United States Patent
Aebi et al.

(10) Patent No.: US 7,632,829 B2
(45) Date of Patent: Dec. 15, 2009

(54) DIAZEPAN DERIVATIVES

(75) Inventors: Johannes Aebi, Binningen (CH); Luke Green, Basel (CH); Patrizio Mattei, Riehen (CH); Fabienne Ricklin, Hombourg (FR); Olivier Roche, Folgensbourg (FR); Peter Zahm, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 167 days.

(21) Appl. No.: 11/788,252

(22) Filed: Apr. 19, 2007

(65) Prior Publication Data

US 2007/0249589 A1 Oct. 25, 2007

(30) Foreign Application Priority Data

Apr. 20, 2006 (EP) .................... 06112832

(51) Int. Cl.
| | | |
|---|---|---|
| C07D 243/14 | (2006.01) | |
| C07D 405/12 | (2006.01) | |
| C07D 401/06 | (2006.01) | |
| C07D 401/14 | (2006.01) | |
| C07D 413/12 | (2006.01) | |
| A61K 31/551 | (2006.01) | |

(52) U.S. Cl. ...................... 514/218; 540/492
(58) Field of Classification Search ............ 514/218; 540/492

See application file for complete search history.

(56) References Cited

FOREIGN PATENT DOCUMENTS

| WO | WO 03/022277 | 3/2003 |
| WO | WO 03/095029 | 11/2003 |
| WO | WO 2004/084898 | 10/2004 |
| WO | WO 2004/092124 | 10/2004 |
| WO | WO 2004/094371 | 11/2004 |
| WO | WO 2007/122104 | 11/2007 |

*Primary Examiner*—Bruck Kifle
(74) *Attorney, Agent, or Firm*—George W. Johnston; Dennis P. Tramaloni

(57) ABSTRACT

The invention is concerned with novel diazepan derivatives of formula (I)

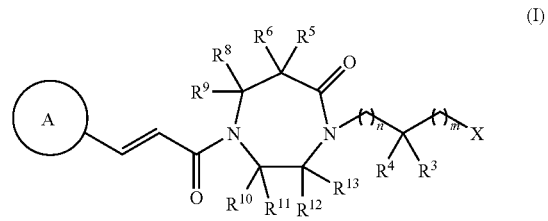

wherein A, X, $R^3$, $R^4$, $R^5$, $R^6$, $R^8$, $R^9$, $R^{10}$, $R^{11}$, $R^{12}$, $R^{13}$, m and n are as defined in the description and in the claims, as well as physiologically acceptable salts thereof. These compounds are antagonists of CCR-2 receptor, CCR-5 receptor and/or CCR-3 receptor and can be used as medicaments.

35 Claims, No Drawings

DIAZEPAN DERIVATIVES

PRIORITY TO RELATED APPLICATIONS

This application claims the benefit of European Application No. 06112832.8, filed Apr. 20, 2006, which is hereby incorporated by reference in its entirety.

BACKGROUND

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The invention is concerned with novel diazepan derivatives of formula (I),

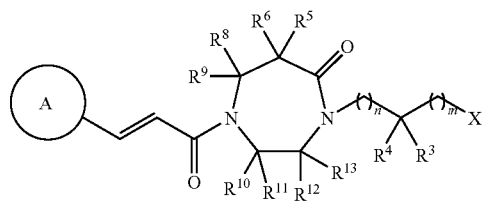

wherein
A is aryl or heteroaryl, said aryl and said heteroaryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said aryl and said heteroaryl being optionally substituted by $C_{1-6}$ alkylenedioxy;

X is —N($R^1$)($R^2$) or —N$^+$($R^1$)($R^2$)($R^7$);

$R^1$ and $R^2$ are, independently to each other, hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$; or $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl;

$R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen; or $R^1$ is hydrogen, $C_{1-6}$ alkyl, $C_{3-6}$ alkenyl, $C_{3-6}$ alkynyl, hydroxy $C_{1-6}$ alkyl, $C_{1-6}$ alkoxy $C_{1-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$;

$R^3$ is hydrogen, $C_{1-6}$ alkyl, $C_{3-7}$ cycloalkyl, $C_{3-7}$ cycloalkyl $C_{1-6}$ alkyl, halogen or halo $C_{1-6}$ alkyl;

$R^2$ and $R^4$, together with the nitrogen atom to which $R^2$ is attached, the carbon atom to which $R^4$ is attached and the $C_{1-2}$ alkylene between said nitrogen atom and said carbon atom, if any, form heterocyclyl optionally substituted by one to three substituents independently selected from the group consisting of $C_{1-6}$ alkyl and fluorine;

$R^5$ and $R^6$ are, independently to each other, hydrogen, fluoro, $C_{1-6}$ alkyl or $C_{3-7}$ cycloalkyl;

$R^7$ is $C_{1-6}$ alkyl;

$R^8$, $R^9$, $R^{10}$, $R^{11}$, $R^{12}$ and $R^{13}$ are, independently to each other, hydrogen, $C_{1-6}$ alkyl or $C_{3-7}$ cycloalkyl;

$R^d$ is hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and the phenyl of said phenyl and said phenyl $C_{1-3}$ alkyl, the heteroaryl of said heteroaryl and said heteroaryl $C_{1-3}$ alkyl, and the heterocyclyl being optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of the heterocyclyl being optionally replaced with a carbonyl group;

$R^a$, $R^b$ and $R^c$ are independently hydrogen or $C_{1-6}$ alkyl;

n is an integer of 0 to 3;

m is an integer of 0 to 3;

m+n is an integer of 1 to 5;

or prodrugs or pharmaceutically acceptable salts thereof.

Further, the invention is concerned with a process and an intermediate for the manufacture of the above compounds, pharmaceutical preparations which contain such compounds, the use of these compounds for the production of pharmaceutical preparations.

The compounds of formula (I) are CCR2 receptor (Chemokine Receptor 2/Monocyte chemotactic protein 1 receptor) antagonists and also CCR-5 receptor (Chemokine Receptor 5) and/or CCR-3 receptor (Chemokine Receptor 3) antagonists. Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

DETAILED DESCRIPTION

The present invention provides the novel compounds of formula (I) which are CCR2 receptor antagonists, with some antagonist activity also at CCR-3 and CCR-5.

Definitions

Unless otherwise indicated, the following definitions are set forth to illustrate and define the meaning and scope of the various terms used to describe the invention herein.

The term "halogen" or "halo" means fluorine, chlorine, bromine and iodine, with chlorine and fluorine being preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl or $C_{1-3}$ alkyl is more preferred. The term "$C_{2-6}$ alkyl" means the same as "$C_{1-6}$ alkyl", except that $C_{2-6}$ alkyl has two to six carbon atoms.

The term "hydroxy $C_{1-6}$ alkyl" means $C_{1-6}$ alkyl substituted by one or more, preferably one hydroxy group(s).

The term "halo $C_{1-6}$ alkyl" means $C_{1-6}$ alkyl substituted by one or more same or different halogen atoms.

The term "$C_{1-2}$ alkylene" means a linear saturated divalent hydrocarbon radical of one to two carbon atoms, such as methylene, ethylene.

The term "$C_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "$C_{7-10}$ bicycloalkyl", alone or in combination with other groups, means a saturated monovalent cyclic hydrocarbon radical of seven to ten ring carbons, having two rings, in which two or more ring carbon atoms of one ring are ring carbon atoms of the other ring, e.g., bicyclo[2.2.1]heptyl.

The term "$C_{1-6}$ alkoxy", alone or in combination with other groups, means the group R'—O—, wherein R' is a $C_{1-6}$ alkyl.

The term "halo $C_{1-6}$ alkoxy", alone or in combination with other groups, means $C_{1-6}$ alkoxy substituted by one or more, preferably one to three halogens.

The term "$C_{1-6}$ alkylenedioxy" means —O—$C_{1-6}$ alkyl-O—. Methylenedioxy or 1,2-ethylenedioxy are preferred.

The term "$C_{3-6}$ alkenyl", alone or in combination with other groups, means a straight-chain or branched hydrocarbon residue comprising a carbon-carbon double bond, having three to six carbon atoms, provided that the carbon atom of the attachment point of the $C_{3-6}$ alkenyl to the rest of the molecule is not bonded to another carbon atom of the $C_{3-6}$ alkenyl by a carbon-carbon double bond. An example of $C_{3-6}$ alkenyl is 2-propenyl.

The term "$C_{3-6}$-alkynyl", alone or in combination with other groups, means a straight-chain or branched hydrocarbon residue comprising a carbon-carbon triple bond, having three to six carbon atoms, provided that the carbon atom of the attachment point of the $C_{3-6}$ alkynyl to the rest of the molecule is not bonded to another carbon atom of the $C_{3-6}$ alkynyl by a carbon-carbon triple bond. An example of $C_{3-6}$ alkynyl is 2-propynyl.

The term "acyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

The term "heterocyclyl", alone or combination with other groups, means non-aromatic mono- or bi-cyclic radicals of four to nine ring atoms in which one to three ring atoms are heteroatoms independently selected from N, O and $S(O)_n$ (where n is an integer from 0 to 2), the remaining ring atoms being C.

The term "aryl", alone or combination with other groups, means phenyl or naphthyl.

The term "heteroaryl", alone or combination with other groups, means a monocyclic or bicyclic radical of 5 to 10 ring atoms having one to three ring heteroatoms independently selected from N, O, and S, the remaining ring atoms being C.

The term "bicyclic radicals" means radicals having two rings, in which two or more ring atoms of one ring are ring carbon atoms of the other ring.

The term, "$C_{1-6}$ alkylsulfonyl", "$C_{1-6}$ alkylsulfinyl" and "$C_{1-6}$ alkylthio" means $C_{1-6}$ alkyl-$SO_2$—, $C_{1-6}$ alkyl-SO— and $C_{1-6}$ alkyl-S—, respectively.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Detailed Description

The invention is concerned with novel diazepan derivatives of formula (I),

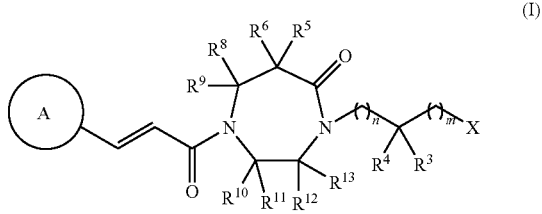

(I)

wherein

A is aryl or heteroaryl, said aryl and said heteroaryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said aryl and said heteroaryl being optionally substituted by $C_{1-6}$ alkylenedioxy;

X is —N($R^1$)($R^2$) or —$N^+$($R^1$)($R^2$)($R^7$);

$R^1$ and $R^2$ are, independently to each other, hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$; or $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl;

$R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen; or $R^1$ is hydrogen, $C_{1-6}$ alkyl, $C_{3-6}$ alkenyl, $C_{3-6}$ alkynyl, hydroxy $C_{1-6}$ alkyl, $C_{1-6}$ alkoxy $C_{1-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$;

$R^3$ is hydrogen, $C_{1-6}$ alkyl, $C_{3-7}$ cycloalkyl, $C_{3-7}$ cycloalkyl $C_{1-6}$ alkyl, halogen or halo $C_{1-6}$ alkyl;

$R^2$ and $R^4$, together with the nitrogen atom to which $R^2$ is attached, the carbon atom to which $R^4$ is attached and the $C_{1-2}$ alkylene between said nitrogen atom and said carbon atom, if any, form heterocyclyl optionally substituted by one to three substituents independently selected from the group consisting of $C_{1-6}$ alkyl and fluorine;

$R^5$ and $R^6$ are, independently to each other, hydrogen, fluoro, $C_{1-6}$ alkyl or $C_{3-7}$ cycloalkyl;

$R^7$ is $C_{1-6}$ alkyl;

$R^8$, $R^9$, $R^{10}$, $R^{11}$, $R^{12}$ and $R^{13}$ are, independently to each other, hydrogen, $C_{1-6}$ alkyl or $C_{3-7}$ cycloalkyl;

$R^d$ is hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$^b$, —$NR^a$—$SO_2$—$NR^bR^c$, —OC(O)$NR^aR^b$, —OC(O)

OR$^a$, C$_{1-6}$ alkylsulfonyl, C$_{1-6}$ alkylsulfinyl, C$_{1-6}$ alkylthio, phenyl, phenyl C$_{1-3}$ alkyl, heteroaryl, heteroaryl C$_{1-3}$ alkyl and heterocyclyl, and the phenyl of said phenyl and said phenyl C$_{1-3}$ alkyl, the heteroaryl of said heteroaryl and said heteroaryl C$_{1-3}$ alkyl, and the heterocyclyl being optionally substituted by one to three substituents independently selected from the group consisting of hydroxy, cyano, NR$^a$R$^b$, halogen, C$_{1-6}$ alkyl, halo C$_{1-6}$ alkyl, hydroxy C$_{1-6}$ alkyl, C$_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, C$_{1-6}$ alkylsulfonyl, C$_{1-6}$ alkylsulfinyl and C$_{1-6}$ alkylthio, and one or two ring carbon atoms of the heterocyclyl being optionally replaced with a carbonyl group;

R$^a$, R$^b$ and R$^c$ are independently hydrogen or C$_{1-6}$ alkyl;

n is an integer of 0 to 3;

m is an integer of 0 to 3;

m+n is an integer of 1 to 5;

or prodrugs or pharmaceutically acceptable salts thereof.

While the broadest definition of this invention is described before, certain compounds of formula (I) are preferred.

A preferred compound of the invention is a compound of formula (I), wherein A is phenyl optionally substituted by one to three substituents independently selected from the group consisting of halogen, benzyloxy, heteroaryl-C$_{1-6}$ alkoxy, C$_{1-6}$ alkyl, C$_{1-6}$ alkoxy and halo C$_{1-6}$ alkoxy, or A is phenyl optionally substituted by C$_{1-6}$ alkylenedioxy. More preferably, A is phenyl substituted by one or two halogen atoms independently selected from the group consisting of chlorine and fluorine. Further more preferably, A is phenyl substituted by two halogen atoms independently selected from the group consisting of chlorine and fluorine at its 3,4 or 3,5 position.

Another preferred compound of the invention is a compound of formula (I), wherein X is —N(R$^1$)(R$^2$). Preferably, at least one of R$^1$ and R$^2$ is other than hydrogen. R$^1$ is preferably hydrogen, C$_{1-6}$ alkyl, or hydroxy C$_{2-6}$ alkyl, more preferably hydrogen or C$_{1-6}$ alkyl, especially hydrogen, and R$^2$ is preferably C$_{3-7}$ cycloalkyl, heterocyclyl, heterocyclyl C$_{1-6}$ alkyl, C$_{7-10}$ bicycloalkyl, hydroxy C$_{2-6}$ alkyl or C$_{1-6}$ alkoxy C$_{2-6}$ alkyl, especially heterocyclyl, in which the cycloalkyl and the heterocyclyl of said heterocyclyl and said heterocyclyl C$_{1-6}$ alkyl are optionally substituted by one or two substituents independently selected from the group consisting of C$_{1-6}$ alkyl, hydroxy, heteroaryl and C$_{1-6}$ alkoxy. When X is —N(R$^1$)(R$^2$), m+n is preferably an integer of 1 or 2, especially 1, and/or R$^3$, R$^4$, R$^5$ and R$^6$ are preferably hydrogen.

In this group ii), preferably A is phenyl optionally substituted by one to three substituents independently selected from the group consisting of halogen, benzyloxy, heteroaryl-C$_{1-6}$ alkoxy, C$_{1-6}$ alkyl, C$_{1-6}$ alkoxy and halo C$_{1-6}$ alkoxy, or A is phenyl optionally substituted by C$_{1-6}$ alkylenedioxy. More preferably, A is phenyl substituted by one or two halogen atoms independently selected from the group consisting of chlorine and fluorine. Further more preferably, A is phenyl substituted by two halogen atoms independently selected from the group consisting of chlorine and fluorine at its 3,4 or 3,5 position.

Another preferred compound of the invention is a compound of formula (I), wherein X is —N(R$^1$)(R$^2$), and R$^1$ and R$^2$, together with the nitrogen atom to which they are attached, form heterocyclyl optionally substituted by one to three substituents independently selected from the group consisting of R$^d$, and one of the ring carbon atoms of said heterocyclyl formed by R$^1$ and R$^2$ being optionally replaced with a carbonyl group; and/or one of the ring carbon atoms of the heterocyclyl formed by R$^1$ and R$^2$ may be a ring carbon atom of another ring which is C$_{3-7}$ cycloalkyl or heterocyclyl, one or two ring carbon atoms of said another ring being optionally replaced by a carbonyl group, and said another ring being optionally substituted by C$_{1-6}$ alkyl.

The heterocyclyl formed by R$^1$ and R$^2$, together with the nitrogen atom to which they are attached, is preferably a mono-cyclic radical of five or six ring atoms in which one more ring atom, in addition ot the nitrogen atom, may be a heteroatom independently selected from N, O and S(O)$_n$ (where n is an integer from 0 to 2), such as piperidyl, pyrrolidinyl, piperazinyl, morpholinyl, thiomorpholinyl or 1,1-dioxo-thiomorphlinyl. The heterocyclyl formed by R$^1$ and R$^2$, together with the nitrogen atom to which they are attached, is preferably piperidyl or pyrrolidinyl.

More preferably, the heterocyclyl formed by R$^1$ and R$^2$, together with the nitrogen atom to which they are attached, is optionally substituted by one or two substituents independently selected from the group consisting of hydroxy, phenyl and hydroxy C$_{1-6}$ alkyl, and/or one of the ring carbon atoms of the heterocyclyl formed by R$^1$ and R$^2$ may be a ring carbon atom of another ring which is five or six membered mono-cyclic heterocyclyl, one or two ring carbon atoms of said another ring being optionally replaced by a carbonyl group.

In this group iii), m+n is preferably an integer of 1 to 3, and R$^3$, R$^4$, R$^5$ and R$^6$ are hydrogen.

Moreover, in this group iii), preferably A is phenyl optionally substituted by one to three substituents independently selected from the group consisting of halogen, benzyloxy, heteroaryl-C$_{1-6}$ alkoxy, C$_{1-6}$ alkyl, C$_{1-6}$ alkoxy and halo C$_{1-6}$ alkoxy, or A is phenyl optionally substituted by C$_{1-6}$ alkylenedioxy. More preferably, A is phenyl substituted by one or two halogen atoms independently selected from the group consisting of chlorine and fluorine. Further more preferably, A is phenyl substituted by two halogen atoms independently selected from the group consisting of chlorine and fluorine at its 3,4 or 3,5 position.

Another preferred compound of the invention is a compound of formula (I), which is 1-[(E)-3-(3,4-Dichloro-phenyl)-acryloyl]-4-(4-piperidin-1-yl-butyl)-[1,4]diazepan-5-one, 1-[(E)-3-(3-Chloro-4-fluoro-phenyl)-acryloyl]-4-(3-piperidin-1-yl-propyl)-[1,4]diazepan-5-one, 1-[(E)-3-(4-Chloro-3-fluoro-phenyl)-acryloyl]-4-(3-piperidin-1-yl-propyl)-[1,4]diazepan-5-one, 8-(3-{4-[(E)-3-(3,4-Dichloro-phenyl)-acryloyl]-7-oxo-[1,4]diazepan-1-yl}-propyl)-1,3,8-triaza-spiro[4.5]decane-2,4-dione, 1-[(E)-3-(3,4-Dichloro-phenyl)-acryloyl]-4-[3-(4-hydroxy-4-phenyl-piperidin-1-yl)-propyl]-[1,4]diazepan-5-one, (+/−)-1-[(E)-3-(3,4-Dichloro-phenyl)-acryloyl]-4-[3-(3-hydroxy-piperidin-1-yl)-propyl]-[1,4]diazepan-5-one, 8-(3-{4-[(E)-3-(3,4-Dichloro-phenyl)-acryloyl]-7-oxo-[1,4]diazepan-1-yl}-propyl)-1-oxa-3,8-diaza-spiro[4.5]decan-2-one, 1-[(E)-3-(3,4-Dichloro-phenyl)-acryloyl]-4-[3-(tetrahydro-pyran-4-ylamino)-ethyl]-[1,4]diazepan-5-one, (S)-1-[(E)-3-(3,4-Dichloro-phenyl)-acryloyl]-4-[3-(2-hydroxymethyl-pyrrolidin-1-yl)-ethyl]-[1,4]diazepan-5-one, or 1-[(E)-3-(3,4-Dichloro-phenyl)-acryloyl]-4-(2-pyrrolidin-1-yl-ethyl)-[1,4]diazepan-5-one, or 1-[(E)-3-(3-Chloro-4-fluoro-phenyl)-acryloyl]-4-[3-((−, cis)-3-hydroxy-4-methyl-piperidin-1-yl)-propyl]-[1,4] diazepan-5-one. or 1-[(E)-3-(3-Chloro-4-fluoro-phenyl)-acryloyl]-4-[3-(3-hydroxy-4,4-dimethyl-piperidin-1-yl)-propyl]-[1,4]diazepan-5-one, or (cis)-1-[(E)-3-(3-Chloro-4-fluoro-phenyl)-acryloyl]-4-[3-(3-hydroxy-5-methyl-piperidin-1-yl)-propyl]-[1,4]diazepan-5-one, or 1-[(E)-3-(3,4-Dichloro-phenyl)-acryloyl]-4-[2-hydroxy-3-(3-hydroxy-4-methyl-piperidin-1-yl)-propyl]-[1,4] diazepan-5-one, or 1-[(E)-3-(3,4-Dichloro-phenyl)-acryloyl]-4-[(S)-2-hydroxy-3-((−)-4-hydroxy-6-aza-spiro[2.5]oct-6-yl)-propyl]-[1,4]diazepan-5-one, or 1-[(E)-3-(3-Chloro-4-fluoro-phenyl)-acryloyl]-4-[(S)-2-hydroxy-3-(3-hydroxy-4,4-dimethyl-piperidin-1-yl)-propyl]-[1,4]diazepan-5-one, or 1-[(E)-3-(3-Chloro-4-fluoro-phenyl)-acryloyl]-4-[(S)-2-hydroxy-3-(cis-3-hydroxy-5-methyl-piperidin-1-yl)-propyl]-[1,4]diazepan-5-one, or 1-[(E)-3-(4-Chloro-3-fluoro-phenyl)-acryloyl]-4-[4-((−)-4-hydroxy-6-aza-spiro[2.5]oct-6-yl)-butyl]-[1,4]diazepan-5-one, or (cis)-1-[(E)-3-(3-Chloro-4-fluoro-phenyl)-acryloyl]-4-[4-(3-hydroxy-5-methyl-piperidin-1-yl)-butyl]-[1,4]diazepan-5-one, or 1-[(E)-3-(3-Chloro-phenyl)-acryloyl]-4-[3-((−)-4-hydroxy-6-aza-spiro[2.5]oct-6-yl)-propyl]-[1,4]diazepan-5-one, or 1-[(E)-3-(5,6-Dichloro-pyridin-3-yl)-acryloyl]-4-[3-((−)-4-hydroxy-6-aza-spiro[2.5]oct-6-yl)-propyl]-[1,4]diazepan-5-one, or 1-[(E)-3-(3-Chloro-4-fluoro-phenyl)-acryloyl]-4-[3-((−)-4-hydroxy-6-aza-spiro[2.5]oct-6-yl)-propyl]-[1,4]diazepan-5-one, or 1-[(E)-3-(3-Chloro-phenyl)-acryloyl]-4-[3-((−)-4-hydroxy-6-aza-spiro[2.5]oct-6-yl)-propyl]-[1,4]diazepan-5-one, or 1-[(E)-3-(5,6-Dichloro-pyridin-3-yl)-acryloyl]-4-[3-((−)-4-hydroxy-6-aza-spiro[2.5]oct-6-yl)-propyl]-[1,4]diazepan-5-one.

General Synthetic Procedures

The compounds of the present invention can be prepared, for example, by the general synthetic procedures described below. Appropriate reaction conditions for the individual reaction steps are known to a person skilled in the art. Starting materials are either commercially available or can be prepared by methods known in the art.

Scheme 1

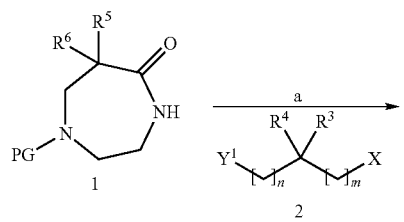

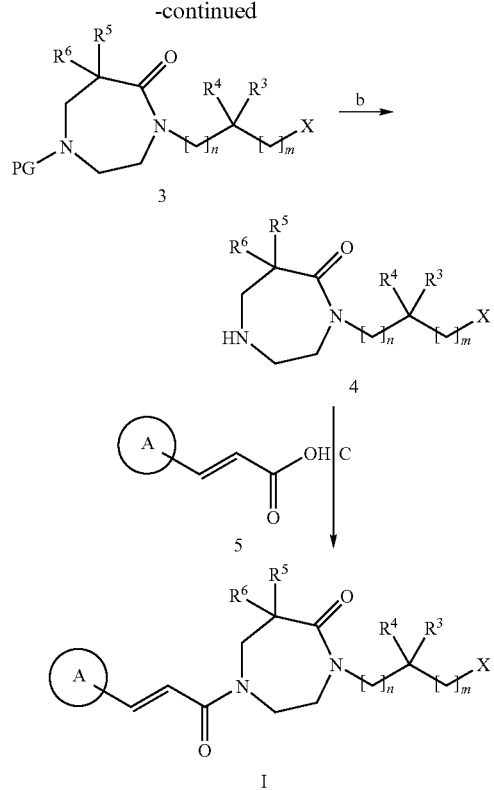

In Scheme 1, PG means protecting group, such as BOC (tert-butyloxy carbonyl), Z(benzyloxy carbonyl). $Y^1$ means bromide, iodide, mesylate or triflate, A, X, $R^3$, $R^4$, $R^5$ and $R^6$, m and n are as defined before. The same reactions described in scheme 1 can be performed with 1 being substituted with $R^5$, $R^6$, $R^8$, $R^9$, $R^{10}$, $R^{11}$, $R^{12}$ and $R^{13}$, as defined before.

Protected 5-oxo-[1,4]diazepanes 1 of scheme 1 are commercially available or can be synthesized by methods known in the art (see e.g. Dickerman, S. C.; Lindwall, H. G. Piperidone chemistry. I. Synthesis of 5-homopiperazinones. Journal of Organic Chemistry (1949), 14 530-6). $R^5$, $R^6$ can be introduced on a suitably protected 5-oxo-[1,4]diazepanes through deprotonation at low temperature and alkylation or fluorination followed by a second deprotonation and alkylation or fluorination, or can also be synthesized from the corresponding piperazinone (see e.g. Design and synthesis of combinatorial scaffolds-diazepinone and homopiperazine. Sun, Chung-Ming. Department of Chemistry, National Dong-Hwa University, Hualien, Taiwan. Letters in Drug Design & Discovery (2005), 2(1), 48-50). $Y^1$ activated building block 2 is commercially available or can be synthesized as described below. The corresponding none activated precursor amines can be synthesized from acids via amide and reduction with methods known in the art, followed optionally by quaternisation. The corresponding acids are commercially available or can be synthesized from epsilon-hydroxy acids via $R^3$ and then $R^4$ alkylation followed optionally by $[CH_2]_{m-1}$ elongation. The $Y^1$ for the amine can then be introduced by activation of the epsilon-hydroxyl group to $Y^1$ ($Y^1$=Cl, e.g. reaction of the alcohol with thionyl chloride in THF 0° C. to 50° C. gives the corresponding chloride). Deprotonation of protected 5-oxo-[1,4]diazepanes 1 in solvents like DMF with e.g. NaH as base at 0° C. to RT followed by reaction with building block 2 at 0° C. to 75° C., preferably 50° C. gives the protected intermediate 3 (step a). Deprotection (e.g. for BOC protected 3, with HCl in dioxane, in $CH_2Cl_2$ and methanol as solvents) gives intermediate 4 as hydrochloride salt (step b) which can be coupled with all possible acids 5 to give the final compound I (step c). Acid 5 can be activated e.g. with oxalyl chloride and catalytic amount of DMF to the ciannamic acid chloride and then reacted with amine 4 in the presence of a base like triethyl amine, or CDI activation DCC, HATU coupling are possible alternatives. Acids 5 can be synthesized from the corresponding aldehydes, or from the corresponding alcohols via oxidation and subsequent Wittig reaction or subsequent Knoevenagel reaction with malonate.

The compounds I with $X=-N(R^1)(R^2)$ can optionally be converted to $X=-N^+(R^1)(R^2)(R^3)$ with $R^3$-halogenide in a solvent like methanol as described in scheme 5 shown below.

In Scheme 2, $Y^1$ means bromide, iodide, mesylate or triflate, A, $R^1$, $R^2$, $R^3$, $R^4$, $R^5$ and $R^6$, m and n are as defined before. The same reactions described in scheme 2 can be performed with 1 being substituted with $R^5$, $R^6$, $R^8$, $R^9$, $R^{10}$, $R^{11}$, $R^{12}$ and $R^{13}$, as defined before.

The free 5-oxo-[1,4]diazepane 1 of scheme 2 is commercially available. $R^5$, $R^6$ can be introduced on a suitable protected 5-oxo-[1,4]diazepanes through deprotonation at low temperature and alkylation or fluorination followed by a second deprotonation and alkylation or fluorination, or can also be synthesized from the corresponding piperazinone (see e.g. Design and synthesis of combinatorial scaffolds-diazepinone and homopiperazine. Sun, Chung-Ming. Department of Chemistry, National Dong-Hwa University, Hualien, Taiwan. Letters in Drug Design & Discovery (2005), 2(1), 48-50).

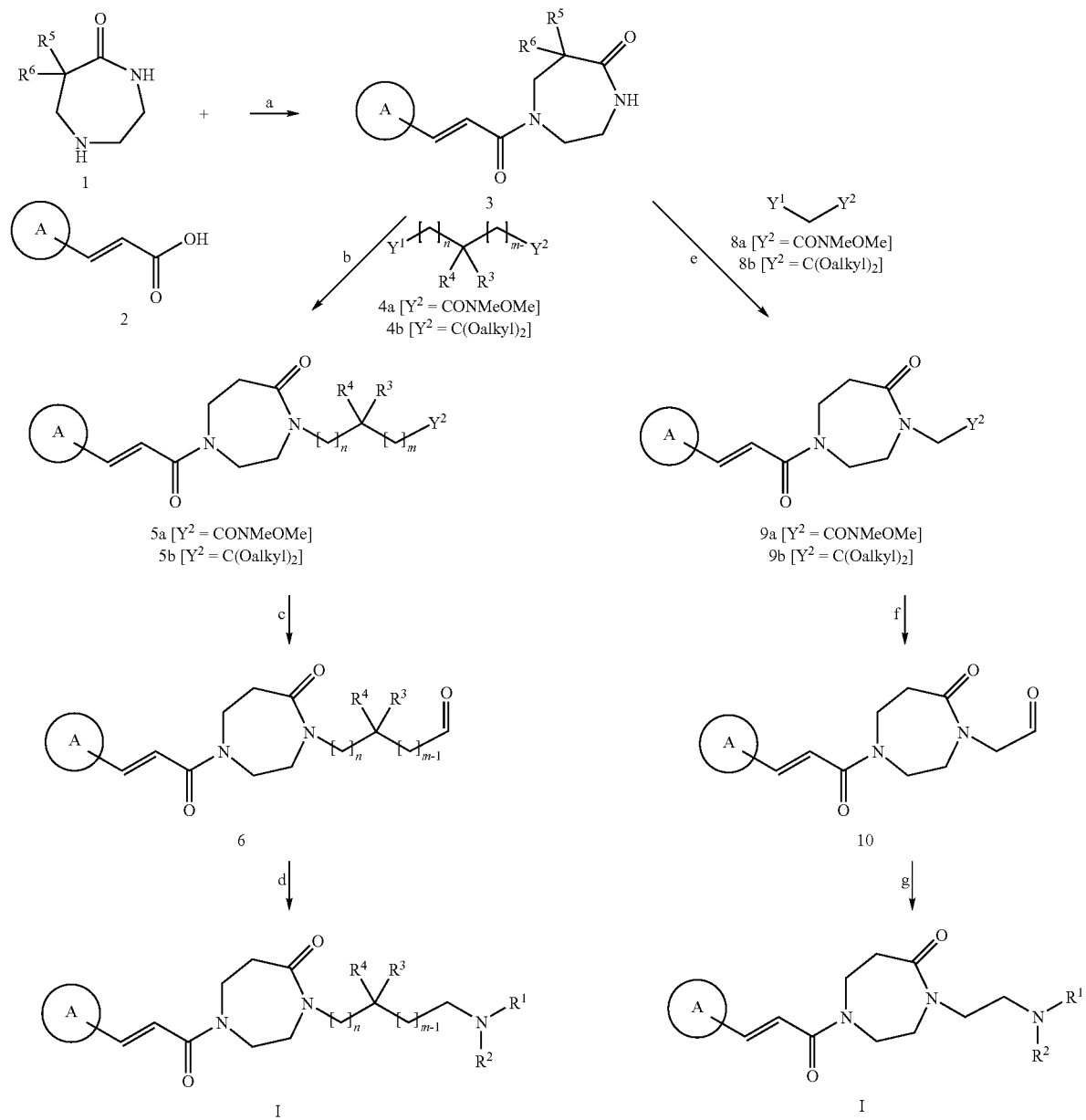

Acids 2 can be synthesized from the corresponding alcohols or aldehyde (via oxidation, for the alcohols) followed by Wittig reaction. Acid 2 can then be activated e.g. with oxalyl chloride and catalytic amount of DMF to the ciannamic acid chloride and then reacted with 5-oxo-[1,4]diazepanes 1 in the presence of a base like triethyl amine, alternatively CDI activation of the acid 2 or DCC or HATU coupling is possible to give intermediate 3 (step a). $Y^1$ activated Weinreb building blocks 4a or 8a are synthesized from the corresponding acids by treatment with N,O-dimethyl-hydroxyl-amine-hydrochloride with EDCI and HOBT in $CH_2Cl_2$ at 0° C. to room temperature. The acids are commercial available or can be synthesized from epsilon-hydroxy acids via $R^3$, $R^4$ alkylation followed optionally by $[CH_2]_{m-1}$ elongation and activation of the hydroxyl group to $Y^1$. The elongation reaction can also lead to aldehydes, which can be transformed to acetals 4b. $Y^1$ activated acetals are also commercial available. Deprotonation of the 5-oxo-[1,4]diazepanes 3 in the presence of 4a, 4b or 8a, 8b in solvents like THF with e.g. NaH as base at 0° C. to RT and then at 50° C. to 75° C. gave intermediate 5a, 5b or 9a, 9b respectively (step b or e). In case of 3-bromo-N-methoxy-N-methyl-propionamide 4a, the first equivalent of NaH is forming the corresponding acrylamide which reacts after additional addition of NaH to the final amide 5a. An LAH— solution, preferable in THF was added to the cooled (preferable at −30° C.) suspension of amide 5a or 9a. After 5 to 15 min, the reaction was cooled (−78° C.) and quenched with acetone and acetic acid to give aldehyde 6 or 10. Aldehydes 6 and 10 are also received from acetal-protected 5b or 9b after cleavage with e.g. formic acid in a mixture of toluene water (step c or f). Reductive amination with $R^1R^2NH$ in $CH_2Cl_2$ with a slight excess of acetic acid and $NaHB(OAc)_3$ at room temperature gives the final compounds I (step d or g).

The compounds I with X=—$N(R^1)(R^2)$ can optionally be converted to X=—$N^+(R^1)(R^2)(R^3)$ with $R^3$-halogenide in a solvent like methanol as described in scheme 5 shown below.

In Scheme 3, $Y^1$ means bromide, iodide, mesylate or triflate, $Y^1$ can be additionally tosylate, $Y^2$ is chloride or ester, or when m is 1, $R^3$, together with $Y^2$ forms epoxy group or —O—$C(CH_3)_2$—O— group, $Y^2$ can be additionally bromide or iodide, A, X, $R^1$, $R^2$, $R^3$, $R^4$, $R^5$ and $R^6$, m and n are as defined before. The same reactions described in scheme 3 can be performed with 1 being substituted with $R^5$, $R^6$, $R^8$, $R^9$, $R^{10}$, $R^{11}$, $R^{12}$ and $R^{13}$, as defined before.

The acylated 5-oxo-[1,4]diazepanes 1 of scheme 3 (corresponds to compound 3 described in scheme 2) can be reacted in two ways to the final compound I. Either directly, where building block 1 was deprotonated e.g. with NaH or potassium tert-butylate in DMA or THF at 0° C. to 65° C. and then reacted with the activated amine 2 (step a). Deprotonation can be carried out with potassium tert-butylate, and THF can be also used as a solvent. Amine 2 is commercially available or can be synthesized by methods known in the art. Amines can be synthesized from acids via amide and reduction to the corresponding amines 2 with methods known in the art followed optionally by quaternisation. The corresponding acids are commercial available or can be synthesized from suitably protected epsilon-hydroxy acids via $R^3$ and then $R^4$ alkylation followed optionally by $[CH_2]_{m-1}$ elongation or $R^3$ modification (e.g. reduction of the ester to the alcohol and protecting it orthogaonal to the epsilon-hydroxy group or alkylation of the alcohol) and activation of the deprotected epsilon-hydroxyl group to $Y^1$ ($Y^1$=Cl, e.g. reaction of the alcohol with thionyl chloride in THF 0° C. to 50° C. gives the corresponding chloride, followed optionally by Finkelstein reaction to the corresponding $Y^1$=Br or $Y^1$=I). Amine 2 can also be synthesized from building block 3 when $Y^2$ is more reactive than $Y^1$ (e.g. $Y^2$=$Y^1$ but preferred reactivity through steric control with the corresponding amine 6). Another possibility is to

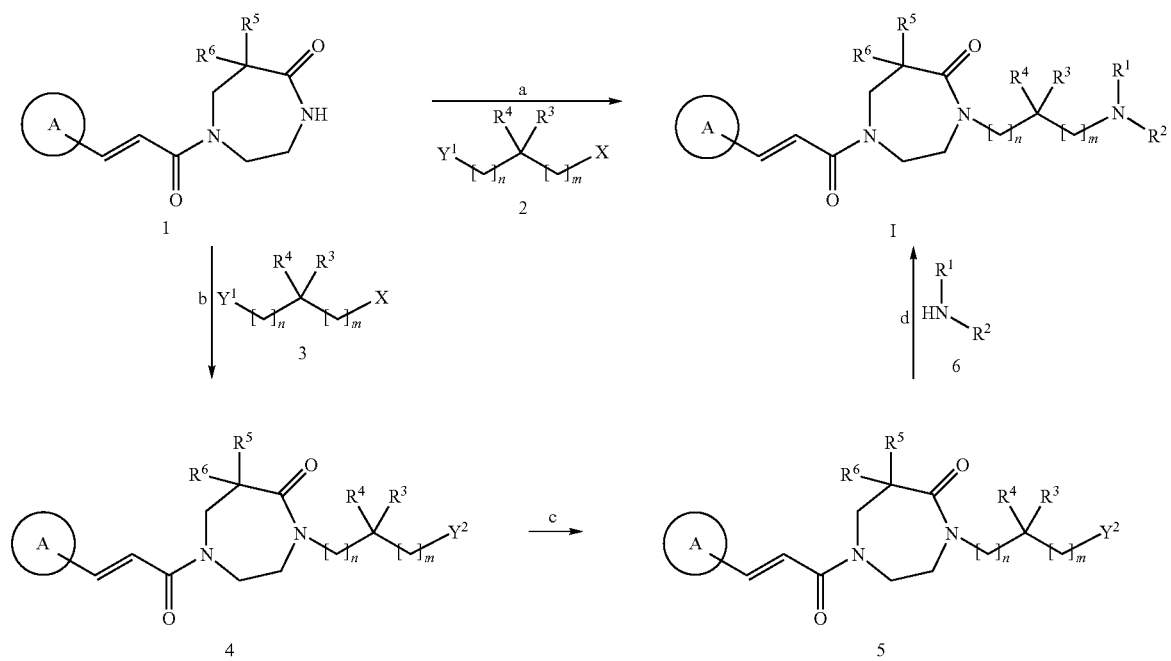

Scheme 3 react the deprotonated acylated 5-oxo-[1,4]diazepanes 1 with building block 3, where the $Y^1$ and $Y^2$ are groups as indicated in the scheme 3 to give intermediate 4 (step b). Building block 3 is commercial available or can be synthesized from epsilon-hydroxy acids via $R^3$ and then $R^4$ alkylation followed optionally by $[CH_2]_{m-1}$ elongation, optionally by introduction of $Y^2$, which is a group with a lower reactivity than $Y^1$. Transformation of the epsilon hydroxyl group to $Y^1$ gives 3. For $Y^2$=chloride, a better leaving group has to be synthesized via Finkelstein reaction (NaI in 2-butanone at 95° C.) to give compound 5 (step c). In case for $Y^2$=ester, sodium borohydride reduction gives the alcohol, which is transferred to the chloride (methansulfonyl chloride/$Et_3N$ in $CH_2Cl_2$) to give 5 ($Y^2$=Cl) (step c). Chloride can optionally be transformed to the iodide 5 ($Y^2$=I) under Finkelstein conditions. Reaction of 5 with an optionally excess of amine 6 in the presence of NaI (for $Y^2$=Cl) or optionally of $Et_3N$, in DMF or DMA gives the final compound I (step d).

In case m is 1, $R^3$, together with $Y^2$ forms epoxy group and $Y^1$=Br or I, building block 3 is an epoxide which reacts with 5-oxo-[1,4]diazepan 1 as described above to the corresponding epoxide 5 ($R^3$ and $Y^2$ form epoxy group and m is 1). Reaction with amine 6 in ethanol or with $Cs_2CO_3$ in DMF or DMA at RT to 80° C. gives the final compound I, which optionally can be separated on a chiral column in the enantiomers. Epoxides 3 are commercially available or can be synthesized from the corresponding alkenes with e.g. m-chloroperbenzoic acid in dichloromethane. For the chiral synthesis, the corresponding commercially available or synthesized chiral 2,2-dimethyl-[1,3]dioxalane 3 (—$R^3$—$Y^2$— is —O—C(Me)$_2$-O—) was used. Acetal 4 ($R^3$ and $Y^2$ form —O—C(Me)$_2$-O—) can be cleaved (Dowex $H^+$ in methanol under reflux), mono mesylated (4, $R^3$=OH, $Y^2$=OMes) and in situ cyclised to the epoxide 5 ($R^3$ and $Y^2$ form epoxy group and m is 1; e.g. mesylchlorid and excess collidine, followed by addition of NaH in DMA at 0° C.). Epoxide 5 was then reacted with amine 6 in ethanol or with $Cs_2CO_3$ in DMF or DMA at 0° C. to 80° C. to give the final compound I. Compound I can further be modified (e.g. $R^3$=COO$C_{1-6}$ alkyl) by hydrolisis with LiOH in THF/ethanol to I (e.g. $R^3$=COO$^-$ $Li^+$) or reduction with $NaBH_4$ in EtOH or $NaBH_4$ in THF to I (e.g. $R^3$=$CH_2OH$). The amines $HNR^1R^2$ 6 are commercial available or can be synthesized by methods known in the art. The $R^d$-substitution can be introduced or manipulated on the appropriate protected amine $NR^1R^2$. Hydroxy groups can be synthesized from ketones, both can be transformed either to mono or di-halogenides. The ketone group in the protected $NR^1R^2$ can be reacted with the metal reagent of $C_{1-6}$ alkyl, phenyl, phenyl $C_{1-3}$ alkyl, heteroaryl, heteroaryl $C_{1-3}$ alkyl and heterocyclyl which are optionally substituted to give the tertiary alcohol. The tertiary alcohol can optionally be eliminated and the double bond hydrogenated to give the corresponding substituted protected $NR^1R^2$. Alternatively, the ketone group in the protected $NR^1R^2$ can be converted to an allylic alcohol via a two step sequence of Wittig reaction to the exomethylene and subsequent allylic oxidation using a suitable reagent e.g. $SeO_2$ to afford the allylic alcohol (as described in J. Org. Chem. 2001, 66, 2487). The resulting allylic alcohol can then be cyclopropanated (e.g with $Et_2Zn$/$CH_2Cl$) to afford the cyclopropanated derivatives, which in turn can be reduced catalytically (e.g. $Pt_2O$ and hydrogen) to afford gem-dimethyl piperidines. Alternatively the cyclopropyl can be introduced directly by double alkylation of the alpha-position of the ketone group in the protected $NR^1R^2$ by deprotonation with a suitable base e.g. tBuOK, and reaction with a double nucleophile as described in Tet. Lett. 1984, 25, 5501. Subsequent reduction of the ketone with e.g. $NaBH_4$ affords the alcohol derivatives. Additionally, spirocyclic derivatives can be prepared from such a suitably protected ketone bearing $NR^1R^2$ as described in J. Org. Chem. 1996, 61, 22, 7650-7651 and J. Med. Chem. 1995, 38, 3772-3779. Substitution on the $C_{1-6}$ alkyl, phenyl, phenyl $C_{1-3}$ alkyl, heteroaryl, heteroaryl $C_{1-3}$ alkyl and heterocyclyl can be further manipulated as discussed below. Cyano groups can be synthesized from amides. $R^aR^b$ in the $NR^aR^b$-substituent can be introduced through orthogonal protection strategy. $C_{1-6}$ alkyl, halo $C_{1-6}$ alkyl, hydroxy $C_{1-6}$ alkyl, acyl can be introduced through enolate alkylation of keton or esters followed by optionally reduction of the ketone to the corresponding methylene group. $C(O)NR^aR^b$ groups are synthesized from acids and amines $HNR^aR^b$, —$NR^a$—C(O)—$R^b$ from amines and acids HOOC—$R^b$, —$NR^a$—C(O)—$OR^b$ from amines and chloro-formates Cl—C(O)—$OR^b$, —$NR^a$—C(O)—$NR^b$ from amines and isocyanates OCN—$R^b$ (which can also be used to generate cyclic ureas as described in WO2005/101989 (A2) where $R^b$ bears a leaving group), —$NR^a$—$SO_2$—$R^b$ from amines and sulfonyl chlorides $ClSO_2$—$R^b$, —$NR^a$—$SO_2$—$NR^bR^c$ from amines and sulfamoyl chlorides which can be synthesized in acetonitrile with $R^bR^cNH$ and sulfuryl chloride at 0° C. to 65° C. In case $R^a$ is an alkyl side chain, this group may be introduced with NaH, $R^a$ halide in DMF at 0° C. to room temperature. The $R^d$-substitution can also be introduced or transformed on the appropriate protected amine $NR^1R^2$ with hydroxy groups: the hydroxy group and isocyanates OCN—$R^b$ gives —OC(O)$NR^aR^b$, the hydroxy group and chloro-formates Cl—C(O)—$OR^b$ gives —OC(O)$OR^b$, the hydroxy group can be akylated. The hydroxy group can be mesylated and reacted with $C_{1-6}$ alkylthiol, which can optionally be oxidized to $C_{1-6}$ alkylsulfonyl- or $C_{1-6}$ alkylsulfinyl-substituents. The mesylate in $NR^1R^2$ can also be reacted with amines $HNR^aR^b$, with NH of heteroaryls or heterocyclyl in the presence of a base. Alternatively, the $R^d$-substitution can also be introduced or transformed on the appropriate protected amine $NR^1R^2$ bearing an ester group, which on reaction with hydrazine at reflux in EtOH affords the corresponding hydrazide which can be then condensed with alkoxyamidines to afford 1,2,4-triazoloyl derivatives. Esters can also be reacted with N-hydroxy-amidines in THF with e.g. NaH as base to [1,2,4]oxadiazols. Acids can be reacted with hydrazides to di acylated hydrazides which can be cyclised with phosphoroxy chloride in acetonitrile to [1,3,4]oxadiazol. Nitriles can be transformed to the corresponding N-hydroxy-amidines and then transformed to the [1,2,4]oxadiazols. Additionally, the appropriately protected amine $NR^1R^2$ derivatives can be prepared from the corresponding pyridine derivatives by reduction to the piperidine under catalytic hydrogenation conditions e.g. $Pt_2O$ or Pd/C and hydrogen as described in WO2004/094371(A2) or by partial reduction of the corresponding pyridinium compounds (prepared by alkylation of the pyridine with a suitable alkylating reagent e.g. benzylbromide) with a suitable reducing agent e.g. $NaBH_4$. The resulting olefins can then be hydroborated e.g. with borane and subsequent oxidative work up to introduce hydroxy groups stereospecifically as described in Tet. Lett. 2000, 41, 5817. Piperidines can also be prepared via condensation of benzylamine, with formaldehyde and the required ketone as described in WO 01/00577A2. The resulting ketopiperidines can be further derivatised as described previously.

Scheme 4

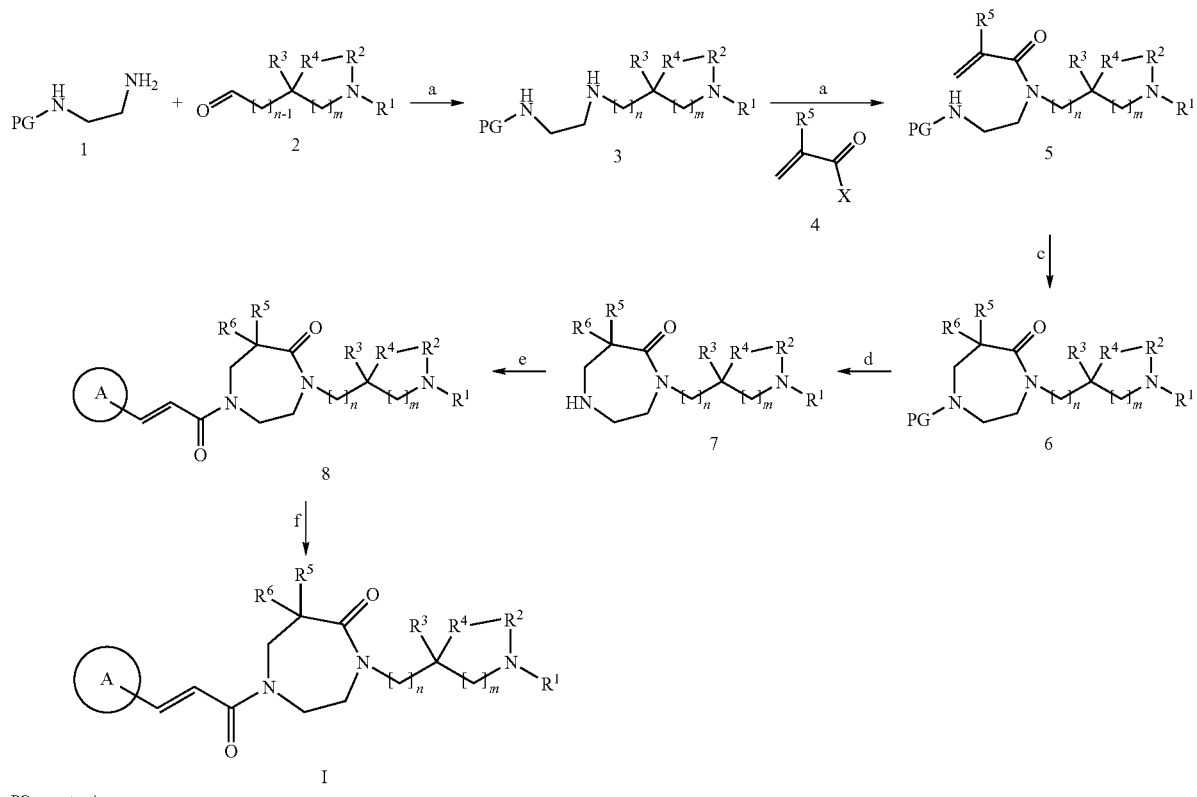

PG = protecting group
X = Cl

The compounds I with X=—N(R$^1$)(R$^2$) can optionally be converted to X=—N$^+$(R$^1$)(R$^2$)(R$^3$) with R$^3$-halogenide in a solvent like methanol as described in scheme 5 shown below.

In Scheme 4, PG means protecting group, such as BOC (tert-butyloxy carbonyl), Z(benzyloxy carbonyl). X is Cl and A, R$^1$, R$^2$, R$^3$, R$^4$, R$^5$ and R$^6$, m and n are as defined before. The same reactions described in scheme 4 can be performed with 1 being substituted with R$^5$, R$^6$, R$^8$, R$^9$, R$^{10}$, R$^{11}$, R$^{12}$ and R$^{13}$, as defined before.

An alternative method for the preparation of 5-oxo-[1,4] diazepanes I in which R$^2$ and R$^4$ are attached to form a heterocyclyl starts from a suitably protected ethylene diamine 1 (e.g. tert-butylcarbonyl), which after reductive amination with aldehyde of the type 2 under standard conditions (CH$_2$Cl$_2$, AcOH, NaBH(OAc)$_3$) will generate amine 3 (step a in Scheme 4). In case of n=0, ketone 2 (e.g. benzylpiperidone) can be reductively aminated as described before or the intermediate imine can be treated with a metalo-R$^3$, to introduce R$^3$. Coupling of this amine 3 with an acryloyl chloride derivative 4 (Schotten-Baumann conditions) affords acrylamide derivative 5 (step b) which can then be cyclised to the diazepan 6 by treatment with a base in a polar solvent e.g. tBuOK in DMF (step c). For the introduction of R$^6$, 6 (R$^6$=H), can be deprotonated at low temperature and then be alkylated or fluorinated, to give the corresponding 6. This can then be elaborated as described earlier (e.g. scheme 1, compound 3 to I) to the desired final compounds I (step e and f).

This reaction sequence can also be used with amines 2, where R$^4$ and R$^2$ do not form a heterocyclyl ring.

The compounds I with X=—N(R$^1$)(R$^2$) can optionally be converted to X=—N$^+$(R$^1$)(R$^2$)(R$^3$) with R$^3$-halogenide in a solvent like methanol as described in scheme 5 shown below.

Scheme 5

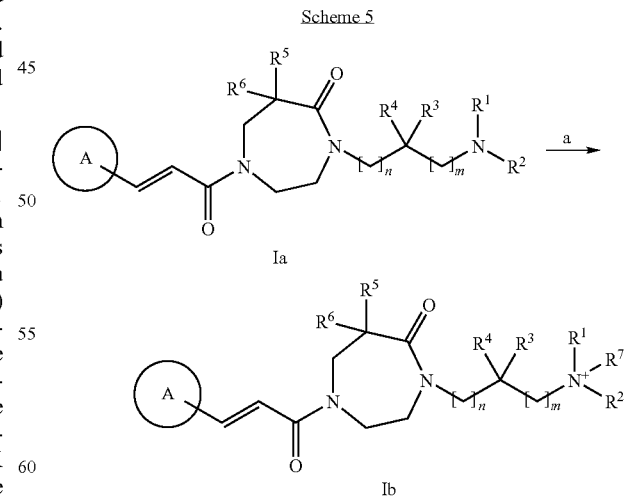

In Scheme 5, A, R$^1$, R$^2$, R$^3$, R$^4$, R$^5$ and R$^6$, m and n are as defined before. The same reactions described in scheme 5 can be performed with 1 being substituted with R$^5$, R$^6$, R$^8$, R$^9$, R$^{10}$, R$^{11}$, R$^{12}$ and R$^{13}$, as defined before.

Scheme 6

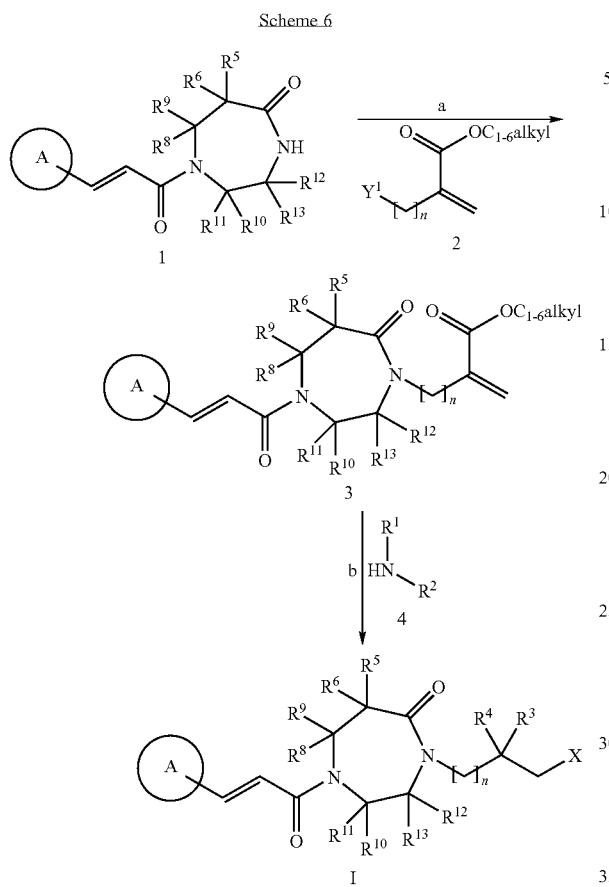

Scheme 7

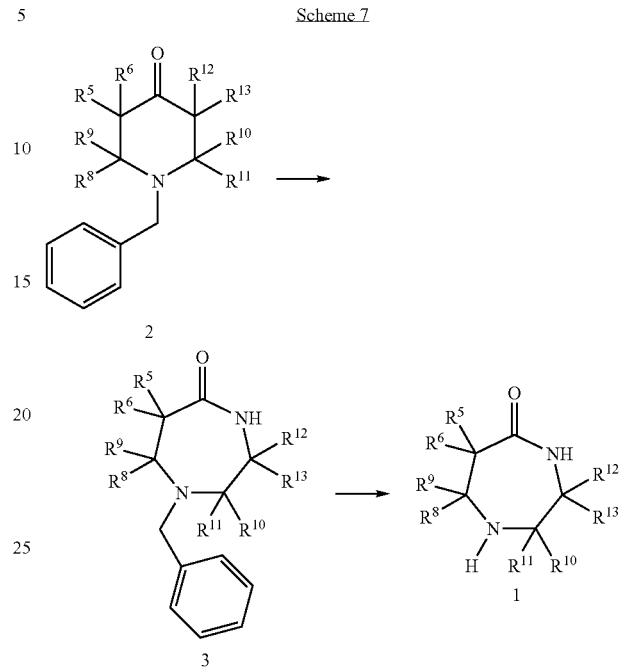

In Scheme 6, $Y^1$ is bromide, iodide, mesylate, tosylate or triflate, A, X, $R^1$, $R^2$, $R^3$, $R^4$, $R^5$, $R^6$, $R^8$, $R^9$, $R^{10}$, $R^{11}$, $R^{12}$ and $R^{13}$ and n are as defined before.

In case $R^3$=COOC$_{1-6}$ alkyl, m=1, building block 2 can be an acrylate which reacts with 5-oxo-[1,4]diazepane 1 in the presence of NaH in DMF or DMA at 0° C. to RT to give intermediate 3. Reaction with amine 4 in acetonitrile with Cs$_2$CO$_3$ at RT gives the final compound I, which optionally can be separated on a chiral column in the enantiomers. Amines 4 are commercial available or can be synthesized as described above. $R^4$ can be introduced at low temperatures via deprotonation and alkylation with a $R^4$-halide. Compound I can further be modified (e.g. $R^3$=COOC$_{1-6}$ alkyl) by hydrolysis with LiOH in THF/ethanol to I (e.g. $R^3$=COO$^-$Li$^+$) or reduction with NaBH$_4$ in EtOH or LiBH$_4$ in THF to I (e.g. $R^3$=CH$_2$OH).

[1,4]-Diazepan-5-ones intermediates of general formula 1 can be synthesized from 1-benzylpiperidin-4-ones of formula 2, as illustrated in Scheme 7. Compounds of formula 2 are either commercially available or can be synthesized according to methods described in the art (e. g., *Heterocycles* 1987, 26, 2165). Schmidt rearrangement or Beckmann rearrangement of 2 (*J. Org. Chem.* 1949, 14, 530) leads to 1-benzyl-[1,4]-diazepan-5-one 3. In the case of unsymmetrically substituted piperidin-4-ones 2, the rearrangement reaction may lead to a mixture of regioisomeric products, which can be separated e. g., by crystallization or chromatography. Finally, 1 is obtained from 3 through hydrogenation at pressures of 1-10 bar, preferably at room temperature, in a solvent such as methanol or ethanol, in the presence of a suitable catalyst such as palladium on activated charcoal.

In Scheme 7, $R^5$, $R^6$, $R^8$, $R^9$, $R^{10}$, $R^{11}$, $R^{12}$ and $R^{13}$ are as defined before. [1,4]-diazepan-5-ones of general formula 1 can also be synthesized as described in Scheme 8 from N-(benzyloxycarbonyl)-β-amino acid esters 2 ($R^a$=methyl or ethyl). Compounds of general formula 2 are either commercially available or may be synthesized according to literature methods (e. g., *Tetrahedron* 2005, 61, 8372). Reaction of 2 with appropriately substituted 2,2-dioxo[1,2,3]oxathiazolidine-3-carboxylic acid tert-butyl esters 3 (*Bioorg. Med. Chem. Lett.* 2006, 16, 1207) in the presence of a base, e. g., potassium tert-butylate or sodium hydride, in a solvent such as 2,2-dimethylpropan-1-ol or N,N-dimethylformamide, at temperatures between 0° C. and 60° C., produces intermediate 4. Cleavage of the Boc protective group (e. g., with hydrogen chloride in 1,4-dioxane or trifluoroacetic acid in dichloromethane), followed by intramolecular ring closure (in the presence of a base such as potassium carbonate, in a solvent such as methanol or ethanol, at temperatures between 0° C. and the boiling point of the solvent), furnishes the [1,4]-diazepan-5-one-1-carboxylic acid benzyl ester 5. The benzyl carbamate group of 5 is removed by hydrogenation at pressures of 1-10 bar, preferably at room temperature, in the presence of a suitable catalyst such as palladium on activated charcoal, thereby leading to 1.

Scheme 8

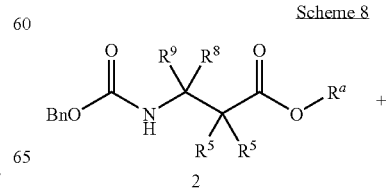

-continued

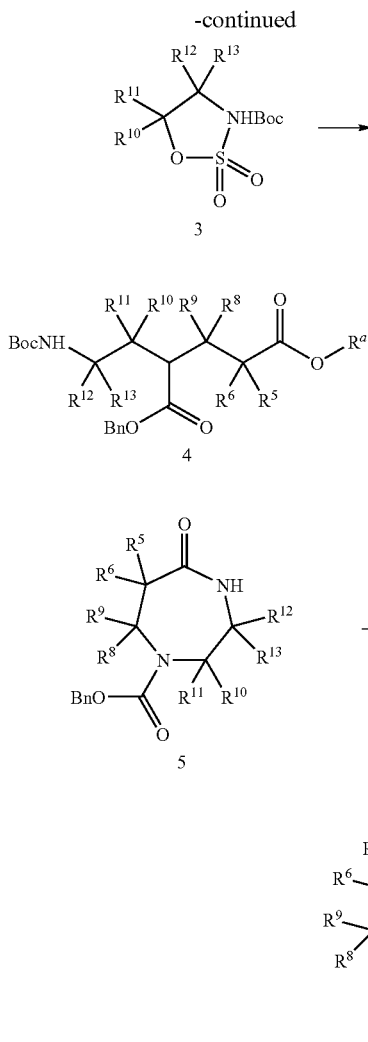

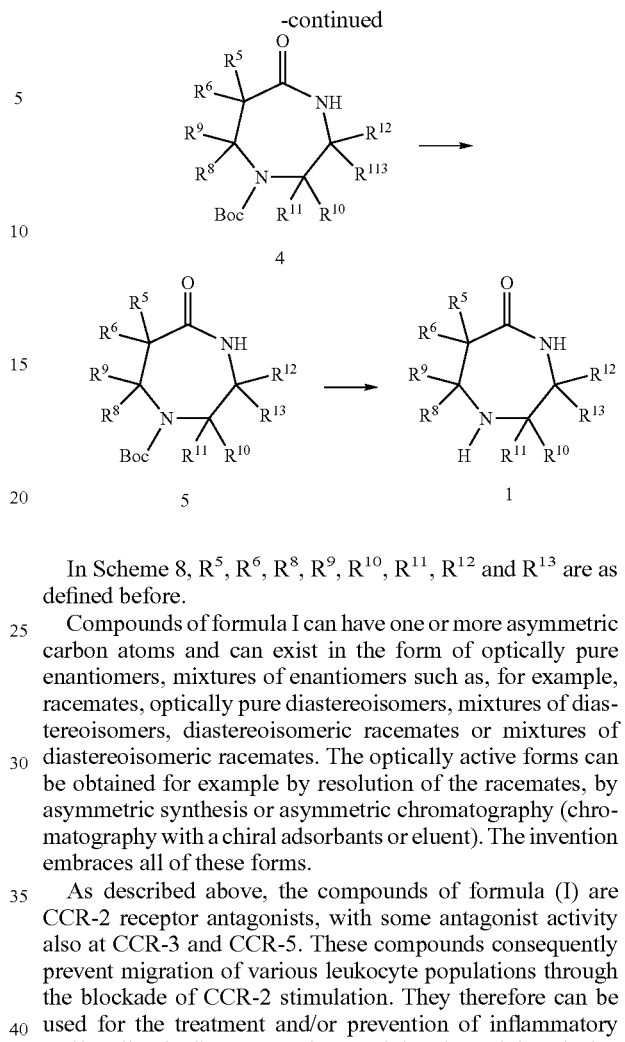

In Scheme 8, $R^5$, $R^6$, $R^8$, $R^9$, $R^{10}$, $R^{11}$, $R^{12}$ and $R^{13}$ are as defined before. [1,4]-diazepan-5-ones of general formula 1 can also be synthesized as described in Scheme 9 from Boc-protected 1,2-diaminoethane derivative 2. Reaction of 2 with 2-propenoic acid ester derivative 3 ($R^a$=methyl or ethyl) in the presence of a base, e. g., sodium hydride or potassium tert-butylate, in a solvent such as N,N-dimethylformamide, leads to [1,4]-diazepan-5-one-1-tert-butyl ester 4. Substituents $R^6$ can be introduced as described in Scheme 1, leading to 5. Finally, cleavage of the tert-butyl carbamate moiety in 5 (e. g., with hydrogen chloride in 1,4-dioxane or trifluoroacetic acid in dichloromethane) leads to 1.

Scheme 9

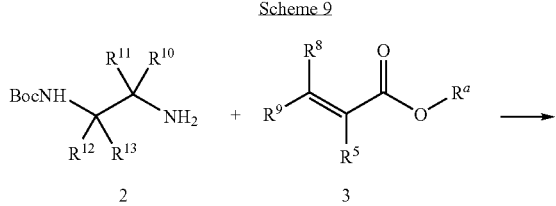

In Scheme 8, $R^5$, $R^6$, $R^8$, $R^9$, $R^{10}$, $R^{11}$, $R^{12}$ and $R^{13}$ are as defined before.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbants or eluent). The invention embraces all of these forms.

As described above, the compounds of formula (I) are CCR-2 receptor antagonists, with some antagonist activity also at CCR-3 and CCR-5. These compounds consequently prevent migration of various leukocyte populations through the blockade of CCR-2 stimulation. They therefore can be used for the treatment and/or prevention of inflammatory and/or allergic diseases, such as peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis and/or burns/ulcers in Diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and asthma. Such medicaments comprise a compound as described above.

The invention also relates to the process and the intermediates for manufacturing the compounds of formula (I) as well as the process for manufacturing the intermediates.

CCR-2 receptor antagonistic activity by the compounds of the present invention can be demonstrated by the following assays.

Receptor Binding Assays

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a topcounter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds I of the present invention exhibit IC50 values in the Ca mobilisation assay of 1 nM to 10 µM, preferably 1 nM to 1.5 µM for CCR2. The following table shows measured values for some selected compounds of the present invention.

| Example Number | IC50(µM) |
|---|---|
| 1 | 0.681 |
| 3 | 1.245 |
| 4 | 0.15 |
| 6 | 1.311 |
| 7 | 1.289 |
| 9 | 0.14 |
| 10 | 0.073 |
| 11 | 0.363 |
| 13 | 0.727 |
| 17 | 0.756 |
| 25 | 1.017 |
| 27 | 0.248 |
| 32 | 1.466 |
| 33 | 0.343 |
| 34 | 1.394 |
| 36 | 0.725 |
| 37 | 0.265 |
| 38 | 0.121 |
| 39 | 0.538 |
| 40 | 0.611 |
| 41 | 1.184 |
| 44 | 0.646 |
| 45 | 0.013 |
| 46 | 0.333 |
| 47 | 0.193 |
| 48 | 0.064 |
| 49 | 0.51 |
| 50 | 0.055 |
| 51 | 0.046 |
| 53 | 0.441 |
| 54 | 0.747 |
| 55 | 0.098 |
| 56 | 1.077 |
| 57 | 0.217 |
| 58 | 0.546 |
| 59 | 0.014 |
| 60 | 0.023 |
| 62 | 0.165 |
| 63 | 0.503 |
| 64 | 0.391 |
| 65 | 0.197 |
| 67 | 0.241 |
| 69 | 0.185 |
| 70 | 0.146 |
| 71 | 0.566 |
| 72 | 0.312 |
| 74 | 0.175 |
| 75 | 0.267 |
| 76 | 0.219 |
| 77 | 0.326 |
| 78 | 0.444 |
| 79 | 0.706 |
| 80 | 0.263 |
| 81 | 0.204 |
| 82 | 0.297 |
| 84 | 0.223 |
| 85 | 1.17 |
| 86 | 1.084 |
| 87 | 0.315 |
| 88 | 0.757 |
| 91 | 0.148 |
| 92 | 0.189 |
| 96 | 1.136 |
| 97 | 1.207 |
| 99 | 1.216 |

-continued

| Example Number | IC50(μM) |
|---|---|
| 101 | 1.229 |
| 102 | 1.025 |
| 103 | 0.388 |
| 104 | 0.598 |
| 105 | 0.806 |
| 106 | 0.523 |
| 108 | 1.199 |
| 109 | 0.521 |
| 110 | 0.641 |
| 111 | 0.335 |
| 117 | 0.459 |
| 120 | 1.143 |
| 124 | 0.667 |
| 134 | 0.6 |
| 136 | 0.688 |
| 138 | 1.261 |
| 153 | 0.446 |
| 154 | 0.373 |
| 155 | 0.37 |
| 157 | 0.703 |
| 159 | 0.258 |
| 160 | 0.232 |
| 161 | 0.047 |
| 162 | 0.319 |
| 163 | 0.56 |
| 164 | 0.544 |
| 165 | 0.345 |
| 166 | 0.212 |
| 167 | 0.028 |
| 169 | 0.255 |
| 170 | 0.448 |
| 171 | 0.995 |
| 172 | 0.105 |
| 175 | 0.096 |
| 177 | 0.954 |
| 178 | 0.201 |
| 179 | 0.003 |
| 180 | 0.319 |
| 181 | 0.003 |
| 183 | 1.227 |
| 186 | 0.038 |
| 187 | 0.385 |
| 188 | 1.338 |
| 189 | 0.008 |
| 190 | 0.118 |
| 191 | 0.025 |
| 192 | 0.015 |
| 193 | 0.644 |
| 194 | 0.494 |
| 195 | 0.453 |
| 196 | 0.864 |
| 198 | 0.739 |
| 199 | 1.336 |
| 201 | 0.656 |
| 205 | 0.325 |
| 208 | 0.78 |
| 209 | 1.392 |
| 210 | 1.136 |
| 211 | 0.363 |
| 212 | 0.437 |
| 213 | 0.421 |
| 214 | 0.592 |
| 215 | 0.356 |
| 216 | 0.726 |
| 217 | 1.212 |
| 219 | 0.045 |
| 220 | 0.169 |
| 221 | 0.478 |
| 223 | 0.013 |
| 224 | 0.014 |
| 225 | 0.243 |
| 226 | 0.464 |
| 227 | 0.409 |
| 228 | 0.149 |
| 229 | 0.154 |
| 230 | 0.215 |
| 231 | 0.218 |

-continued

| Example Number | IC50(μM) |
|---|---|
| 232 | 0.091 |
| 233 | 0.359 |
| 235 | 0.112 |
| 236 | 0.565 |
| 238 | 0.054 |
| 240 | 0.105 |
| 241 | 0.765 |
| 242 | 0.124 |
| 243 | 0.133 |
| 244 | 0.66 |
| 246 | 0.421 |
| 247 | 0.613 |
| 248 | 0.226 |
| 249 | 1.253 |
| 250 | 0.812 |
| 251 | 0.008 |
| 252 | 0.12 |
| 253 | 0.132 |
| 254 | 0.108 |
| 255 | 0.561 |
| 256 | 1.074 |
| 257 | 0.182 |
| 258 | 0.375 |
| 259 | 0.057 |
| 260 | 0.009 |
| 261 | 0.009 |
| 262 | 0.004 |
| 266 | 0.077 |
| 267 | 0.214 |
| 268 | 0.215 |
| 269 | 0.619 |
| 270 | 0.01 |
| 271 | 0.055 |
| 272 | 0.191 |
| 273 | 0.313 |
| 274 | 0.004 |
| 275 | 1.093 |
| 277 | 1.292 |
| 278 | 0.54 |
| 279 | 0.005 |
| 280 | 0.021 |
| 281 | 0.129 |
| 282 | 0.212 |
| 283 | 0.311 |
| 284 | 0.717 |
| 285 | 0.644 |
| 287 | 0.848 |
| 288 | 0.206 |
| 289 | 0.296 |
| 290 | 0.199 |
| 291 | 0.404 |
| 293 | 1.118 |
| 296 | 0.298 |
| 298 | 0.281 |
| 300 | 0.981 |
| 301 | 0.977 |
| 303 | 0.257 |
| 305 | 0.192 |
| 306 | 0.391 |
| 307 | 0.437 |
| 309 | 0.016 |
| 315 | 0.717 |
| 316 | 0.755 |
| 317 | 0.528 |
| 318 | 0.707 |
| 319 | 0.265 |
| 320 | 1.489 |
| 322 | 1.199 |
| 324 | 0.215 |
| 325 | 0.741 |
| 326 | 0.999 |
| 327 | 0.002 |
| 328 | 0.028 |
| 329 | 0.137 |
| 330 | 0.006 |
| 331 | 0.059 |
| 332 | 0.002 |

| Example Number | IC50(µM) |
|---|---|
| 333 | 0.301 |
| 334 | 0.004 |
| 335 | 0.013 |
| 336 | 0.003 |
| 337 | 0.071 |
| 338 | 0.553 |
| 339 | 1.358 |
| 340 | 0.019 |
| 342 | 0.003 |
| 343 | 0.011 |
| 344 | 0.026 |
| 347 | 0.864 |
| 348 | 0.765 |
| 355 | 0.982 |
| 356 | 0.552 |
| 357 | 0.385 |
| 358 | 0.873 |
| 359 | 0.807 |
| 360 | 0.179 |
| 361 | 0.226 |
| 362 | 0.504 |
| 363 | 0.073 |
| 364 | 0.531 |
| 370 | 0.341 |
| 372 | 1.234 |
| 374 | 0.58 |
| 375 | 0.274 |
| 376 | 0.416 |
| 377 | 0.697 |
| 378 | 1.239 |
| 379 | 1.498 |
| 381 | 0.236 |
| 382 | 0.246 |
| 383 | 0.198 |
| 384 | 0.334 |
| 385 | 0.31 |
| 386 | 0.38 |
| 387 | 0.584 |
| 388 | 0.381 |
| 389 | 0.323 |
| 390 | 1.102 |
| 392 | 0.054 |
| 393 | 0.878 |
| 394 | 0.551 |
| 395 | 0.996 |
| 397 | 0.944 |
| 398 | 1.065 |
| 399 | 0.72 |
| 400 | 0.264 |
| 401 | 0.092 |
| 402 | 0.291 |
| 404 | 0.095 |
| 405 | 0.807 |
| 407 | 0.264 |
| 409 | 0.382 |
| 411 | 0.199 |
| 412 | 0.342 |
| 413 | 0.077 |
| 414 | 0.065 |
| 415 | 0.027 |
| 416 | 0.011 |
| 418 | 1.473 |
| 419 | 0.25 |
| 420 | 0.052 |
| 421 | 0.064 |
| 422 | 0.07 |
| 423 | 0.016 |
| 424 | 0.119 |
| 425 | 0.089 |
| 426 | 0.07 |
| 427 | 0.259 |
| 428 | 0.113 |
| 429 | 0.086 |
| 430 | 0.352 |
| 431 | 0.448 |
| 432 | 0.016 |
| 433 | 0.244 |
| 434 | 0.14 |
| 435 | 0.281 |
| 436 | 0.746 |
| 437 | 0.463 |
| 438 | 0.369 |
| 439 | 0.263 |
| 440 | 0.103 |
| 441 | 0.022 |
| 442 | 0.085 |
| 444 | 0.032 |
| 445 | 0.354 |
| 446 | 0.626 |
| 447 | 0.092 |
| 448 | 0.181 |
| 450 | 0.243 |
| 451 | 0.682 |
| 453 | 0.033 |
| 454 | 0.23 |
| 455 | 0.106 |
| 456 | 0.016 |
| 457 | 0.283 |
| 458 | 0.148 |
| 459 | 0.267 |
| 460 | 0.832 |
| 461 | 0.614 |
| 462 | 0.041 |
| 463 | 0.348 |
| 464 | 0.226 |
| 465 | 0.376 |
| 466 | 0.389 |
| 467 | 1.16 |
| 468 | 0.347 |
| 469 | 0.061 |
| 470 | 0.085 |
| 471 | 0.043 |
| 472 | 0.418 |
| 473 | 0.051 |
| 474 | 0.106 |
| 475 | 0.02 |
| 476 | 0.018 |
| 477 | 0.313 |
| 478 | 0.998 |
| 479 | 0.232 |
| 480 | 0.053 |
| 481 | 0.009 |
| 482 | 0.013 |
| 485 | 0.075 |
| 486 | 0.205 |
| 487 | 0.014 |
| 488 | 0.618 |
| 490 | 0.026 |
| 491 | 0.216 |
| 492 | 0.026 |
| 493 | 0.015 |
| 494 | 0.006 |
| 495 | 0.019 |
| 496 | 0.007 |
| 497 | 0.026 |
| 498 | 0.011 |
| 499 | 0.084 |
| 500 | 0.451 |
| 501 | 0.155 |
| 502 | 0.253 |
| 503 | 0.051 |
| 504 | 0.316 |

Chemotaxis Assay

The chemotaxis assay was performed with THP1-4x cells (Mirzadegan et al. 2000, The Journal of Biological Chemistry 275, 33, 25562-25571) similar as described earlier (Kruszynski et al. 2005, Journal of Peptide Science, in press.).

THP1-4x were cultured in RPMI1640, 2 mM L-glutamine, 0.15% Na-bicarbonat, 0.25% D-glucose, 10 mM Hepes, 100 mM Na-pyruvate, 50 mM β-mercaptoethanol, 10% FBS. Isolated cells were labelled in culture medium with 2.5 μg/ml calcein-AM (Molecular Probes) for 60 minutes at 37° C. Excess calcein was removed and cells were washed in D-PBS$^{++}$, 2% FBS.

Cells ($1 \times 10^5$) with or without various concentrations of test compounds were loaded on the top of 8-μm polycarbonate filter in a 96-well-modified Boyden chamber (NeuroProbe). Beneath the filter 10 nM MCP-1 (R&D Systems; Roche) with or without test compounds or D-PBS$^{++}$, 2% FBS was placed in the corresponding well. The closed chambers were incubated for 1 hour at 37° C., 5% $CO_2$. Remaining cells in the top compartment were wiped off and migrated cells were measured as fluorescence in the bottom compartment in a FLU-Ostar (Galaxy BMG) at 485 nm excitation and 530 nm emission. Specific migration is defined as total migration towards MCP-1 minus the background migration towards D-PBS$^{++}$, 2% FBS. The ability of test compounds to antagonize CCR2-chemotaxis is reported as concentration required to inhibit 50% of specific migration ($IC_{50}$) towards MCP-1.

The compounds I of the present invention exhibit IC50 values in the chemotaxis assay of 1 nM to 10 μM, preferably 1 nM to 250 nM for CCR2. The following table shows measured values for some selected compounds of the present invention.

| Example | IC50(nM) |
| --- | --- |
| Example 48 | 13 |
| Example 59 | 77 |
| Example 81 | 71 |
| Example 160 | 101 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case (therapeutically effective amount). For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations:
AcOH=Acetic acid, BOC=t-Butyloxycarbonyl, BuLi=Butyllithium, CDI=1,1-carbonyldiimidazole, $CH_2Cl_2$=dichloromethane, DCE=1,2-dichloroethane, DIBALH=Di-i-butylaluminium hydride, DCC=N,N'-Dicyclohexylcarbodiimide, DMA=N,N-Dimethylacetamide, DMAP=4-Dimethylaminopyridine, DMF=N,N-Dimethylformamide, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HATU=O-(7-azabenzotriazol-1-yl)-1,1,3,3-tetramethyluronium hexafluorophosphate, HOBT=1-Hydroxybenzo-triazole, Huenig's base=$iPr_2NEt$=N-Ethyl diisopropylamine, LAH=Lithium aluminium hydride, LDA=Lithium diisopropylamide, $LiBH_4$=Lithium borohydride, MeOH=Methanol, NaI=Sodium iodide, Red-Al=Sodium bis(2-methoxyethoxy)aluminium hydride, TBDMSCl=t-Butyldimethylsilyl chloride, TFA=Trifluoroacetic acid, THF=Tetrahydrofurane, quant=quantitative.

General Remarks

All reactions were performed under argon.

Intermediate 1

{4-[(E)-3-(3,4-Dichloro-phenyl)-acryloyl]-7-oxo-[1,4]diazepan-1-yl}-acetaldehyde 1-[(E)-3-(3,4-Dichloro-phenyl)-acryloyl]-[1,4]diazepan-5-one A solution of 9.77 g (43.65 mmol) of (E)-3,4-dichlorocinnamic acid in 250 ml of $CH_2Cl_2$ was treated at RT with 3 drops of DMF. 4.15 ml (48.02 mmol, 1.1 eq) of oxalyl chloride in 30 ml $CH_2Cl_2$ were added dropwise and stirring was continued for 3 h. The solution was evaporated, redissolved in 170 ml of $CH_2Cl_2$, cooled (0° C.) and treated with a solution of 4.48 g (39.29 mmol, 0.9 eq) of 2,3,6,7-tetrahydro-(1H)-1,4-diazepin-5(4H)-one and 12.17 ml (87.30 mmol, 2 eq) of triethylamine in 80 ml of $CH_2Cl_2$. The reaction was warmed up over night to RT, then partitioned between $CH_2Cl_2$/MeOH 9:1 (×3)/ aqueous 10% $KHSO_4$, the organic phases were washed with aqueous saturated $NaHCO_3$ and aqueous 10% NaCl, dried over $Na_2SO_4$ and evaporated. The residue was dissolved and evaporated with toluene and crystallized with $CH_2Cl_2/Et_2O$ to give 7.99 g (58%) of the title compound as white solid. MS: 312.8 ($MH^+$, 2Cl).

2-{4-[(E)-3-(3,4-Dichloro-phenyl)-acryloyl]-7-oxo-[1,4]diazepan-1-yl}-N-methoxy-N-methyl-acetamide A suspension of 5.01 g (16.00 mmol) of 1-[(E)-3-(3,4-dichloro-phenyl)-acryloyl]-[1,4]diazepan-5-one and 3.20 g (17.60 mmol) of 2-bromo-N-methoxy-N-methyl-acetamide (intermediate 1D) in 110 ml of THF was treated at 0° C. with 0.84 g (19.20 mmol) of NaH (55% in oil) in two portions. The reaction was warmed up to RT over night and stirred for 2.5 h at 75° C. The reaction was cooled and neutralized with cold aqueous 10% $KHSO_4$ and extracted with EtOAc (3×). The organic phases were washed with aqueous saturated $NaHCO_3$, aqueous 10% NaCl, dried over $Na_2SO_4$ evaporated and purified by flash silica gel column ($CH_2Cl_2$/MeOH 99:1 to 97.5:2.5) to yield 3.49 g (53%) of the light yellow crystalline title compound. MS: 414.1 ($MH^+$, 2Cl).

{4-[(E)-3-(3,4-Dichloro-phenyl)-acryloyl]-7-oxo-[1,4]diazepan-1-yl}-acetaldehyde 7.92 ml (7.92 mmol) of a LAH-solution (1.0 M in THF) was dropped to a cooled (−30° C.) suspension of 3.28 g (7.92 mmol) of 2-{4-[(E)-3-(3,4-dichloro-phenyl)-acryloyl]-7-oxo-[1,4]diazepan-1-yl}-N-methoxy-N-methyl-acetamide in 260 ml of THF. The reaction was stirred for 5 min at −30° C. and then cooled to −78° C. The reaction was stopped by adding first 12.8 ml (174.24 mmol) of acetone and afterwards 0.9 mL (15.84 mmol) of acetic acid. The reaction was then powered to an aqueous 10% $KHSO_4$ solution and extracted with ether (3×), the organic phase was dried over $Na_2SO_4$ evaporated dissolved in toluene and evaporated (3×) to yield 2.12 g (75%) of the title compound as light yellow foam. MS: 355.0 ($MH^+$, 2Cl).

2-Bromo-N-methoxy-N-methyl-acetamide used in intermediate 1B was synthesized as follows:

2-Bromo-N-methoxy-N-methyl-acetamide

A solution of 13.90 g (100 mmol) of bromoacetic acid in 1.3 l $CH_2Cl_2$ was treated with 15.61 g (160 mmol) of N,O-dimethyl-hydroxylamine hydrochloride, 17.63 ml (160 mmol) of N-methylmorpholine and at 0° C. with 24.92 g (130 mmol) of EDCI and 3.07 g (20 mmol) of HOBT. The cooling bath was allowed to come to RT and after 3.5 h the reaction was extracted with aqueous 10% $KHSO_4/Et_2O$ (3×). The organic phases were washed with aqueous saturated $NaHCO_3$, 10% NaCl and dried over $Na_2SO_4$ to yield after careful evaporation of the solvent 11.85 g (65%) of the title compound as a light yellow liquid. MS: 181.1 ($M^+$, 1Br).

Intermediate 2

3-{4-[(E)-3-(3,4-Dichloro-phenyl)-acryloyl]-7-oxo-[1,4]diazepan-1-yl}-propionaldehyde 3-{4-[(E)-3-(3,4-Dichloro-phenyl)-acryloyl]-7-oxo-[1,4]diazepan-1-yl}-N-methoxy-N-methyl-propionamide A suspension of 10.02 g (32.00 mmol) of 1-[(E)-3-(3,4-dichloro-phenyl)-acryloyl]-[1,4]diazepan-5-one (intermediate 1A]) and 6.27 g (32.00 mmol) of 3-bromo-N-methoxy-N-methyl-propionamide (intermediate 2C]) in 225 ml of THF was treated at 0° C. with 1.54 g (35.20 mmol) of NaH (55% in oil) in two portions. The suspension was stirred 4 h at RT, cooled and treated again at 0° C. with 1.54 g (35.20 mmol) of NaH (55% in oil) in two portions. The reaction was warmed up to RT over night, treated a third time at 0° C. with 1.54 g (35.20 mmol) of NaH (55% in oil) in two portions and stirred for 30 min at 50° C. After 20 h at RT, the reaction was neutralized with cold aqueous 10% $KHSO_4$ and extracted with EtOAc (3×). The organic phases were washed with aqueous saturated $NaHCO_3$, aqueous 10% NaCl, dried over $Na_2SO_4$ evaporated and purified by flash silica gel column ($CH_2Cl_2$/MeOH 99:1 to 97.5:2.5) to yield 8.97 g (65%) of the title compound as an off-white foam. MS: 428.2 ($MH^+$, 2Cl).

3-{4-[(E)-3-(3,4-Dichloro-phenyl)-acryloyl]-7-oxo-[1,4]diazepan-1-yl}-propionaldehyde In analogy to the procedure described in intermediate 1C, 3-{4-[(E)-3-(3,4-dichloro-phenyl)-acryloyl]-7-oxo-[1,4]diazepan-1-yl}-N-methoxy-N-methyl-propionamide gave the title compound as white solid. MS: 368.9 ($MH^+$, 2Cl).

3-Bromo-N-methoxy-N-methyl-propionamide used in intermediate 2A] was synthesized as follows:

3-Bromo-N-methoxy-N-methyl-propionamide

In analogy to the procedure described in intermediate 1D, 3-bromopropionic acid gave the title compound as a light yellow liquid. MS: 195.9 ($MH^+$, 1Br).

Intermediate 3

{4-[(E)-3-(3-Chloro-phenyl)-acryloyl]-7-oxo-[1,4]diazepan-1-yl}-acetaldehyde

1-[(E)-3-(3-Chloro-phenyl)-acryloyl]-[1,4]diazepan-5-one

In analogy to the procedure described in intermediate 1A, (E)-3-chlorocinnamic acid and 2,3,6,7-tetrahydro-(1H)-1,4-diazepin-5(4H)-one gave the title compound as a white solid. MS: 278.9 ($MH^+$, 1Cl).

1-[(E)-3-(3-Chloro-phenyl)-acryloyl]-4-(2,2-diethoxy-ethyl)-[1,4]diazepan-5-one

A solution of 5.02 g (18.00 mmol) of 1-[(E)-3-(3-chloro-phenyl)-acryloyl]-[1,4]diazepan-5-one in 140 ml of DMA was treated at RT with 0.86 g (19.80 mmol) of NaH (55% in oil) in four portions. After 1 h 3.72 ml (21.60 mmol) of 2-bromo-1,1-diethoxy-ethane were added over 30 min. The reaction was stirred over night and heated for 1 h at 75° C. The reaction was cooled and neutralized with cold aqueous saturated NaHCO$_3$ and extracted with Et$_2$O (3×). The organic phases were washed with aqueous saturated NaHCO$_3$, aqueous 10% NaCl, dried over Na$_2$SO$_4$ evaporated and purified by flash silica gel column (CH$_2$Cl$_2$/MeOH 99:1 to 98:2) to yield 1.87 g (26%) of the title compound as a yellow viscous oil. MS: 395.4 (MH$^+$, Cl).

{4-[(E)-3-(3-Chloro-phenyl)-acryloyl]-7-oxo-[1,4]diazepan-1-yl}-acetaldehyde

A solution of 1.00 g (2.53 mmol) of 1-[(E)-3-(3-chloro-phenyl)-acryloyl]-4-(2,2-diethoxy-ethyl)-[1,4]diazepan-5-one in 10 ml of toluene was treated at RT with 5.22 ml formic acid and 1.5 ml water. The reaction was stirred for 1.5 h, evaporated and neutralized with aqueous saturated NaHCO$_3$ and extracted with Et$_2$O (3×). The organic phases were washed with aqueous 10% NaCl, dried over Na$_2$SO$_4$ evaporated and purified by flash silica gel column (EtOAc) to yield 0.37 g (45%) of the title compound as off-white foam. MS: 321.3 (MH$^+$, Cl).

Intermediate 4

4-(3-Piperidin-1-yl-propyl)-[1,4]diazepan-5-one-dihydrochloride

5-Oxo-4-(3-piperidin-1-yl-propyl)-[1,4]diazepane-1-carboxylic acid tert-butyl ester A solution of 8.52 g (39.75 mmol) of 5-oxo-[1,4]diazepane-1-carboxylic acid tert-butyl ester in 200 ml of DMA was treated at 0° C. with 2.60 g (59.62 mmol) of NaH (55% in oil) in small portions. The reaction was stirred 1 h at this temperature, then the free 1-(3-chloropropyl)piperidine in 200 ml toluene was dropped in (49.62 g (250.42 mmol, 6.3 eq.) 1-(3-chloropropyl)piperidine hydrochloride were dissolved in 262 ml of 1N NaOH and extracted with toluene (200 ml). The organic phase was dried over Na$_2$SO$_4$). The reaction was warmed up to RT and stirred over night. After 2 h at 50° C. and cooling to RT, the reaction was neutralized with water (50 ml), evaporated and then dissolved in aqueous saturated NaHCO$_3$/Et$_2$O. After reextraction with Et$_2$O, the organic phase was dried (Na$_2$SO$_4$), evaporated and crystallized from pentane to yield 12.08 g (90%) of the title compound as white crystals. MS: 340.2 (MH$^+$).

4-(3-Piperidin-1-yl-propyl)-[1,4]diazepan-5-one-dihydrochloride

A solution of 7.3 g (21.50 mmol) of 5-oxo-4-(3-piperidin-1-yl-propyl)-[1,4]diazepane-1-carboxylic acid tert-butyl ester was dissolved in 140 ml CH$_2$Cl$_2$, cooled to 0° C. and treated with 54 ml (215.03 mmol) of 4M HCl in dioxane, then warmed to RT. After 3 h, 40 ml of MeOH were added to dissolve the precipitation and stirring was continued over night. The solution was evaporated, dissolved in toluene and evaporated (2×) to yield 7.71 g (quantitative) of the title compound as a white solid. MS: 240.1 (MH$^+$).

Intermediate 5

4-(2-Pyrrolidin-1-yl-ethyl)-[1,4]di-azepan-5-one-dihydrochloride

5-Oxo-4-(2-pyrrolidin-1-yl-ethyl)-[1,4]diazepane-1-carboxylic acid tert-butyl ester In analogy to the procedure described in intermediate 4A, 5-oxo-[1,4]diazepane-1-carboxylic acid tert-butyl ester and 1-(2-chloro-ethyl)-pyrrolidine gave the title compound as light yellow solid. MS: 312.0 (MH$^+$).

4-(2-Pyrrolidin-1-yl-ethyl)-[1,4]di-azepan-5-one-dihydrochloride

In analogy to the procedure described in intermediate 4B, 5-oxo-4-(2-pyrrolidin-1-yl-ethyl)-[1,4]diazepane-1-carboxylic acid tert-butyl ester gave the title compound as off-white powder.
MS: 212.1 (MH$^+$).

Intermediate 6

6-Fluoro-3-piperidin-4-yl-1H-indole

Prepared following the protocol published in Eur. J. Med. Chem. 1987, 22, 33-43.

Intermediate 7

Piperidin-4-yl-imidazolidin-2-one

Prepared following the protocol published in WO2005/101989 (A2)

Intermediate 8

4-(5-Methyl-4H-[1,2,4]triazol-3-yl)-piperidine hydrochloride 4-(5-Methyl-4H-[1,2,4]triazol-3-yl)-piperidine-1-carboxylic acid tert-butyl ester 4-Hydrazinocarbonyl-piperidine-1-carboxylic acid tert-butyl ester (1.19 g, 5 mmol) was mixed with ethylacetimidate hydrochloride (0.91 g, 7 mmol) in DMF (5 ml) and Et$_3$N (2 ml, 15 mmol) was added. The reaction was stirred for 1 h after which time the DMF was evaporated, the residue redissolved in AcOH and 0.5 g of ammonium acetate added and the reaction heated to 100° C. for a further 3 h. The reaction was then concentrated, redissolved in CH$_2$Cl$_2$, washed with NaHCO$_3$, dried (Na$_2$SO$_4$) and concentrated. The residue was purified by flash column chromatography (CH$_2$Cl$_2$:MeOH 1:0-9:1) to afford the title product (0.14 g, 10%) as a colourless gum. MS: 267.4 (MH$^+$)

4-(5-Methyl-4H-[1 2,4]triazol-3-yl)-piperidine hydrochloride 4-(5-Methyl-4H-[1,2,4]triazol-3-yl)-piperidine-1-carboxylic acid tert-butyl ester (0.12 g, 0.5 mmol) was dissolved in a solution of HCl in 1,4-dioxane (5 ml, 4 M), stirred for 2 h and then concentrated to afford the title product (0.1 g, quant) as a yellow solid. $^1$H NMR (300 MHz, MeOD) δ 2.09-2.20 (2H, m), 2.36-2.40 (2H, m), 2.74 (3H, s), 3.22-3.33 (2H, m), 3.41-3.60 (3H, m).

Intermediate 9

1,3,8-Triaza-spiro[4.5]decan-4-one

Prepared following the protocol published in J. Med. Chem. 1998, 41, 25, 5084-5093.

Intermediate 10

4-Hydroxy-piperidine-4-carboxylic acid amide

Prepared following the protocol published in WO2005/110416 (A2).

Intermediate 11

1,3,8-Triaza-spiro[4.5]decane-2,4-dione

Prepared according to the procedure published in J. Org. Chem. 1996, 61, 22, 7650-7651.

Intermediate 12

4-(1H-Pyrazol-3-yl)-piperidine

Prepared according to the procedure published in WO2004/094371(A2).

Intermediate 13 trans-4-Amino-1-pyridin-2-yl-cyclohexanol

Prepared according to the procedure published in WO2005/060665(A2).

Intermediate 14

Oxa-3,8-diaza-spiro[4.5]decan-2-one

Prepared according to the procedure published in J. Med. Chem. 1995, 38, 3772-3779.

Intermediate 15

4-Oxazol-2-yl-piperidin-4-ol hydrochloride

4-Hydroxy-4-oxazol-2-yl-piperidine-1-carboxylic acid tert-butyl ester

To a solution of oxazole (1 g, 14 mmol) in anhydrous THF (10 ml) was added borane. THF complex (14 ml, 1M in THF, 14 mmol) and the mixture stirred for 1 h, after which time the reaction was cooled to −78° C. and nBuLi (9 ml, 1.6 M in hexanes, 14 mmol) added dropwise and the reaction stirred for a further 1 h. A solution of Boc-piperidone (3.2g, 16 mmol) in THF (10 ml) is then added, the reaction stirred for a further 4 h at −78° C. before allowing the reaction to reach room temperature overnight. The solvent is then evaporated, the residue redissolved in EtOAc, washed with saturated ammonium chloride solution, dried ($Na_2SO_4$) and concentrated. Purification by flash column chromatography (EtOAc: Heptane 3:7) affords the title product (1.9 g, 44%) as a colourless gum, contaminated with an unknown byproduct. MS: 269.2 ($MH^+$)

4-Hydroxy-4-oxazol-2-yl-piperidine-1-carboxylic acid tert-butyl ester (0.1 g, 0.4 mmol) was dissolved in a solution of HCl in dioxane (5 ml, 4 M in dioxane) and stirred for 1 h.

The reaction was then concentrated to dryness to afford the title product (0.08 g, quant) as white solid.
MS: 169.1 ($MH^+$)

Intermediate 16

4-Methyl-piperidin-4-ol

Prepared according to the procedure published in J. Med. Chem. 1965, 8, 766-776.

Intermediate 17

2,8-Diaza-spiro[4.5]decane-1,3-dione

Prepared according to the procedure published in J. Med. Chem. 1995, 38, 3772-3779.

Intermediate 18

2,8-Diaza-spiro[4.5]decan-3-one

Prepared according to the procedure published in J. Med. Chem. 1995,.38, 3772-3779.

Intermediate 19

4-Hydroxy-piperidine-4-carboxylic acid amide

Prepared according to the procedure published in WO2004/043925(A2)

Intermediate 20

(+/−)-cis-(3-Methoxy-tetrahydro-pyran-4-yl)-amine

A slurry of 3-methoxy-tetrahydro-pyran-4-one (0.4 g, 3 mmol—described in WO03/093266(A1)), ammonium formate (1.9 g, 30 mmol), 10% palladium on charcoal (1 g) in water:MeOH (1:5, 6 ml) was stirred overnight after which time it was filtered through Hyflo, the mixture concentrated to remove the MeOH, the residue taken up in $Et_2O$, dried ($Na_2SO_4$) and concentrated to afford the title product (0.2 g, 49%) as a yellow oil (contaminated by 10-20% of the trans isomer). $^1$H NMR (300 MHz, $CDCl_3$) (cis isomer) δ 1.60-1.80 (2H, m), 2.95-3.00 (1H, m), 3.22-3.43 (5H, m). 3.82-3.95 (1H, m), 4.01-4.13 (1H, m).

Intermediate 21

(2S,4R)-4-hydroxy-2-hydroxymethyl-pyrrolidine

Prepared according to the procedure published in WO92/03464.

Intermediate 22

(2S,4S)-4-hydroxy-2-hydroxymethyl-pyrrolidine

Prepared analogously to intermediate 21 from cis-4-hydroxy-L-proline.

Intermediate 23

(2S,3S)-3-Hydroxy-pyrrolidine-2-carboxylic acid methyl ester

Prepared from trans-3-hydroxy-L-proline (Tetrahedron Letters 2001, 42, 49, 8571-8574).

Intermediate 24

(2R,3S)-3-Hydroxy-2-hydroxymethyl-pyrrolidine

Prepared analogously to intermediate 21 from trans-3-hydroxy-L-proline.

Intermediate 25

(cis)-(rac)-3,4-Bis-(tert-butyl-dimethyl-silanyloxy)-piperidine

Prepared via (cis)-(rac)-3,4-dihydroxy-piperidine-1-carboxylic acid benzyl ester (Tetrahedron 2006, 62, 3284-3291), followed by silylation (tert-Butyl-chloro-dimethyl-silane/imidazol in DMF) and hydrogenation (10% Pd/C, $H_2$ in ethanol).

Intermediate 26

(trans)-(rac)-3,4-Bis-(tert-butyl-dimethyl-silanyloxy)-piperidine

Prepared via (trans)-(rac)-3,4-dihydroxy-piperidine-1-carboxylic acid benzyl ester (Tetrahedron 2006, 62, 3284-3291), followed by silylation (tert-Butyl-chloro-dimethyl-silane/imidazol in DMF) and hydrogenation (10% Pd/C, $H_2$ in ethanol).

Intermediate 27

Oxa-8-aza-spiro[4.5]decane triofluoroacetate

Prepared analogously to Bioorganic & Medicinal Chemistry Letters (2002), 12(13), 1759-1762.

Intermediate 28

4-[1,2,4]Triazol-1-yl-piperidine hydrochloride

Prepared according to the procedure published in WO2004094371.

Intermediate 29

N-Piperidin-4-yl-methanesulfonamide hydrochloride

Prepared according to the procedure published in US2005043298

Intermediate 30

(rac)-(3-Methyl-piperidin-3-yl)-methanol hydrochloride (rac)-3-Methyl-piperidine-1,3-dicarboxylic acid 1-tert-butyl ester 3-ethyl ester A solution of 2.42 ml (2.0 M in THF/n-heptane/ethylbenzene, 5.55 mmol) LDA in 10 ml THF was treated slowly at −78° C. with 2.00 g (7.77 mmol) ethyl 1-BOC-3-piperidinecarboxylate in 7 ml THF. After 30 min at −78° C., a solution of 2.42 ml (38.86 mmol) iodomethane was added. Over night, the solution was naturally warmed to RT, poured on aqueous 10% $KHSO_4$ solution and extracted with ether (3×). The organic phase was dried ($Na_2SO_4$) and evaporated to give 2.81 g of a mixture containing 40% of the desired compound and 60% of starting material. Repetition of the procedure above gave 2.81 g (quant.) of crude title compound containing ca 10% of staring material. MS: 272.3 ($MH^+$).

(rac)-3-Hydroxymethyl-3-methyl-piperidine-1-carboxylic acid tert-butyl ester 6.14 ml (1.2 M in toluene, 7.37 mmol) of DIBALH was dropped to a dry ice cooled (−30° C.) solution of 1.00 g (3.69 mmol) crude 3-methyl-piperidine-1,3-dicarboxylic acid 1-tert-butyl ester 3-ethyl ester in 2 ml of THF. The reaction was warmed up (0° C. for 1 h), continued for 3 h, cooled (−15° C.) and treated again with 0.61 ml (1.2 M in toluene, 0.74 mmol) of DIBALH. After 1 h the reaction was warmed up to 0° C. and neutralized with aqueous 10% $KHSO_4$ solution. The mixture was extracted with ether (3×), the organic phases were washed with a aqueous 10% NaCl solution, dried ($Na_2SO_4$) and evaporated to give after flash silica gel column (n-heptane/EtOAc 9:1) 0.61 g (73%) of the title compound as yellow oil. MS: 230.0 ($MH^+$).

(rac)-(3-Methyl-piperidin-3-yl)-methanol hydrochloride

A solution of 0.20 g (0.87 mmol) of (rac)-3-hydroxymethyl-3-methyl-piperidine-1-carboxylic acid tert-butyl ester was dissolved in 5 ml of $CH_2Cl_2$, treated at 0° C. with a solution of HCl in dioxane (2.18 ml, 4 M in dioxane) and stirred for 2 h at RT. The reaction was then concentrated to dryness and re-evaporated with toluene to afford the title product (0.17 g, quant.) as white solid. MS: 130.1 ($MH^+$)

Intermediate 31

(rac)-3-Methoxymethyl-3-methyl-piperidine hydrochloride (rac)-3-Methoxymethyl-3-methyl-piperidine-1-carboxylic acid tert-butyl ester A solution of 0.37 g (1.60 mmol) of (rac)-3-hydroxymethyl-3-methyl-piperidine-1-carboxylic acid tert-butyl ester (intermediate 30B) and 0.20 ml (3.20 mmol) of iodomethane in 15 ml of DMF was treated at 0° C. with 0.08 g (1.92 mmol) of NaH (55% in oil). The reaction was stirred for 2 h at 0° C., neutralized with cold aqueous 10% $KHSO_4$ and extracted with $Et_2O$ (3×). The organic phases were washed with aqueous saturated $NaHCO_3$, aqueous 10% NaCl, dried over $Na_2SO_4$ evaporated and purified by flash silica gel column (n-heptane/EtOAc 95:5) to yield 0.25 g (64%) of the title compound as colorless liquid. MS: 244.1 ($MH^+$).

(rac)-3-Methoxymethyl-3-methyl-piperidine hydrochloride

In analogy to the procedure described for intermediate 30C, (rac)-3-methoxymethyl-3-methyl-piperidine-1-carboxylic acid tert-butyl ester gave the title compound as white powder.
MS: 144.0 ($MH^+$).

Intermediate 32

(4-Methyl-piperidin-4-yl)-methanol trifluoro-acetate

In analogy to the procedure described for intermediate 30A to 30C, ethyl 1-BOC-4-piperidinecarboxylate gave after TFA deprotection (instead of HCl in dioxane) the title compound as colorless oil.

Intermediate 33

4-Methoxymethyl-4-methyl-piperidine hydrochloride

In analogy to the procedure described for intermediate 31A to 31B, 4-hydroxymethyl-4-methyl-piperidine-1-carboxylic acid tert-butyl ester gave the title compound as white solid.

Intermediate 34

(rac)-(2-Methyl-piperidin-2-yl)-methanol hydrochloride

In analogy to the procedure described for intermediate 30A to 30C, ethyl 1-BOC-2-piperidinecarboxylate gave the title compound as light yellow powder.

Intermediate 35

(rac)-3-Hydroxymethyl-piperidin-4-ol hydrochloride 1:1 diast. Mixture

A) (rac)-3-Hydroxymethyl-piperidin-4-ol hydrochloride 1:1 diast. Mixture

A solution of 1 g (4.52 mmol) (rac)-1-benzyl-3-hydroxymethyl-piperidin-4-ol (ca 1:1 diast mixture, Synthesis (1999), 11, 1937-1943) in 25 ml of MeOH was treated with a solution of HCl in dioxane (1.24 ml, 4 M in dioxane, 4.97 mmol) and 95 mg of Pd(OH)$_2$/C (20%) and was stirred over H$_2$-atmosphere for 16 h. After filtration, new catalyst was added (95 mg of Pd(OH)$_2$/C (20%)) and stirred over H$_2$-atmosphere for 2 days. After filtration, the solution was evaporated under reduced pressure to yield 0.66 g (86%) of the title compound as a ca 1:1 cis/trans mixture, MS: 132.3 (MH$^+$).

Intermediate 36

(rac)-3-Methoxymethyl-piperidin-4-ol hydrochloride (rac)-4-Methoxy-3-methoxymethyl-piperidine-1-carboxylic acid tert-butyl ester and 4-Hydroxy-3-methoxymethyl-piperidine-1-carboxylic acid tert-butyl ester A solution of 0.61 g (2.62 mmol) of (rac)-4-hydroxy-3-hydroxymethyl-piperidine-1-carboxylic acid tert-butyl ester (Bioorganic & Medicinal Chemistry Letters (2005), 15(5), 1375-1378) in 25 ml of DMF was treated at 0° C. with 0.13 g (2.88 mmol) of NaH (55% in oil) and after 30 min slowly with 0.18 ml (2.88 mmol) of iodomethane in 14 ml of THF. The reaction was stirred for 3 h at 0° C., neutralized with cold aqueous 10% KHSO$_4$ and extracted with Et$_2$O (3×). The organic phases were washed with aqueous 10% NaCl, dried over Na$_2$SO$_4$ evaporated and purified by flash silica gel column (n-heptane/EtOAc 95:5 to 1:1) to yield 0.073 g (11%) of 4-methoxy-3-methoxymethyl-piperidine-1-carboxylic acid tert-butyl ester as light yellow oil, MS: 260.0 (MH$^+$) and 0.46 g (71%) of (rac)-4-hydroxy-3-methoxymethyl-piperidine-1-carboxylic acid tert-butyl ester as a light yellow oil containing ca 25% of (rac)-3-hydroxymethyl-4-methoxy-piperidine-1-carboxylic acid tert-butyl ester. MS: 246.1 (MH$^+$).

(rac)-3-Methoxymethyl-piperidin-4-ol hydrochloride

In analogy to the procedure described for intermediate 30C, (rac)-4-hydroxy-3-methoxymethyl-piperidine-1-carboxylic acid tert-butyl ester gave the title compound as light yellow gum, containing 25% of (rac)-(4-methoxy-piperidin-3-yl)-methanol hydrochloride. MS: 146.3 (MH$^+$).

Intermediate 37

(rac)-4-Methoxy-3-methoxymethyl-piperidine hydrochloride

In analogy to the procedure described for intermediate 30C, (rac)-4-methoxy-3-methoxymethyl-piperidine-1-carboxylic acid tert-butyl ester (intermediate 36A) gave the title compound as light yellow gum. MS: 160.2 (MH$^+$).

Intermediate 38

Piperidin-4-yl-carbamic acid methyl ester hydrochloride

4-Methoxycarbonylamino-piperidine-1-carboxylic acid tert-butyl ester

A solution of 4.00 g (2.00 mmol) of 4-amino-1-BOC-piperidine and 4.18 ml (3.00 mmol) of Et$_3$N in 50 ml of CH$_2$Cl$_2$ was treated at 0° C. with 1.62 ml (2.10 mmol) of methyl chloroformate. The reaction was stirred for 16 h at RT, neutralized with aqueous 10% KHSO$_4$ and extracted with CH$_2$Cl$_2$ (3×). The organic phases were washed with aqueous 10% NaCl, dried over Na$_2$SO$_4$ evaporated and purified by flash silica gel column (n-heptane/EtOAc 1:1 to 1:2) to yield 3.30 g (64%) of the title compound as white solid. MS: 259.2 (MH$^+$).

Piperidin-4-yl-carbamic acid methyl ester hydrochloride

In analogy to the procedure described for intermediate 30C, 4-methoxycarbonylamino-piperidine-1-carboxylic acid tert-butyl ester gave the title compound as white solid. MS: 158.3 (M$^+$).

Intermediate 39

Methyl-piperidin-4-yl-carbamic acid methyl ester hydrochloride 4-(Methoxycarbonyl-methyl-amino)-piperidine-1-carboxylic acid tert-butyl ester A solution of 1.01 g (3.91 mmol) of 4-methoxycarbonylamino-piperidine-1-carboxylic acid tert-butyl ester (intermediate 38A) in 15 ml of DMF was treated at 0° C. with 0.26 g (5.86 mmol) of NaH (55% in oil) and after 30 min with 1.95 ml (31.28 mmol) of iodomethane. The reaction was stirred for 16 h at RT, neutralized with cold aqueous 10% KHSO$_4$ and extracted with Et$_2$O (3×). The organic phases were washed with aqueous 10% NaCl, dried over Na$_2$SO$_4$ evaporated and purified by flash silica gel column (n-heptane/EtOAc 1:1) to yield 0.99 g (93%) of the title compound as colorless oil. MS: 273.1 (MH$^+$).

Methyl-piperidin-4-yl-carbamic acid methyl ester hydrochloride

In analogy to the procedure described for intermediate 30C, 3-methoxymethyl-3-methyl-piperidine-1-carboxylic acid tert-butyl ester gave the title compound as white solid. MS: 173.0 (MH$^+$).

Intermediate 40

(rac)-Piperidin-3-yl-carbamic acid methyl ester hydrochloride

(rac)-3-Methoxycarbonylamino-piperidine-1-carboxylic acid tert-butyl ester

In analogy to the procedure described for intermediate 38A, (rac)-3-amino-1-BOC-piperidine gave the title compound as off-white gum. MS: 258.9 (MH$^+$).

(rac)-Piperidin-3-yl-carbamic acid methyl ester hydrochloride

In analogy to the procedure described for intermediate 30C, (rac)-3-methoxycarbonylamino-piperidine-1-carboxylic acid tert-butyl ester gave the title compound as off-white solid. MS: 159.2 (MH$^+$).

Intermediate 41

Ethyl-carbamic acid piperidin-4-yl ester hydrochloride

4-Ethylcarbamoyloxy-piperidine-1-carboxylic acid tert-butyl ester

A solution of 1.50 g (7.45 mmol) of N-BOC-4-hydroxypoperidine in 20 ml of DMF was treated at RT with 0.74 (7.45 mmol) of copper(I) chloride and 0.59 ml (7.45 mmol) of ethyl isocyanate. The reaction was stirred for 4 h at 0° C. and the partitioned between aqueous 10% NaCl and Et$_2$O (3×). The organic phases were washed with aqueous 10% NaCl, dried over Na$_2$SO$_4$ evaporated and purified by flash silica gel column (n-heptane/EtOAc 4:1 to 2:1) to yield 1.66 g (82%) of the title compound as light yellow oil. MS: 273.1 (MH$^+$).

Ethyl-carbamic acid piperidin-4-yl ester hydrochloride

In analogy to the procedure described for intermediate 30C, 4-ethylcarbamoyloxy-piperidine-1-carboxylic acid tert-butyl ester gave the title compound as white powder. MS: 173.0 (MH$^+$).

Intermediate 42

4-(5-Methyl-[1,3,4]oxadiazol-2-yl)-piperidine

4-(N'-Acetyl-hydrazinocarbonyl)-piperidine-1-carboxylic acid benzyl ester

A suspension of 0.80 g (3.04 mmol) of 1-[(benzyloxy) carbonyl]-4-piperidinecarboxylic acid and 0.25 g (3.34 mmol) in 28 ml CH$_2$Cl$_2$ of N-acethyl hydrazine was treated at 0° C. with 0.73 g (3.80 mmol) of EDCI. Over night, the suspension was naturally warmed to RT, poured on aqueous 10% KHSO$_4$ solution and extracted with CH$_2$Cl$_2$ (3×). The organic phases were washed with aqueous saturated NaHCO$_3$ and aqueous 10% NaCl, dried (Na$_2$SO$_4$) and evaporated to give 0.84 g (87%) of the title compound as white solid. MS: 320.2 (MH$^+$).

4-(5-Methyl-[1,3,4]oxadiazol-2-yl)-piperidine-1-carboxylic acid benzyl ester A suspension of 2.00 g (6.26 mmol) of 4-(N'-acetyl-hydrazinocarbonyl)-piperidine-1-carboxylic acid benzyl ester in 30 ml acetonitril was treated at RT with 0.69 ml (7.51 mmol) of phosphoroxychloride. The suspension was stirred 1 h at RT and the refluxed for 2 h, evaporated, dissolved in CH$_2$Cl$_2$ and neutralized with aqueous saturated NaHCO$_3$ solution. The aqueous phase was extracted with CH$_2$Cl$_2$ (2×). The organic phase was dried (Na$_2$SO$_4$) and and evaporated to give after flash silica gel column (EtOAc) 1.69 g (89%) of the title compound as light yellow oil. MS: 302.1 (MH$^+$).

4-(5-Methyl-[1,3,4]oxadiazol-2-yl)-piperidine

A suspension of 100 mg (0.33 mmol) of 4-(5-methyl-[1,3,4]oxadiazol-2-yl)-piperidine-1-carboxylic acid benzyl ester in 5 ml EtOAc and 10 mg Pd/C 10% was hydrogenated (1 atm) for 1 h. The reaction was filtered (Celite) and evaporated to give 55.4 mg (99%) of the title compound as white solid. MS: 167.9 (MH$^+$).

Intermediate 43

4-(3-Methyl-[1,2,4]oxadiazol-5-yl)-piperidine hydrochloride

4-(3-Methyl-[1,2,4]oxadiazol-5-yl)-piperidine-1-carboxylic acid tert-butyl ester A solution 1.30 g (17.49 mmol) of acetamide oxime in 55 ml THF was treated with 0.76 g (17.49 mmol) of NaH (55% in oil) and the corresponding suspension stirred for 45 min at RT. 3.00 g (11.66 mmol) of ethyl 1-tert-butoxycarbonylpiperidine-4-carboxylate dissolved in 15 ml of THF was added and heated at 65° C. for 2 h. The solution was cooled to RT, poured on aqueous saturated NH$_4$Cl solution and extracted with Et$_2$O (3×). The organic phases were washed with aqueous saturated NaHCO$_3$ and aqueous 10% KHSO$_4$, dried (Na$_2$SO$_4$) and evaporated to give 2.19 g (70%) of the title compound as orange liquid. MS: 268.2 (MH$^+$).

4-(3-Methyl-[1,2,4]oxadiazol-5-yl)-piperidine hydrochloride

In analogy to the procedure described for intermediate 30C, 4-(3-methyl-[1,2,4]oxadiazol-5-yl)-piperidine-1-carboxylic acid tert-butyl ester gave the title compound as off-white solid. MS: 168.1 (MH$^+$)).

Intermediate 44

(rac, cis)-2-Hydroxyrnethyl-piperidin-4-ol hydrochloride

(rac, cis)-4-Hydroxy-piperidine-2-carboxylic acid methyl ester hydrochloride A solution of 1.09 g (5.00 mmol) (1RS,5SR)-2-benzyl-6-oxa-2-aza-bicyclo[3.2.1]octan-7-one (Journal of Organic Chemistry (1996), 61(6), 2226-31) in 25 ml of MeOH was treated with a solution of HCl in dioxane (1.38 ml, 4 M in dioxane, 5.50 mmol) and 109 mg of Pd(OH)$_2$/C (20%) and was stirred over H$_2$-atmosphere for 2.5 h. After filtration, the solution was evaporated under reduced pressure and precipitated from CH$_2$Cl$_2$/Et$_2$O to yield 0.81 g (83%) of the title compound as an off-white powder, MS: 160.2 (MH$^+$).

(rac, cis)-4-Hydroxy-piperidine-1,2-dicarboxylic acid 1-tert-butyl ester 2-methyl ester A solution of 0.70 g (4.40 mmol) (rac, cis)-4-hydroxy-piperidine-2-carboxylic acid methyl ester hydrochloride and 1.01 g (4.62 mmol) di-tert-butyl-dicarbonate in 10 ml CH$_2$Cl$_2$ was slowly treated with 0.77 ml (5.50 mmol) Et$_3$N. The reaction was stirred for 30 min at RT, poured on ice cold aqueous 10% KHSO$_4$ solution and extracted with Et$_2$O (3×). The organic phases were washed with aqueous 10% KHSO$_4$ and aqueous 10% NaCl, dried (Na$_2$SO$_4$) and evaporated to give 1.09 g (96%) of the title compound as light yellow oil. MS: 259.9 (MH$^+$).

(rac, cis)-4-(tert-Butyl-dimethyl-silanyloxy)-piperidine-1,2-dicarboxylic acid 1-tert-butyl ester 2-methyl ester A solution of 1.00 g (3.88 mmol) (rac, cis)-4-hydroxy-piperidine-1,2-dicarboxylic acid 1-tert-butyl ester 2-methyl ester and 0.87 g (12.79 mmol) imidazole in 2.5 ml DMF was cooled to 0° C. and treated with 0.64 g (7.7 mmol, 1.1 eq) TBDMSCl. After 30 min, the solution was stirred at RT for 1 h. Additional 0.12 g (0.78 mmol, 1.1 eq) TBDMSCl were added and stirred for additional 3 h. The solution was added to ice water and extracted with Et$_2$O (3×). The organic phases were washed with water and aqueous 10% NaCl, dried (Na$_2$SO$_4$) and evaporated to give after flash silica gel column (n-heptane/EtOAc 1:9 to 1:4) 1.04 g (72%) of the title compound as colorless oil. MS: 374.3 (MH$^+$).

(rac, cis)-4-(tert-Butyl-dimethyl-silanyloxy)-2-hydroxymethyl-piperidine-1-carboxylic acid tert-butyl ester 4.46 ml (1.2 M in toluene, 5.35 mmol) of DIBALH was dropped to a dry ice cooled (−30° C.) solution of 1.00 g (2.68 mmol) (rac, cis)-4-(tert-butyl-dimethyl-silanyloxy)-piperidine-1,2-dicarboxylic acid 1-tert-butyl ester 2-methyl ester in 15 ml of THF. The reaction was warmed up (0° C. for 1 h), continued for 1.5 h, cooled (−15° C.) and treated again with 0.45 ml (1.2 M in toluene, 0.54 mmol) of DIBALH. After 2 h at 0° C., the reaction was neutralized with aqueous 10% KHSO$_4$ solution. The mixture was extracted with ether (3×), the organic phases were washed with a aqueous 10% NaCl solution, dried (Na$_2$SO$_4$) and evaporated to give 0.98 g (quantitative) of the title compound as light yellow waxy solid. MS: 346.2 (MH$^+$).

(rac, cis)-2-Hydroxymethyl-piperidin-4-ol hydrochloride

A solution of 0.16 g (0.45 mmol) of (rac, cis)-4-(tert-butyl-dimethyl-silanyloxy)-2-hydroxymethyl-piperidine-1-carboxylic acid tert-butyl ester dissolved in 1 ml of MeOH was treated at 0° C. with a solution of HCl in dioxane (1.12 ml, 4 M in dioxane) and stirred for 30 min at 0° C. The reaction was then concentrated to dryness, re-evaporated with toluene and precipitated with CH$_2$Cl$_2$/Et$_2$O to give 0.05 g (68%) of the title product as white solid. MS: 132.3 (MH$^+$)

Intermediate 45

(rac, cis)-2-Methoxymethyl-piperidin-4-ol hydrochloride (rac, cis)-4-(tert-Butyl-dimethyl-silanyloxy)-2-methoxymethyl-piperidine-1-carboxylic acid tert-butyl ester In analogy to the procedure described for intermediate 31A, (rac, cis)-4-(tert-butyl-dimethyl-silanyloxy)-2-hydroxymethyl-piperidine-1-carboxylic acid tert-butyl ester (intermediate 44D) gave the title compound as colorless oil. MS: 360.3 (MH$^+$).

(rac, cis)-2-Methoxymethyl-piperidin-4-ol hydrochloride

In analogy to the procedure described for intermediate 44E, (rac)-cis-4-(tert-butyl-dimethyl-silanyloxy)-2-methoxymethyl-piperidine-1-carboxylic acid tert-butyl ester gave after precipitation with MeOH/Et$_2$O the title compound as white solid. MS: 146.0 (MH$^+$).

Intermediate 46

(rac, trans)-2-Hydroxymethyl-piperidin-4-ol hydrochloride (rac, cis)-1-Benzyl-4-hydroxy-piperidine-2-carboxylic acid methyl ester A solution of 4.35 g (20.00 mmol) (1RS,5SR)-2-benzyl-6-oxa-2-aza-bicyclo[3.2.1]octan-7-one (Journal of Organic Chemistry (1996), 61(6), 2226-31) in 100 ml of MeOH was treated at 0° C. with a solution of HCl in dioxane (5.50 ml, 4 M in dioxane, 220 mmol) and was stirred for 24 h at RT. The solution was evaporated under reduced pressure, partitioned in water acidified with 0.1 N HCl/Et$_2$O and washed with Et$_2$O (2×). The aqueous phase was basified with aqueous saturated NaHCO$_3$ and extracted with Et$_2$O (3×). These organic phases were washed with 10% NaCl, dried over Na$_2$SO$_4$ and evaporated to give 4.25 g (85%) of the title compound as a viscous yellow oil, MS: 250.0 (MH$^+$).

(rac, trans)-1-Benzyl-4-formyloxy-piperidine-2-carboxylic acid methyl ester

A solution of 1.84 ml (8.00 mmol) of di-tert-butyl azodicarboxylate in 3.1 ml of THF was slowly added (during 10 min, exothermic!) to a solution of 1.00 g (4.00 mmol) (rac, cis)-1-benzyl-4-hydroxy-piperidine-2-carboxylic acid methyl ester, 2.10 g (8.00 mmol) triphenylphosphine and 0.30 (8.00 mmol) formic acid in 11 ml THF. During the addition, the reaction was cooled to RT with a water bath. The resulting suspension was stirred at RT for 16 h, then added to diluted aqueous 10% KHSO$_4$ and washed with Et$_2$O (3×). The aqueous phase was basified with NaHCO$_3$ and extracted with Et$_2$O (3×). The organic phases were washed with aqueous 10% NaCl dried over Na$_2$SO$_4$ and evaporated to give 0.93 g of crude product. Flash silica gel column (n-heptane/EtOAc 95/5) gave 0.53 g (47%) of the title compound as light yellow oil. MS: 278.0 (MH$^+$).

(rac, trans)-1-Benzyl-2-hydroxymethyl-piperidin-4-ol 7.51 ml (1.2 M in toluene, 9.01 mmol) of DIBALH was dropped to a dry ice cooled (−30° C.) solution of 0.50 g (1.80 mmol) (rac, trans)-1-benzyl-4-formyloxy-piperidine-2-carboxylic acid methyl ester in 9 ml of THF. The reaction was warmed up (0° C. for 1 h), and stirred for 1 h at this temperature, then added to diluted aqueous 10% $KHSO_4$ and washed with $Et_2O$ (3×). The aqueous phase was basified with $NaHCO_3$, saturated with NaCl and extracted with EtOAc (3×). The organic phase was dried over $Na_2SO_4$ and evaporated to give 0.34 g (85%) of the title compound as off-white solid. MS: 222.0 ($MH^+$).

(rac, trans)-2-Hydroxymethyl-piperidin-4-ol hydrochloride

In analogy to the procedure described for intermediate 35A, (rac, trans)-1-benzyl-2-hydroxymethyl-piperidin-4-ol gave after precipitation with $CH_2Cl_2/Et_2O$ the title compound as white powder. MS: 132.3 ($MH^+$).

Intermediate 47

(rac, cis)-4-Hydroxymethyl-piperidin-3-ol hydrochloride

(rac, cis)-4-Hydroxymethyl-piperidin-3-ol hydrochloride

In analogy to the procedure described for intermediate 35A, (rac, cis)-1-benzyl-4-hydroxymethyl-piperidin-3-ol (Helvetica Chimica Acta, Volume 87, Number 10, 2629-2661) gave the title compound as light brown solid. MS: 132.3 ($MH^+$).

Intermediate 48

(rac, trans)-4-Hydroxymethyl-piperidin-3-ol hydrochloride

(rac, trans)-4-Hydroxymethyl-piperidin-3-ol hydrochloride

In analogy to the procedure described for intermediate 35A, (rac, trans)-1-benzyl-4-hydroxymethyl-piperidin-3-ol (Helvetica Chimica Acta, Volume 87, Number 10, 2629-2661) gave the title compound as orange solid. MS: 132.16 ($MH^+$).

Intermediate 49

(rac, cis)-4-Methoxymethyl-piperidin-3-ol hydrochloride

(rac, cis)-1-Benzyl-4-methoxymethyl-piperidin-3-ol, (rac, cis)-1-Benzyl-3-methoxy-piperidin-4-yl)-methanol and ((rac, cis)-1-Benzyl-3-methoxy-4-methoxymethyl-piperidine A solution of 0.80 g (3.63 mmol) of (rac, cis)-1-benzyl-4-hydroxymethyl-piperidin-3-ol (Helvetica Chimica Acta, Volume 87, Number 10, 2629-2661) in 40 ml of THF was treated at 0° C. with 0.45 g (3.99 mmol) of potassium tert-butylate and after 10 min with slowly with 0.25 ml (3.99 mmol) of iodomethane in 20 ml of THF. Over night, the solution was naturally warmed to RT, partitioned between $Et_2O$/aqueous saturated $NaHCO_3$ and extracted again with $Et_2O$ (2×). The organic phases were washed with aqueous saturated $NaHCO_3$, dried over $Na_2SO_4$ evaporated and gave after purification on a flash isolute $NH_2$-column (n-heptane/EtOAc 95:5 to 4:1) 0.33 g (39%) of (rac, cis)-1-benzyl-4-methoxymethyl-piperidin-3-ol as light yellow oil, MS: 236.1 ($MH^+$), Rf=0.39 on silicagel with n-heptane/EtOAc 1:1;

0.17 g (20%) of (rac, cis)-1-benzyl-3-methoxy-piperidin-4-yl)-methanol as light yellow oil, MS: 236.1 ($MH^+$), Rf=0.19 on silicagel with n-heptane/EtOAc 1:1;

and 0.09 g (10%) (rac, cis)-1-benzyl-3-methoxy-4-methoxymethyl-piperidine as light yellow oil, MS: 250.2 ($MH^+$), Rf=0.02 on silicagel with n-heptane/EtOAc 1:1.

(rac, cis)-4-Methoxymethyl-piperidin-3-ol hydrochloride

A solution of 0.31 g (1.39 mmol) (rac, cis)-1-benzyl-4-methoxymethyl-piperidin-3-ol in 6 ml of EtOH was treated with a solution of 1.43 ml of aqueous 1 N HCl and 30 mg of Pd/C (10%) and was stirred over $H_2$-atmosphere for 2 day. After filtration, the solution was evaporated, suspended in acetonitrile and evaporated again under reduced pressure to yield 0.25 g (quantitative) of the title compound as a white solid. MS: 146.3 ($MH^+$).

Intermediate 50

(rac, cis)-(3-Methoxy-piperidin-4-yl)-methanol hydrochloride

(rac, cis)-(3-Methoxy-piperidin-4-yl)-methanol hydrochloride

In analogy to the procedure described for intermediate 49B, (rac, cis)-1-benzyl-3-methoxy-piperidin-4-yl)-methanol (intermediate 49A) gave the title compound as light yellow oil. MS: 146.3 ($MH^+$).

Intermediate 51

(rac, cis)-3-Methoxy-4-methoxymethyl-piperidine hydrochloride

(rac, cis)-3-Methoxy-4-methoxymethyl-piperidine hydrochloride

In analogy to the procedure described for intermediate 49B, (rac, cis)-1-benzyl-3-methoxy-piperidin-4-yl)-methanol (intermediate 49A) gave the title compound as light brown oil. MS: 160.2 ($MH^+$).

Intermediate 52

(rac, cis)-4-Hydroxymethyl-4-methyl-piperidin-3-ol hydrochloride

(rac)-1-Benzyl-4-methyl-3-oxo-piperidine-4-carboxylic acid ethyl ester

A milky solution of 7.75 g (69.02 mmol) of potassium tert-butylate in 125 ml of THF was cooled (0° C.) and treated portion wise with 10.44 g (34.00 mmol) of ethyl-N-benzyl-3-oxo-4-piperidin-carboxylate hydrochloride so the temperature did not rise over 5° C. After 1 h at RT, the reaction was cooled (0° C.) and ad treated slowly with 5.07 ml (35.70 mmol) of iodomethane in 4 ml of THF. After 4.5 h at RT, the reaction was cooled (0° C.) and neutralized with 40 ml of aqueous saturated NH$_4$Cl solution. The aqueous phase was extracted with Et$_2$O (3×). The organic phases were washed with aqueous saturated NaCl, dried over Na$_2$SO$_4$ and evaporated to give 4.97 g (53%) of the title compound as orange oil. MS: 276.1 (MH$^+$).

(rac, cis)-1-Benzyl-4-hydroxymethyl-4-methyl-piperidin-3-ol and (rac, trans)-1-Benzyl-4-hydroxymethyl-4-methyl-piperidin-3-ol 24.33 ml (1.2 M in toluene, 29.20 mmol) of DIBALH was dropped to a dry ice cooled (−30° C.) solution of 2.01 g (7.30 mmol) (rac)-1-benzyl-4-methyl-3-oxo-piperidine-4-carboxylic acid ethyl ester in 37 ml of THF. Over night, the solution was naturally warmed to RT, cooled (0° C.) and treated again with 6.08 ml (1.2 M in toluene, 7.30 mmol) of DIBALH. After 4 h at RT, the reaction was neutralized with ice cooled aqueous 10% KHSO$_4$ solution. The mixture was extracted with ether (3×), the organic phases were washed with aqueous 10% KHSO$_4$ and aqueous 10% NaCl solution, dried (Na$_2$SO$_4$) and evaporated to give after flash silica gel column (CH$_2$Cl$_2$/MeOH 99:1 to 95:5) 0.28 g (16%) of (rac, cis)-1-benzyl-4-hydroxymethyl-4-methyl-piperidin-3-ol as a viscous orange oil, MS: 236.1 (MH$^+$), 0.20 g (12%) of a cis/trans mixture of (rac)-1-benzyl-4-hydroxymethyl-4-methyl-piperidin-3-ol and 0.19 g (11%) (rac, trans)-1-benzyl-4-hydroxymethyl-4-methyl-piperidin-3-ol as a viscous orange oil. MS: 236.3 (MH$^+$)

(rac, cis)-4-Hydroxymethyl-4-methyl-piperidin-3-ol hydrochloride

In analogy to the procedure described for intermediate 49B, hydrogenation of (rac, cis)-1-benzyl-4-hydroxymethyl-4-methyl-piperidin-3-ol (intermediate 52B) in MeOH gave after 2.5 days the title compound as light yellow solid. MS: 146.1 (MH$^+$).

Intermediate 53

(rac, trans)-4-Hydroxymethyl-4-methyl-piperidin-3-ol hydrochloride (rac, trans)-4-Hydroxymethyl-4-methyl-piperidin-3-ol hydrochloride In analogy to the procedure described for intermediate 35A, hydrogenation of (rac, trans)-1-benzyl-4-hydroxymethyl-4-methyl-piperidin-3-ol (intermediate 52B) in MeOH gave after 3 days the title compound as light yellow waxy solid. MS: 146.1 (MH$^+$).

Intermediate 54

1-[(E)-3-(3-Chloro-4-fluoro-phenyl)-acryloyl]-[1,4]diazepan-5-one

1-[(E)-3-(3-Chloro-4-fluoro-phenyl)-acryloyl]-[1,4]diazepan-5-one

In analogy to the procedure described for intermediate 1A, (E)-3-chloro-4-fluorocinnamic acid and 2,3,6,7-tetrahydro-(1H)-1,4-diazepin-5(4H)-one gave the title compound as white solid. MS: 297.2 (MH$^+$, 1Cl).

Intermediate 55

1-[(E)-3-(3,4-Difluoro-phenyl)-acryloyl]-[1,4]diazepan-5-one

1-[(E)-3-(3,4-Difluoro-phenyl)-acryloyl]-[1,4]diazepan-5-one

In analogy to the procedure described for intermediate 1A, (E)-4,4-difluorocinnamic acid and 2,3,6,7-tetrahydro-(1H)-1,4-diazepin-5(4H)-one gave the title compound as white solid.
MS: 281.2 (MH$^+$).

Intermediate 56

1-[(E)-3-(3-Chloro-4-fluoro-phenyl)-acryloyl]-4-((R)-2-oxiranyl-ethyl)-[1,4]diazepan-5-one 1-[(E)-3-(3-Chloro-4-fluoro-phenyl)-acryloyl]-4-((R)-2-oxiranyl-ethyl)-[1,4]diazepan-5-one In analogy to the procedure described for example 172A to 172C, 1-[(E)-3-(3-Chloro-4-fluoro-phenyl)-acryloyl]-[1,4]diazepan-5-one (intermediate 54) and methanesulfonic acid 2-((R)-2,2-dimethyl-[1,3]dioxolan-4-yl)-ethyl ester gave the title compound as pink oil. MS: 367.0 (MH$^+$, 1Cl).

Intermediate 57

1-[(E)-3-(4-Chloro-3-fluoro-phenyl)-acryloyl]-4-(4-iodo-butyl)-[1,4]diazepan-5-one 1-[(E)-3-(4-Chloro-3-fluoro-phenyl)-acryloyl]-[1,4]diazepan-5-one In analogy to the procedure described for intermediate 1A, (E)-4-chloro-3-fluorocinnamic acid and 2,3,6,7-tetrahydro-(1H)-1,4-diazepin-5(4H)-one gave the title compound as white solid. MS: 297.3 (MH$^+$).

1-[(E)-3-(4-Chloro-3-fluoro-phenyl)-acryloyl]-4-(4-iodo-butyl)-[1,4]diazepan-5-one In analogy to the procedure described for example 9A and 9B, 1-[(E)-3-(4-chloro-3-fluoro-phenyl)-acryloyl]-[1,4]diazepan-5-one gave the title compound as light yellow solid. MS: 478.8 (MH$^+$, 1Cl).

Intermediate 58

(rac)-1-[(E)-3-(3,4-Difluoro-phenyl)-acryloyl]-4-(2-oxiranyl-ethyl)-[1,4]diazepan-5-one (rac)-1-[(E)-3-(3,4-Difluoro-phenyl)-acryloyl]-4-(2-oxiranyl-ethyl)-[1,4]diazepan-5-one In analogy to the procedure described for example 170A, 1-[(E)-3-(3,4-difluoro-phenyl)-acryloyl]-[1,4]diazepan-5-one (intermediate 55) and (rac)-2-(2-bromo-ethyl)-oxirane (Journal of Organic Chemistry (1969), 34(12), 4060-5) gave the title compound as light yellow viscous oil. MS: 351.3 (MH$^+$).

Intermediate 59

3-{4-[(E)-3-(3-Chloro-4-fluoro-phenyl)-acryloyl]-7-oxo-[1,4]diazepan-1-yl}-propionaldehyde 3-{4-[(E)-3-(3-Chloro-4-fluoro-phenyl)-acryloyl]-7-oxo-[1,4]diazepan-1-yl}-propionaldehyde In analogy to the procedure described for intermediate 2A and 2B, 1-[(E)-3-(3-Chloro-4-fluoro-phenyl)-acryloyl]-[1,4]diazepan-5-one (intermediate 54) gave the title compound as colorless gum. MS: 353.2 (MH$^+$, 1Cl).

Intermediate 60

3-{4-[(E)-3-(4-Chloro-3-fluoro-phenyl)-acryloyl]-7-oxo-[1,4]diazepan-1-yl}-propionaldehyde 3-{4-[(E)-3-(4-Chloro-3-fluoro-phenyl)-acryloyl]-7-oxo-[1,4]diazepan-1-yl}-propionaldehyde In analogy to the procedure described for intermediate 2A and 2B, 1-[(E)-3-(3-Chloro-4-fluoro-phenyl)-acryloyl]-[1,4]diazepan-5-one (intermediate 57A) gave the title compound as white solid. MS: 353.1 (MH$^+$, 1Cl).

Intermediate 61

5-Oxo-4-(3-oxo-propyl)-[1,4]diazepane-1-carboxylic acid tert-butyl ester

5-Oxo-4-(3-oxo-propyl)-[1,4]diazepane-1-carboxylic acid tert-butyl ester

In analogy to the procedure described for intermediate 2A and 2B, 5-oxo-[1,4]diazepane-1-carboxylic acid tert-butyl ester gave the title compound as colorless oil. MS: 215.3 (M$^+$-tert-butyl).

Intermediate 62

(rac, cis)-2-Hydroxymethyl-piperidin-3-ol (rac)-3-Hydroxy-2-hydroxymethyl-piperidine-1-carboxylic acid tert-butyl ester A suspension of 5 g (31.00 mmol) of 2-hydroxymethyl-pyridin-3-ol hydrochlorid and 2.50 g 5% Rh/Alox in 100 ml AcOEt was stirred under hydrogen atmosphere 20 h at 25° C. and 8 bar. The suspension was filtered and evaporated to give an yellow oil. The crude product was treated with 8.78 g (40.00 mmol) BOC$_2$O and 12 ml (93.00 mmol) Hunig's base in 30 ml DMF under ice cooling for 25 h. An extraction (water/brine/AcOEt) and two crystallizations (AcOEt, MeCN/CH$_2$Cl$_2$) gave 1.77 g (25%) of the title compound as a white solid. MS: 232.0 (MH$^+$).

(rac, cis)-2-Hydroxymethyl-piperidin-3-ol hydrochlorid 0.80 g (3.46 mmol) of (rac)-3-hydroxy-2-hydroxymethyl-piperidine-1-carboxylic acid tert-butyl ester in 10 ml dioxane was treated with 4M HCl/dioxane for 18 h at RT to give the title compound as white solid 0.15 g (100%). MS: 132.2 (MH$^+$).

Intermediate 63

(rac, cis)-6-Methoxymethyl-piperidin-3-ol

5-Benzyloxy-4-chloro-2-methoxymethyl-pyridine

A solution of 9.30 g (172 mmol) of sodium methylate in 132 ml methanol was added drop wise to a solution of 5-benzyloxy-4-chloro-2-chloromethyl-pyridine (Australian Journal of chemistry, 1977, 30, 649) in 130 ml DMSO. The suspension was heated at 100° C. for 6 h, poured on ice, extracted with four portions of CH$_3$Cl. The organic phases were dried (Na$_2$SO$_4$), evaporated and distilled (Kp 0.2 mm Hg, 150-152° C.) to give 12.80 g (91%) of the title compound. MS: 264.0 (MH$^+$).

(rac, cis)-6-Methoxymethyl-piperidin-3-ol

A suspension of 1.00 g (3.79 mmol) of 5-benzyloxy-4-chloro-2-methoxymethyl-pyridine and 0.20 g 5% Rh/Alox in 25 ml methanol was stirred under hydrogen atmosphere 20 h at 50° C. and 8 bar. The suspension was filtered, evaporated and purified by silica gel column (AcOEt) to give 0.55 g (99%, 84% cis- and 16% trans-isomer) of the titled compound as a light yellow oil
MS: 146.3 (MH$^+$).

Intermediate 64

(rac, cis)-2-Methoxymethyl-6-methyl-piperidin-3-ol

[3-(4-Methoxy-benzyloxy)-6-methyl-pyridin-2-yl]-methanol 1.39 g (10 mmol) of the commercial 3-hydroxy-6-methyl-2-pyridinemethanol in 15 ml DMF was cooled (0° C.), treated with 0.52 g (13.00 mmol) of NaH (55% in oil) and after 30 min, with 1.35 mL (10.00 mmol) p-methoxybenzylchlorid. The suspension was stirred 1 h at 0° C. and 2 h at RT. The reaction mixture was diluted with CH$_2$Cl$_2$ and washed with 1M NaOH and brine. The organic layers were dried over magnesium sulfate, evaporated, purified by silica gel column (AcOEt) and crystallized (AcOEt/n-n-heptane) to give 1.55 g (60%) of the title compound as a white solid. MS: 260.0 (MH$^+$).

3-(4-Methoxy-benzyloxy)-2-methoxymethyl-6-methyl-pyridine 1.55 g (6.00 mmol) of [3-(4-Methoxy-benzyloxy)-6-methyl-pyridin-2-yl]-methanol in cold 10 ml THF (0° C.) was treated 30 min with 0.41 g (10.30 mmol) of NaH (55% in oil), then 0.43 ml (6.90 mmol) of iodomethane was added and the yellow suspension stirred 1 h. An extraction (water/CH$_2$Cl$_2$) and a chromatography (silica gel, AcOEt/n-n-heptane) delivered 1.41 g (86%) of the title compound as a yellow oil. MS: 274.3 (MH$^+$).

(rac, cis)-2-Methoxymethyl-6-methyl-piperidin-3-ol 3-(4-Methoxy-benzyloxy)-2-methoxymethyl-6-methyl-pyridine was hydrogenated using the method described in intermediate 63B to give the title compound as a white solid. MS: 160.2 (MH$^+$).

Intermediate 65

(rac, cis)-6-Hydroxymethyl-piperidin-3-ol (rac)-5-Hydroxy-2-methyl-piperidine-1-carboxylic acid tert-butyl ester and (rac, cis)-5-Hydroxy-2-hydroxymethyl-piperidine-1-carboxylic acid tert-butyl ester 1.50 g (9.28 mmol) of 6-Hydroxymethyl-pyridin-3-ol hydrochlorid was hydrogenated under the conditions described in intermediate 63B. The crude product was dissolved in 5 ml DMF, 5.60 ml (32.00 mmol) of Hunig's base and 3.56 g (16.00 mmol) of $BOC_2O$ were added and the yellow solution was stirred 18 h at RT. Evaporation, extraction (AcOEt/water/brine) and chromatography (silica gel, AcOEt/MeOH) gave 0.35 g (15%) (rac)-5-hydroxy-2-methyl-piperidine-1-carboxylic acid tert-butyl ester; MS: 216.4 ($MH^+$)
and 0.24 g (10%) (rac, cis)-5-hydroxy-2-hydroxymethyl-piperidine-1-carboxylic acid tert-butyl ester of the title compound as a light yellow oil. MS: 232.1 ($MH^+$).

(rac, cis)-6-Hydroxymethyl-piperidin-3-ol hydrochlorid

In analogy to intermediate 62B, (rac, cis)-5-hydroxy-2-hydroxymethyl-piperidine-1-carboxylic acid tert-butyl ester gave the title compound was obtained as a light brown solid. MS: 132.0 ($MH^+$).

Intermediate 66

(rac)-6-Methyl-piperidin-3-ol

In analogy to intermediate 62B, 5-hydroxy-2-methyl-piperidine-1-carboxylic acid tert-butyl ester (intermediate 65A) gave title compound as a light brown solid. MS: 116.3 ($MH^+$).

Intermediate 67

(rac)-5-Methoxy-piperidin-2-yl)-methanol

In analogy to the procedure described for intermediate 63B, (5-methoxy-pyridin-2-yl)-methanol gave the title compound as a light yellow oil. MS: 146.3 ($MH^+$).

Intermediate 68

4-Methoxy-6-methoxymethyl-piperidin-3-ol; hydrochloride

4-Methoxy-6-methoxymethyl-pyridin-3-ol [prepared from 5-benzyloxy-4-chloro-2-methoxymethyl-pyridine (intermediate 63A) by reaction with 1) NaOMe, 2) MCPBA, 3) $PdC/H_2$] was hydrogenated in analogy to intermediate 63B to give the title compound as a white solid MS: 176.2 ($MH^+$).

Intermediate 69

N-(2R,4S,5R)-(5-Methoxy-2-methoxymethyl-piperidin-4-yl)-acetamide and N-(2S,4R,5S)-(5-Methoxy-2-methoxymethyl-piperidin-4-yl)-acetamide 0.60 g (2.93 mmol) of 5-Methoxy-2-methoxymethyl-pyridin-4-ylamine (prepared by treatment of the 5-methoxy-2-methoxymethyl-pyran-4-one with aqueous 25% ammonia at 100° C.) in 10 mL $CH_2Cl_2$ was treated at 0° C. with 0.26 mL (3.65 mmol) acetyl chloride and 1.25 ml (7.30 ml) Hunig's base. After 20 min, the suspension was diluted with $CH_2Cl_2$ and washed with aqueous 10% $Na_2CO_3$ and brine. The organic layers were dried over magnesium sulfate and evaporated to give 0.71 g of the title compound as a yellow gum. The crude product was hydrogenated in analogy to intermediate 63B. A chromatography (silica gel, AcOEt/MeOH) and crystallization (AcOEt/n-n-heptane) gave 0.09 g (11%) of the title compound as a white solid. MS: 217.2 ($MH^+$).

Intermediate 70

(rac, trans)-6-Methyl-piperidin-3-ol g (9.16 mmol) of 6-Methyl-pyridin-3-ol was hydrogenated under the conditions described in intermediate 63B, then chromatographed (silica gel, AcOEt/MeOH) to give 161 mg (15%) of the title compound as a white solid. MS: 116.2 ($MH^+$).

Intermediate 71

(rac)-2,6-Bis-methoxymethyl-piperidin-3-ol 2.00 g (8.15 mmol) of (5-benzyloxy-6-hydroxymethyl-pyridin-2-yl)-methanol (prepared from 2,6-bis-hydroxymethyl-pyridin-3-ol by treatment with benzylbromide, $K_2CO_3$ in MeCN, WO 2006100305) was reacted in analogy to intermediate 64B and intermediate 64C to give 0.83 g (74%) of the title compound as a yellow oil. MS: 190.4 ($MH^+$).

Intermediate 72

(rac)-2-(6-Hydroxymethyl-piperidin-3-yloxy)-acetamide 2-(6-Hydroxymethyl-pyridin-3-yloxy)-acetamide 1.25 g (6.35 mmol) of (6-Hydroxymethyl-pyridin-3-yloxy)-acetic acid methyl ester (prepared from 6-methylpyridin-3-ol by reaction with: 1) Chloro-acetic acid methyl ester, 2) m-Cl-perbenzoic acid and 3) trifluoroacetic acid anhydride) was treated with 31 ml 7M $NH_3$ in MeOH for 2.5 h at RT. The suspension was evaporated to give 1.19 g (100%) of the title compound as a white solid. MS: 183.3 ($MH^+$).

(rac)-2-(6-Hydroxymethyl-piperidin-3-yloxy)-acetamide 2-(6-Hydroxymethyl-pyridin-3-yloxy)-acetamide was hydrogenated as described in intermediate 63B, to give the title compound as a yellow gum. MS: 189.4 ($MH^+$).

Intermediate 73

(rac)-2-Methoxymethyl-piperidin-3-ol

In analogy to the procedure described for intermediate 64, 2-hydroxymethyl-pyridin-3-ol gave the title compound as yellow oil. MS: 146.4 ($MH^+$).

Intermediate 74

(rac, trans)-6-Methoxymethyl-piperidin-3-ol

(rac, cis)-5-hydroxy-2-methoxymethyl-piperidine-1-carboxylic acid tert-butyl ester and

(rac, trans)-5-hydroxy-2-methoxymethyl-piperidine-1-carboxylic acid tert-butyl ester In analogy to the procedure described for intermediate 65A, crude (rac)-6-methoxymethyl-piperidin-3-ol (intermediate 63B) gave after separation by silica gel column (AcOEt) 34% of the (rac, cis)-5-hydroxy-2-methoxymethyl-piperidine-1-carboxylic acid tert-butyl ester and 6% of the (rac, trans)-5-hydroxy-2-methoxymethyl-piperidine-1-carboxylic acid tert-butyl ester as a light yellow liquid. MS: 246.3 (MH$^+$).

(rac, trans)-6-Methoxymethyl-piperidin-3-ol hydrochlorid

In analogy to the procedure described for intermediate 62B, (rac, trans)-5-hydroxy-2-methoxymethyl-piperidine-1-carboxylic acid tert-butyl ester gave the title compound as a white solid. MS: 146.4 (MH$^+$).

Intermediate 75

(rac, cis)-5-Methyl-piperidin-3-ol hydrochloride

(rac, cis)-3-Hydroxy-5-methyl-piperidine-1-carboxylic acid tert-butyl ester and

(rac, cis)-3-Hydroxy-5-hydroxymethyl-piperidine-1-carboxylic acid tert-butyl ester A solution of 1.20 g (9.59 mmol) of 5-hydroxymethyl-pyridin-3-ol (Jensen, Henrik Helligso; Lyngbye, Laila; Jensen, Astrid; Bols, Mikael. Chemistry—A European Journal (2002), 8(5), 1218-1226) in 1.3 ml of aqueous 25% HCl and 10 ml of MeOH was hydrogenated with 0.60 g 10% Pd/C at 50 bar and 120° C. for 20 h. Filtration and reaction with new catalyst with the same conditions gave crude product which was reacted with di-tert-butyl-dicarbonate in analogy to intermediate 44B. Purification by silica gel column (n-n-heptane/iso-propanol 95:5 to 1:1) gave 0.50 g (27%) of (rac, cis)-3-hydroxy-5-methyl-piperidine-1-carboxylic acid tert-butyl ester as light yellow oil, MS: 216.2 (MH$^+$)

and 0.15 g (8%) of rac-3-hydroxy-5-hydroxymethyl-piperidine-1-carboxylic acid tert-butyl ester as light yellow oil. MS: 232.0 (MH$^+$).

(rac, cis)-5-Methyl-piperidin-3-ol hydrochloride

In analogy to the procedure described for intermediate 62B, (rac, cis)-3-hydroxy-5-methyl-piperidine-1-carboxylic acid tert-butyl ester gave the title compound as a white solid. MS: 116.3 (MH$^+$).

Intermediate 76

(rac)-5-Hydroxymethyl-piperidin-3-ol hydrochloride

(rac)-5-Hydroxymethyl-piperidin-3-ol hydrochloride

In analogy to the procedure described for intermediate 62B, rac-3-hydroxy-5-hydroxymethyl-piperidine-1-carboxylic acid tert-butyl ester gave the title compound as orange gum. MS: 132.2 (MH$^+$).

Intermediate 77

(rac)-1-[(E)-3-(3,4-Dichloro-phenyl)-acryloyl]-3-methyl-[1,4]diazepan-5-one

(rac)-1-Benzyl-3-methyl-[1,4]diazepan-5-one

Sodium azide (1.58 g, 24.4 mmol) was added portionwise over 6 h to a solution of 1-benzyl-3-methylpiperidin-4-one (5.00 g, 24.4 mmol) at 0° C., then the reaction mixture was allowed to reach room temperature over 16 h. The reaction mixture was then poured upon ice/40% aq. sodium hydroxide solution/ethyl acetate, the organic layer was washed with brine, dried (MgSO$_4$), and evaporated. Recrystallization in n-heptane/ethyl acetate 2:1 (60 ml) produced the title compound (2.59 g, 49%). White solid, MS: 219.3 (MH$^+$).

(rac)-3-Methyl-[1,4]diazepan-5-one

A mixture of 1-benzyl-3-methyl-[1,4]diazepan-5-one (1.88 g, 8.62 mmol) and palladium (10% on activated charcoal, 188 mg) in ethanol (50 ml) was stirred at room temperature under a hydrogen atmosphere (3 bar). After 18 h, the catalyst was removed by filtration and the filtrate evaporated to afford the title compound (1.12 g, 99%). White solid, MS: m/e=128 (M$^+$).

(rac)-1-[(E)-3-(3,4-Dichloro-phenyl)-acryloyl]-3-methyl-[1,4]diazepan-5-one In analogy to the procedure described in intermediate 1A, (E)-3,4-dichlorocinnamic acid and 3-methyl-[1,4]diazepan-5-one gave the title compound as a white solid. MS: 327.2 (MH$^+$).

Intermediate 78

(rac)-1-[(E)-3-(3,4-Dichloro-phenyl)-acryloyl]-7-methyl-[1,4]diazepan-5-one

(rac)-7-Methyl-5-oxo-[1,4]diazepane-1-carboxylic acid benzyl ester 2,2-dioxo-[1,2,3]oxathiazolidine-3-carboxylic acid tert-butyl ester (WO2002072584; 454 mg, 2.03 mmol) was added to a solution of 3-benzyloxycarbonylamino-butyric acid ethyl ester (450 mg, 1.69 mmol) and potassium tert-butylate (228 mg, 2.03 mmol). The reaction mixture was stirred for 72 h at room temperature and heated at 50° C. for another 24 h. After cooling, the reaction mixture was partitioned between 10% aq. citric acid solution and ethyl acetate, the organic layer was washed with brine, dried (MgSO$_4$), and evaporated. The residue was taken up in dichloromethane (10 ml), treated with trifluoroacetic acid (2.5 ml), stirred at room temperature for 45 min, then evaporated. The residue was dissolved in methanol (10 ml), then potassium carbonate (3.08 g, 22.3 mmol) was added and the reaction mixture was stirred at room temperature for 16 h. After evaporation, the residue was partitioned between ethyl acetate and 1 M aq. sodium hydroxide solution. The organic layer was washed with brine, dried (MgSO$_4$), and evaporated. Chromatography (SiO$_2$; CH$_2$Cl$_2$/MeOH/NH$_4$OH 95:5:0.25) produced the title compound (205 mg, 46%). Colorless gum, MS: 263.2 (MH$^+$).

(rac)-7-Methyl-[1,4]diazepan-5-one

A mixture of 7-methyl-5-oxo-[1,4]diazepane-1-carboxylic acid benzyl ester (201 mg, 0.77 mmol) and palladium (10% on activated charcoal, 80 mg) in ethanol (2 ml) was stirred at room temperature under a hydrogen atmosphere (3 bar). After 20 h, the catalyst was removed by filtration and the filtrate evaporated to afford the title compound (81 mg, 82%). White solid, MS: 128 (M$^+$).

(rac)-1-[(E)-3-(3,4-Dichloro-phenyl)-acryloyl]-7-methyl-[1,4]diazepan-5-one

-(7-Azobenzotriazol-1-yl)-1,1,3,3-tetramethyluronium hexafluorophosphate (343 mg, 0.90 mmol) was added to a solution of 3,4-dichlorocinnamic acid (130 mg, 0.60 mmol), 7-methyl-[1,4]diazepan-5-one (77 mg, 0.60 mmol), and 4-methylmorpholine (304 mg, 3.01 mmol) in N,N-dimethylformamide (1 ml). The reaction mixture was stirred for 3 h at room temperature, then partitioned between n-heptane/ethyl acetate 1:1 and water. The organic layer was washed with brine, dried (MgSO$_4$), and evaporated. Chromatography (SiO$_2$; CH$_2$Cl$_2$MeOH/NH$_4$OH 95:5:0.25) produced the title compound (193 mg 98%). Colorless gum, MS: 327.1 (MH$^+$).

Intermediate 79

(R)-1-[(E)-3-(3,4-Dichloro-phenyl)-acryloyl]-2-methyl-[1,4]diazepan-5-one

(R)-2-methyl-5-oxo-[1,4]diazepane-1-carboxylic acid benzyl ester

In analogy to the procedure described in intermediate 78A, 3-benzyloxycarbonylamino-propanoic acid methyl ester and (S)-5-methyl-2,2-dioxo-[1,2,3]oxathiazolidine-3-carboxylic acid tert-butyl ester (*Bioorg. Med. Chem. Lett.* 2006, 16, 1207) gave the title compound. Colorless gum, MS: m/e=263.1 (MH$^+$).

(R)-2-Methyl-[1,4]diazepan-5-one

In analogy to the procedure described in intermediate 78B, (R)-2-methyl-5-oxo-[1,4]diazepane-1-carboxylic acid benzyl ester gave the title compound. Colorless gum, MS: m/e=128 (M$^+$).

(R)-1-[(E)-3-(3,4-Dichloro-phenyl)-acryloyl]-2-methyl-[1,4]diazepan-5-one

In analogy to the procedure described in intermediate 78C, (E)-3,4-dichlorocinnamic acid and (R)-2-methyl-[1,4]diazepan-5-one gave the title compound as a colorless gum, MS: m/e=327.3 (MH$^+$).

Intermediate 80

(rac)-1-[(E)-3-(3,4-Dichloro-phenyl)-acryloyl]-6-methyl-[1,4]diazepan-5-one

(rac)-6-Methyl-5-oxo-[1,4]diazepane-1-carboxylic acid tert-butyl ester

Sodium hydride (60% dispersion in mineral oil, 275 mg, 6.88 mmol) was added at room temperature to a solution of tert-butyl N-(2-aminoethyl)carbamate (1.00 g, 6.24 mmol), then after 30 min ethyl methacrylate (712 mg, 6.24 mmol) was added. The reaction mixture was stirred at room temperature over 16 h, then partitioned between ethyl acetate/n-heptane 1:1 and water. The organic layer was washed with brine, dried (MgSO$_4$), and evaporated. Chromatography (SiO2; ethyl acetate, then CH$_2$Cl$_2$/MeOH/NH$_4$OH 95:5:0.25) produced the title compound (51 mg, 4%). White solid, MS: m/e=229.4 (MH$^+$).

(rac)-6-Methyl-[1,4]diazepan-5-one hydrochloride

6-Methyl-5-oxo-[1,4]diazepane-1-carboxylic acid tert-butyl ester (42 mg, 0.18 mmol) was suspended in hydrogen chloride solution (4 M in 1,4-dioxane, 0.5 ml) and stirred at room temperature for 4 h, then volatile material was removed by distillation, to afford the title compound (29 mg, 96%). Colorless gum, MS: 129.1 ([M–Cl]$^+$).

(rac)-1-[(E)-3-(3,4-Dichloro-phenyl)-acryloyl]-6-methyl-[1,4]diazepan-5-one

In analogy to the procedure described in intermediate 78C, (E)-3,4-dichlorocinnamic acid and 6-methyl-[1,4]diazepan-5-one hydrochloride gave the title compound as a colorless gum, MS: 327.1 (MH$^+$).

Intermediate 81

(rac)-6-Aza-spiro[2.5]octan-4-ol hydrochloride

A] (rac)-6-Aza-spiro[2.5]octane-6-carboxylic acid tert-butyl ester

To a solution of Et$_2$Zn (37.5 ml, 1.1M solution in toluene, 0.04 mmol) in DCE (80 ml) at 0° C. was added chloroiodomethane (5.99 ml, 0.08 mmol) under Ar. This mixture was stirred for 15 minutes before a solution of 3-hydroxy-4-methylene-piperidine-1-carboxylic acid tert-butyl ester (J. Org. Chem. 2001, 66, 2487) (4.19 g, 0.02 mmol) in DCE (10 ml) was added, after which time the reaction was stirred for 0.5 h at 0° C. and then allowed to reach room temperature, stirring for a further 1 h. The reaction was then quenched by addition of saturated NH$_4$Cl, separated, and the organic dried (Na$_2$SO$_4$) and concentrated. Purfication by flash column chromatography (EtOAc:n-heptane 2:8-1:1) afforded the title product (2.4 g, 54%) as a crystalline solid. MS: 228.2 (MH$^+$).

(rac)-6-Aza-spiro[2.5]octan-4-ol hydrochloride

Intermediate 81A (0.52 g, 2 mmol) was dissolved in 10 ml of HCl in dioxane (4M), stirred for ten minutes. The reaction was then concentrated to afford the title product (0.38 g, quant.) as a white powder. MS: 128.1 (MH$^+$).

Intermediate 82

(+)-6-Aza-spiro[2.5]octan-4-ol hydrochloride

The title compound was prepared by chiral separation of Intermediate 81A on a Chiralpak AD column (Isopropanol: n-heptane 5:95) and subsequent analogous deprotection with HCl in dioxane. MS: 128.1 (MH$^+$).

Intermediate 83

(−)-6-Aza-spiro[2.5]octan-4-ol hydrochloride

The title compound was prepared by chiral separation of Intermediate 81A on a Chiralpak AD column (Isopropanol:

n-heptane 5:95) and subsequent analogous deprotection with HCl in dioxane. MS: 128.1 (MH+).

Intermediate 84

(rac)-3-Hydroxy-4,4-dimethyl-piperidine hydrochloride (rac)-3-Hydroxy-4,4-dimethyl-piperidine-1-carboxylic acid tert-butyl ester Intermediate 81A (0.43 g, 1.9 mmol) was dissolved in AcOH (7 ml) with platinum oxide (0.4 g, 1.9 mmol) and stirred under hydrogen atmosphere (balloon) for 2 d. The reaction was then filtered through Hyflo and concentrated to afford the title product (0.41 g, 94%) as oil. MS: 230.2 (MH+).

(rac)-3-Hydroxy-4,4-dimethyl-piperidine hydrochloride

Intermediate 84A was deprotected with HCl in dioxane to afford the title product as a white powder. MS: 130.1 (MH+).

Intermediate 85

(+, cis)-4-Methyl-piperidin-3-ol hydrochloride (rac, trans)-3-Hydroxy-4-methyl-piperidine-1-carboxylic acid tert-butyl ester (rac, trans)-1-Benzyl-4-methyl-piperidin-3-ol (Tet. Lett. 2000, 5817) (13.0 g, 63 mmol) was dissolved in MeOH with Pd(OH)$_2$/C (4 g) and stirred under a hydrogen atmosphere (balloon) for 16 h after which time Boc$_2$O (13.8 g, 63 mmol) was added, the reaction stirred for 1 h, filtered through Hyflo and concentrated to afford the title product (13.3 g, 98%) as a crystalline solid. MS: 216.2 (MH+).

(rac, cis)-4-Methyl-3-(4-nitro-benzoyloxy)-piperidine-1-carboxylic acid tert-butyl ester Intermediate 85A (6.0 g, 28 mmol) was dissolved in THF (40 ml) with PPh$_3$ (8.9 g, 34 mmol), 4-nitrobenzoic acid (5.7 g, 34 mmol) and cooled to 0° C. before dropwise addition of diisopropyldiazadicarboxylate (6.9 g, 34 mmol). The ice bath was removed and the reaction allowed coming to room temperature, stirring for 16 h. The reaction was then directly absorbed onto silica gel and purified by flash column chromatography (EtOAc:n-heptane 2:8) to afford the title product (4.0 g, 40%) as a white solid. MS: 365.2 (MH+).

(rac, cis)-3-Hydroxy-4-methyl-piperidine-1-carboxylic acid tert-butyl ester

Intermediate 85B (5.0 g, 14 mmol) was dissolved in MeOH (70 ml) and NaOH (4.5 ml, 6N in water, 27 mmol) was added. The reaction was stirred for 1 h after which time the solvent removed under vacuum, the residue portioned between water and CH$_2$Cl$_2$ and the organic collected, dried (Na$_2$SO$_4$) and concentrated to afford the title product (2.6 g, 87%) as a crystalline solid. MS: 216.1 (MH+).

(+, cis)-3-hydroxy-4-methyl-piperidine-1-carboxylic acid tert-butyl ester

Intermediate 85C was separated on a Chiralpak AD column (Isopropanol:n-heptane 5:95) to afford the title compound. MS: 216.1 (MH+).

(+, cis)-4-Methyl-piperidin-3-ol hydrochloride

Intermediate 85D was deprotected with HCl in dioxane to afford the title compounds as a white powder. MS: 116.2 (MH+).

Intermediate 86

(−, cis)-4-Methyl-piperidin-3-ol hydrochloride

The title compound was prepared in analogy to Intermediate 85D and subsequently deprotected with HCl in dioxane to afford the title product as a white powder. MS: 116.2 (MH+).

Intermediate 87

(rac, trans)-2-Methyl-piperidin-3-ol hydrochloride (rac, trans)-3-Hydroxy-2-methyl-piperidine-1-carboxylic acid tert-butyl ester Hydroxy-2-methylpyridine (2.0 g, 18 mmol) was dissolved in MeOH (40 ml) with 5% Rh on alumina (0.27 g) and heated to 30° C. at 90 bar of hyrdogen atmosphere for 22 h. The reaction was then filtered through Hyflo, Boc$_2$O (4.0 g, 18 mmol) added and the reaction stirred for 1 h before removing the solvent under vacuum. The residue was redissolved in CH$_2$Cl$_2$, washed with 10% citric acid solution, dried (Na$_2$SO$_4$) and concentrated. Purification by flash column chromatography (EtOAc:n-heptane 3:7-1:1) afforded the title product (0.7 g, 18%) of the title product as a light yellow liquid. MS: 216.1 (MH+). A small quantity of (rac, cis)-3-hydroxy-2-methyl-piperidine-1-carboxylic acid tert-butyl ester (0.06 g, 2%) was also obtained from the column. MS: 216.1 (MH+).

(rac, trans)-2-Methyl-piperidin-3-ol hydrochloride

Intermediate 87A (0.7 g, 3 mmol) was deprotected using HCl in dioxane affording the title product (0.45 g, 91%) as a white powder. MS: 116.1 (MH+).

Intermediate 88

(rac, cis)-2-Methyl-piperidin-3-ol hydrochloride

The byproduct (rac, cis)-3-hydroxy-2-methyl-piperidine-1-carboxylic acid tert-butyl ester from the reaction to make intermediate 87A was deprotected with HCl in dioxane to afford the title compound. MS: 116.1 (MH+).

Intermediate 89

(rac, trans)-4-Fluoro-piperidin-3-ol hydrochloride (rac, trans)-4-Fluoro-piperidin-3-ol-1-carboxylic acid tert-butyl ester (rac)-7-Oxa-3-aza-bicyclo[4.1.0]heptane-3-carboxylic acid tert-butyl ester (Heter. 1994, 39, 163) (2.0 g, 10 mmol) was dissolved in a mixture of DCE (1.5 ml) and trisHF.Et$_3$N (1.6 g, 10 mmol) and heated to 80° C. for 12 h after which time the reaction was diluted with CH$_2$Cl$_2$, washed with sat. NaHCO$_3$, then sat. NH$_4$Cl, dried (Na$_2$SO$_4$) and concentrated. Purification by flash column chromatography (EtOAc:n-heptane 3:7) afforded the title compound (1.5 g, 66%) as a yellow liquid. MS: 220.1 (MH+). Also obtained was the regioisomer (rac, trans)-3-fluoro-4-hydroxy-piperidine-1-carboxylic acid tert-butyl ester (0.26 g, 12%) as a yellow oil. MS: 220.1 (MH+).

(rac, trans)-4-Fluoro-piperidin-3-ol hydrochloride

Intermediate 89A (0.5 g, 2 mmol) was deprotected with HCl in dioxane affording the title product (0.34 g, 95%) as a white powder. MS: 120.1 (MH+).

Intermediate 90

(rac, trans)-3-Fluoro-piperidin-4-ol hydrochloride

The byproduct (rac, trans)-3-fluoro-4-hydroxy-piperidine-1-carboxylic acid tert-butyl ester ester from the reaction to make intermediate 89A was deprotected with HCl in dioxane to afford the title compound. MS: 120.1 (MH+).

Intermediate 91

(rac)-4-Methyl-piperidin-3-ol hydrochloride

3-Hydroxy-4-methyl-piperidine-1-carboxylic acid tert-butyl ester

Hydroxy-4-methylpyridine (0.98 g, 9 mmol) was dissolved in a AcOH (50 ml) and $Pt_2O$ (0.10 g) added. The mixture was heated to 100° C. under 100 bar of hydrogen pressure for 20 h. The reaction was then filtered through Hyflo and concentrated. The residue was dissolved in $CH_2Cl_2$ (30 ml) and $Et_3N$ (2.75 ml, 20 mmol) and $Boc_2O$ (2.2 g, 10 mmol) added and the mixture stirred for 1 h. The reaction was then washed with 10% citric acid solution, dried ($Na_2SO_4$) and concentrated. Purification by flash column chromatography (EtOAc:n-heptane 3:7) afforded the title product (0.63 g, 33%), a 3:1 mixture of diasteriomers (cis:trans) as a colourless oil. MS: 216.1 (MH+).

(rac)-4-Methyl-piperidin-3-ol hydrochloride

Intermediate 91A was deprotected with HCl in dioxane to afford the title product as a white powder. MS: 116.1 (MH+).

Intermediate 92

4-[3-((−)-4-hydroxy-6-aza-spiro[2.5]oct-6-yl)-propyl]-[1,4]diazepan-5-one dihydrochloride 4-[3-((−)-4-hydroxy-6-aza-spiro[2.5]oct-6-yl)-propyl]-5-oxo-[1,4]diazepane-1-carboxylic acid tert-butyl ester 5-Oxo-4-(3-oxo-propyl)-[1,4]diazepane-1-carboxylic acid tert-butyl ester (intermediate 61) (0.19 g, 0.7 mmol) was reacted with (−)-6-Aza-spiro[2.5]octan-4-ol hydrochloride (intermediate 83) (0.12 g, 0.7 mmol) in DCE:EtOH (1:1, 6 ml), AcOH (0.18 ml) and pyridine-borane complex (0.18 ml, 8M in pyridine, 1.4 mmol) for 20 minutes. The reaction was then concentrated, redissolved in $CH_2Cl_2$ and washed with sat. $NaHCO_3$, dried ($Na_2SO_4$) and concentrated. The residue was purified by flash column chromatography ($CH_2Cl_2$: MeOH 8:2) to afford the title product (0.25 g, 91%) as a gum. MS: 382.4 (MH+).

4-[3-((−)-4-hydroxy-6-aza-spiro[2.5]oct-6-yl)-propyl]-[1,4]diazepan-5-one dihydrochloride Intermediate 92A was deprotected with HCl in dioxane to afford the title product as a white powder. MS: 282.3 (MH+).

Intermediate 93

(rac, cis)-3-Fluoro-piperidin-4-ol hydrochloride

3-Fluoro-4-hydroxy-piperidine-1-carboxylic acid tert-butyl ester

Fluoro-4- oxo-piperidine-1-carboxylic acid tert-butyl ester (Chem. Europ. J. 2005, 5, 1579) (1.0 g, 5 mmol) was dissolved in MeOH (5 ml), cooled to 0° C. and sodium borohydride (0.2 g, 5 mmol) was added portionwise. The reaction was allowed to reach room temperature and stirred overnight after which time the solvent was removed under vacuum, the residue redissolved in $CH_2Cl_2$, washed with water, dried ($Na_2SO_4$) and concentrated. The product was purified by flash column chromatography (EtOAc:n-heptane 3:7-1:1) to afford the title compound (0.67 g, 67%) as a white solid. $^1H$ NMR (400 MHz, DMSO) δ 1.19-1.68 (11H, m), 2.80-3.0 (1H, m), 3.06-3.17 (1H, m), 3.59-3.70 (2H, m), 3.90-3.97 (1H, m), 4.55 (1H, dt, J 52, 4 Hz).

(rac, cis)-3-Fluoro-piperidin-4-ol hydrochloride

Intermediate 93A was deprotected with HCl in dioxane to afford the title compound as a white powder. MS: 120.1 (MH+).

Intermediate 94

(rac)-3-Methyl-piperidin-4-ol (rac)-1-Benzyl-3-methyl-piperidin-4-ol

Benzyl-3- methyl-piperidin-4-one (2.0 g, 10 mmol) was dissolved in MeOH (10 ml), cooled to 0° C. and sodium borohydride (0.2 g, 5 mmol) was added portionwise. The reaction was allowed to reach room temperature and stirred overnight after which time the solvent was removed under vacuum, the residue redissolved in $CH_2Cl_2$, washed with water, dried ($Na_2SO_4$) and concentrated to afford the title compound (2.1 g, quant), a 3:1 mixture of diasteriomers (trans:cis) as gum. MS: 206.2 (MH+).

(rac)-3-Methyl-piperidin-4-ol

Intermediate 94A (0.93 g) was dissolved in EtOH (10 ml) and $Pd(OH)_2/C$ (0.2 g) and cyclohexen (2 ml) added. The reaction was heated to reflux for 16 h after which time it was filtered through Hyflo and concentrated, affording the title product (0.52 g, quant) a brown oil.
MS: 116.1 (MH+).

Intermediate 95

(rac, trans)-3-Methyl-piperidin-4-ol hydrochloride (rac, trans)-4-Hydroxy-3-methyl-piperidine-1-carboxylic acid tert-butyl ester Benzyl-5-methyl-1,2,3,6-tetrahydro-pyridine (Tet. Lett. 1998, 39, 5417) (7.7 g, 41 mmol) was dissolved in THF (100 ml) and sodium borohydride (2.6 g, 69 mmol) added. The mixture was cooled to 0° C. and borontrifluoride etherate (6.2 ml, 49 mmol) added, the reaction allowed to reach room temperature and subsequently stirred for 1 h. The reaction was recooled to 0° C., a small quantity of water added to quench any remaining borane, and then a suspension of Oxone (42.6 g, 69 mmol) in water (100 ml) was added and the reaction again allowed to reach room temperature (1 h). The reaction was filtered, extacted with EtOAc, the aqeous phase made basic by addition of solid NaOH, and then reextracted with $CH_2Cl_2$, dried ($Na_2SO_4$) and concentrated. The crude residue (5.2 g) was redissolved in MeOH, Pd(OH)$_2$/C added and the reaction stirred under an atmosphere of hydrogen (balloon) for 16 h after which time $Boc_2O$ (5.5 g, 25 mmol) was added, the reaction stirred for 1 h, and then filtered through Hyflo and concentrated. Purification by flash column chromatography (EtOAc:n-heptane 4:6) afforded the title product (2.1 g, 39%) as a colourless gum. MS: 216.2 ($MH^+$).

(rac, trans)-3-Methyl-piperidin-4-ol hydrochloride

Intermediate 95A was deprotected with HCl in dioxane to afford the title product as a white powder. MS: 116.2 ($MH^+$).

Intermediate 96

(rac, cis)-3-Methyl-piperidin-4-ol hydrochloride (rac, cis)-3-Methyl-4-(4-nitro-benzoyloxy)-piperidine-1-carboxylic acid tert-butyl ester Intermediate 95A (0.6 g, 3 mmol) was converted to the 4-nitrobenzoic ester analogously to Intermediate 85B affording the titled product (0.9 g, 90%) as a white solid. MS: 365.2 ($MH^+$).

(rac, cis)-4-Hydroxy-3-methyl-piperidine-1-carboxylic acid tert-butyl ester

Intermediate 96A (0.86 g, 2 mmol) was saponified analogously to intermediate 85C affording the title product (0.5 g, 98%) as a colourless oil. MS: 216.4 ($MH^+$).

(rac, cis)-3-Methyl-piperidin-4-ol hydrochloride

Intermediate 96B was deprotected with HCl in dioxane to afford the title product as a white powder. MS: 116.1 ($MH^+$).

Intermediate 97

(rac)-3,3-Dimethyl-piperidin-4-ol (rac)-1-Benzyl-3,3-dimethyl-piperidin-4-ol

Benzyl-3,3-dimethyl-piperidin-4-one (WO 01/00577 A2) (5.0 g, 23 mmol) was dissolved in MeOH (25 ml), cooled to 0° C. and sodium borohydride (1.0 g, 25 mmol) was added portionwise. The reaction was allowed to reach room temperature and stirred overnight after which time the solvent was removed under vacuum, the residue redissolved in $CH_2Cl_2$, washed with water, dried ($Na_2SO_4$) and concentrated to afford the title compound (4.9 g, 97%). MS: 220.4 ($MH^+$).

(rac)-3,3-Dimethyl-piperidin-4-ol

Intermediate 97A (4.9 g) was dissolved in EtOH (50 ml) and Pd(OH)$_2$/C (0.3 g) and cyclohexene (6 ml) added. The reaction was heated to reflux for 16 h after which time it was filtered through Hyflo and concentrated, affording the title product (0.5 g, quant) a white crystalline solid. MS: 130.1 ($MH^+$).

Intermediate 98

(rac)-5-Aza-spiro[2.5]octan-8-ol

8-Oxo-5-aza-spiro[2.5]octane-5-carboxylic acid tert-butyl ester

4-Oxo-piperidine-1-carboxylic acid tert-butyl ester (1.0 g, 5 mmol) was dissolved in tBuOH (10 ml) with tBuOK (1.1 g, 10 mmol) and stirred for 15 minutes before portionwise addition of (2-chloro-ethyl)-dimethyl-sulfonium iodide (Tet. Lett. 1984, 25, 5501) (1.1 g, 5 mmol) over 1 h. The reaction was stirred for 16 h after which time it was partioned between water and $CH_2Cl_2$, the organic collected, dried ($Na_2SO_4$) and concentrated. Flash column chromatography (EtOAc:n-heptane 1:9-3:7) afforded the titled product (0.2 g, 19%) as a colourless oil. MS: 130.1 ($MH^+$).

(rac)-8-Hydroxy-5-aza-spiro[2.5]octane-5-carboxylic acid tert-butyl ester

Intermediate 98A (0.2 g, 1 mmol) was dissolved in MeOH (5 ml) and sodium borohydride (0.04 g, 1 mmol) added. The reaction was stirred for 1 h, concentrated, partitioned between $CH_2Cl_2$ and water, the organic collected, dried ($Na_2SO_4$) and concentrated. Flash column chromatography (EtOAc:n-heptane 3:7-1:1) afforded the titled prouduct (0.15 g, 68%) as colourless gum. MS: 228.1 ($MH^+$).

(rac)-5-Aza-spiro[2.5]octan-8-ol

Intermediate 98B was deprotected with HCl in dioxane to afford the titled product as a white poweder. MS: 128.1 ($MH^+$).

Intermediate 99

1-[(E)-3-(3-Chloro-4-fluoro-phenyl)-acryloyl]-4-(4-iodo-butyl)-[1,4]diazepan-5-one 1-[(E)-3-(3-Chloro-4-fluoro-phenyl)-acryloyl]-4-(4-iodo-butyl)-[1,4]diazepan-5-one In analogy to the procedure described for example 9A and 9B, 1-[(E)-3-(3-chloro-4-fluoro-phenyl)-acryloyl]-[1,4]diazepan-5-one (intermediate 54) gave the title compound as yellow foam. MS: 478.9 ($MH^+$).

Intermediate 100

(rac, trans)-4-Methyl-piperidin-3-ol hydrochloride

The title compound was prepared from intermediate 85B, (rac, trans)-3-Hydroxy-4-methyl-piperidine-1-carboxylic acid tert-butyl ester, by deprotection with HCl in dioxane. MS:116.2 ($MH^+$).

Intermediate 101

(rac)-3-Methyl-piperidin-3-ol hydrochloride

The title compound was prepared in analogy to intermediate 16. MS:116.2 ($MH^+$).

Intermediate 102

Oxa-4,9-diaza-spiro[5.5]undecan-3-one

The title compound was prepared as described in J. Med. Chem. 1983, 26, 6, 855.

Example 1

1-[(E)-3-(3-Chloro-phenyl)-acryloyl]-4-(2-pyrrolidin-1-yl-ethyl)-[1,4]diazepan-5-one 1-[(E)-3-(3-Chloro-phenyl)-acryloyl]-4-(2-pyrrolidin-1-yl-ethyl)-[1,4]diazepan-5-one In analogy to the procedure described in intermediate 4A, 1-[(E)-3-(3-chloro-phenyl)-acryloyl]-[1,4]diazepan-5-one (intermediate 3A]) and 1-(2-chloro-ethyl)-pyrrolidine gave the title compound as off-white powder. MS: 376.5 (MH+, Cl).

Example 2

4-[2-(4-Acetyl-piperazin-1-yl)-ethyl]-1-[(E)-3-(3-chloro-phenyl)-acryloyl]-[1,4]diazepan-5-one 4-[2-(4-Acetyl-piperazin-1-yl)-ethyl]-1-[(E)-3-(3-chloro-phenyl)-acryloyl]-[1,4]diazepan-5-one In analogy to the procedure described in intermediate 4A, 1-[(E)-3-(3-chloro-phenyl)-acryloyl]-[1,4]diazepan-5-one (intermediate 3A]) and 1-[4-(2-chloro-ethyl)-piperazin-1-yl]-ethanone gave the title compound as off-white foam. MS: 433.2 (MH+, Cl).

Example 3

1-[(E)-3-(3,4-Dichloro-phenyl)-acryloyl]-4-(2-piperidin-1-yl-ethyl)-[1,4]diazepan-5-one 1-[(E)-3-(3,4-Dichloro-phenyl)-acryloyl]-4-(2-piperidin-1-yl-ethyl)-[1,4]diazepan-5-one In analogy to the procedure described in intermediate 4A, 1-[(E)-3-(3,4-dichloro-phenyl)-acryloyl]-[1,4]diazepan-5-one (intermediate 1A) and 1-(2-chloro-ethyl)-piperidine gave the title compound as white solid. MS: 424.1 (MH+, 2Cl).

Example 4

1-[(E)-3-(3,4-Dichloro-phenyl)-acryloyl]-4-(3-piperidin-1-yl-propyl)-[1,4]diazepan-5-one 1-[(E)-3-(3,4-Dichloro-phenyl)-acryloyl]-4-(3-piperidin-1-yl-propyl)-[1,4]diazepan-5-one In analogy to the procedure described in intermediate 4A, 1-[(E)-3-(3,4-dichloro-phenyl)-acryloyl]-[1,4]diazepan-5-one (intermediate 1A) and 1-(3-chloro-propyl)-piperidine gave the title compound as light yellow solid. MS: 438.1 (MH+, 2Cl).

Example 5

1-[(E)-3-(3-Chloro-phenyl)-acryloyl]-4-(2-morpholin-4-yl-ethyl)-[1,4]diazepan-5-one {4-[(E)-3-(3-Chloro-phenyl)-acryloyl]-7-oxo-[1,4]diazepan-1-yl}-acetic acid ethyl ester A solution of 4.33 g (15.53 mmol) of 1-[(E)-3-(3-chloro-phenyl)-acryloyl]-[1,4]diazepan-5-one (intermediate 3A) in 80 ml of DMF was treated at 0° C. with 0.75 g (17.09 mmol) of NaH (55% in oil) in two portions and after 30 min with 1.89 ml (17.09 mmol) of bromo-acetic acid ethyl ester in 1 ml of DMF. The reaction was stirred for 5 h at RT, cooled (0° C.) and treated again with 0.20 g (4.66 mmol) of NaH (55% in oil) and after 20 min with 0.34 ml (3.11 mmol) of bromo-acetic acid ethyl ester. The reaction was warmed up to RT over night, cooled and neutralized with cold aqueous 10% KHSO4 and extracted with Et2O (3×). The organic phases were washed with aqueous saturated NaHCO3, aqueous 10% NaCl, dried over Na2SO4 evaporated and purified by flash silica gel column (EtOAc/n-heptane 1:1 to 9:1) to yield 2.92 g (52%) of the title compound as light yellow viscous oil. MS: 365.0 (MH+, Cl).

1-[(E)-3-(3-Chloro-phenyl)-acryloyl]-4-(2-hydroxy-ethyl)-[1,4]diazepan-5-one

A solution of 2.16 g (5.91 mmol) of {4-[(E)-3-(3-chloro-phenyl)-acryloyl]-7-oxo-[1,4]diazepan-1-yl}-acetic acid ethyl ester in 30 ml of ethanol was treated at 0° C. with 0.45 g (11.81 mmol) of sodium borohydride in 30 ml of ethanol during 20 min. The reaction was stirred for 21 h at RT, cooled (0° C.) and treated again with 0.45 g (11.81 mmol) of sodium borohydride. After 22 h at RT the reaction neutralized with cold aqueous 10% KHSO4 and extracted with EtOAc (3×). The organic phases were washed with aqueous 10% NaCl, dried over Na2SO4 evaporated and purified by flash silica gel column (EtOAc and then EtOAc/EtOH 1 to 7.5%) to yield 1.50 g (79%) of the title compound as light white foam. MS: 323.1 (MH+, Cl).

4-(2-Chloro-ethyl)-1-[(E)-3-(3-chloro-phenyl)-acryloyl]-[1,4]diazepan-5-one

To an ice-cooled solution of 2.13 g (3.50 mmol) of 1-[(E)-3-(3-chloro-phenyl)-acryloyl]-4-(2-hydroxy-ethyl)-[1,4]diazepan-5-one and 0.73 ml (5.25 mmol) of Et3N in 35 ml of dichloromethane were added 0.29 ml (3.68 mmol) of methanesulfonyl chloride under stirring within 5 min keeping the temperatue at 0° C. The reaction was stirred at room temperature for 1 h 45 min. Water was added and after 5 min, the reaction was then partitioned between ether and aqueous saturated NaHCO3. The water phase was extracted again with ether (2×), the organic phases were washed with aqueous 10% NaCl, dried (Na2SO4) and concentrated to yield 1.22 g (87%) of the title compound as yellow viscous oil. MS: 341.0 (MH+, 2Cl).

1-[(E)-3-(3-Chloro-phenyl)-acryloyl]-4-(2-morpholin-4-yl-ethyl)-[1,4]diazepan-5-one A solution of 0.085 g (0.25 mmol) of 4-(2-chloro-ethyl)-1-[(E)-3-(3-chloro-phenyl)-acryloyl]-[1,4]diazepan-5-one in 1.3 ml of DMA was treated with 0.04 ml (0.50 mmol) of morpholine and stirred for 8 h at RT, a crystal of NaI was added and stirring was continued for 40 h. The reaction was extracted with aqueous saturated NaHCO$_3$/EtOAc (3×). The organic phases were washed with aqueous 10% NaCl, dried (Na$_2$SO$_4$), concentrated and evaporated. Purification by catridges, Si-Amine, 70 ml, 20 g (EtOAc) gave 0.008 g (8%) of the title compound as off-white viscous oil. MS: 392.0 (MH$^+$, Cl).

Example 6

1-[(E)-3-(3,4-Dichloro-phenyl)-acryloyl]-4-(3-morpholin-4-yl-propyl)-[1,4]diazepan-5-one 1-[(E)-3-(3,4-Dichloro-phenyl)-acryloyl]-4-[3-(tetrahydro-pyran-2-yloxy)-propyl]-[1,4]diazepan-5-one In analogy to the procedure described in example 5A, 1-[(E)-3-(3,4-dichloro-phenyl)-acryloyl]-[1,4]diazepan-5-one (intermediate 1A]) and 2-(3-bromo-propoxy)-tetrahydro-pyran gave the title compound as white solid. MS: 455.3 (MH$^+$, 2Cl).

1-[(E)-3-(3,4-Dichloro-phenyl)-acryloyl]-4-(3-hydroxy-propyl)-[1,4]diazepan-5-one A solution of 1.30 g (2.85 mmol) of 1-[(E)-3-(3,4-dichloro-phenyl)-acryloyl]-4-[3-(tetrahydro-pyran-2-yloxy)-propyl]-[1,4]diazepan-5-one in 6 ml of methanol was treated with 0.22 g (0.86 mmol) of pyridinium toluene-4-sulfonate and stirred at 55° C. for 30 min. The reaction was cooled and extracted with aqueous 10% KHSO$_4$/Et$_2$O (3×). The organic phases were washed with aqueous saturated NaHCO$_3$, aqueous 10% NaCl, dried (Na$_2$SO$_4$) and evaporated to give after crystallization (Et$_2$O) 0.98 g (92%) of the title compound as white solid.
MS: 371.0 (MH$^+$, 2Cl).

Methanesulfonic acid 3-{4-[(E)-3-(3,4-dichlorophenyl)-acryloyl]-7-oxo-[1,4]diazepan-1-yl}-propyl ester In analogy to the procedure described in example 5C, 1-[(E)-3-(3,4-dichloro-phenyl)-acryloyl]-4-(3-hydroxy-propyl)-[1,4]diazepan-5-one and methanesulfonyl chloride gave the crude title compound as white foam and as a mixture of mainly mesylate and some chloride.
MS: 448.2 (M$^+$, 2Cl).

1-[(E)-3-(3,4-Dichloro-phenyl)-acryloyl]-4-(3-iodopropyl)-[1,4]diazepan-5-one

A solution of 0.50 g (1.11 mmol) of crude methanesulfonic acid 3-{4-[(E)-3-(3,4-dichloro-phenyl)-acryloyl]-7-oxo-[1,4]diazepan-1-yl}-propyl ester in 20 ml of 2-butanone was treated with 0.33 g (2.23 mmol) of sodium iodide and stirred at 95° C. for 30 min. The reaction was cooled, evaporated, suspended in 60 ml dichloromethane/Et$_2$O (1:3), filtered and the organic solvent discarded. The residue was then washed again with dichloromethane to give after evaporation 0.27 g (51%) of the title compound as white solid. MS: 481.0 (MH$^+$, 2Cl).

1-[(E)-3-(3,4-Dichloro-phenyl)-acryloyl]-4-(3-morpholin-4-yl-propyl)-[1,4]diazepan-5-one In analogy to the procedure described in example 5D, 1-[(E)-3-(3,4-dichloro-phenyl)-acryloyl]-4-(3-iodo-propyl)-[1,4]diazepan-5-one and morpholine (with no additional sodium iodide) gave after flash silica gel column purification (CH$_2$Cl$_2$/EtOAc 99:1 to 96:4) the title compound as a light yellow viscous oil. MS: 440.2 (MH$^+$, 2Cl).

Example 7

1-[(E)-3-(3,4-Difluoro-phenyl)-acryloyl]-4-(3-piperidin-1-yl-propyl)-[1,4]diazepan-5-one 1-[(E)-3-(3,4-Difluoro-phenyl)-acryloyl]-4-(3-piperidin-1-yl-propyl)-[1,4]diazepan-5-one In analogy to the procedure described in intermediate 1A, (E)-3,4-difluorocinnamic acid and 4-(3-piperidin-1-yl-propyl)-[1,4]diazepan-5-one-dihydrochloride (intermediate 4B, suspended in CH$_2$Cl$_2$ with 4 equivalent of Et$_3$N) gave after purification on catridges, Si-Amine, 70 ml, 20 g (EtOAc) the title compound as a white powder. MS: 406.2 (MH$^+$).

Example 8

4-(3-Piperidin-1-yl-propyl)-1-[(E)-3-(3-trifluoromethyl-phenyl)-acryloyl]-[1,4]diazepan-5-one 4-(3-Piperidin-1-yl-propyl)-1-[(E)-3-(3-trifluoromethyl-phenyl)-acryloyl]-[1,4]diazepan-5-one In analogy to the procedure described in intermediate 1A, (E)-3-(trifluoromethyl)cinnamic acid and 4-(3-piperidin-1-yl-propyl)-[1,4]diazepan-5-one-dihydrochloride (intermediate 4B, suspended in CH$_2$Cl$_2$ with 4 equivalent of Et$_3$N) gave after purification on catridges, Si-Amine, 70 mL, 20 g (EtOAc) the title compound as a light yellow viscous oil. MS: 438.4 (MH$^+$).

Example 9

1-[(E)-3-(3,4-Dichloro-phenyl)-acryloyl]-4-(4-piperidin-1-yl-butyl)-[1,4]diazepan-5-one 4-(4-Chloro-butyl)-1-[(E)-3-(3,4-dichloro-phenyl)-acryloyl]-[1,4]diazepan-5-one In analogy to the procedure described in example 5A, 1-[(E)-3-(3,4-dichloro-phenyl)-acryloyl]-[1,4]diazepan-5-one (intermediate 1A]) and 1-chloro-4-iodobutane gave the title compound as orange solid. MS: 403.2 (MH$^+$, 3Cl).

1-[(E)-3-(3,4-Dichloro-phenyl)-acryloyl]-4-(4-iodobutyl)-[1,4]diazepan-5-one

In analogy to the procedure described in example 6D, 4-(4-chloro-butyl)-1-[(E)-3-(3,4-dichloro-phenyl)-acryloyl]-[1,4]diazepan-5-one and sodium iodide were stirred at 90° C. for 26 h to give the title compound as orange foam. MS: 495.0 (MH$^+$, 2Cl).

1-[(E)-3-(3,4-Dichloro-phenyl)-acryloyl]-4-(4-piperidin-1-yl-butyl)-[1,4]diazepan-5-one In analogy to the procedure described in example 5D, 1-[(E)-3-(3,4-dichloro-phenyl)-acryloyl]-4-(4-iodo-butyl)-[1,4]diazepan-5-one and piperidine (with no additional sodium iodide) gave the title compound as white powder. MS: 452.2 (MH$^+$, 2Cl).

Example 10

1-[(E)-3-(3,4-Dichloro-phenyl)-acryloyl]-4-{4-[methyl-(tetrahydro-pyran-4-yl)-amino]-butyl}-[1,4]diazepan-5-one 1-[(E)-3-(3,4-Dichloro-phenyl)-acryloyl]-4-{4-[methyl-(tetrahydro-pyran-4-yl)-amino]-butyl}-[1,4]diazepan-5-one A solution of 0.100 g (0.20 mmol) of 1-[(E)-3-(3,4-dichloro-phenyl)-acryloyl]-4-(4-iodo-butyl)-[1,4]diazepan-5-one (example 9B) in 3.1 ml of DMA was treated with free methyl-(tetrahydro-pyran-4-yl)-amine in 1 ml of toluene [0.035 g (0.22 mmol) methyl-(tetrahydro-pyran-4-yl)-amine hydrochloride were dissolved in 0.8 ml of 0.5 N NaOH was extracted with toluene (2 ml). The organic phase was dried over $Na_2SO_4$] and stirred for 22 h at RT, 0.06 ml (0.40 mmol) of $Et_3N$ was added and stirring was continued for 18 h at 50° C. Again methyl-(tetrahydro-pyran-4-yl)-amine in 1 ml of $CH_2Cl_2$ [0.035 g (0.22 mmol) methyl-(tetrahydro-pyran-4-yl)-amine hydrochloridewere dissolved in 0.5 ml aqueous 10% NaCl solution/0.4 ml of 1 N NaOH was extracted with $CH_2Cl_2$ (1 ml). The organic phase was dried over $Na_2SO_4$] was added and heated for 9 h at 50° C. The reaction was extracted with aqueous saturated $NaHCO_3/Et_2O$ (3×). The organic phases were washed with aqueous 10% NaCl, dried ($Na_2SO_4$), concentrated and evaporated. Purification by catridges, Si-Amine, 70 ml, 20 g (n-heptane/EtOAc 1:4 to 1:9) gave 0.004 g (4%) of the title compound as a light yellow semisolid. MS: 482.3 ($MH^+$, 2Cl).

Example 11

1-[(E)-3-(3-Chloro-4-fluoro-phenyl)-acryloyl]-4-(3-piperidin-1-yl-propyl)-[1,4]diazepan-5-one 1-[(E)-3-(3-Chloro-4-fluoro-phenyl)-acryloyl]-4-(3-piperidin-1-yl-propyl)-[1,4]diazepan-5-one A suspension of 0.099 g (0.32 mmol) 4-(3-piperidin-1-yl-propyl)-[1,4]diazepan-5-one-dihydrochloride (intermediate 4B) and 0.077 g (0.38 mmol) of (E)-3-chloro-4-fluorocinnamic acid in 3 ml of $CH_2Cl_2$ was treated with 0.09 ml (0.64 mmol) of $Et_3N$ at RT, cooled (0° C.) and treated with a 0.085 g (0.41 mmol) of N,N'-dicyclohexylcarbodiimide. The reaction was warmed up over night to RT, then partitioned between EtOAc (×3)/saturated $NaHCO_3$. The organic phases were washed with aqueous 10% NaCl, dried over $Na_2SO_4$ and evaporated to give after purification on catridges, Si-Amine, 70 ml, 20 g (EtOAc/n-heptane 9:1) 0.075 g (64%) of the title compound as a white solid. MS: 422.1 ($MH^+$, Cl).

Example 12

1-[(E)-3-(5,6-Dichloro-pyridin-3-yl)-acryloyl]-4-(3-piperidin-1-yl-propyl)-[1,4]diazepan-5-one (E)-3-(5,6-Dichloro-pyridin-3-yl)-acrylic acid methyl ester To a solution of (5,6-Dichloro-pyridin-3-yl)-methanol (1.8 g, 10 mmol) in $CH_2Cl_2$ (20 ml) was added manganese dioxide (4.4 g, 50 mmol). The reaction was stirred for 16 h after which time it was filtered through a pad of Hyflo and a fresh portion of manganese dioxide (1.8 g, 20 mmol) added and the reaction stirred for a further 4 h. The manganese dioxide was removed by filtration through Hyflo and the reaction concentrated affording crude 5,6-dichloro-pyridine-3-carbaldehyde (1.4 g, 81%). This was then dissolved in toluene (20 ml) and (methoxycarbonylmethylene)triphenylphosphorane (4.1 g, 12 mmol) added and the mixture heated to reflux for 1 h after which time the mixture was diluted with $CH_2Cl_2$, silica gel added and the mixture concentrated to dryness. The absorbed product was then purified by flash column chromatography (EtOAc:Heptane 1:1) furnishing the title compound (1.5 g, 81%) as a white solid.

MS: 232.0 ($MH^+$, 2Cl).

(E)-3-(5,6-Dichloro-pyridin-3-yl)-acrylic acid (E)-3-(5,6-Dichloro-pyridin-3-yl)-acrylic acid methyl ester (1.54 g, 7 mmol) was suspended in MeOH (20 ml) and aqueous sodium hydroxide (1.1 ml, 6M, 7 mmol) added. The mixture was heated to reflux for 20 min after which time the reaction was concentrated, the residue taken up in water and the pH adjusted to 1 by addition of 1M HCl. The product could then be isolated by filtration affording the title compound (1.11 g, 77%) as a white solid. MS: 216.0 ($M-H^-2Cl$).

E)-3-(5,6-Dichloro-pyridin-3-yl)-acryloyl]-4-(3-piperidin-1-yl-propyl)-[1,4]diazepan-5-one To a suspension of (E)-3-(5,6-Dichloro-pyridin-3-yl)-acrylic acid (26 mg, 0.12 mmol), 4-(3-piperidin-1-yl-propyl)-[1,4]diazepan-5-one-dihydrochloride (intermediate 4) (24 mg, 0.1 mmol), O-(7-azabenotriazol-1-yl)-1,1,3,3-tetramethyluronium hexafluorophosphate (46 mg, 0.12 mmol) in DMF (1 ml) was added $Et_3N$(21 ul, 0.15 mmol) and the mixture shaken fro 1 h. The reaction was then directly purified by preparative HPLC affording the title product (14 mg, 32%) as a white powder. MS: 439.4 ($MH^+$, 2Cl).

Example 13

1-[(E)-3-(4-Chloro-3-fluoro-phenyl)-acryloyl]-4-(3-piperidin-1-yl-propyl)-[1,4]diazepan-5-one 1-[(E)-3-(4-Chloro-3-fluoro-phenyl)-acryloyl]-4-(3-piperidin-1-yl-propyl)-[1,4]diazepan-5-one In analogy to the procedure described in intermediate 1A, 4-(3-piperidin-1-yl-propyl)-[1,4]diazepan-5-one-dihydrochloride (intermediate 4B) and (E)-4-chloro-3-fluorocinnamic acid gave after work up with EtOAc (×3)/saturated $NaHCO_3$ and precipitation (n-pentane) the title compound as off-white solid. MS: 422.2 ($MH^+$, Cl).

Examples 14-26

General Procedure for Examples 14-26

A solution CDI (0.016 g, 0.1 mmol) in DMF (0.5 ml) was added to the appropriate cinnamic acid (0.1 mmol) and the solution shaken for 1 h after which time a solution of 4-(2-pyrrolidin-1-yl-ethyl)-[1,4]di-azepan-5-one-dihydrochloride (intermediate 5) ( 0.027 g, 0.1 mmol), $Et_3N$ (28 ul, 0.2 mmol) in DMF (0.5 ml) was added and the shaking continued for 16 h. The reactions were then directly purified by preparative HPLC.

TABLE 1

| Example No. | Compound Name | Cinnamic Acid | MS: (MH+) |
|---|---|---|---|
| 14 | 4-(2-Pyrrolidin-1-yl-ethyl)-1-[(E)-3-(4-trifluoromethyl-phenyl)-acryloyl]-[1,4]diazepan-5-one | 4-Trifluoromethylcinnamic acid | 410.5 |
| 15 | 4-(2-Pyrrolidin-1-yl-ethyl)-1-[(E)-3-(4-methoxy-phenyl)-acryloyl]-[1,4]diazepan-5-one | 4-Methoxycinnamic acid | 372.5 |
| 16 | 4-(2-Pyrrolidin-1-yl-ethyl)-1-[(E)-3-(2,4-dichloro-phenyl)-acryloyl]-[1,4]diazepan-5-one | 2,4-Dichlorocinnamic acid | 410.5 |
| 17 | 1-[(E)-3-(4-Benzyloxy-phenyl)-acryloyl]-4-(2-pyrrolidin-1-yl-ethyl)-[1,4]diazepan-5-one | 4-Benzyloxycinnamic acid | 448.6 |
| 18 | 1-(E)-(3-Benzo[1,3]dioxol-5-yl-acryloyl)-4-(2-pyrrolidin-1-yl-ethyl)-[1,4]diazepan-5-one | 3,4-Methylenedioxycinnamic acid | 386.5 |
| 19 | 4-(2-Pyrrolidin-1-yl-ethyl)-1-[(E)-3-(2,4-difluoro-phenyl)-acryloyl]-[1,4]diazepan-5-one | 2,4-Difluorocinnamic acid | 378.5 |
| 20 | 1-[(E)-3-(3,5-Difluoro-phenyl)-acryloyl]-4-(2-pyrrolidin-1-yl-ethyl)-[1,4]diazepan-5-one | 3,5-Difluorocinnamic acid | 378.5 |
| 21 | 4-(2-Pyrrolidin-1-yl-ethyl)-1-[(E)-3-phenyl-acryloyl]-[1,4]diazepan-5-one | Cinnamic acid | 342.5 |
| 22 | 4-(2-Pyrrolidin-1-yl-ethyl)-1-[(E)-3-(2-methoxy-phenyl)-acryloyl]-[1,4]diazepan-5-one | 2-Methoxycinnamic acid | 372.5 |
| 23 | 4-(2-Pyrrolidin-1-yl-ethyl)-1-[(E)-3-(4-fluoro-phenyl)-acryloyl]-[1,4]diazepan-5-one | 4-Fluorocinnamic acid | 360.5 |
| 24 | 4-(2-Pyrrolidin-1-yl-ethyl)-1-[(E)-3-(3-fluoro-phenyl)-acryloyl]-[1,4]diazepan-5-one | 3-Fluorocinnamic acid | 360.5 |
| 25 | 1-(E)-(3-Naphthalen-2-yl-acryloyl)-4-(2-pyrrolidin-1-yl-ethyl)-[1,4]diazepan-5-one | 2-Napthyacrylic acid | 392.5 |
| 26 | 4-(2-Pyrrolidin-1-yl-ethyl)-1-[(E)-3-(4-chloro-phenyl)-acryloyl]-[1,4]diazepan-5-one | 4-Chlorocinnamic acid | 376.2 |

Examples 27-34

General Procedure for Examples 27-34

A solution of {4-[(E)-3-(3-chloro-phenyl)-acryloyl]-7-oxo-[1,4]diazepan-1-yl}-acetaldehyde (intermediate 3) (0.031 g, 0.1 mmol) in DCE (0.5 ml) was added to the appropriate amine (0.1 mmol) followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

TABLE 2

| Example No. | Compound Name | Amine | MS: (MH+) |
|---|---|---|---|
| 27 | 1-[(E)-3-(3-Chloro-phenyl)-acryloyl]-4-{3-[4-(6-fluoro-1H-indol-3-yl)-piperidin-1-yl]-ethyl}-[1,4]diazepan-5-one | 6-Fluoro-3-piperidin-4-yl-1H-indole (intermediate 6) | 522.8 |
| 28 | 1-[(E)-3-(3-chloro-phenyl)-acryloyl]-4-{3-[4-(2-oxo-imidazolidin-1-yl)-piperidin-1-yl]-ethyl}-[1,4]diazepan-5-one | 1-Piperidin-4-yl-imidazolidin-2-one (intermediate 7) | 473.8 |
| 29 | 1-[(E)-3-(3-Chloro-phenyl)-acryloyl]-4-{3-[4-(5-methyl-1H-[1,2,4]triazol-3-yl)-piperidin-1-yl]-ethyl}-[1,4]diazepan-5-one | 4-(5-Methyl-4H-[1,2,4]triazol-3-yl)-piperidine hydrochloride (intermediate 8) | 470.8 |
| 30 | 4-[2-(4-Benzyl-piperidin-1-yl)-ethyl]-1-[(E)-3-(3-chloro-phenyl)-acryloyl]-[1,4]diazepan-5-one | 4-Benzylpiperidine | 479.8 |
| 31 | 1-[(E)-3-(3-Chloro-phenyl)-acryloyl]-4-[3-(4-hydroxy-4-phenyl-piperidin-1-yl)-propyl]-[1,4]diazepan-5-one | 4-Hydroxy-4-phenyl-piperidine | 481.8 |

TABLE 2-continued

| Example No. | Compound Name | Amine | MS: (MH+) |
|---|---|---|---|
| 32 | 1-[(E)-3-Chloro-phenyl-acryloyl]-4-{2-[4-phenyl-piperidin-1-yl]-ethyl}-[1,4]diazepan-5-one | 4-Phenylpiperidine | 465.8 |
| 33 | 1-[(E)-3-(3-Chloro-phenyl)-acryloyl]-4-[3-(4-(4-fluoro-phenyl)-piperidin-1-yl)-ethyl]-[1,4]diazepan-5-one | 4-(4-Fluoro-phenyl)-piperidine | 483.8 |
| 34 | 1-[(E)-3-(3-Chloro-phenyl)-acryloyl]-4-{2-[4-(3-chloro-phenyl)-piperidin-1-yl]-ethyl}-[1,4]diazepan-5-one | 4-(3-Chloro-phenyl)-piperidine | 499.8 |

Examples 35-92

General Procedure for Examples 35-92

A solution of 3-{4-[(E)-3-(3,4-dichloro-phenyl)-acryloyl]-7-oxo-[1,4]diazepan-1-yl}-propionaldehyde (intermediate 2) (0.037 g, 0.1 mmol) in DCE (0.5 ml) was added to the appropriate amine (0.1 mmol) followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

TABLE 3

| Example No. | Compound Name | Amine | MS: (MH+) |
|---|---|---|---|
| 35 | 4-[3-(4-Cyclopropanecarbonyl-piperazin-1-yl)-propyl]-1-[(E)-3-(3,4-dichloro-phenyl)-acryloyl]-[1,4]diazepan-5-one | Cyclopropyl-piperazin-1-yl-methanone | 507.2 |
| 36 | 4-[3-(Cyclopentyl-amino)-propyl]-1-[(E)-3-(3,4-dichloro-phenyl)-acryloyl]-[1,4]diazepan-5-one | Cyclopentylamine | 438.2 |
| 37 | 4-[-3-(Cyclopentyl-methyl-amino)-propyl]-1-[(E)-3-(3,4-dichloro-phenyl)-acryloyl]-[1,4]diazepan-5-one | Cyclopentyl-methyl-amine | 452.2 |
| 38 | (+/−)-4-[3-(Bicyclo[2.2.1]hept-2-ylamino)-propyl]-1-[(E)-3-(3,4-dichloro-phenyl)-acryloyl]-[1,4]diazepan-5-one | (+/−)-endo-2-Norbonylamine hydrochloride | 464.2 |
| 39 | 4-[3-(Cyclohexyl-methyl-amino)-propyl]-1-[(E)-3-(3,4-dichloro-phenyl)-acryloyl]-[1,4] diazepan-5-one | Cylcohexyl-methyl-amine | 466.2 |
| 40 | 1-[(E)-3-(3,4-Dichloro-phenyl)-acryloyl]-4-[3-(1,1-dioxo-thiomorpholin-4-yl)-propyl]-[1,4]diazepan-5-one | Thiomorpholine-1,1-dioxide | 488.1 |
| 41 | 1-[(E)-3-(3,4-Dichloro-phenyl)-acryloyl]-4-{3-[(2-methoxy-ethyl)-methyl-amino]-propyl}-[1,4]diazepan-5-one | (2-Methoxy-ethyl)-methyl-amine | 442.2 |
| 42 | 1-[(E)-3-(3,4-Dichloro-phenyl)-acryloyl]-4-{3-[(2-hydroxy-ethyl)-methyl-amino]-propyl}-[1,4]diazepan-5-one | (2-Hydroxy-ethyl)-methyl-amine | 428.2 |
| 43 | 4-{3-[Bis-(2-hydroxy-ethyl)-amino]-propyl}-1-[(E)-3-(3,4-dichloro-phenyl)-acryloyl]-[1,4]diazepan-5-one | 2-(2-Hydroxy-ethylamino)-ethanol | 458.2 |
| 44 | (+/−)-N-[1-(E)-(3-{4-[3-(3,4-Dichloro-phenyl)-acryloyl]-7-oxo-[1,4] diazepan-1-yl}-propyl)-pyrrolidin-3-yl]-acetamide | (+/−)-N-Pyrrolidin-3-yl-acetamide | 481.2 |
| 45 | 1-[(E)-3-(3,4-Dichloro-phenyl)-acryloyl]-4-[3-(4-phenyl-piperidin-1-yl)-propyl]-[1,4]diazepan-5-one | 4-Phenyl-piperidine | 514.2 |
| 46 | 1-[(E)-3-(3,4-Dichloro-phenyl)-acryloyl]-4-(3-pyrrolidin-1-yl-propyl)-[1,4]diazepan-5-one | Pyrollidine | 424.2 |
| 47 | (S)-1-[(E)-3-(3,4-Dichloro-phenyl)-acryloyl]-4-[3-(2-hydroxymethyl-pyrrolidin-1-yl)-propyl]-[1,4]diazepan-5-one | (S)-Prolinol | 454.2 |

TABLE 3-continued

| Example No. | Compound Name | Amine | MS: (MH+) |
|---|---|---|---|
| 48 | 8-(3-{4-[(E)-3-(3,4-Dichloro-phenyl)-acryloyl]-7-oxo-[1,4]diazepan-1-yl}-propyl)-1,3,8-triaza-spiro[4.5]decane-2,4-dione | 1,3,8-Triaza-Spiro[4.5]decane-2,4-dione (intermediate 11) | 522.2 |
| 49 | 4-[(E)-3-(4-Benzyl-4-hydroxy-piperidin-1-yl)-propyl]-1-[(E)-3-(3,4-dichloro-phenyl)-acryloyl]-[1,4]diazepan-5-one | 4-Benzyl-piperidin-4-ol | 544.2 |
| 50 | 1-[(E)-3-(3,4-Dichloro-phenyl)-acryloyl]-4-[3-(4-methyl-piperidin-1-yl)-propyl]-[1,4]diazepan-5-one | 4-Methyl-piperidine | 452.2 |
| 51 | 1-[(E)-3-(3,4-Dichloro-phenyl)-acryloyl]-4-(3-thiomorpholin-4-yl-propyl)-[1,4]diazepan-5-one | Thiomorpholine | 456.1 |
| 52 | (+/−)-1-[(E)-3-(3,4-Dichloro-phenyl)-acryloyl]-4-[3-([1,4]dioxan-2-ylmethyl-methyl-amino)-propyl]-[1,4]diazepan-5-one | (1,4)-dioxan-2-yl-methylamine | 484.2 |
| 53 | 1-[(E)-3-(3,4-Dichloro-phenyl)-acryloyl]-4-[3-(4-hydroxy-3,4,5,6-tetrahydro-2H-[4,4']bipyridinyl-1-yl)-propyl]-[1,4]diazepan-5-one | 4-Hydroxy-4-pyrid-4-yl(piperidine) | 531.2 |
| 54 | cis/trans-1-[(E)-3-(3,4-Dichloro-phenyl)-acryloyl]-4-{3-[methyl-(4-methyl-cyclohexyl)-amino]-propyl}-[1,4]diazepan-5-one | cis/trans-Methyl-(4-methyl-cyclohexyl)-amine | 480.3 |
| 55 | 1-[(E)-3-(3,4-Dichloro-phenyl)-acryloyl]-4-[3-(4,4-difluoro-piperidin-1-yl)-propyl]-[1,4]diazepan-5-one | 4,4-Difluororpiperidine | 474.2 |
| 56 | 1-[(E)-3-(3,4-Dichloro-phenyl)-acryloyl]-4-{3-[4-(2-oxo-imidazolidin-1-yl)-piperidin-1-yl]-propyl}-[1,4]diazepan-5-one | Piperidin-4-yl-imidazolidin-2-one (intermediate 7) | 522.2 |
| 57 | 1-[(E)-3-(3,4-Dichloro-phenyl)-acryloyl]-4-{3-[4-(1H-pyrazol-3-yl)-piperidin-1-yl]-propyl}-[1,4]diazepan-5-one | 4-(1H-Pyrazol-3-yl)-piperidine (intermediate 12) | 504.2 |
| 58 | 1-[(E)-3-(3,4-Dichloro-phenyl)-acryloyl]-4-{3-[4-(5-methyl-1H-[1,2,4]triazol-3-yl)-piperidin-1-yl]-propyl}-[1,4]diazepan-5-one | 4-(5-Methyl-4H-[1,2,4]triazol-3-yl)-piperidine hydrochloride (intermediate 8) | 519.2 |
| 59 | 1-[(E)-3-(3,4-Dichloro-phenyl)-acryloyl]-4-[3-(4-hydroxy-4-phenyl-piperidin-1-yl)-propyl]-[1,4]diazepan-5-one | 4-Phenyl-piperidin-4-ol | 530.5 |
| 60 | 1-(-3-{4-[(E)-3-(3,4-Dichloro-phenyl)-acryloyl]-7-oxo-[1,4]diazepan-1-yl}-propyl)-4-phenyl-piperidine-4-carbonitrile | 4-Phenyl-piperidine-4-carbonitrile | 539.5 |
| 61 | 1-[(E)-3-(3,4-Dichloro-phenyl)-acryloyl]-4-[3-(4-morpholin-4-yl-piperidin-1-yl)-propyl]-[1,4]diazepan-5-one | 4-Piperidin-4-yl-morpholine | 523.5 |
| 62 | (+/−)-1-[(E)-3-(3,4-Dichloro-phenyl)-acryloyl]-4-[3-(2-methyl-piperidin-1-yl)-propyl]-[1,4]diazepan-5-one | (+/−)-2-Methylpiperidine | 452.4 |
| 63 | 1-[(E)-3-(3,4-Dichloro-phenyl)-acryloyl]-4-[3-(tetrahydro-pyran-4-ylamino)-propyl]-[1,4]diazepan-5-one | Tetrahydro-pyran-4-ylamine | 454.5 |
| 64 | cis/trans-1-[(E)-3-(3,4-Dichloro-phenyl)-acryloyl]-4-[3-(2-methyl-cyclohexylamino)-propyl]-[1,4]diazepan-5-one | cis/trans-2-Methylcyclohexylamine | 466.4 |
| 65 | trans-1-[(E)-3-(3,4-Dichloro-phenyl)-acryloyl]-4-[3-(4-hydroxy-4-pyridin-2-yl-cyclohexylamino)-propyl]-[1,4]diazepan-5-one | trans-4-Amino-1-pyridin-2-yl-cyclohexanol (intermediate 13) | 545.5 |
| 66 | trans-1-[(E)-3-(3,4-Dichloro-phenyl)-acryloyl]-4-[2-(4-hydroxy-cyclohexylamino)propyl]-[1,4]diazepan-5-one | trans-4-Amino-cyclohexanol | 468.5 |
| 67 | 4-(3-{4-[(E)-3-(3,4-Dichloro-phenyl)-acryloyl]-7-oxo-[1,4]diazepan-1-yl}-propylamino)-cyclohexanecarboxylic acid ethyl ester | Piperidine-4-carboxylic acid ethyl ester | 510.2 |

TABLE 3-continued

| Example No. | Compound Name | Amine | MS: (MH+) |
|---|---|---|---|
| 68 | 1-[(E)-3-(3,4-Dichloro-phenyl)-acryloyl]-4-{3-[(3-hydroxy-propyl)-amino]-propyl}-[1,4]diazepan-5-one | 3-Amino-propan-1-ol | 428.2 |
| 69 | 1-[(E)-3-(3,4-Dichloro-phenyl)-acryloyl]-4-[3-(4'-hydroxy-3',4',5',6'-tetrahydro-2'H-[2,4']bipyridinyl-1'-yl)-propyl]-[1,4]diazepan-5-one | 4-Hydroxy-4-pyrid-2-yl(piperidine) | 531.2 |
| 70 | 1-[(E)-3-(3,4-Dichloro-phenyl)-acryloyl]-4-[3-(4'-hydroxy-3',4',5',6'-tetrahydro-2'H-[3,4']bipyridinyl-1'-yl)-propyl]-[1,4]diazepan-5-one | 4-Hydroxy-4-pyrid-3-yl(piperidine) | 531.2 |
| 71 | (+/−)-1-[(E)-3-(3,4-Dichloro-phenyl)-acryloyl]-4-[3-(3-hydroxy-pyrrolidin-1-yl)-propyl]-[1,4]diazepan-5-one | (+/−) 3-Hydroxy-pyrollidine | 440.2 |
| 72 | 1-[(E)-3-(3,4-Dichloro-phenyl)-acryloyl]-4-[3-(4-trifluoromethyl-piperidin-1-yl)-propyl]-[1,4]diazepan-5-one | 4-Trifluoromethyl-piperidine | 506.2 |
| 73 | 1-[(E)-3-(3,4-Dichloro-phenyl)-acryloyl]-4-[3-(4-methanesulfonyl-piperazin-1-yl)-propyl]-[1,4]diazepan-5-one | 1-Methanesulfonyl-piperazine | 517.2 |
| 74 | 1-[(E)-3-(3,4-Dichloro-phenyl)-acryloyl]-4-[3-(4-fluoro-piperidin-1-yl)-propyl]-[1,4]diazepan-5-one | 4-Fluoro-piperidine | 456.2 |
| 75 | 1-[(E)-3-(3,4-Dichloro-phenyl)-acryloyl]-4-[3-(4-methyl-piperazin-1-yl)-propyl]-[1,4]diazepan-5-one | 1-Methyl-piperazine | 517.2 |
| 76 | 4-[3-(4-Methyl-4-hydroxy-piperidin-1-yl)-propyl]-1-[(E)-3-(3,4-dichloro-phenyl)-acryloyl]-[1,4]diazepan-5-one | 4-Methyl-piperidin-4-ol | 456.2 |
| 77 | 4-(3-{4-[(E)-3-(3,4-Dichloro-phenyl)-acryloyl]-7-oxo-[1,4]diazepan-1-yl}-propylamino)-cyclohexanecarboxylic acid amide | Piperidine-4-carboxylic acid amide | 481.2 |
| 78 | 1-[(E)-3-(3,4-Dichloro-phenyl)-acryloyl]-4-{3-[methyl-(tetrahydro-pyran-4-yl)-amino]-propyl}-[1,4]diazepan-5-one | Methyl-(tetrahydro-pyran-4-yl)-amine | 468.2 |
| 79 | 1-[(E)-3-(3,4-Dichloro-phenyl)-acryloyl]-4-[3-(4-methoxy-piperidin-1-yl)-propyl]-[1,4]diazepan-5-one | 4-Methoxy-piperidine | 468.3 |
| 80 | (+/−)-1-[(E)-3-(3,4-Dichloro-phenyl)-acryloyl]-4-[3-(3-methoxy-piperidin-1-yl)-propyl]-[1,4]diazepan-5-one | 3-Methoxy-piperidine | 468.1 |
| 81 | (+/−)-1-[(E)-3-(3,4-Dichloro-phenyl)-acryloyl]-4-[3-(3-hydroxy-piperidin-1-yl)-propyl]-[1,4]diazepan-5-one | (+/−) 3-Hydroxy-piperidine | 454 |
| 82 | [1-(3-{4-[(E)-3-(3,4-Dichloro-phenyl)-acryloyl]-7-oxo-[1,4]diazepan-1-yl}-propyl)-piperidin-4-yl]-carbamic acid ethyl ester | Ethyl piperidin-4-yl carbamate | 525.1 |
| 83 | N-[1-(3-{4-[(E)-3-(3,4-Dichloro-phenyl)-acryloyl]-7-oxo-[1,4]diazepan-1-yl}-propyl)-piperidin-4-yl]-acetamide | N-Piperidin-4-yl-acetamide | 495.1 |
| 84 | 8-(3-{4-[(E)-3-(3,4-Dichloro-phenyl)-acryloyl]-7-oxo-[1,4]diazepan-1-yl}-propyl)-1-oxa-3,8-diaza-spiro[4.5]decan-2-one | Oxa-3,8-diaza-spiro[4.5]decan-2-one (intermediate 14) | 509.3 |
| 85 | 1-[(E)-3-(3,4-Dichloro-phenyl)-acryloyl]-4-[3-(4-hydroxy-4-oxazol-2-yl-piperidin-1-yl)-propyl]-[1,4]diazepan-5-one | 4-Oxazol-2-yl-piperidin-4-ol hydrochloride (intermediate 15) | 521.0 |
| 86 | 1-(3-{4-[(E)-3-(3,4-Dichloro-phenyl)-acryloyl]-7-oxo-[1,4]diazepan-1-yl}-propyl)-piperidine-4-carboxylic acid methylamide | Piperidine-4-carboxylic acid methylamide | 495.0 |
| 87 | 8-(3-{4-[(E)-3-(3,4-Dichloro-phenyl)-acryloyl]-7-oxo-[1,4]diazepan-1-yl}-propyl)-2,8-diaza-spiro[4.5]decane-1,3-dione | 2,8-Diaza-spiro[4.5]decane-1,3-dione (intermediate 17) | 521.1 |

TABLE 3-continued

| Example No. | Compound Name | Amine | MS: (MH+) |
|---|---|---|---|
| 88 | 8-(3-{4-[(E)-3-(3,4-Dichloro-phenyl)-acryloyl]-7-oxo-[1,4]diazepan-1-yl}-propyl)-2,8-diaza-spiro[4.5]decan-3-one | 2,8-Diaza-spiro[4.5]decan-3-one (intermediate 18) | 507.4 |
| 89 | 8-(3-{4-[(E)-3-(3,4-Dichloro-phenyl)-acryloyl]-7-oxo-[1,4]diazepan-1-yl}-propyl)-1,3,8-triaza-spiro[4.5]decan-4-one | 1,3,8-Triaza-spiro[4.5]decan-4-one (intermediate 9) | 508.2 |
| 90 | 1-(3-{4-[3-(3,4-Dichloro-phenyl)-acryloyl]-7-oxo-[1,4]diazepan-1-yl}-propyl)-4-hydroxy-piperidine-4-carboxylic acid amide | 4-Hydroxy-piperidine-4-carboxylic acid amide (intermediate 19) | 497.2 |
| 91 | (R)-1-[(E)-3-(3,4-Dichloro-phenyl)-acryloyl]-4-[3-(3-hydroxy-piperidin-1-yl)-propyl]-[1,4]diazepan-5-one | (R)-3-Hydroxypiperidine | 454.2 |
| 92 | (S)-1-[(E)-3-(3,4-Dichloro-phenyl)-acryloyl]-4-[3-(3-hydroxy-piperidin-1-yl)-propyl]-[1,4]diazepan-5-one | (S)-3-Hydroxypiperidine | 454.2 |

Examples 93-151

General Procedure for Examples 93-151

A solution of 3-{4-[(E)-3-(3,4-dichloro-phenyl)-acryloyl]-7-oxo-[1,4]diazepan-1-yl}-acetaldehyde (intermediate 3) (0.036 g, 0.1 mmol) in DCE (0.5 ml) was added to the appropriate amine (0.1 mmol) followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

TABLE 4

| Example No. | Compound Name | Amine | MS: (MH+) |
|---|---|---|---|
| 93 | (S)-1-[(E)-3-(3,4-Dichloro-phenyl)-acryloyl]-4-[3-(2-methoxymethyl-pyrrolidin-1-yl)-ethyl]-[1,4]diazepan-5-one | (S)-2-Methoxymethyl-pyrrolidine | 454.1 |
| 94 | (R)-1-[(E)-3-(3,4-Dichloro-phenyl)-acryloyl]-4-[3-(2-methoxymethyl-pyrrolidin-1-yl)-ethyl]-[1,4]diazepan-5-one | (R)-2-Methoxymethyl-pyrrolidine | 454.1 |
| 95 | (R)-1-[(E)-3-(3,4-Dichloro-phenyl)-acryloyl]-4-[3-(2-hydroxymethyl-pyrrolidin-1-yl)-ethyl]-[1,4]diazepan-5-one | (R)-Prolinol | 440.1 |
| 96 | 1-[(E)-3-(3,4-Dichloro-phenyl)-acryloyl]-4-[3-(4-hydroxy-4-phenyl-piperidin-1-yl)-ethyl]-[1,4]diazepan-5-one | 4-Phenyl-piperidin-4-ol | 516.5 |
| 97 | 1-[(E)-3-(3,4-Dichloro-phenyl)-acryloyl]-4-[2-(4-hydroxymethyl-piperidin-1-yl)-ethyl]-[1,4]diazepan-5-one | 4-Methyl-piperidin-4-ol | 454.4 |
| 98 | 1-[(E)-3-(3,4-Dichloro-phenyl)-acryloyl]-4-[3-(4'-hydroxy-3',4',5',6'-tetrahydro-2'H-[2,4']bipyridinyl-1'-yl)-ethyl]-[1,4]diazepan-5-one | 4-Hydroxy-4-pyrid-2-yl(piperidine) | 517.5 |
| 99 | 1-[(E)-3-(3,4-Dichloro-phenyl)-acryloyl]-4-[3-(4'-hydroxy-3',4',5',6'-tetrahydro-2'H-[3,4']bipyridinyl-1'-yl)-ethyl]-[1,4]diazepan-5-one | 4-Hydroxy-4-pyrid-3-yl(piperidine) | 517.5 |
| 100 | 1-[(E)-3-(3,4-Dichloro-phenyl)-acryloyl]-4-[3-(4-hydroxy-3,4,5,6-tetrahydro-2H-[4,4']bipyridinyl-1-yl)-ethyl]-[1,4]diazepan-5-one | 4-Hydroxy-4-pyrid-4-yl(piperidine) | 517.5 |
| 101 | 1-(-3-{4-[(E)-3-(3,4-Dichloro-phenyl)-acryloyl]-7-oxo-[1,4]diazepan-1-yl}-ethyl)-4-phenyl-piperidine-4-carbonitrile | 4-Phenyl-piperidine-4-carbonitrile | 525.5 |
| 102 | (+/−)-1-[(E)-3-(3,4-Dichloro-phenyl)-acryloyl]-4-[3-(2-methyl-piperidin-1-yl)-ethyl]-[1,4]diazepan-5-one | (+/−)-2-Methylpiperidine | 438.4 |
| 103 | 1-[(E)-3-(3,4-Dichloro-phenyl)-acryloyl]-4-[3-(tetrahydro-pyran-4-ylamino)-ethyl]-[1,4]diazepan-5-one | Tetrahydro-pyran-4-ylamine | 440.4 |

TABLE 4-continued

| Example No. | Compound Name | Amine | MS: (MH+) |
|---|---|---|---|
| 104 | cis/trans-1-[(E)-3-(3,4-Dichloro-phenyl)-acryloyl]-4-[3-(2-methyl-cyclohexylamino)-ethyl]-[1,4]diazepan-5-one | cis/trans-2-Methylcyclohexylamine | 452.4 |
| 105 | trans-1-[(E)-3-(3,4-Dichloro-phenyl)-acryloyl]-4-[3-(4-hydroxy-4-pyridin-2-yl-cyclohexylamino)-ethyl]-[1,4]diazepan-5-one | trans-4-Amino-1-pyridin-2-yl-cyclohexanol (intermediate 13) | 531.5 |
| 106 | trans-1-[(E)-3-(3,4-Dichloro-phenyl)-acryloyl]-4-[2-(4-hydroxy-cyclohexylamino)-ethyl]-[1,4]diazepan-5-one | trans-4-Amino-cyclohexanol | 454.4 |
| 107 | 4-[3-(4-Cyclopropanecarbonyl-piperazin-1-yl)-ethyl]-1-[(E)-3-(3,4-dichloro-phenyl)-acryloyl]-[1,4]diazepan-5-one | Cyclopropyl-piperazin-1-yl-methanone | 493.2 |
| 108 | 4-[3-(Cyclopentyl-amino)-ethyl]-1-[(E)-3-(3,4-dichloro-phenyl)-acryloyl]-[1,4]diazepan-5-one | Cyclopentylamine | 424.2 |
| 109 | 4-[-3-(Cyclopentyl-methyl-amino)-ethyl]-1-[(E)-3-(3,4-dichloro-phenyl)-acryloyl]-[1,4]diazepan-5-one | Cyclopentyl-methyl-amine | 438.1 |
| 110 | (+/−)-4-[3-(Bicyclo[2.2.1]hept-2-ylamino)ethyl]-1-[(E)-3-(3,4-dichloro-phenyl)-acryloyl]-[1,4]diazepan-5-one | (+/−)-endo-2-Norbonylamine hydrochloride | 450.2 |
| 111 | 4-[3-(Cyclohexy-methyl-amino)-ethyl]-1-[(E)-3-(3,4-dichloro-phenyl)-acryloyl]-[1,4]diazepan-5-one | Cylcohexyl-methyl-amine | 452.1 |
| 112 | 1-[(E)-3-(3,4-Dichloro-phenyl)-acryloyl]-4-[3-(1,1-dioxo-thiomorpholin-4-yl)-ethyl]-[1,4]diazepan-5-one | Thiomorpholine-1,1-dioxide | 474.0 |
| 113 | 1-[(E)-3-(3,4-Dichloro-phenyl)-acryloyl]-4-{3-[(2-methoxy-ethyl)-methyl-amino]-ethyl}-[1,4]diazepan-5-one | (2-Methoxy-ethyl)-methyl-amine | 428.1 |
| 114 | 1-[(E)-3-(3,4-Dichloro-phenyl)-acryloyl]-4-{3-[(2-hydroxy-ethyl)-methyl-amino]-ethyl}-[1,4]diazepan-5-one | (2-Hydroxy-ethyl)-methyl-amine | 414.1 |
| 115 | 4-{3-[Bis-(2-hydroxy-ethyl)-amino]-ethyl}-1-[(E)-3-(3,4-dichloro-phenyl)-acryloyl]-[1,4]diazepan-5-one | 2-(2-Hydroxy-ethylamino)-ethanol | 444.2 |
| 116 | (+/−)-N-[1-((E)-3-{4-[3-(3,4-Dichloro-phenyl)-acryloyl]-7-oxo-[1,4]diazepan-1-yl}-ethyl)-pyrrolidin-3-yl]-acetamide | (+/−)N-Pyrrolidin-3-yl-acetamide | 467.2 |
| 117 | (S)-1-[(E)-3-(3,4-Dichloro-phenyl)-acryloyl]-4-[3-(2-hydroxymethyl-pyrrolidin-1-yl)-ethyl]-[1,4]diazepan-5-one | (S)-Prolinol | 440.1 |
| 118 | 8-(3-{4-[(E)-3-(3,4-Dichloro-phenyl)-acryloyl]-7-oxo-[1,4]diazepan-1-yl}-ethyl)-1,3,8-triaza-spiro[4.5]decane-2,4-dione | 1,3,8-Triaza-spiro[4.5]decane-2,4-dione (intermediate 11) | 508.2 |
| 119 | 4-[(E)-3-(4-Benzyl-4-hydroxy-piperidin-1-yl)-ethyl]-1-[(E)-3-(3,4-dichloro-phenyl)-acryloyl]-[1,4]diazepan-5-one | 4-Benzyl-piperidin-4-ol | 530.1 |
| 120 | 1-[(E)-3-(3,4-Dichloro-phenyl)-acryloyl]-4-[3-(4-methyl-piperidin-1-yl)-ethyl]-[1,4]diazepan-5-one | 4-Methyl-piperidine | 438.2 |
| 121 | 1-[(E)-3-(3,4-Dichloro-phenyl)-acryloyl]-4-(3-thiomorpholin-4-yl-ethyl)-[1,4]diazepan-5-one | Thiomorpholine | 442.1 |
| 122 | 1-[(E)-3-(3,4-Dichloro-phenyl)-acryloyl]-4-(2-morpholin-4-yl-ethyl)-[1,4]diazepan-5-one | Morpholine | 426.1 |
| 123 | (+/−)-1-[(E)-3-(3,4-Dichloro-phenyl)-acryloyl]-4-[3-([1,4]dioxan-2-ylmethyl-methyl-amino)-ethyl]-[1,4]diazepan-5-one | (1,4)-Dioxan-2-yl-methylamine | 470.1 |
| 124 | cis/trans-1-[(E)-3-(3,4-Dichloro-phenyl)-acryloyl]-4-{3-[methyl-(4-methyl-cyclohexyl)-amino]-ethyl}-[1,4]diazepan-5-one | cis/trans-Methyl-(4-methyl-cyclohexyl)-amine | 466.3 |
| 125 | 1-[(E)-3-(3,4-Dichloro-phenyl)-acryloyl]-4-[3-(4,4-difluoro-piperidin-1-yl)-ethyl]-[1,4]diazepan-5-one | 4,4-Difluororpiperidine | 460.1 |

TABLE 4-continued

| Example No. | Compound Name | Amine | MS: (MH+) |
|---|---|---|---|
| 126 | 1-[(E)-3-(3,4-Dichloro-phenyl)-acryloyl]-4-{3-[4-(2-oxo-imidazolidin-1-yl)-piperidin-1-yl]-ethyl}-[1,4]diazepan-5-one | Piperidin-4-yl-imidazolidin-2-one (intermediate 7) | 508.1 |
| 127 | 1-[(E)-3-(3,4-Dichloro-phenyl)-acryloyl]-4-{3-[4-(1H-pyrazol-3-yl)-piperidin-1-yl]-ethyl}-[1,4]diazepan-5-one | 4-(1H-Pyrazol-3-yl)-piperidine (intermediate 12) | 490.2 |
| 128 | 4-(3-{4-[(E)-3-(3,4-Dichloro-phenyl)-acryloyl]-7-oxo-[1,4]diazepan-1-yl}-ethylamino)-cyclohexanecarboxylic acid ethyl ester | Piperidine-4-carboxylic acid ethyl ester | 496.2 |
| 129 | 1-[(E)-3-(3,4-Dichloro-phenyl)-acryloyl]-4-[3-(4-trifluoromethyl-piperidin-1-yl)-ethyl]-[1,4]diazepan-5-one | 4-Trifluoromethyl-piperidine | 492.1 |
| 130 | 1-[(E)-3-(3,4-Dichloro-phenyl)-acryloyl]-4-[3-(4-fluoro-piperidin-1-yl)-ethyl]-[1,4]diazepan-5-one | 4-Fluoro-piperidine | 442.1 |
| 131 | 1-[(E)-3-(3,4-Dichloro-phenyl)-acryloyl]-4-[2-(4-methyl-piperazin-1-yl)-ethyl]-[1,4]diazepan-5-one | 1-Methyl-piperazine | 439.2 |
| 132 | 4-[3-(4-Methyl-4-hydroxy-piperidin-1-yl)-ethyl]-1-[(E)-3-(3,4-dichloro-phenyl)-acryloyl]-[1,4]diazepan-5-one | 4-Methyl-piperidin-4-ol | 454.1 |
| 133 | 4-(3-{4-[(E)-3-(3,4-Dichloro-phenyl)-acryloyl]-7-oxo-[1,4]diazepan-1-yl}-ethylamino)-cyclohexanecarboxylic acid amide | Piperidine-4-carboxylic acid amide | 467.1 |
| 134 | 1-[(E)-3-(3,4-Dichloro-phenyl)-acryloyl]-4-{3-[methyl-(tetrahydro-pyran-4-yl)-amino]-ethyl}-[1,4]diazepan-5-one | Methyl-(tetrahydro-pyran-4-yl)-amine | 454.2 |
| 135 | 1-[(E)-3-(3,4-Dichloro-phenyl)-acryloyl]-4-{3-[(3-hydroxy-propyl)-amino]-ethyl}-[1,4]diazepan-5-one | 3-Amino-propan-1-ol | 414.1 |
| 136 | 1-[(E)-3-(3,4-Dichloro-phenyl)-acryloyl]-4-[2-(1-isopropyl-piperidin-4-ylamino)-ethyl]-[1,4]diazepan-5-one | 1-Isopropyl-piperidin-4-ylamine | 481.2 |
| 137 | 1-[(E)-3-(3,4-Dichloro-phenyl)-acryloyl]-4-[2-(1-methyl-piperidin-4-ylamino)-ethyl]-[1,4]diazepan-5-one | 1-Methyl-piperidin-4-ylamine | 453 |
| 138 | cis/trans-1-[(E)-3-(3,4-Dichloro-phenyl)-acryloyl]-4-{3-[(4-methyl-cyclohexyl)-amino]-ethyl}-[1,4]diazepan-5-one | Cis/trans-4-Methyl-cyclohexylamine | 452.1 |
| 139 | 1-[(E)-3-(3,4-Dichloro-phenyl)-acryloyl]-4-[3-(4-hydroxy-piperidin-1-yl)-ethyl]-[1,4]diazepan-5-one | Piperidin-4-ol | 440.1 |
| 140 | (+/−)-cis-1-[(E)-3-(3,4-Dichloro-phenyl)-acryloyl]-4-{2-[(3-methoxy-tetrahydro-pyran-4-yl)-amino]-ethyl}-[1,4]diazepan-5-one | (+/−)-cis-(3-Methoxy-tetrahydro-pyran-4-yl)-amine (intermediate 20) | 470.1 |
| 141 | 1-[(E)-3-(3,4-Dichloro-phenyl)-acryloyl]-4-[2-((R)-3-hydroxy-piperidin-1-yl)-ethyl]-[1,4]diazepan-5-one | (R)-3-Hydroxypiperidine | 440.2 |
| 142 | 1-[(E)-3-(3,4-Dichloro-phenyl)-acryloyl]-4-[2-((S)-3-hydroxy-piperidin-1-yl)-ethyl]-[1,4]diazepan-5-one | (S)-3-Hydroxypiperidine | 440.2 |
| 143 | 1-[(E)-3-(3,4-Dichloro-phenyl)-acryloyl]-4-[2-((R)-3-hydroxy-pyrrolidin-1-yl)-ethyl]-[1,4]diazepan-5-one | (R)-3-hydroxy-pyrrolidine | 426.1 |
| 144 | 1-[(E)-3-(3,4-Dichloro-phenyl)-acryloyl]-4-[2-((S)-3-hydroxy-pyrrolidin-1-yl)-ethyl]-[1,4]diazepan-5-one | (S)-3-hydroxy-pyrrolidine | 426.1 |
| 145 | (S)-1-(2-{4-[(E)-3-(3,4-Dichloro-phenyl)-acryloyl]-7-oxo-[1,4]diazepan-1-yl}-ethyl)-pyrrolidine-2-carboxylic acid methylamide | (S)-pyrrolidine-2-carboxylic acid methylamide | 467.2 |
| 146 | (S)-1-(2-{4-[(E)-3-(3,4-Dichloro-phenyl)-acryloyl]-7-oxo-[1,4]diazepan-1-yl}-ethyl)-pyrrolidine-2-carboxylic acid amide | (S)-pyrrolidine-2-carboxylic acid amide | 453.1 |
| 147 | 1-[(E)-3-(3,4-Dichloro-phenyl)-acryloyl]-4-[2-((S)-3-ethoxy-pyrrolidin-1-yl)-ethyl]-[1,4]diazepan-5-one | (S)-3-ethoxy-pyrrolidine | 454.2 |

TABLE 4-continued

| Example No. | Compound Name | Amine | MS: (MH+) |
|---|---|---|---|
| 148 | 1-[(E)-3-(3,4-Dichloro-phenyl)-acryloyl]-4-[2-((2S,4R)-4-hydroxy-2-hydroxymethyl-pyrrolidin-1-yl)-ethyl]-[1,4]diazepan-5-one | (2S,4R)-4-hydroxy-2-hydroxymethyl-pyrrolidine (intermediate 21) | 456.1 |
| 149 | 1-[(E)-3-(3,4-Dichloro-phenyl)-acryloyl]-4-[2-((2S,4S)-4-hydroxy-2-hydroxymethyl-pyrrolidin-1-yl)-ethyl]-[1,4]diazepan-5-one | (2S,4S)-4-hydroxy-2-hydroxymethyl-pyrrolidine (intermediate 22) | 456.1 |
| 150 | 1-[(E)-3-(3,4-Dichloro-phenyl)-acryloyl]-4-[2-((2R,3S)-3-hydroxy-2-hydroxymethyl-pyrrolidin-1-yl)-ethyl]-[1,4]diazepan-5-one | (2R,3S)-3-hydroxy-2-hydroxymethyl-pyrrolidine | 456.1 |
| 151 | (2S,3S)-1-(2-{4-[(E)-3-(3,4-Dichloro-phenyl)-acryloyl]-7-oxo-[1,4]diazepan-1-yl}-ethyl)-3-hydroxy-pyrrolidine-2-carboxylic acid methyl ester | (2S,3S)-3-hydroxy-pyrrolidine-2-carboxylic acid methyl ester | 484.1 |

Example 152

(+/−)-cis-1-[(E)-3-(3,4-Dichloro-phenyl)-acryloyl]-4-{2-[(3-methoxy-tetrahydro-pyran-4-yl)-methyl-amino]-ethyl}-[1,4]diazepan-5-one To the crude reaction mixture from (+/−)-cis-1-[(E)-3-(3,4-dichloro-phenyl)-acryloyl]-4-{2-[(3-methoxy-tetrahydro-pyran-4-yl)-amino]-ethyl}-[1,4]diazepan-5-one (example 140) was added 2 drops of 36% aqueous formaldehyde solution and the mixture shaken for 1 h. The reaction was then concentrated and the residue purified by flash column chromatography ($CH_2Cl_2$:MeOH 1:0-8:2) affording the titled product (21 mg, 44%) as a colourless solid. MS: 484.1 (MH+, 2Cl).

Example 153

8-(3-{4-[(E)-3-(3,4-Dichloro-phenyl)-acryloyl]-7-oxo-[1,4]diazepan-1-yl}-propyl)-8-methyl-2,4-dioxo-1,3-diaza-8-azonia-spiro[4.5]decane iodide To a solution of 8-(3-{4-[(E)-3-(3,4-Dichloro-phenyl)-acryloyl]-7-oxo-[1,4]diazepan-1-yl}-propyl)-1,3,8-triaza-spiro[4.5]decane-2,4-dione (example 48) (10 mg, 19 umol) in MeOH (0.5 ml) was added iodomethane (10 uL, 95 umol) and the reaction left for 2 days at room temperature. Concentration of the mixture affording the title product (13 mg, 98%) as a white solid. MS: 536.1 (M+, 2Cl).

Example 154

1-(3-{4-[3-(3,4-Dichloro-phenyl)-acryloyl]-7-oxo-[1,4]diazepan-1-yl}-propyl)-1-methyl-piperidinium iodide To a solution of 1-[(E)-3-(3,4-Dichloro-phenyl)-acryloyl]-4-(3-piperidin-1-yl-propyl)-[1,4]diazepan-5-one (example 4) (27 mg, 62 umol) in MeOH (0.5 ml) was added iodomethane (40 uL, 620 umol) and the reaction left for overnight at room temperature. Concentration of the mixture affording the title product (35 mg, 98%) as a white solid. MS: 452.2 (M+, 2Cl).

Example 155

1-[(E)-3-(3,4-Dichloro-phenyl)-acryloyl]-4-(4-morpholin-4-yl-butyl)-[1,4]diazepan-5-one 1-[(E)-3-(3,4-Dichloro-phenyl)-acryloyl]-4-(4-morpholin-4-yl-butyl)-[1,4]diazepan-5-one In analogy to the procedure described in example 5D, 1-[(E)-3-(3,4-dichloro-phenyl)-acryloyl]-4-(4-iodo-butyl)-[1,4]diazepan-5-one (example 9C) and morpholine (10 eq, with no additional sodium iodide) gave the title compound as light yellow oil. MS: 454.2 (MH+, 2Cl).

Example 156

1-[(E)-(3-Phenyl-acryloyl)]-4-(3-piperidin-1-yl-propyl)-[1,4]diazepan-5-one

1-[(E)-(3-Phenyl-acryloyl)]-4-(3-piperidin-1-yl-propyl)-[1,4]diazepan-5-one

In analogy to the procedure described in example 11A, 4-(3-piperidin-1-yl-propyl)-[1,4]diazepan-5-one-dihydrochloride (intermediate 4B) and (E)-cinnamic acid gave the title compound as off-white solid. MS: 370.2 (MH+).

Example 157

1-((E)-3-Naphthalen-2-yl-acryloyl)-4-(3-piperidin-1-yl-propyl)-[1,4]diazepan-5-one 1-((E)-3-Naphthalen-2-yl-acryloyl)-4-(3-piperidin-1-yl-propyl)-[1,4]diazepan-5-one In analogy to the procedure described in example 11A, 4-(3-piperidin-1-yl-propyl)-[1,4]diazepan-5-one-dihydrochloride (intermediate 4B) and 2-naphthylacrylic acid gave the title compound as white solid. MS: 420.2 (MH+)

Example 158

4-(1-Benzyl-piperidin-4-yl)-1-[(E)-3-(3,4-dichloro-phenyl)-acryloyl]-[1,4]diazepan-5-one {2-[Acryloyl-(1-benzyl-piperidin-4-yl)-amino]-ethyl}-carbamic acid tert-butyl ester To a solution of benzylpiperidone (5 g, 26 mmol) and (2-amino-ethyl)-carbamic acid tert-butyl ester (4.23 g, 26 mmol) and acetic acid (2.5 ml, 53 mmol) in $CH_2Cl_2$ (50.0 ml) was slowly added $NaBH(OAc)_3$ (6.69 g, 32 mmol). On completion of the addition the reaction was stirred for 0.5 h. Saturated $NaHCO_3$ (30 ml) was then cautiously added until the pH was basic. A solution of acroyl chloride (2.3 ml, 29 mmol) in $CH_2Cl_2$ (10.0 ml) was then added and the reaction stirred for a further 1 h. The organic layer was then separated, dried ($Na_2SO_4$) and concentrated. The product was isolated by flash column chromatography (EtOAc) to afford the title compound as a light yellow foam (6 g, 58%). MS: 388.2 (MH$^+$).

4-(1-Benzyl-piperidin-4-yl)-5-oxo-[1,4]diazepane-1-carboxylic acid tert-butyl ester To a solution of {2-[Acryloyl-(1-benzyl-piperidin-4-yl)-amino]-ethyl}-carbamic acid tert-butyl ester (4.6 g, 12 mmol) in DMF (40 ml) was added potassium tert-butoxide (0.1 g, 1 mmol) and the reaction stirred for 2 h after which time it was concentrated, the residue dissolved in $CH_2Cl_2$, washed with saturated $NaHCO_3$, dried ($Na_2SO_4$), and concentrated. The product was isolated by flash column chromatography ($CH_2Cl_2$:MeOH 9:1) to afford the title compound (3.5 g, 75%) as a white solid. MS: 388.3 (MH$^+$)

4-(1-Benzyl-piperidin-4-yl)-1-[(E)-3-(3,4-dichloro-phenyl)-acryloyl]-[1,4]diazepan-5-one 4-(1-Benzyl-piperidin-4-yl)-5-oxo-[1,4]diazepane-1-carboxylic acid tert-butyl ester (1.5 g, 4 mmol) was dissolved in trifluoroacetic acid (10 ml) and the reaction stirred for 1 h. The reaction was concentrated to dryness, portioned between $CH_2Cl_2$ (20 ml) and saturated $NaHCO_3$ (20 ml) and a solution of (E)-3-(3,4-dichloro-phenyl)-acryloyl chloride (prepared by Vilsmeier-Heck reaction on the acid) (0.9 g, 4 mmol) in $CH_2Cl_2$ (10 ml) was added dropwise. The reaction was stirred for 0.5 h after which time the organic was collected, dried ($Na_2SO_4$), and concentrated to afford the title compound (1.8 g, 92%) as a white solid. MS: 486.9 (MH$^+$, 2Cl).

Example 159

1-[(E)-3-(3,4-Dichloro-phenyl)-acryloyl]-4-[3-(4-hydroxy-piperidin-1-yl)-propyl]-[1,4]diazepan-5-one In analogy to examples 35-91, 3-{4-[(E)-3-(3,4-dichloro-phenyl)-acryloyl]-7-oxo-[1,4]diazepan-1-yl}-propionaldehyde (intermediate 2) was reacted with piperidine-4-ol to afford the title product as a white solid. MS: 454.4 (MH$^+$, 2Cl).

Example 160

1-[(E)-3-(3,4-Dichloro-phenyl)-acryloyl]-4-(2-pyrrolidin-1-yl-ethyl)-[1,4]diazepan-5-one In analogy to examples 14-26, 4-(2-pyrrolidin-1-yl-ethyl)-[1,4]diazepan-5-one-dihydrochoride (intermediate 5) was reacted with 3,4-dichlorocinammic acid to afford the title compound as a white solid. MS: 410.3 (MH$^+$, 2Cl).

Example 161

1-[(E)-3-(3,4-Dichloro-phenyl)-acryloyl]-4-[4-(3-hydroxy-piperidin-1-yl)-butyl]-[1,4]diazepan-5-one (rac)-1-[(E)-3-(3,4-Dichloro-phenyl)-acryloyl]-4-[4-(3-hydroxy-piperidin-1-yl)-butyl]-[1,4]diazepan-5-one In analogy to the procedure described in example 5D, 1-[(E)-3-(3,4-dichloro-phenyl)-acryloyl]-4-(3-iodo-propyl)-[1,4]diazepan-5-one and (rac)-3-hydroxy-piperidine (10 equivalents, with no additional sodium iodide) gave after purification on a flash isolute $NH_2$-column (n-heptane/EtOAc 1:4 to 1:9 and EtOAc) the title compound as a light yellow oil. MS: 468.1 (MH$^+$, 2Cl).

Example 162

1-[(E)-3-(3,4-Dichloro-phenyl)-acryloyl]-4-(5-piperidin-1-yl-pentyl)-[1,4]diazepan-5-one 4-(5-Chloro-pentyl)-1-[(E)-3-(3,4-dichloro-phenyl)-acryloyl]-[1,4]diazepan-5-one In analogy to the procedure described in example 5A, 1-[(E)-3-(3,4-dichloro-phenyl)-acryloyl]-[1,4]diazepan-5-one (intermediate 1A]) and 1-chloro-5-iodopentane gave the title compound as yellow oil. MS: 416.9 (MH$^+$, 3Cl).

1-[(E)-3-(3,4-Dichloro-phenyl)-acryloyl]-4-(5-iodo-pentyl)-[1,4]diazepan-5-one

In analogy to the procedure described in example 6D, 4-(5-chloro-pentyl)-1-[(E)-3-(3,4-dichloro-phenyl)-acryloyl]-[1,4]diazepan-5-one and sodium iodide were stirred at 90° C. for 20 h to give the title compound as orange oil. MS: 509.2 (MH$^+$, 2Cl).

1-[(E)-3-(3,4-Dichloro-phenyl)-acryloyl]-4-(5-piperidin-1-yl-pentyl)-[1,4]diazepan-5-one In analogy to the procedure described in example 5D, 1-[(E)-3-(3,4-dichloro-phenyl)-acryloyl]-4-(5-iodo-pentyl)-[1,4]diazepan-5-one and piperidine (10 equivalents, with no additional sodium iodide) gave the title compound as yellow oil. MS: 466.2 (MH$^+$, 2Cl).

Example 163

1-[(E)-3-(3,4-Dichloro-phenyl)-acryloyl]-4-[4-((3RS,4SR)-3,4-dihydroxy-piperidin-1-yl)-butyl]-[1,4]diazepan-5-one hydrochlorid 4-{4-[(3RS,4SR)-3,4-Bis-(tert-butyl-dimethyl-silanyloxy)-piperidin-1-yl]-butyl}-1-[(E)-3-(3,4-dichloro-phenyl)-acryloyl]-[1,4]diazepan-5-one A solution of 0.279 g (0.56 mmol) of 1-[(E)-3-(3,4-dichloro-phenyl)-acryloyl]-4-(4-iodo-butyl)-[1,4]diazepan-5-one (example 9B) in 2 ml of DMA was treated with 0.195 ml (0.56 mmol) of (cis)-(rac)-3,4-Bis-(tert-butyl-dimethyl-silanyloxy)-piperidine (intermediate 25) and 0.184 g (0.56 mmol) of cesium carbonate. After 2.25 h at RT, CH$_2$Cl$_2$ was added, filtrated and evaporated. Purification by catridges, Si-Amine, 50 g, (EtOAc/n-heptane 4:1) gave 0.300 g (75%) of the title compound as light brown foam. MS: 712.6 (MH$^+$, 2Cl).

1-[(E)-3-(3,4-Dichloro-phenyl)-acryloyl]-4-[4-((3RS,4SR)-3,4-dihydroxy-piperidin-1-yl)-butyl]-[1,4]diazepan-5-one hydrochlorid A solution of 0.100 g (0.14 mmol) of 4-{4-[(3RS,4SR)-3,4-bis-(tert-butyl-dimethyl-silanyloxy)-piperidin-1-yl]-butyl}-1-[(E)-3-(3,4-dichloro-phenyl)-acryloyl]-[1,4]diazepan-5-one in 2 mL of MeOH was cooled (0° C.), treated with 0.35 ml (1.40 mmol) of 4M HCl in dioxane and stirred at RT for 2 h. The solution was evaporated, dissolved in toluene and evaporated (2×) to yield 0.053 g (73%) of the title compound as light brown foam. MS: 484.2 (MH$^+$, 2Cl).

Example 164

1-[(E)-3-(3,4-Dichloro-phenyl)-acryloyl]-4-[4-((3RS,4RS)-3,4-dihydroxy-piperidin-1-yl)-butyl]-[1,4]diazepan-5-one hydrochloride 4-{4-[(3RS,4RS)-3,4-Bis-(tert-butyl-dimethyl-silanyloxy)-piperidin-1-yl]-butyl}-1-[(E)-3-(3,4-dichloro-phenyl)-acryloyl]-[1,4]diazepan-5-one In analogy to the procedure described in example 163A, 1-[(E)-3-(3,4-dichloro-phenyl)-acryloyl]-4-(4-iodo-butyl)-[1,4]diazepan-5-one (example 9B) and (trans)-(rac)-3,4-Bis-(tert-butyl-dimethyl-silanyloxy)-piperidine (intermediate 26) gave the title compound as colorless oil.
MS: 712.5 (MH$^+$, 2Cl).

1-[(E)-3-(3,4-Dichloro-phenyl)-acryloyl]-4-[4-((3RS,4RS)-3,4-dihydroxy-piperidin-1-yl)-butyl]-[1,4]diazepan-5-one hydrochloride In analogy to the procedure described in example 163B, 4-{4-[(3RS,4RS)-3,4-bis-(tert-butyl-dimethyl-silanyloxy)-piperidin-1-yl]-butyl}-1-[(E)-3-(3,4-dichloro-phenyl)-acryloyl]-[1,4]diazepan-5-one gave the title compound as off-white solid. MS: 484.4 (MH$^+$, 2Cl).

Example 165

1-[(E)-3-(3,4-Dichloro-phenyl)-acryloyl]-4-[4-((3RS,4RS)-3,4-dihydroxy-piperidin-1-yl)-butyl]-[1,4]diazepan-5-one 1-[(E)-3-(3,4-Dichloro-phenyl)-acryloyl]-4-[4-((3RS,4RS)-3,4-dihydroxy-piperidin-1-yl)-butyl]-[1,4]diazepan-5-one A solution of 0.025 g (0.05 mmol) 1-[(E)-3-(3,4-dichloro-phenyl)-acryloyl]-4-[4-((3RS,4RS)-3,4-dihydroxy-piperidin-1-yl)-butyl]-[1,4]diazepan-5-one was dissolved in EtOAc and washed with aqueous saturated NaHCO$_3$. The water phase was extracted with EtOAc(2×), the organic phases washed with aqueous saturated NaHCO$_3$, dried over Na$_2$SO$_4$ and evaporated to give 0.017 g (73%) of the title compound as colorless foam. MS: 484.2 (MH$^+$, 2Cl).

Example 166

(rac)-1-[(E)-3-(3,4-Dichloro-phenyl)-acryloyl]-4-(2-hydroxy-3-piperidin-1-yl-propyl)-[1,4]diazepan-5-one (rac)-1-[(E)-3-(3,4-Dichloro-phenyl)-acryloyl]-4-oxiranylmethyl-1,41diazepan-5-one A solution of 1.50 g (4.79 mmol) of 1-[(E)-3-(3,4-dichloro-phenyl)-acryloyl]-[1,4]diazepan-5-one (intermediate 1A) in 30 ml of DMF, with 0.29 g (6.71 mmol) of NaH (55% in oil) was stirred for 30 min at 0° C. and then treated slowly with 0.47 ml (5.75 mmol) of 2-bromomethyl-oxirane in 15 ml DMF. After 3.5 h at 0° C., the reaction was extracted with aqueous saturated NaHCO$_3$/EtOAc (3×). The organic phases were washed with aqueous saturated NaHCO$_3$, dried over Na$_2$SO$_4$ and evaporated to yield 2.79 g (quantitative) of the crude title compound as off-white semisolid, which was used directly in the next steps. MS: 368.9 (MH$^+$, 2Cl).

(rac)-1-[(E)-3-(3,4-Dichloro-phenyl)-acryloyl]-4-(2-hydroxy-3-piperidin-1-yl-propyl)-[1,4]diazepan-5-one A solution of 0.30 g (0.81 mmol) of (rac)-1-[(E)-3-(3,4-dichloro-phenyl)-acryloyl]-4-oxiranylmethyl-[1,4]diazepan-5-one in 0.3 ml of DMA was treated with 0.19 ml (1.22 mmol) of piperidine and 0.265 g (0.81 mmol) of cesium carbonate. The reaction was stirred over night at RT, CH$_2$Cl$_2$ was added, filtrated and evaporated. Crystallization (CH$_2$Cl$_2$/Et$_2$O) gave 0.16 g (43%) of the title compound as pink crystalline solid. MS: 454.2 (MH$^+$, 2Cl).

Example 167

1-[(E)-3-(3,4-Dichloro-phenyl)-acryloyl]-4-((S)-2-hydroxy-3-piperidin-1-yl-propyl)-[1,4]diazepan-5-one 1-[(E)-3-(3,4-Dichloro-phenyl)-acryloyl]-4-((R)-2,2-dimethyl-[1,3]dioxolan-4-ylmethyl)-[1,4]diazepan-5-one A solution of 6.26 g (20.00 mmol) of 1-[(E)-3-(3,4-dichloro-phenyl)-acryloyl]-[1,4]diazepan-5-one (intermediate 1A]) in 200 ml of THF was treated at 0° C. with 2.47 g (22.00 mmol) of potassium tert-butylate and after 10 min with 5.73 (20.00 mmol) of toluene-4-sulfonic acid (S)-2,2-dimethyl-[1,3]dioxolan-4-ylmethyl ester. The reaction was stirred for 14 h at RT, 28 h at reflux temperature, cooled and extracted with aqueous saturated $NaHCO_3$/$Et_2O$ (3×). The organic phases were washed with aqueous saturated $NaHCO_3$, aqueous 10% NaCl, dried over $Na_2SO_4$ evaporated and purified by flash silica gel column ($CH_2Cl_2$/MeOH 97.5/2.5) to yield 4.27 g (50%) of the title compound as off-white powder. MS: 427.1 ($MH^+$, 2Cl).

1-[(E)-3-(3,4-Dichloro-phenyl)-acryloyl]-4-((R)-2,3-dihydroxy-propyl)-[1,4]diazepan-5-one A solution of 4.16 g (9.72 mmol) of 1-[(E)-3-(3,4-dichloro-phenyl)-acryloyl]-4-((R)-2,2-dimethyl-[1,3]dioxolan-4-ylmethyl)-[1,4]diazepan-5-one in 35 ml of methanol and 3.8 ml of water was treated with 1.95 g of Dowex 50WX8 (activated with aqueous 25% HCl and washed neutral wit water). The reaction was stirred for 10 h at reflux temperature, cooled, evaporated, dissolved in $CH_2Cl_2$, dried over $Na_2SO_4$ and evaporated to yield 3.37 g (89%) of the title compound as light yellow foam. MS: 387.1 ($MH^+$, Cl).

1-[(E)-3-(3,4-Dichloro-phenyl)-acryloyl]-4-(R)-1-oxiranylmethyl-[1,4]diazepan-5-one An ice-cooled solution of 0.50 g (1.30 mmol) of 1-[(E)-3-(3,4-dichloro-phenyl)-acryloyl]-4-((R)-2,3-dihydroxy-propyl)-[1,4]diazepan-5-one and 1.72 ml (13.00 mmol) of 2,4,6-trimethyl-pyridine in 5.2 ml of DMF was treated with 0.11 ml (1.36 mmol) of methanesulfonyl chloride in 0.3 mL of DMF. The reaction was stirred 2.5 h at 0° C. and 1 h at RT. After cooling (0° C.), 0.13 g (2.86 mmol) of NaH (55% in oil) was added and the reaction was continued at this temperature for 16 h. The solution was poured on cold aqueous 10% $KH_2PO_4$ and extracted with $Et_2O$ (3×). The organic phases were washed with aqueous 10% $KH_2PO_4$ (2×), aqueous saturated $NaHCO_3$ and aqueous 10% NaCl, dried ($Na_2SO_4$) and concentrated to yield after precipitation ($CH_2Cl_2$/n-pentane) 0.38 g (78%) of the title compound as light yellow powder. MS: 368.9 ($MH^+$, 2Cl).

1-[(E)-3-(3,4-Dichloro-phenyl)-acryloyl]-4-((S)-2-hydroxy-3-piperidin-1-yl-propyl)-[1,4]diazepan-5-one A suspension of 0.10 g (0.27 mmol) of 1-[(E)-3-(3,4-dichloro-phenyl)-acryloyl]-4-(R)-1-oxiranylmethyl-[1,4]diazepan-5-one in 0.27 ml of EtOH was treated at 0° C. with 0.04 ml (0.40 mmol) of piperidine. The reaction was stirred for 20 h at RT, then evaporated, suspended in toluene and evaporated again. Precipitation ($CH_2Cl_2$/$Et_2O$/-n-pentane) gave 0.10 g (84%) of the title compound as off-white powder with 90% ee. MS: 454.1 ($MH^+$, 2Cl). (The enatiomeric purity was determined with a chiralpak-ADH column, 25 cm*4.6 mm, No.DL182 and 30% n-heptane+70% (EtOH+0.01M $NH_4AcOH$) as eluent. The purity corresponds to the purity of toluene-4-sulfonic acid (S)-2,2-dimethyl-[1,3]dioxolan-4-ylmethyl ester).

Example 168

1-[(E)-3-(3,4-Dichloro-phenyl)-acryloyl]-4-((R)-2-hydroxy-3-piperidin-1-yl-propyl)-[1,4]diazepan-5-one 1-[(E)-3-(3,4-Dichloro-phenyl)-acryloyl]-4-((R)-2-hydroxy-3-piperidin-1-yl-propyl)-[1,4]diazepan-5-one 135 mg of (rac)-1-[(E)-3-(3,4-Dichloro-phenyl)-acryloyl]-4-((S)-2-hydroxy-3-piperidin-1-yl-propyl)-[1,4]diazepan-5-one (example 166) were separated with a chiralpak-ADH column, 5 µM, 25 cm*20 mm, Daicel, Cat.-No. 19345 and 25% n-heptane+75% (EtOH/MeOH 25:75 v/v) as eluent. 48.9 mg (36%) of 1-[(E)-3-(3,4-dichloro-phenyl)-acryloyl]-4-((S)-2-hydroxy-3-piperidin-1-yl-propyl)-[1,4]diazepan-5-one (99.4% ee) (example 167D) and 50 mg (37%) of 1-[(E)-3-( 3,4-dichloro-phenyl)-acryloyl]-4-((R)-2-hydroxy-3-piperidin-1-yl-propyl)-[1,4]diazepan-5-one (99.6% ee) was isolated as a white foam. MS: 454.1 ($MH^+$, 2Cl). (The enatiomeric purity was determined with a chiralpak-ADH column, Daicel, Cat.-No. 19325, 25 cm*4.6 mm and 35% n-heptan+65% EtOH as eluent).

Example 169

(rac)-1-[(E)-3-(3,4-Dichloro-phenyl)-acryloyl]-4-[3-(4-fluoro-piperidin-1-yl)-2-hydroxy-propyl]-[1,4]diazepan-5-one (rac)-1-[(E)-3-(3,4-Dichloro-phenyl)-acryloyl]-4-[3-(4-fluoro-piperidin-1-yl)-2-hydroxy-propyl]-[1,4]diazepan-5-one A solution of 0.080 g (0.22 mmol) of (rac)-1-[(E)-3-(3,4-dichloro-phenyl)-acryloyl]-4-oxiranylmethyl-[1,4]diazepan-5-one (example 166A) in 0.5 ml of MeOH was treated with 0.038 (0.26 mmol) of 4-fluoropiperidine hydrochloride and 0.15 ml (1.08 mmol) of $Et_3N$ in 0.5 ml of MeOH. The reaction was stirred for 24 h at RT, partitioned between aqueous saturated $NaHCO_3$ and extracted with $Et_2O$ (3×). The organic phase was dried over $Na_2SO_4$ and evaporated to give after flash silica gel column ($CH_2Cl_2$/MeOH 98:2) 0.0099 g (10%) of the title compound as white foam. MS: 471.9 ($MH^+$, 2Cl).

Example 170

(rac)-1-[(E)-3-(3,4-Dichloro-phenyl)-acryloyl]-4-(3-hydroxy-4-piperidin-1-yl-butyl)-[1,4]diazepan-5-one (rac) 1-[(E)-3-(3,4-Dichloro-phenyl)-acryloyl]-4-(2-oxiranyl-ethyl)-[1,4]diazepan-5-one In analogy to the procedure described for example 166A, 1-[(E)-3-(3,4-dichloro-phenyl)-acryloyl]-[1,4]diazepan-5-one (intermediate 1A) and (rac)-2-(2-bromo-ethyl)-oxirane (Journal of Organic Chemistry (1969), 34(12), 4060-5) gave after extraction with $Et_2O$ instead of EtOAc the title compound as yellow oil. MS: 383.2 ($MH^+$, 2Cl).

(rac) 1-[(E)-3-(3,4-Dichloro-phenyl)-acryloyl]-4-(3-hydroxy-4-piperidin-1-yl-butyl)-[1,4]diazepan-5-one In analogy to the procedure described for example 167D, (rac)-1-[(E)-3-(3,4-dichloro-phenyl)-acryloyl]-4-(2-oxiranyl-ethyl)-[1,4]diazepan-5-one and piperidine gave the title compound as yellow oil. MS: 468.1 (MH⁺, 2Cl).

Example 171

(rac)-1-[(E)-3-(3,4-Dichloro-phenyl)-acryloyl]-4-[3-hydroxy-4-(3-hydroxy-piperidin-1-yl)-butyl]-[1,4]diazepan-5-one (rac)-1-[(E)-3-(3,4-Dichloro-phenyl)-acryloyl]-4-[3-hydroxy-4-(3-hydroxy-piperidin-1-yl)-butyl]-[1,4]diazepan-5-one In analogy to the procedure described for example 167D, (rac)-1-[(E)-3-(3,4-dichloro-phenyl)-acryloyl]-4-(2-oxiranyl-ethyl)-[1,4]diazepan-5-one and 3-hydroxypiperidine gave the title compound as yellow oil. MS: 484.2 (MH⁺, 2Cl).

Example 172

1-[(E)-3-(3,4-Dichloro-phenyl)-acryloyl]-4-((R)-3-hydroxy-4-piperidin-1-yl-butyl)-[1,4]diazepan-5-one 1-[(E)-3-(3,4-Dichloro-phenyl)-acryloyl]-4-[2-((R)-2,2-dimethyl-[1,3]dioxolan-4-yl)-ethyl]-[1,4]diazepan-5-one In analogy to the procedure described for example 167A, 1-[(E)-3-(3,4-dichloro-phenyl)-acryloyl]-[1,4]diazepan-5-one (intermediate 1A]) and methanesulfonic acid 2-((R)-2,2-dimethyl-[1,3]dioxolan-4-yl)-ethyl ester (prepared from 2-((R)-2,2-dimethyl-[1,3]dioxolan-4-yl)-ethanol and methanesulfonyl chloride) gave after reaction at RT, the title compound as an off-white foam. MS: 441.1 (MH⁺, 2Cl).

1-[(E)-3-(3,4-Dichloro-phenyl)-acryloyl]-4-((R)-3,4-dihydroxy-butyl)-[1,4]diazepan-5-one In analogy to the procedure described for example 167B, 1-[(E)-3-(3,4-dichloro-phenyl)-acryloyl]-4-[2-((R)-2,2-dimethyl-[1,3]dioxolan-4-yl)-ethyl]-[1,4]diazepan-5-one gave after 3 h at reflux, the title compound as a white foam. MS: 401.2 (MH⁺, 2Cl).

1-[(E)-3-(3,4-Dichloro-phenyl)-acryloyl]-4-((R)-2-oxiranyl-ethyl)-[1,4]diazepan-5-one In analogy to the procedure described for example 167C, 1-[(E)-3-(3,4-dichloro-phenyl)-acryloyl]-4-((R)-3,4-dihydroxy-butyl)-[1,4]diazepan-5-one gave the title compound as an off-white foam. MS: 383.0 (MH⁺, 2Cl).

1-[(E)-3-(3,4-Dichloro-phenyl)-acryloyl]-4-((R)-3-hydroxy-4-piperidin-1-yl-butyl)-[1,4]diazepan-5-one In analogy to the procedure described for example 167D, 1-[(E)-3-(3,4-dichloro-phenyl)-acryloyl]-4-((R)-2-oxiranyl-ethyl)-[1,4]diazepan-5-one the title compound as an white foam with 94% ee. MS: 368.3 (MH⁺, 2Cl). (The enatiomeric purity was determined with a chiralpak-ADH column, 25 cm*4.6 mm, No.DL182 and 50% n-heptan+50% (EtOH+ 0.01M NH₄AcOH) as eluent. The purity corresponds to the purity of 2-((R)-2,2-dimethyl-[1,3]dioxolan-4-yl)-ethanol).

Example 173

1-((Z)-3-Naphthalen-1-yl-acryloyl)-4-(3-piperidin-1-yl-propyl)-[1,4]diazepan-5-one 1-((Z)-3-Naphthalen-1-yl-acryloyl)-4-(3-piperidin-1-yl-propyl)-[1,4]diazepan-5-one In analogy to the procedure described for example 11A, 4-(3-piperidin-1-yl-propyl)-[1,4]diazepan-5-one-dihydrochloride (intermediate 4B) and (Z)-3-naphthalen-1-yl-acrylic acid gave the title compound as light yellow foam. MS: 420.1 (MH⁺).

Example 174

1-[(E)-3-(3,4-Dichloro-phenyl)-acryloyl]-4-(2,2-dimethyl-3-piperidin-1-yl-propyl)-[1,4]diazepan-5-one 2,2-Dimethyl-3-piperidin-1-yl-propan-1-ol A solution of 3.00 g (17.96 mmol) of 3-bromo-2,2-dimethyl-propan-1-ol, 17.78 ml (179.59 mmol) of piperidine, 2.48 g (17.96 mmol) of K₂CO₃ and 2.69 g (17.96 mmol) of potassium iodide in 20 ml of DMA were stirred at 70° C. for 20 h. After filtration and evaporation of the solvents, the crude product was dissolved in diluted aqueous HCl solution and washed with EtOAc (3x). The aqueous phase was basified with KHCO₃ and some drops of 1N NaOH and extracted with EtOAc (3x). The organic phase was dried (Na₂SO₄) and evaporated to give 0.57 g (18%) of the title compound as yellow liquid. MS: 172.0 (MH⁺).

Methanesulfonic acid
2,2-dimethyl-3-piperidin-1-yl-propyl ester

A solution of 0.51 g (2.99 mmol) of 2,2-dimethyl-3-piperidin-1-yl-propan-1-ol in 7 ml of dichloromethane was treated at 0° C. with 0.24 ml (179.59 mmol) of methanesulfonyl chloride and stirred at RT for 2.5 h. The reaction was extracted with aqueous saturated NaHCO₃ /Et₂O (3x). The organic phases were washed with aqueous saturated NaHCO₃, dried over Na₂SO₄ and evaporated to give 0.85 g (quantitative) of the title compound as light brown oil. MS: 249.2 (M⁺).

1-(3-Iodo-2,2-dimethyl-propyl)-piperidine

In analogy to the procedure described for example 6D, methanesulfonic acid 2,2-dimethyl-3-piperidin-1-yl-propyl ester and sodium iodide stirred at 95° C. for 3 h gave the title compound as brown oil. MS: 282.1 (MH⁺).

1-[(E)-3-(3,4-Dichloro-phenyl)-acryloyl]-4-(2,2-dimethyl-3-piperidin-1-yl-propyl)-[1,4]diazepan-5-one In analogy to the procedure described for intermediate 4A, 1-[(E)-3-(3,4-dichloro-phenyl)-acryloyl]-[1,4]diazepan-5-one (intermediate 1A]) and 1-(3-iodo-2,2-dimethyl-propyl)-piperidine stirred 2 h at RT, gave the title compound as white solid. MS: 466.3 (MH⁺, 2Cl).

Example 175

1-[(E)-3-(3-Chloro-4-fluoro-phenyl)-acryloyl]-4-((S)-2-hydroxy-3-piperidin-1-yl-propyl)-[1,4]diazepan-5-one 1-[(E)-3-(3-Chloro-4-fluoro-phenyl)-acryloyl]-4-(R)-1-oxiranylmethyl-[1,4]diazepan-5-one In analogy to the procedure described for example 167A to 167C, 1-[(E)-3-(3-chloro-4-fluoro-phenyl)-acryloyl]-[1,4]diazepan-5-one (intermediate 54) and toluene-4-sulfonic acid (S)-2,2-dimethyl-[1,3]dioxolan-4-ylmethyl ester gave the title compound as light yellow viscous oil. MS: 353.1 (MH$^+$, 1Cl).

1-[(E)-3-(3-Chloro-4-fluoro-phenyl)-acryloyl]-4-((S)-2-hydroxy-3-piperidin-1-yl-propyl)-[1,4]diazepan-5-one In analogy to the procedure described for example 167D, 1-[(E)-3-(3-chloro-4-fluoro-phenyl)-acryloyl]-4-(R)-1-oxiranylmethyl-[1,4]diazepan-5-one and piperidine gave the title compound as off-white foam. MS: 438.3 (MH$^+$, 1Cl).

Example 176

(rac)-1-[(E)-3-(3,4-Dichloro-phenyl)-acryloyl]-4-(2-hydroxy-2-methyl-3-piperidin-1-yl-propyl)-[1,4]diazepan-5-one (rac)-1-[(E)-3-(3,4-Dichloro-phenyl)-acryloyl]-4-(2-hydroxy-2-methyl-3-piperidin-1-yl-propyl)-[1,4]diazepan-5-one In analogy to the procedure described for example 166, 1-[(E)-3-(3,4-dichloro-phenyl)-acryloyl]-[1,4]diazepan-5-one (intermediate 1A) and 2-chloromethyl-2-methyloxirane with 0.3 equivalent of potassium iodide gave the intermediate 1-[(E)-3-(3,4-dichloro-phenyl)-acryloyl]-4-(2-methyl-oxiranylmethyl)-[1,4]diazepan-5-one which was reacted with no work up with piperidine in ethanol to give the title compound as light yellow waxy solid. MS: 468.2 (MH$^+$, 2Cl).

Example 177

(rac)-1-[(E)-3-(3,4-Difluoro-phenyl)-acryloyl]-4-(2-hydroxy-3-piperidin-1-yl-propyl)-[1,4]diazepan-5-one (rac)-1-[(E)-3-(3,4-Difluoro-phenyl)-acryloyl]-4-oxiranylmethyl-[1,4]diazepan-5-one In analogy to the procedure described for example 166A, 1-[(E)-3-(3,4-difluoro-phenyl)-acryloyl]-[1,4]diazepan-5-one (intermediate 55) and 2-bromomethyl-oxirane gave the title compound as yellow oil. MS: 337.2 (MH$^+$).

(rac)-1-[(E)-3-(3,4-Difluoro-phenyl)-acryloyl]-4-(2-hydroxy-3-piperidin-1-yl-propyl)-[1,4]diazepan-5-one In analogy to the procedure described for example 166B, (rac)-1-[(E)-3-(3,4-difluoro-phenyl)-acryloyl]-4-oxiranylmethyl-[1,4]diazepan-5-one and piperidine gave the title compound as light yellow viscous oil. MS: 422.2 (MH$^+$).

Example 178

1-[(E)-3-(3,4-Dichloro-phenyl)-acryloyl]-4-((S)-3-hydroxy-4-piperidin-1-yl-butyl)-[1,4]diazepan-5-one 1-[(E)-3-(3,4-Dichloro-phenyl)-acryloyl]-4-((S)-3,4-dihydroxy-butyl)-[1,4]diazepan-5-one In analogy to the procedure described for example 167A and 167B, 1-[(E)-3-(3,4-dichloro-phenyl)-acryloyl]-[1,4]diazepan-5-one (intermediate 1A]) and methanesulfonic acid 2-((S)-2,2-dimethyl-[1,3]dioxolan-4-yl)-ethyl ester (prepared from 2-((S)-2,2-dimethyl-[1,3]dioxolan-4-yl)-ethanol and methanesulfonyl chloride) gave the title compound as an white foam. MS: 401.3 (MH$^+$, 2Cl).

Methanesulfonic acid (S)-4-{4-[(E)-3-(3,4-dichloro-phenyl)-acryloyl]-7-oxo-[1,4]diazepan-1-yl}-2-hydroxy-butyl ester In analogy to the procedure described for example 167C, 1-[(E)-3-(3,4-dichloro-phenyl)-acryloyl]-4-((S)-3,4-dihydroxy-butyl)-[1,4]diazepan-5-one with 2,4,6-trimethyl-pyridine and methanesulfonyl chloride in CH$_2$Cl$_2$ gave the intermediate mesylate as an white foam. MS: 479.0 (MH$^+$, 2Cl).

1-[(E)-3-(3,4-Dichloro-phenyl)-acryloyl]-4-((S)-3-hydroxy-4-piperidin-1-yl-butyl)-[1,4]diazepan-5-one In analogy to the procedure described for example 166B, Methanesulfonic acid (S)-4-{4-[(E)-3-(3,4-dichloro-phenyl)-acryloyl]-7-oxo-[1,4]diazepan-1-yl}-2-hydroxy-butyl ester with catalytic amount of sodium iodide, 1.2 equivalent of cesium carbonate and 5 equivalent of piperidine gave after 2 h at 60° C. the epoxide as intermediate. A further equivalent of cesium carbonate was added and the reaction heated at 80° C. over night to give the title compound as a colorless gum with 99% ee. MS: 368.1 (MH$^+$, 2Cl). (The enatiomeric purity was determined with a chiralpak-ADH column, 25 cm*4.6 mm, No.DL182 and 50% n-heptane+50% (EtOH+0.01M NH$_4$AcOH) as eluent. The purity corresponds to the purity of 2-((S)-2,2-dimethyl-[1,3]dioxolan-4-yl)-ethanol).

Example 179

(rac)-2-{4-[(E)-3-(3,4-Dichloro-phenyl)-acryloyl]-7-oxo-[1,4]diazepan-1-yl}-5-piperidin-1-yl-pentanoic acid methyl ester (rac)-5-Bromo-2-{4-[(E)-3-(3,4-dichloro-phenyl)-acryloyl]-7-oxo-[1,4]diazepan-1-yl}-pentanoic acid methyl ester A solution of 0.501 g (1.60 mmol) of 1-[(E)-3-(3,4-dichloro-phenyl)-acryloyl]-[1,4]diazepan-5-one (intermediate 1A) and 0.447 g (1.60 mmol) of methyl 2,5-dibromopentane in 7 ml of DMF was treated at 0° C. with 0.077 g (1.76 mmol) of NaH (55% in oil). The reaction was stirred for 20 h at RT, cooled (0° C.) and treated again with 0.224 g (0.80 mmol) of methyl 2,5-dibromopentane and 0.038 g (0.88 mmol) of NaH (55% in oil). After 1 h at 0° C. and 3 h at RT, the reaction was neutralized with cold aqueous 10% KHSO$_4$ and extracted with Et$_2$O (3×). The organic phases were washed with aqueous 10% KHSO$_4$, aqueous 10% NaCl, dried over Na$_2$SO$_4$ evaporated and purified by flash silica gel column (CH$_2$Cl$_2$/Et$_2$O 95:5 to 70:30) to yield 0.39 g (48%) of the title compound as white foam. MS: 505.1 (MH$^+$, 1Br).

(rac)-2-{4-[(E)-3-(3,4-Dichloro-phenyl)-acryloyl]-7-oxo-[1,4]diazepan-1-yl}-5-iodo-pentanoic acid methyl ester In analogy to the procedure described in example 6D, 4-(5-chloro-pentyl)-1-[(E)-3-(3,4-dichloro-phenyl)-acryloyl]-[1,4]diazepan-5-one and sodium iodide were stirred at RT for 4 h to give the title compound as yellow foam. MS: 552.2 (MH$^+$, 2Cl).

(rac)-2-{4-[(E)-3-(3,4-Dichloro-phenyl)-acryloyl]-7-oxo-[1,4]diazepan-1-yl}-5-piperidin-1-yl-pentanoic acid methyl ester A solution of 0.111 g (0.20 mmol) of 2-{4-[(E)-3-(3,4-dichloro-phenyl)-acryloyl]-7-oxo-[1,4]diazepan-1-yl}-5-iodo-pentanoic acid methyl ester in 1 ml of DMA was treated at 0° C. with 0.021 ml (0.21 mmol) of piperidine and stirred 30 min at 0° C. and 1 h at RT. 0.065 g (0.20 mmol) of cesium carbonate was added at 0° C. and stirring was continued for 2 h. After additional 3 h at RT, the reaction was extracted with aqueous saturated NaHCO$_3$/Et$_2$O (3×). The organic phases were washed with aqueous saturated NaHCO$_3$, aqueous 10% NaCl, dried over Na$_2$SO$_4$ evaporated and precipitated with CH$_2$Cl$_2$/n-pentane to yield 0.86 g (84%) of the title compound as a white foam. MS: 510.3 (MH$^+$, 2Cl).

Example 180

Lithium; (rac)-2-{4-[(E)-3-(3,4-dichloro-phenyl)-acryloyl]-7-oxo-[1,4]diazepan-1-yl}-5-piperidin-1-yl-pentanoate

Lithium; (rac)-2-{4-[(E)-3-(3,4-dichloro-phenyl)-acryloyl]-7-oxo-[1,4]diazepan-1-yl]}-5-piperidin-1-yl-pentanoate A solution of 0.041 g (0.08 mmol) of the above prepared (rac)-2-{4-[(E)-3-(3,4-dichloro-phenyl)-acryloyl]-7-oxo-[1,4]diazepan-1-yl}-5-piperidin-1-yl-pentanoic acid methyl ester in 4 ml of THF/MeOH (1:1), treated at 0° C. with 0.084 mL (0.08 mmol) of 1 N LiOH, and kept at ambient temperature for 20 h. Water (0.32 ml) was added and heated for 1 h at 40° C. The reaction was evaporated and precipitated with CH$_2$Cl$_2$/Et$_2$O to give 0.028 g (70%) of the title compound as white powder. MS: 494.2 (M−H$^-$, 2Cl).

Example 181

(rac)-1-[(E)-3-(3,4-Dichloro-phenyl)-acryloyl]-4-(1-hydroxymethyl-4-piperidin-1-yl-butyl)-[1,4]diazepan-5-one

(rac)-1-[(E)-3-(3,4-Dichloro-phenyl)-acryloyl]-4-(1-hydroxymethyl-4-piperidin-1-yl-butyl)-[1,4]diazepan-5-one A solution of 0.041 g (0.08 mmol) of (rac)-2-{4-[(E)-3-(3,4-dichloro-phenyl)-acryloyl]-7-oxo-[1,4]diazepan-1-yl}-5-piperidin-1-yl-pentanoic acid methyl ester in 0.5 ml of ethanol was treated at 0° C. with 0.006 g (0.16 mmol) of sodium borohydride in 0.5 ml of ethanol during 5 min. The reaction was stirred for 21 h at RT, cooled (0° C.) and treated again with 0.006 g (0.16 mmol) of sodium borohydride in 0.5 ml ethanol. After 5 h at RT the reaction was neutralized with cold aqueous 10% KHSO$_4$ and extracted with cold saturated NaHCO$_3$/EtOAc (3×). The organic phases were washed with aqueous 10% NaCl, dried over Na$_2$SO$_4$, evaporated and purified by flash silica gel column (CH$_2$Cl$_2$/MeOH 9:1 to 4:1 and then, to elute the product, with CH$_2$Cl$_2$/MeOH/25% NH$_4$OH 9:1:0.1) to yield after precipitation with CH$_2$Cl$_2$/n-penatne 0.022 g (57%) of the title compound as white foam. MS: 482.3 (MH$^+$, 2Cl).

Example 182

(rac)-3-{4-[(E)-3-(3,4-Dichloro-phenyl)-acryloyl]-7-oxo-[1,4]diazepan-1-yl}-2-piperidin-1-ylmethyl-propionic acid ethyl ester

2-{4-[(E)-3-(3,4-Dichloro-phenyl)-acryloyl]-7-oxo-[1,4]diazepan-1-ylmethyl}-acrylic acid ethyl ester A suspension of 2.50 g (7.98 mmol) of 1-[(E)-3-(3,4-dichloro-phenyl)-acryloyl]-[1,4]diazepan-5-one (intermediate 1A) and 1.15 ml (7.98 mmol) of ethyl 2-(bromomethylacrylate) in 80 ml of DMF was treated at −20° C. with 0.38 g (8.78 mmol) of NaH (55% in oil) and warmed up naturally to 18° C. (2.5 h). After cooling (0° C.) additionally 0.12 ml (0.80 mmol) of ethyl 2-(bromomethylacrylate) was added and after 30 min no starting material was left, based on TLC. The reaction was extracted with aqueous 10% KHSO$_4$/ether (3×), the organic phases were washed with a aqueous 10% NaCl solution, dried (Na$_2$SO$_4$) and evaporated to give 3.51 g (quantitative, 90% purity) of the crude title compound as light yellow viscous oil, which was used directly in the next step. MS: 425.1 (MH$^+$, 2Cl).

(rac)-3-{4-[(E)-3-(3,4-Dichloro-phenyl)-acryloyl]-7-oxo-[1,4]diazepan-1-yl}-2-piperidin-1-ylmethyl-propionic acid ethyl ester A suspension of 0.80 g (1.88 mmol) of 2-{4-[(E)-3-(3,4-dichloro-phenyl)-acryloyl]-7-oxo-[1,4]diazepan-1-ylmethyl}-acrylic acid ethyl ester, 0.56 ml (5.64 mmol) of piperidine and 1.83 g (5.61 mmol) of cesium carbonate in 32 ml of acetonitrile was stirred over night at RT. Additional 0.37 ml (3.76 mmol) of piperidine were added and after 1 h, cesium carbonate was filtrated and the solvent evaporated. Purification by flash silica gel column (CH$_2$Cl$_2$/MeOH 98:2 to 96:4) gave 0.43 g (44%) of the title compound as colorless foam. MS: 510.4 (MH$^+$, 2Cl).

Example 183

Lithium; (rac)-3-{4-[(E)-3-(3,4-dichloro-phenyl)-acryloyl]-7-oxo-[1,4]diazepan-1-yl}-2-piperidin-1-ylmethyl-propionate

Lithium; (rac)-3-{4-[(E)-3-(3,4-dichloro-phenyl)-acryloyl]-7-oxo-[1,4]diazepan-1-yl}-2-piperidin-1-ylmethyl-propionate In analogy to the procedure described in example 180, (rac)-3-{4-[(E)-3-(3,4-dichloro-phenyl)-acryloyl]-7-oxo-[1,4]diazepan-1-yl}-2-piperidin-1-ylmethyl-propionic acid ethyl ester gave the title as colorless solid. MS: 480.1 (M−H$^-$, 2Cl).

Examples 184-187

The following examples were produced from the appropriate [1,4]-diazepan-5-one derivative and 1-(3-chloropropyl) piperidine in analogy to the procedure described in intermediate 4A:

| Example No. | Compound Name | [1,4]-diazepan-5-one derivative | MS: (MH+) |
|---|---|---|---|
| 184 | (rac)-1-[(E)-3-(3,4-Dichloro-phenyl)-acryloyl]-3-methyl-4-(3-piperidin-1-yl-propyl)-[1,4]diazepan-5-one | (rac)-1-[(E)-3-(3,4-Dichloro-phenyl)-acryloyl]-3-methyl-[1,4]diazepan-5-one (Intermediate 77) | 452.2 |
| 185 | (rac)-1-[(E)-3-(3,4-Dichloro-phenyl)-acryloyl]-7-methyl-4-(3-piperidin-1-yl-propyl)-[1,4]diazepan-5-one | (rac)-1-[(E)-3-(3,4-Dichloro-phenyl)-acryloyl]-7-methyl-[1,4]diazepan-5-one (Intermediate 78) | 452.1 |
| 186 | (R)-1-[(E)-3-(3,4-Dichloro-phenyl)-acryloyl]-2-methyl-4-(3-piperidin-1-yl-propyl)-[1,4]diazepan-5-one | (R)-1-[(E)-3-(3,4-Dichloro-phenyl)-acryloyl]-2-methyl-[1,4]diazepan-5-one (Intermediate 79) | 452.1 |
| 187 | (rac)-1-[(E)-3-(3,4-Dichloro-phenyl)-acryloyl]-6-methyl-4-(3-piperidin-1-yl-propyl)-[1,4]diazepan-5-one | (rac)-1-[(E)-3-(3,4-Dichloro-phenyl)-acryloyl]-6-methyl-[1,4]diazepan-5-one (Intermediate 80) | 452.2 |

Example 188

1-[(E)-3-(3-Chloro-phenyl)-acryloyl]-4-(3-piperidin-1-yl-propyl)-[1,4]diazepan-5-one To a suspension of (E)-3-(3-Chloro-phenyl)-acrylic acid acid (26 mg, 0.12 mmol), 4-(3-piperidin-1-yl-propyl)-[1,4]diazepan-5-one-dihydrochloride (intermediate 4) (24 mg, 0.1 mmol), O-(7-azabenotriazol-1-yl)-1,1,3,3-tetramethyluronium hexafluorophosphate (46 mg, 0.12 mmol) in DMF (1 ml) was added Et₃N (21 ul, 0.15 mmol) and the mixture shaken for 1 h. The reaction was then directly purified by preparative HPLC affording the title product (28 mg, 69%) as a white powder. MS: 404.2 (MH+).

Examples 189-224

General Procedure for Examples 189-224

A solution of 3-{4-[(E)-3-(3-Chloro-4-fluoro-phenyl)-acryloyl]-7-oxo-[1,4]diazepan-1-yl}-propionaldehyde (intermediate 59) (0.1 mmol) in DCE (0.5 ml) was added to the appropriate amine (0.1 mmol), which are either commercially available or are described in the intermediate section, followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

| Example No. | Compound Name | Amine | MS: (MH+) |
|---|---|---|---|
| 189 | 1-[(E)-3-(3-Chloro-4-fluoro-phenyl)-acryloyl]-4-[3-((−)-4-hydroxy-6-aza-spiro[2.5]oct-6-yl)-propyl]-[1,4]diazepan-5-one | (−)-6-Aza-Spiro[2.5]octan-4-ol (intermediate 83) | 464.4 |
| 190 | 1-[(E)-3-(3-Chloro-4-fluoro-phenyl)-acryloyl]-4-[3-((+, cis)-3-hydroxy-4-methyl-piperidin-1-yl)-propyl]-[1,4]diazepan-5-one | (3S,4S))-4-Methyl-piperidin-3-ol (intermediate 85) | 452.4 |
| 191 | 1-[(E)-3-(3-Chloro-4-fluoro-phenyl)-acryloyl]-4-[3-((−, cis)-3-hydroxy-4-methyl-piperidin-1-yl)-propyl]-[1,4]diazepan-5-one | (−,cis)-4-Methyl-piperidin-3-ol (intermediate 86) | 452.4 |
| 192 | 1-[(E)-3-(3-Chloro-4-fluoro-phenyl)-acryloyl]-4-[3-((+)-4-hydroxy-6-aza-spiro[2.5]oct-6-yl)-propyl]-[1,4]diazepan-5-one | (+)-6-Aza-spiro[2.5]octan-4-ol (intermediate 82) | 464.4 |
| 193 | 1-[(E)-3-(3-Chloro-4-fluoro-phenyl)-acryloyl]-4-[3-((R)-3-hydroxy-piperidin-1-yl)-propyl]-[1,4]diazepan-5-one | (R)-piperidin-3-ol | 438.2 |
| 194 | 8-(3-{4-[(E)-3-(3-Chloro-4-fluoro-phenyl)-acryloyl]-7-oxo-[1,4]diazepan1-yl}-propyl)-1,3,8-triazaspiro[4.5]decane-2,4-dione | 1,3,8-Triaza-spiro[4.5]decane-2,4-dione (intermediate 11) | 506.2 |
| 195 | 8-(3-{4-[(E)-3-(3-Chloro-4-fluoro-phenyl)-acryloyl]-7-oxo-[1,4]diazepan1-yl}-propyl)-1-oxa-3,8-diazaspiro[4.5]decan-2-one | 2,8-Diaza-spiro[4.5]decan-1-one (intermediate 14) | 493.2 |
| 196 | 1-[(E)-3-(3-Chloro-4-fluoro-phenyl)-acryloyl]-4-[3-(4-hydroxy-piperidin-1-yl)-propyl]-[1,4]diazepan-5-one | piperidin-4-ol | 438.2 |

-continued

| Example No. | Compound Name | Amine | MS: (MH+) |
|---|---|---|---|
| 197 | 1-[(E)-3-(3-Chloro-4-fluoro-phenyl)-acryloyl]-4-[3-(tetrahydro-pyran-4-ylamino)-propyl]-[1,4]diazepan-5-one | Tetrahydro-pyran-4-ylamine | 438.2 |
| 198 | 8-(3-{4-[(E)-3-(3-Chloro-4-fluoro-phenyl)-acryloyl]-7-oxo-[1,4]diazepan-1-yl}-propyl)-2,8-diaza-spiro[4.5]decan-3-one | 2,8-Diaza-spiro[4.5]decan-3-one (intermediate 18) | 491.2 |
| 199 | 1-(3-{4-[(E)-3-(3-Chloro-4-fluoro-phenyl)-acryloyl]-7-oxo-[1,4]diazepan-1-yl}-propyl)-piperidine-4-carbonitrile | Piperidine-4-carbonitrile | 447.2 |
| 200 | N-[1-(3-{4-[(E)-3-(3-Chloro-4-fluoro-phenyl)-acryloyl]-7-oxo-[1,4]diazepan-1-yl}-propyl)-piperidin-4-yl]-methanesulfonamide | N-Piperidin-4-yl-methanesulfonamide (intermediate 29) | 515.2 |
| 201 | [1-(3-{4-[(E)-3-(3-Chloro-4-fluoro-phenyl)-acryloyl]-7-oxo-[1,4]diazepan-1-yl}-propyl)-piperidin-4-yl]-carbamic acid methyl ester | Piperidin-4-yl-carbamic acid methyl ester (intermediate 38) | 495.2 |
| 202 | Ethyl-carbamic acid 1-(3-{4-[(E)-3-(3-chloro-4-fluoro-phenyl)-acryloyl]-7-oxo-[1,4]diazepan-1-yl}-propyl)-piperidin-4-yl ester | Ethyl-carbamic acid piperidin-4-yl ester (intermediate 41) | 509.2 |
| 203 | 1-[(E)-3-(3-Chloro-4-fluoro-phenyl)-acryloyl]-4-{3-[4-(3-methyl-[1,2,4]oxadiazol-5-yl)-piperidin-1-yl]-propyl}-[1,4]diazepan-5-one | 4-(5-Methyl-[1,3,4]oxadiazol-2-yl)-piperidine (intermediate 42) | 504.2 |
| 204 | 1-[(E)-3-(3-Chloro-4-fluoro-phenyl)-acryloyl]-4-{3-[4-(5-methyl-[1,3,4]oxadiazol-2-yl)-piperidin-1-yl]-propyl}-[1,4]diazepan-5-one | 4-(5-Methyl-[1,3,4]oxadiazol-2-yl)-piperidine (intermediate 43) | 504.2 |
| 205 | (rac)-1-[(E)-3-(3-Chloro-4-fluoro-phenyl)-acryloyl]-4-[3-(3-hydroxy-3-methyl-piperidin-1-yl)-propyl]-[1,4]diazepan-5-one | (rac)-3-methyl-piperidin-3-ol (intermediate 101) | 452.2 |
| 206 | 1-[(E)-3-(3-Chloro-4-fluoro-phenyl)-acryloyl]-4-[3-(4-dimethylamino-piperidin-1-yl)-propyl]-[1,4]diazepan-5-one | 4-dimethylamino-piperidine | 465.2 |
| 207 | 1-[(E)-3-(3-Chloro-4-fluoro-phenyl)-acryloyl]-4-[3-(4-[1,2,4]triazol-1-yl)-piperidin-1-yl)-propyl]-[1,4]diazepan-5-one | 4-(2H-[1,2,4]Triazol-1-yl)-piperidine (intermediate 28) | 489.2 |
| 208 | (rac,trans)-1-[(E)-3-(3-Chloro-4-fluoro-phenyl)-acryloyl]-4-[3-(3-hydroxy-2-methyl-piperidin-1-yl)-propyl]-[1,4]diazepan-5-one | (rac,trans)-2-Methyl-piperidin-3-ol (intermediate 87) | 452.2 |
| 209 | (rac,cis)-1-[(E)-3-(3-Chloro-4-fluoro-phenyl)-acryloyl]-4-[3-(3-hydroxy-2-methyl-piperidin-1-yl)-propyl]-[1,4]diazepan-5-one | (rac,cis)-2-Methyl-piperidin-3-ol (intermediate 88) | 452.2 |
| 210 | (rac)-1-[(E)-3-(3-Chloro-4-fluoro-phenyl)-acryloyl]-4-[3-(2-hydroxymethyl-piperidin-1-yl)-propyl]-[1,4]diazepan-5-one | (rac)-2-hydroxymethyl-piperidine | 452.2 |
| 211 | (rac)-1-[(E)-3-(3-Chloro-4-fluoro-phenyl)-acryloyl]-4-[3-(3-hydroxymethyl-piperidin-1-yl)-propyl]-[1,4]diazepan-5-one | (rac)-3-hydroxymethyl-piperidine | 452.2 |
| 212 | 1-[(E)-3-(3-Chloro-4-fluoro-phenyl)-acryloyl]-4-[3-(4-hydroxymethyl-piperidin-1-yl)-propyl]-[1,4]diazepan-5-one | 4-hydroxymethyl-piperidine | 452.2 |
| 213 | (rac,trans)-1-[(E)-3-(3-Chloro-4-fluoro-phenyl)-acryloyl]-4-[3-(4-fluoro-3-hydroxy-piperidin-1-yl)-propyl]-[1,4]diazepan-5-one | (rac,trans)-4-Fluoro-piperidin-3-ol (intermediate 89) | 456.2 |
| 214 | (rac,trans)-1-[(E)-3-(3-Chloro-4-fluoro-phenyl)-acryloyl]-4-[3-(3-fluoro-4-hydroxy-piperidin-1-yl)-propyl]-[1,4]diazepan-5-one | (rac,trans)-3-Fluoro-piperidin-4-ol (intermediate 90) | 456.2 |
| 215 | (rac)-1-[(E)-3-(3-Chloro-4-fluoro-phenyl)-acryloyl]-4-[3-(cis-3-hydroxy-4-hydroxymethyl-piperidin-1-yl)-propyl]-[1,4]diazepan-5-one | (rac,cis)-4-hydroxymethyl-piperidin-3-ol (intermediate 47) | 468.3 |

| Example No. | Compound Name | Amine | MS: (MH+) |
|---|---|---|---|
| 216 | (rac)-1-[(E)-3-(3-Chloro-4-fluoro-phenyl)-acryloyl]-4-[3-(cis-3-hydroxy-4-methoxymethyl-piperidin-1-yl)-propyl]-[1,4]diazepan-5-one | (rac,cis)-4-methoxymethyl piperidin-3-ol (intermediate 49) | 482.3 |
| 217 | (rac)-1-[(E)-3-(3-Chloro-fluoro-phenyl)-acryloyl]-4-[3-(trans-3-hydroxy-4-hydroxymethyl-piperidin-1-yl)-propyl]-[1,4]diazepan-5-one | (rac,trans)-4-hydroxymethyl piperidin-3-ol (intermediate 48) | 468.3 |
| 218 | (rac)-1-[(E)-3-(3-Chloro-4-fluoro-phenyl)-acryloyl]-4-[3-(cis-3-methoxy-4-hydroxymethyl-piperidin-1-yl)-propyl]-[1,4]diazepan-5-one | (rac,cis)-3-methoxy-piperidin-4-yl-methanol (intermediate 50) | 482.3 |
| 219 | (rac)-1-[(E)-3-(3-Chloro-4-fluoro-phenyl)-acryloyl]-4-[3-(cis-3-hydroxy-4-hydroxymethyl-4-methyl-piperidin-1yl)-propyl]-[1,4]diazepan-5-one | (rac,cis)-4-hydroxymethyl-4-methyl-piperidin-3-ol (intermediate 52) | 482.4 |
| 220 | (rac)-1-[(E)-3-(3-Chloro-4-fluoro-phenyl)-acryloyl]-4-[3-(trans-3-hydroxy-4-hydroxymethyl-4-methyl-piperidin-1-yl)-propyl]-[1,4]diazepan-5-one | (rac,trans)-4-hydroxymethyl-4-methyl-piperidin-3-ol (intermediate 53) | 482.3 |
| 221 | (rac)-1-[(E)-3-(3-Chloro-fluoro-phenyl)-acryloyl]-4-[3-(5-hydroxy-2-methyl-piperidin-1-yl)-propyl]-[1,4]diazepan-5-one | (rac)-6-methyl-piperidin-3-ol (intermediate 66) | 452.3 |
| 222 | (rac)-1-[(E)-3-(3-Chloro-4-fluoro-phenyl)-acryloyl]-4-[3-(5-hydroxy-2-hydroxymethyl-piperidin-1-yl)-propyl]-[1,4]diazepan-5-one | (rac)-6-hydroxymethyl-piperidin-2-ol (intermediate 65) | 468.3 |
| 223 | (rac)-1-[(E)-3-(3-Chloro-4-fluoro-phenyl)-acryloyl]-4-[3-(3-hydroxy-4,4-dimethyl-piperidin-1-yl)-propyl]-[1,4]diazepan-5-one | (rac)-4,4-dimethyl-piperidin-3-ol (intermediate 84) | 466.3 |
| 224 | (rac,cis)-1-[(E)-3-(3-Chloro-4-fluoro-phenyl)-acryloyl]-4-[3-(3-hydroxy-5-methyl-piperidin-1-yl)-propyl]-[1,4]diazepan-5-one | (rac,cis)-5-methyl-piperidin-3-ol (intermediate 75) | 452.3 |

Examples 225-279

General Procedure for Examples 225-279

A solution of 3-{4-[(E)-3-(3,4-dichloro-phenyl)-acryloyl]-7-oxo-[1,4]diazepan-1-yl}-propionaldehyde (intermediate 2) (0.1 mmol) in DCE (0.5 ml) was added to the appropriate amine (0.1 mmol) which are either commercially available or are described in the intermediate section, followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

| Example No. | Compound Name | Amine | MS: (MH+) |
|---|---|---|---|
| 225 | (rac,trans)-1-[(E)-3-(3,4-Dichlorophenyl)-acryloyl]-4-[3-(3-hydroxy-2-methyl-piperidin-1-yl)-propyl]-[1,4]diazepan-5-one | (rac,trans)-2-methyl-piperidin-3-ol (intermediate 87) | 468.2 |
| 226 | (rac,cis)-1-[(E)-3-(3,4-Dichloro-phenyl)-acryloyl]-4-[3-(3-hydroxy-2-methyl-piperidin-1-yl)-propyl]-[1,4]diazepan-5-one | (rac, cis)-2-methyl-piperidin-3-ol (intermediate 88) | 468.2 |
| 227 | (rac)-1-[(E)-3-(3,4-Dichloro-phenyl)-acryloyl]-4-[3-(2-hydroxymethyl-piperidin-1-yl)-propyl]-[1,4]diazepan-5-one | (rac)-2-hydroxymethyl-piperidine | 468.2 |
| 228 | (rac)-1-[(E)-3-(3,4-Dichloro-phenyl)-acryloyl]-4-[3-(3-hydroxymethyl-piperidin-1-yl)-propyl]-[1,4]diazepan-5-one | (rac)-3-hydroxymethyl-piperidine | 468.2 |
| 229 | 1-[(E)-3-(3,4-Dichloro-phenyl)-acryloyl]-4-[3-(4-hydroxymethyl-piperidin-1-yl)-propyl]-[1,4]diazepan-5-one | 4-hydroxymethyl-piperidine | 468.2 |

-continued

| Example No. | Compound Name | Amine | MS: (MH+) |
|---|---|---|---|
| 230 | (rac,trans)-1-[(E)-3-(3,4-Dichloro-phenyl)-acryloyl]-4-[3-(4-fluoro-3-hydroxy-piperidin-1-yl)-propyl]-[1,4]diazepan-5-one | (rac,trans)-4-Fluoro-piperidin-3-ol (intermediate 89) | 472.2 |
| 231 | (rac,trans)-1-[(E)-3-(3,4-Dichloro-phenyl)-acryloyl]-4-[3-(3-fluoro-4-hydroxy-piperidin-1-yl)-propyl]-[1,4]diazepan-5-one | (rac,trans)-3-Fluoro-piperidin-4-ol (intermediate 90) | 472.2 |
| 232 | (rac)-1-[(E)-3-(3,4-Dichloro-phenyl)-acryloyl]-4-[3-(3-hydroxy-3-methyl-piperidin-1-yl)-propyl]-[1,4]diazepan-5-one | (rac)-3-methyl-piperidin-3-ol (intermediate 101) | 468.2 |
| 233 | (rac, cis)-1-[(E)-3-(3,4-Dichloro-phenyl)-acryloyl]-4-[3-(3-fluoro-4-hydroxy-piperidin-1-yl)-propyl]-[1,4]diazepan-5-one | (rac, cis)-3-Fluoro-piperidin-4-ol (intermediate 93) | 472.3 |
| 234 | 1-[(E)-3-(3,4-Dichloro-phenyl)-acryloyl]-4-{3-[4-(2-methoxy-ethyl)-piperazin-1-yl]-propyl}-[1,4]diazepan-5-one | 1-(2-Methoxy-ethyl)-piperazine | 497.3 |
| 235 | (rac)-1-[(E)-3-(3,4-Dichloro-phenyl)-acryloyl]-4-[3-(3-methyl-piperidin-1-yl)-propyl]-[1,4]diazepan-5-one | (rac)-3-methyl-piperidine | 452.3 |
| 236 | (rac)-1-[(E)-3-(3,4-Dichloro-phenyl)-acryloyl]-4-[3-(3-methoxymethyl-piperidin-1-yl)-propyl]-[1,4]diazepan-5-one | (rac)-3-methoxymethyl-piperidine | 482.3 |
| 237 | 1-[(E)-3-(3,4-Dichloro-phenyl)-acryloyl]-4-[3-(3-oxo-piperazin-1-yl)-propyl]-[1,4]diazepan-5-one | Piperazin-2-one | 453.3 |
| 238 | (rac)-1-[(E)-3-(3,4-Dichloro-phenyl)-acryloyl]-4-[3-(3-hydroxy-4-methyl-piperidin-1-yl)-propyl]-[1,4]diazepan-5-one | (rac)-4-methyl-piperidin-3-ol (intermediate 91) | 468.3 |
| 239 | 1-[(E)-3-(3,4-Dichloro-phenyl)-acryloyl]-4-[3-(5-oxo-[1,4]diazepan-1-yl)-propyl]-[1,4]diazepan-5-one | [1,4]Diazepan-5-one | 467.2 |
| 240 | 1-[(E)-3-(3,4-Dichloro-phenyl)-acryloyl]-4-[3-(4-isopropyl-piperazin-1-yl)-propyl]-[1,4]diazepan-5-one | 1-Isopropyl-piperazine | 481.3 |
| 241 | 1-[(E)-3-(3,4-Dichloro-phenyl)-acryloyl]-4-[3-(4-cyclopropyl-piperazin-1-yl)-propyl]-[1,4]diazepan-5-one | 1-Cyclopropyl-piperazine | 479.3 |
| 242 | 1-[(E)-3-(3,4-Dichloro-phenyl)-acryloyl]-4-[3-(4-cyclopentyl-piperazin-1-yl)-propyl]-[1,4]diazepan-5-one | 1-Cyclopentyl-piperazine | 507.3 |
| 243 | (rac)-1-[(E)-3-(3,4-Dichloro-phenyl)-acryloyl]-4-[3-(4-hydroxy-3-methyl-piperidin-1-yl)-propyl]-[1,4]diazepan-5-one | (rac)-3-methyl-piperidin-4-ol (intermediate 94) | 468.3 |
| 244 | [1-(3-{4-[(E)-3-(3,4-Dichloro-phenyl)-acryloyl]-7-oxo-[1,4]diazepan-1-yl}-propyl)-piperidin-4-yl]-carbamic acid methyl ester | Piperidin-4-yl-carbamic acid methyl ester (intermediate 38) | 511.3 |
| 245 | [1-(3-{4-[(E)-3-(3,4-Dichloro-phenyl)-acryloyl]-7-oxo-[1,4]diazepan-1-yl}-propyl)-piperidin-4-yl]-methyl-carbamic acid methyl ester | Methyl-piperidin-4-yl-carbamic acid methyl ester (intermediate 39) | 525.3 |
| 246 | (rac)-1-[(E)-3-(3,4-Dichloro-phenyl)-acryloyl]-4-[3-(4-isopropyl-3-methyl-piperazin-1-yl)-propyl]-[1,4]diazepan-5-one | (rac)-1-Isopropyl-2-methyl-piperazine | 495.7 |
| 247 | 1-[(E)-3-(3,4-Dichloro-phenyl)-acryloyl]-4-[3-(4-methoxymethyl-piperidin-1-yl)-propyl]-[1,4]diazepan-5-one | 4-methoxymethyl-piperidine | 482.3 |
| 248 | (rac)-1-[(E)-3-(3,4-Dichloro-phenyl)-acryloyl]-4-[3-(3-hydroxymethyl-3-methyl-piperidin-1-yl)-propyl]-[1,4]diazepan-5-one | (rac)-(3-methyl-piperidin-3-yl) methanol (intermediate 30) | 482.3 |
| 249 | (rac)-1-[(E)-3-(3,4-Dichloro-phenyl)-acryloyl]-4-[3-(3-methoxymethyl-3-methyl-piperidin-1-yl)-propyl]-[1,4]diazepan-5-one | (rac)-3-methoxymethyl-3-methyl-piperidine (intermediate 31) | 496.3 |

-continued

| Example No. | Compound Name | Amine | MS: (MH+) |
|---|---|---|---|
| 250 | (rac)-1-[(E)-3-(3,4-Dichloro-phenyl)-acryloyl]-4-[3-(2-hydroxymethyl-2-methyl-piperidin-1-yl)-propyl]-[1,4]diazepan-5-one | (rac)-(2-methyl-piperidin-2-yl) methanol (intermediate 34) | 482.3 |
| 251 | (rac)-1-[(E)-3-(3,4-Dichloro-phenyl)-acryloyl]-4-[3-(4-hydroxy-6-aza-spiro[2.5]oct-6-yl)-propyl]-[1,4]diazepan-5-one | (rac)-6-Aza-spiro[2.5]octan-4-ol (intermediate 81) | 480.3 |
| 252 | (rac)-1-[(E)-3-(3,4-Dichloro-phenyl)-acryloyl]-4-[3-(8-hydroxy-5-aza-spiro[2.5]oct-5-yl)-propyl]-[1,4]diazepan-5-one | (rac)-5-Aza-spiro[2.5]octan-8-ol (intermediate 98) | 480.3 |
| 253 | (rac)-1-[(E)-3-(3,4-Dichloro-phenyl)-acryloyl]-4-[3-(cis-4-hydroxy-3-methyl-piperidin-1-yl)-propyl]-[1,4]diazepan-5-one | (rac, cis)-3-methyl-piperidin-4-ol (intermediate 96) | 468.3 |
| 254 | 1-[(E)-3-(3,4-Dichloro-phenyl)-acryloyl]-4-[3-(4-hydroxymethyl-4-methyl-piperidin-1-yl)-propyl]-[1,4]diazepan-5-one | (4-methyl-piperidin-4-yl) methanol (intermediate 32) | 482.3 |
| 255 | (rac)-1-[(E)-3-(3,4-Dichloro-phenyl)-acryloyl]-4-[3-(2-hydroxymethyl-2-methyl-pyrrolidin-1-yl)-propyl]-[1,4]diazepan-5-one | (rac)-2-hydroxymethyl-2-methyl-pyrrolidine | 468.3 |
| 256 | (rac)-[1-(3-{4-[(E)-3-(3,4-Dichloro-phenyl)-acryloyl]-7-oxo-[1,4]diazepan-1-yl}-propyl)-piperidin-3-yl]-carbamic acid methyl ester | (rac)-Piperidin-3-yl-carbamic acid methyl ester (intermediate 40) | 511.3 |
| 257 | (rac)-1-[(E)-3-(3,4-Dichloro-phenyl)-acryloyl]-4-[3-(4-hydroxy-3,3-dimethyl-piperidin-1-yl)-propyl]-[1,4]diazepan-5-one | (rac)-3,3-dimethyl-piperidin-4-ol (intermediate 97) | 482.4 |
| 258 | 1-[(E)-3-(3,4-Dichloro-phenyl)-acryloyl]-4-[3-(4-isobutyl-piperazin-1-yl)-propyl]-[1,4]diazepan-5-one | 1-Isobutyl-piperazine | 495.4 |
| 259 | 1-[(E)-3-(3,4-Dichloro-phenyl)-acryloyl]-4-[3-((+, cis)-3-hydroxy-4-methyl-piperidin-1-yl)-propyl]-[1,4]diazepan-5-one | (+,cis)-4-Methyl-piperidin-3-ol (intermediate 85) | 468.3 |
| 260 | 1-[(E)-3-(3,4-Dichloro-phenyl)-acryloyl]-4-[3-((−, cis)-3-hydroxy-4-methyl-piperidin-1-yl)-propyl]-[1,4]diazepan-5-one | (−,cis)-4-Methyl-piperidin-3-ol (intermediate 86) | 468.3 |
| 261 | 1-[(E)-3-(3,4-Dichloro-phenyl)-acryloyl]-4-[3-((+)-4-hydroxy-6-aza-spiro[2.5]oct-6-yl)-propyl]-[1,4]diazepan-5-one | (+)-6-Aza-spiro[2.5]octan-4-ol (intermediate 82) | 480.3 |
| 262 | 1-[(E)-3-(3,4-Dichloro-phenyl)-acryloyl]-4-[3-((−)-4-hydroxy-6-aza-spiro[2.5]oct-6-yl)-propyl]-[1,4]diazepan-5-one | (−)-6-Aza-spiro[2.5]octan-4-ol (intermediate 83) | 480.3 |
| 263 | (rac)-4-(3-{4-[(E)-3-(3,4-Dichloro-phenyl)-acryloyl]-7-oxo-[1,4]diazepan-1-yl}-propyl)-piperazine-2-carboxylic acid methyl ester | (rac)-Piperazine-2-carboxylic acid methyl ester | 497.3 |
| 264 | 1-[(E)-3-(3,4-Dichloro-phenyl)-acryloyl]-4-[3-(4-methyl-3-oxo-piperazin-1-yl)-propyl]-[1,4]diazepan-5-one | 1-Methyl-piperazin-2-one | 467.3 |
| 265 | (rac)-(3-{4-[(E)-3-(3,4-Dichloro-phenyl)-acryloyl]-7-oxo-[1,4]diazepan-1-yl}-propyl)-1-oxa-4,9-diaza-spiro[5.5]undecan-3-one | (rac)-1-Oxa-4,9-diaza-spiro[5.5]undecan-3-one (intermediate 102) | 523.4 |
| 266 | (rac,cis)-1-[(E)-3-(3,4-Dichloro-phenyl)-acryloyl]-4-[3-(3-hydroxy-4-hydroxymethyl-piperidin-1-yl)-propyl]-[1,4]diazepan-5-one | (rac,cis)-4-hydroxymethyl-piperidin-3-ol (intermediate 47) | 484.3 |
| 267 | (rac,cis)-1-[(E)-3-(3,4-Dichloro-phenyl)-acryloyl]-4-[3-(3-hydroxy-4-methoxymethyl-piperidin-1-yl)-propyl]-[1,4]diazepan-5-one | (rac,cis)-4-methoxymethyl-piperidin-3-ol (intermediate 49) | 498.3 |
| 268 | (rac,trans)-1-[(E)-3-(3,4-Dichloro-phenyl)-acryloyl]-4-[3-(3-hydroxy-4-hydroxymethyl-piperidin-1-yl)-propyl]-[1,4]diazepan-5-one | (rac,trans)-4-hydroxymethyl-piperidin-3-ol (intermediate 48) | 484.3 |

-continued

| Example No. | Compound Name | Amine | MS: (MH+) |
|---|---|---|---|
| 269 | (rac,cis)-1-[(E)-3-(3,4-Dichloro-phenyl)-acryloyl]-4-[3-(3-methoxy-4-hydroxymethyl-piperidin-1-yl)-propyl]-[1,4]diazepan-5-one | (rac,cis)-3-methoxymethyl-piperidin-4-ol (intermediate 50) | 498.3 |
| 270 | (rac,cis)-1-[(E)-3-(3,4-Dichloro-phenyl)-acryloyl]-4-[3-(3-hydroxy-4-hydroxymethyl-4-methyl-piperidin-1-yl)-propyl]-[1,4]diazepan-5-one | (rac,cis)-4-hydroxymethyl-4-methyl-piperidin-3-ol (intermediate 52) | 498.3 |
| 271 | (rac,trans)-1-[(E)-3-(3,4-Dichloro-phenyl)-acryloyl]-4-[3-(3-hydroxy-4-hydroxymethyl-4-methyl-piperidin-1-yl)-propyl]-[1,4]diazepan-5-one | (rac,trans)-4-hydroxymethyl-4-methyl-piperidin-3-ol (intermediate 53) | 498.3 |
| 272 | (rac)-1-[(E)-3-(3,4-Dichloro-phenyl)-acryloyl]-4-[3-(5-hydroxy-2-methyl-piperidin-1-yl)-propyl]-[1,4]diazepan-5-one | (rac)-6-methyl-piperidin-3-ol (intermediate 66) | 468.3 |
| 273 | (rac)-1-[(E)-3-(3,4-Dichloro-phenyl)-acryloyl]-4-[3-(5-hydroxy-2-hydroxymethyl-piperidin-1-yl)-propyl]-[1,4]diazepan-5-one | (rac)-6-hydroxymethyl-piperidin-3-ol (intermediate 65) | 484.3 |
| 274 | (rac)-1-[(E)3-(3,4-Dichloro-phenyl)-acryloyl]-4-[3-(3-hydroxy-4,4-dimethyl-piperidin-1-yl)-propyl]-[1,4]diazepan-5-one | (rac)-4,4-dimethyl-piperidin-3-ol (intermediate 97) | 482.3 |
| 275 | (rac,cis)-1-[(E)-3-(3,4-Dichloro-phenyl)-acryloyl]-4-[3-(3-methoxy-tetrahydro pyran-4-ylamino)-propyl]-[1,4]diazepan-5-one | (rac,cis)-3-Methoxy-tetrahydro-pyran-4-ylamine (intermediate 20) | 484.2 |
| 276 | (rac)-1-[(E)-3-(3,4-Dichloro-phenyl)-acryloyl]-4-[3-(3-dimethylamino-piperidin-1-yl)-propyl]-[1,4]diazepan-5-one | (rac)-3-dimethylamino-piperidine | 481.2 |
| 277 | (rac)-1-[(E)-3-(3,4-Dichloro-phenyl)-acryloyl]-4-[3-(3-dimethylamino-pyrollidin-1-yl)-propyl]-[1,4]diazepan-5-one | (rac)-3-dimethylamino-pyrollidine | 467.2 |
| 278 | (rac)-1-[(E)-3-(3,4-Dichloro-phenyl)-acryloyl]-4-[3-(3-diethylamino-pyrollidin-1-yl)-propyl]-[1,4]diazepan-5-one | (rac)-3-diethylamino-pyrollidine | 495.2 |
| 279 | (rac,cis)-1-[(E)-3-(3,4-Dichloro-phenyl)-acryloyl]-4-[3-(3-hydroxy-5-methyl-piperidin-1-yl)-propyl]-[1,4]diazepan-5-one | (rac,cis)-5-methyl-piperidin-3-ol (intermediate 75) | 468.3 |

Examples 280-326

General Procedure for Examples 280-326

A solution of (rac)-1-[(E)-3-(3, 4-Dichloro-phenyl)-acryloyl]-4-oxiranylmethyl-[1,4]diazepan-5-one (example 166A) (0.1 mmol) in DMA (0.5 ml) was added to the appropriate amine (0.15 mmol), which are either commercially available or are described in the intermediate section, and a generous spatula of cesium carbonate added. The reaction was then shaken overnight at 80° C., filtered, and directly purifed purified by preparative HPLC.

| Example No. | Compound Name | Amine | MS: (MH+) |
|---|---|---|---|
| 280 | (rac)-1-[(E)-3-(3,4-Dichloro-phenyl)-acryloyl]-4-[2-hydroxy-3-(3-hydroxy-4-methyl-piperidin-1-yl)-propyl]-[1,4]diazepan-5-one | (rac)-4-methyl-piperidin-3-ol (intermediate 91) | 484.3 |
| 281 | (rac)-1-[(E)-3-(3,4-Dichloro-phenyl)-acryloyl]-4-[2-hydroxy-3-(3-hydroxy-piperidin-1-yl)-propyl]-[1,4]diazepan-5-one | (rac)-3-hydroxypiperidine | 470.2 |
| 282 | (rac)-1-[(E)-3-(3,4-Dichloro-phenyl)-acryloyl]-4-[2-hydroxy-3-((trans)-3-hydroxy-2-methyl-piperidin-1-yl)-propyl]-[1,4]diazepan-5-one | (rac,trans)-2-methyl-piperidin-3-ol (intermediate 87) | 484.3 |

| Example No. | Compound Name | Amine | MS: (MH+) |
|---|---|---|---|
| 283 | (rac)-1-[(E)-3-(3,4-Dichloro-phenyl)-acryloyl]-4-[2-hydroxy-3-(3-methoxy-piperidin-1-yl)-propyl]-[1,4]diazepan-5-one | (rac)-3-methoxypiperidine | 484.3 |
| 284 | (rac)-1-[(E)-3-(3,4-Dichloro-phenyl)-acryloyl]-4-[3-(trans-4-fluoro-3-hydroxy-piperidin-1-yl)-2-hydroxy-propyl]-[1,4]diazepan-5-one | (rac,trans)-4-Fluoro-piperidin-3-ol (intermediate 89) | 488.2 |
| 285 | 1-[(E)-3-(3,4-Dichloro-phenyl)-acryloyl]-4-[2-hydroxy-3-(4-hydroxy-piperidin-1-yl)-propyl]-[1,4]diazepan-5-one | Piperidin-4-ol | 470.2 |
| 286 | (rac)1-[(E)-3-(3,4-Dichloro-phenyl)-acryloyl]-4-[3-(trans-3-fluoro-4-hydroxy-piperidin-1-yl)-2-hydroxy-propyl]-[1,4]diazepan-5-one | (rac,trans)-3-fluoro-piperidin-4-ol (intermediate 90) | 488.3 |
| 287 | (rac)-1-[(E)-3-(3,4-Dichloro-phenyl)-acryloyl]-4-[3-(cis-4-fluoro-3-hydroxy-piperidin-1-yl)-2-hydroxy-propyl]-[1,4]diazepan-5-one | (rac, cis)-3-fluoro-piperidin-4-ol (intermediate 93) | 488.2 |
| 288 | (rac)-1-[(E)-3-(3,4-Dichloro-phenyl)-acryloyl]-4-[2-hydroxy-3-(3-methyl-piperidin-1-yl)-propyl]-[1,4]diazepan-5-one | (rac)-3-methylpiperidine | 468.3 |
| 289 | (rac)-1-[(E)-3-(3,4-Dichloro-phenyl)-acryloyl]-4-[2-hydroxy-3-(3-hydroxymethyl-piperidin-1-yl)-propyl]-[1,4]diazepan-5-one | (rac)-3-hydroxymethyl-piperidine | 484.3 |
| 290 | (rac)-1-[(E)-3-(3,4-Dichloro-phenyl)-acryloyl]-4-[2-hydroxy-3-(2-hydroxymethyl-piperidin-1-yl)-propyl]-[1,4]diazepan-5-one | (rac)-2-hydroxymethyl-piperidine | 484.3 |
| 291 | (rac)-(1-[(E)-3-(3,4-Dichloro-phenyl)-acryloyl]-4-[2-hydroxy-3-(4-hydroxymethyl-piperidin-1-yl)-propyl]-[1,4]diazepan-5-one | Piperidin-4-ol | 484.3 |
| 292 | (rac)-1-[(E)-3-(3,4-Dichloro-phenyl)-acryloyl]-4-[2-hydroxy-3-(3-hydroxy-pyrrolidin-1-yl)-propyl]-[1,4]diazepan-5-one | (rac)-3-hydroxy-pyrrolidine | 456.2 |
| 293 | (rac)-1-[(E)-3-(3,4-Dichloro-phenyl)-acryloyl]-4-[2-hydroxy-3-(3-methoxymethyl-piperidin-1-yl)-propyl]-[1,4]diazepan-5-one | (rac)-3-methoxymethyl-piperidine | 498.3 |
| 294 | (rac)-[1-(3-{4-[(E)-3-(3,4-Dichloro-phenyl)-acryloyl]-7-oxo-[1,4]diazepan-1-yl}-2-hydroxy-propyl)-piperidin-4-yl]-carbamic acid methyl ester | Piperidin-4-yl-carbamic acid methylester (intermediate 38) | 527.3 |
| 295 | (rac)-[1-(3-{4-[(E)-3-(3,4-Dichloro-phenyl)-acryloyl]-7-oxo-[1,4]diazepan-1-yl}-2-hydroxy-propyl)-piperidin-4-yl]-methyl-carbamic acid methyl ester | Methyl-piperidin-4-yl-carbamic acid methyl ester (intermediate 39) | 541.3 |
| 296 | (rac)-1-[(E)-3-(3,4-Dichloro-phenyl)-acryloyl]-4-[2-hydroxy-3-(4-isopropyl-piperazin-1-yl)-propyl]-[1,4]diazepan-5-one | 1-Isopropyl-piperazine | 497.4 |
| 297 | (rac)-1-[(E)-3-(3,4-Dichloro-phenyl)-acryloyl]-4-[3-(4-cyclopropyl-piperazin-1-yl)-2-hydroxy-propyl]-[1,4]diazepan-5-one | 1-Cyclopropyl-piperazine | 495.3 |
| 298 | (rac)-1-[(E)-3-(3,4-Dichloro-phenyl)-acryloyl]-4-[3-(4-cyclopentyl-piperazin-1-yl)-2-hydroxy-propyl]-[1,4]diazepan-5-one | 1-Cyclopentyl-piperazine | 523.4 |
| 299 | (rac)-1[(E)-3-(3,4-Dichloro-phenyl)-acryloyl]-4-{2-hydroxy-3-[4-(2-methoxy-ethyl)-piperazin-1-yl]-propyl}-[1,4]diazepan-5-one | 1-(2-Methoxy-ethyl)-piperazine | 513.4 |
| 300 | (rac)-1-[(E)-3-(3,4-Dichloro-phenyl)-acryloyl]-4-[2-hydroxy-3-(4-hydroxy-3-methyl-piperidin-1-yl)-propyl]-[1,4]diazepan-5-one | (rac)-3-methyl-piperidin-4-ol (intermediate 94) | 484.3 |
| 301 | (rac)-1-[(E)-3-(3,4-Dichloro-phenyl)-acryloyl]-4-[2-hydroxy-3-(4-isopropyl-3-methyl-piperazin-1-yl)-propyl]-[1,4]diazepan-5-one | (rac)-1-Isopropyl-2-methyl-piperazine | 511.3 |

-continued

| Example No. | Compound Name | Amine | MS: (MH+) |
|---|---|---|---|
| 302 | (rac)-1-[(E)-3-(3,4-Dichloro-phenyl)-acryloyl]-4-[2-hydroxy-3-(4-methyl-piperazin-1-yl)-propyl]-[1,4]diazepan-5-one | 1-Methyl-piperazine | 469.3 |
| 303 | (rac)-1-[(E)-3-(3,4-Dichloro-phenyl)-acryloyl]-4-[2-hydroxy-3-(3-hydroxy-3-methyl-piperidin-1-yl)-propyl]-[1,4]diazepan-5-one | (rac)-3-methyl-piperidin-3-ol (intermediate 101) | 484.3 |
| 304 | (rac)-1-[(E)-3-(3,4-Dichloro-phenyl)-acryloyl]-4-[2-hydroxy-3-(4-methoxymethyl-piperidin-1-yl)-propyl]-[1,4]diazepan-5-one | 4-methoxymethyl-piperidine | 498.3 |
| 305 | (rac)-1-[(E)-3-(3,4-Dichloro-phenyl)-acryloyl]-4-[2-hydroxy-3-(3-hydroxymethyl-3-methyl-piperidin-1-yl)-propyl]-[1,4]diazepan-5-one | (rac)-(3-methyl-piperidin-3-yl) methanol (intermediate 30) | 498.3 |
| 306 | (rac)-1-[(E)-3-(3,4-Dichloro-phenyl)-acryloyl]-4-[2-hydroxy-3-(3-methoxymethyl-3-methyl-piperidin-1-yl)-propyl]-[1,4]diazepan-5-one | (rac)-3-methoxymethyl-3-methyl-piperidine (intermediate 31) | 512.3 |
| 307 | (rac)-1-[(E)-3-(3,4-Dichloro-phenyl)-acryloyl]-4-[2-hydroxy-3-(2-hydroxy-2-hydroxymethyl-piperidin-1-yl)-propyl]-[1,4]diazepan-5-one | (rac)-(2-methyl-piperidin-2-yl) methanol (intermediate 34) | 498.3 |
| 308 | (rac)-1-[(E)-3-(3,4-Dichloro-phenyl)-acryloyl]-4-[2-hydroxy-3-(cis-4-hydroxy-2-hydroxymethyl-piperidin-1-yl)-propyl]-[1,4]diazepan-5-one | (rac,cis)-2-hydroxymethyl-piperidin-4-ol (intermediate 45) | 500.3 |
| 309 | (rac)-1-[(E)-3-(3,4-Dichloro-phenyl)-acryloyl]-4-[2-hydroxy-3-(4-hydroxy-6-aza-spiro[2.5]oct-6-yl)-propyl]-[1,4]diazepan-5-one | (rac)-6-Aza-spiro[2.5]octan-4-ol (intermediate 81) | 496.5 |
| 310 | (rac)-1-[(E)-3-(3,4-Dichloro-phenyl)-acryloyl]-4-[2-hydroxy-3-(4-hydroxy-3-hydroxymethyl-piperidin-1-yl)-propyl]-[1,4]diazepan-5-one | (rac)-3-hydroxymethyl-piperidin-4-ol (intermediate 35) | 500.5 |
| 311 | (rac)-1-[(E)-3-(3,4-Dichloro-phenyl)-acryloyl]-4-[2-hydroxy-3-(4-hydroxy-3-methoxymethyl-piperidin-1-yl)-propyl]-[1,4]diazepan-5-one | (rac)-3-methoxymethyl-piperidin-4-ol (intermediate 35) | 514.5 |
| 312 | (rac)-1-[(E)-3-(3,4-Dichloro-phenyl)-acryloyl]-4-[2-hydroxy-3-(4-methoxy-3-methoxymethyl-piperidin-1-yl)-propyl]-[1,4]diazepan-5-one | (rac)-4-methoxy-3-methoxymethyl-piperidine (intermediate 37) | 528.5 |
| 313 | (rac)1-[(E)-3-(3,4-Dichloro-phenyl)-acryloyl]-4-[2-hydroxy-3-(trans-4-hydroxy-2-hydroxymethyl-piperidin-1-yl)-propyl]-[1,4]diazepan-5-one | (rac,trans)-2-hydroxymethyl-piperidin-4-ol (intermediate 46) | 500.5 |
| 314 | (rac)-N-[1-(3-{4-[(E)-3-(3,4-Dichloro-phenyl)-acryloyl]-7-oxo-[1,4]diazepan-1-yl}-2-hydroxy-propyl)-piperidin-4-yl]-acetamide | N-Piperidin-4-yl-acetamide | 511.5 |
| 315 | (rac)-1-[(E)-3-(3,4-Dichloro-phenyl)-acryloyl]-4-[2-hydroxy-3-(trans-3-hydroxy-4-methyl-piperidin-1-yl)-propyl]-[1,4]diazepan-5-one | (rac,trans)-4-methyl-piperidin-3-ol (intermediate 100) | 484.5 |
| 316 | (rac)-1-[(E)-3-(3,4-Dichloro-phenyl)-acryloyl]-4-[2-hydroxy-3-(trans-4-hydroxy-3-methyl-piperidin-1-yl)-propyl]-[1,4]diazepan-5-one | (rac,trans)-3-methyl-piperidin-4-ol (intermediate 95) | 484.5 |
| 317 | (rac)1-[(E)-3-(3,4-Dichloro-phenyl)-acryloyl]-4-[2-hydroxy-3-(8-hydroxy-5-aza-spiro[2.5]oct-5-yl)-propyl]-[1,4]diazepan-5-one | (rac)-5-Aza-spiro[2.5]octan-8-ol (intermediate 81) | 496.3 |
| 318 | (rac)-1-[3-(3,4-Dichloro-phenyl)-acryloyl]-4-[2-hydroxy-3-(cis-4-hydroxy-3-methyl-piperidin-1-yl)-propyl]-[1,4]diazepan-5-one | (rac,cis)-3-methyl-piperidin-4-ol (intermediate 96) | 484.3 |
| 319 | (rac)-1-[(E)-3-(3,4-Dichloro-phenyl)-acryloyl]-4-[2-hydroxy-3-(4-hydroxymethyl-4-methyl-piperidin-1-yl)-propyl]-[1,4]diazepan-5-one | (4-methyl-piperidin-4-yl) methanol (intermediate 32) | 498.3 |
| 320 | (rac)-1-[(E)-3-(3,4-Dichloro-phenyl)-acryloyl]-4-{2-hydroxy-3-[(2-hydroxy-ethyl)-methyl-amino]-propyl}-[1,4]diazepan-5-one | 2-Methylamino-ethanol | 444.3 |

-continued

| Example No. | Compound Name | Amine | MS: (MH+) |
|---|---|---|---|
| 321 | (rac)-1-[(E)-3-(3,4-Dichloro-pheny)-acryloyl]-4-{3-[ethyl-(2-hydroxy-ethyl)-amino]-2-hydroxy-propyl}-[1,4]diazepan-5-one | 2-Ethylamino-ethanol | 458.3 |
| 322 | (rac)-1-[3-(3,4-Dichloro-phenyl)-acryloyl]-4-[2-hydroxy-3-(2-hydroxymethyl-2-methyl-pyrrolidin-1-yl)-propyl]-[1,4]diazepan-5-one | (rac)-2-hydroxymethyl-2-methyl-pyrrolidine | 484.3 |
| 323 | (rac)-[1-(3-{4-[(E)-3-(3,4-Dichloro-phenyl)-acryloyl]-7-oxo-[1,4]diazepan-1-yl}-2-hydroxy-propyl)-piperidin-3-yl]-carbamic acid methyl ester | (rac)-Piperidin-3-yl-carbamic acid methyl ester (intermediate 40) | 527.3 |
| 324 | (rac)-1-[(E)-3-(3,4-Dichloro-phenyl)-acryloyl]-4-[2-hydroxy-3-(4-hydroxy-3,3-dimethyl-piperidin-1-yl)-propyl]-[1,4]diazepan-5-one | (rac)-3,3-dimethyl-piperidin-4-ol (intermediate 97) | 498.3 |
| 325 | (rac)-1-[3-(3,4-Dichloro-phenyl)-acryloyl]-4-[2-hydroxy-3-(4-isobutyl-piperazin-1-yl)-propyl]-[1,4]diazepan-5-one | 1-Isobutyl-piperazine | 511.4 |
| 326 | (rac)-1-[(E)-3-(3,4-Dichloro-phenyl)-acryloyl]-4-[2-hydroxy-3-(1-oxa-8-aza-spiro[4.5]dec-8-yl)-propyl]-[1,4]diazepan-5-one | 1-Oxa-8-aza-spiro[4.5]decane (intermediate 27) | 510.3 |

Examples 327-335

General Procedure for Examples 327-335

A solution of 1-[(E)-3-(3,4-Dichloro-phenyl)-acryloyl]-4-(R)-1-oxiranylmethyl-[1,4]diazepan-5-one (example 167C) (0.1 mmol) in DMA (0.5 ml) was added to the appropriate amine (0.15 mmol), which are either commercially available or are described in the intermediate section, and a generous spatula of cesium carbonate added. The reaction was then shaken overnight at 80° C., filtered, and directly purifed purified by preparative HPLC.

| Example No. | Compound Name | Amine | MS: (MH+) |
|---|---|---|---|
| 327 | 1-[(E)-3-(3,4-Dichloro-phenyl)-acryloyl]-4-[(S)-2-hydroxy-3-((−)-4-hydroxy-6-aza-spiro[2.5]oct-6-yl)-propyl]-[1,4]diazepan-5-one | (−)-6-Aza-spiro[2.5]octan-4-ol (intermediate 83) | 496.3 |
| 328 | 1-[(E)-3-(3,4-Dichloro-phenyl)-acryloyl]-4-[(S)-2-hydroxy-3-(cis-3-hydroxy-4-hydroxymethyl-piperidin-1-yl)-propyl]-[1,4]diazepan-5-one | (rac,cis)-4-hydroxymethyl-piperidin-3-ol (intermediate 47) | 500.3 |
| 329 | 1-[(E)-3-(3,4-Dichloro-phenyl)-acryloyl]-4-[(S)-2-hydroxy-3-(cis-3-hydroxy-4-methoxymethyl-piperidin-1-yl)-propyl]-[1,4]diazepan-5-one | (rac,cis)-4-methoxymethyl-piperidin-3-ol (intermediate 49) | 514.3 |
| 330 | 1-[(E)-3-(3,4-Dichloro-phenyl)-acryloyl]-4-[(S)-2-hydroxy-3-((cis)-3-hydroxy-4-hydroxymethyl-4-methyl-piperidin-1-yl)-propyl]-[1,4]diazepan-5-one | (rac,cis)-4-hydroxymethyl-4-methyl-piperidin-3-ol (intermediate 52) | 514.3 |
| 331 | 1-[(E)-3-(3,4-Dichloro-phenyl)-acryloyl]-4-[(S)-2-hydroxy-3-((trans)-3-hydroxy-4-hydroxymethyl-4-methyl-piperidin-1-yl)-propyl]-[1,4]diazepan-5-one | (rac,trans)-4-hydroxymethyl-4-methyl-piperidin-3-ol (intermediate 53) | 514.3 |
| 332 | 1-[(E)-3-(3,4-Dichloro-phenyl)-acryloyl]-4-[(S)-2-hydroxy-3-((+)-4-hydroxy-6-aza-spiro[2.5]oct-6-yl)-propyl]-[1,4]diazepan-5-one | (+)-6-Aza-spiro[2.5]octan-4-ol (intermediate 82) | 496.3 |
| 333 | 1-[(E)-3-(3,4-Dichloro-phenyl)-acryloyl]-4-[(S)-2-hydroxy-3-(trans-3-hydroxy-4-hydroxymethyl-piperidin-1-yl)-propyl]-[1,4]diazepan-5-one | (rac,trans)-4-hydroxymethyl-piperidin-3-ol (intermediate 48) | 500.3 |
| 334 | 1-[(E)-3-(3,4-Dichloro-phenyl)-acryloyl]-4-[(S)-2-hydroxy-3-(3-hydroxy-4,4-dimethyl-piperidin-1-yl)-propyl]-[1,4]diazepan-5-one | (rac)-4,4-dimethyl-piperidin-3-ol (intermediate 84) | 498.3 |

| Example No. | Compound Name | Amine | MS: (MH+) |
|---|---|---|---|
| 335 | 1-[(E)-3-(3,4-Dichloro-phenyl)-acryloyl]-4-[(S)-2-hydroxy-3-(cis-3-hydroxy-5-methyl-piperidin-1-yl)-propyl]-[1,4]diazepan-5-one | (rac, cis)-5-methyl-piperidin-3-ol (intermediate 75) | 484.3 |

Examples 336-344

General Procedure for Examples 336-344

A solution of 1-[(E)-3-(3-Chloro-4-fluoro-phenyl)-acryloyl]-4-((R)-2-oxiranyl-ethyl)-[1,4]diazepan-5-one (intermediate 56) (0.1 mmol) in DMA (0.5 ml) was added to the appropriate amine (0.15 mmol), which are either commercially available or are described in the intermediate section, and a generous spatula of cesium carbonate added. The reaction was then shaken overnight at 80° C., filtered, and directly purifed purified by preparative HPLC.

| Example No. | Compound Name | Amine | MS: (MH+) |
|---|---|---|---|
| 336 | 1-[(E)-3-(3-Chloro-4-fluoro-phenyl)-acryloyl]-4-[(S)-2-hydroxy-3-((−)-4-hydroxy-6-aza-spiro[2.5]oct-6-yl)-propyl]-[1,4]diazepan-5-one | (−)-6-Aza-spiro[2.5]octan-4-ol (intermediate 83) | 480.3 |
| 337 | 1-[(E)-3-(3-Chloro-4-fluoro-phenyl)-acryloyl]-4-[(S)-2-hydroxy-3-(cis-3-hydroxy-4-hydroxymethyl-piperidin-1-yl)-propyl]-[1,4]diazepan-5-one | (rac,cis)-4-hydroxymethyl-piperidin-3-ol (intermediate 47) | 484.3 |
| 338 | 1-[(E)-3-(3-Chloro-4-fluoro-phenyl)-acryloyl]-4-[(S)-2-hydroxy-3-(cis-3-hydroxy-4-methoxymethyl-piperidin-1-yl)-propyl]-[1,4]diazepan-5-one | (rac,cis)-4-methoxymethyl-piperidin-3-ol (intermediate 49) | 498.3 |
| 339 | 1-[(E)-3-(3-Chloro-4-fluoro-phenyl)-acryloyl]-4-[(S)-2-hydroxy-3-(trans-3-hydroxy-4-hydroxymethyl-piperidin-1-yl)-propyl]-[1,4]diazepan-5-one | (rac,trans)-4-hydroxymethyl-piperidin-3-ol (intermediate 48) | 484.3 |
| 340 | 1-[(E)-3-(3-Chloro-4-fluoro-phenyl)-acryloyl]-4-[(S)-2-hydroxy-3-((cis)-3-hydroxy-4-hydroxymethyl-4-methyl-piperidin-1-yl)-propyl]-[1,4]diazepan-5-one | (rac,cis)-4-hydroxymethyl-4-methyl-piperidin-3-ol (intermediate 52) | 498.3 |
| 341 | 1-[(E)-3-(3-Chloro-4-fluoro-phenyl)-acryloyl]-4-[(S)-2-hydroxy-3-((trans)-3-hydroxy-4-hydroxymethyl-4-methyl-piperidin-1-yl)-propyl]-[1,4]diazepan-5-one | (rac,trans)-4-hydroxymethyl-4-methyl-piperidine-3-ol (intermediate 53) | 498.3 |
| 342 | 1-[(E)-3-(3-Chloro-4-fluoro-phenyl)-acryloyl]-4-[(S)-2-hydroxy-3-((+)-4-hydroxy-6-aza-spiro[2.5]oct-6-yl)-propyl]-[1,4]diazepan-5-one | (+)-6-Aza-Spiro[2.5]octan-4-ol (intermediate 82) | 480.3 |
| 343 | 1-[(E)-3-(3-Chloro-4-fluoro-phenyl)-acryloyl]-4-[(S)-2-hydroxy-3-(3-hydroxy-4,4-dimethyl-piperidin-1-yl)-propyl]-[1,4]diazepan-5-one | (rac)-4,4-dimethyl-piperidin-3-ol (intermediate 84) | 482.3 |
| 344 | 1-[(E)-3-(3-Chloro-4-fluoro-phenyl)-acryloyl]-4-[(S)-2-hydroxy-3-(cis-3-hydroxy-5-methyl-piperidin-1-yl)-propyl]-[1,4]diazepan-5-one | (rac,cis)-5-methyl-piperidin-3-ol (intermediate 75) | 468.3 |

Examples 345-357

General Procedure for Examples 345-357

A solution of 3-{4-[(E)-3-(3,4-dichloro-phenyl)-acryloyl]-7-oxo-[1,4]diazepan-1-yl}-acetaldehyde (intermediate 3) (0.1 mmol) in DCE (0.5 ml) was added to the appropriate amine (0.1 mmol), which are either commercially available or are described in the intermediate section, followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

| Example No. | Compound Name | Amine | MS: (MH⁺) |
|---|---|---|---|
| 345 | (rac)-1-[(E)-3-(3,4-Dichloro-phenyl)-acryloyl]-4-[2-(3-dimethylamino-piperidin-1-yl)-ethyl]-[1,4]diazepan-5-one | (rac)-3-dimethylamino-piperidine | 469.2 |
| 346 | (rac)-1-[(E)-3-(3,4-Dichloro-phenyl)-acryloyl]-4-[2-(3-dimethylamino-pyrollidin-1-yl)-ethyl]-[1,4]diazepan-5-one | (rac)-3-dimethylamino-pyrollidine | 453.2 |
| 347 | (rac)-1-[(E)-3-(3,4-Dichloro-phenyl)-acryloyl]-4-[2-(3-diethylamino-pyrollidin-1-yl)-ethyl]-[1,4]diazepan-5-one | (rac)-3-diethylamino-pyrollidine | 481.2 |
| 348 | (rac)-1-[(E)-3-(3,4-Dichloro-phenyl)-acryloyl]-4-[2-(2-methyl-pyrrolidin-1-yl)-ethyl]-[1,4]diazepan-5-one | (rac)-2-methyl-pyrrolidine | 424.3 |
| 349 | (rac)1-[(E)-3-(3,4-Dichloro-phenyl)-acryloyl]-4-[2-(trans-2,5-dimethyl-pyrrolidin-1-yl)-ethyl]-[1,4]diazepan-5-one | (rac,trans)-2,5-dimethyl-pyrrolidine | 438.3 |
| 350 | (rac)-1-[(E)-3-(3,4-Dichloro-phenyl)-acryloyl]-4-[2-(2-hydroxymethyl-2-methyl-pyrrolidin-1-yl)-ethyl]-[1,4]diazepan-5-one | (rac)-2-hydroxymethyl-2-methyl-pyrrolidine | 454.3 |
| 351 | (rac)-[1-(2-{4-[(E)-3-(3,4-Dichloro-phenyl)-acryloyl]-7-oxo-[1,4]diazepan-1-yl}-ethyl)-piperidin-3-yl]-carbamic acid methyl ester | (rac)-Piperidin-3-yl-carbamic acid methyl ester (intermediate 40) | 497.3 |
| 352 | (rac)-1-[(E)-3-(3,4-Dichloro-phenyl)-acryloyl]-4-[2-(4-hydroxy-3,3-dimethyl-piperidin-1-yl)-ethyl]-[1,4]diazepan-5-one | (rac)-3,3-dimethyl-piperidin-4-ol (intermediate 97) | 468.3 |
| 353 | 1-[(E)-3-(3,4-Dichloro-phenyl)-acryloyl]-4-[2-(4-isobutyl-piperazin-1-yl)-ethyl]-[1,4]diazepan-5-one | 1-Isobutyl-piperazine | 481.3 |
| 354 | (rac)-N-[1-(2-{4-[(E)-3-(3,4-Dichloro-phenyl)-acryloyl]-7-oxo-[1,4]diazepan-1-yl}-ethyl)-piperidin-3-yl]-acetamide | (rac)-N-Piperidin-3-yl-acetamide | 481.3 |
| 355 | (rac,trans)-1-[(E)-3-(3,4-Dichloro-phenyl)-acryloyl]-4-[2-(2-hydroxy-cyclohexylamino)-ethyl]-[1,4]diazepan-5-one | (rac,trans)-2-hydroxy-cyclohexylamine | 454.2 |
| 356 | 4-(2-Cyclohexylamino-ethyl)-1-[(E)-3-(3,4-dichloro-phenyl)-acryloyl]-[1,4]diazepan-5-one | cyclohexylamine | 454.2 |
| 357 | (rac,cis)-1-[(E)-3-(3,4-Dichloro-phenyl)-acryloyl]-4-[2-(2-hydroxy-cyclohexylamino)-ethyl]-[1,4]diazepan-5-one | (rac,cis)-2-hydroxy-cyclohexylamine | 454.2 |

Examples 358-381

General Procedure for Examples 358-381

A solution of (rac)-1-[(E)-3-(3,4-dichloro-phenyl)-acryloyl]-4-oxiranylmethyl-[1,4]diazepan-5-one (example 166A) (0.1 mmol) in DMA (0.5 ml) was added to the appropriate amine (0.15 mmol), which are either commercially available or are described in the intermediate section, and a generous spatula of cesium carbonate added. The reaction was then shaken overnight at 80° C., filtered, and directly purifed purified by preparative HPLC.

| Example No. | Compound Name | Amine | MS: (MH+) |
|---|---|---|---|
| 358 | (rac)-1-[(E)-3-(3,4-Dichloro-phenyl)-acryloyl]-4-[3-hydroxy-4-(4-hydroxy-3-methyl-piperidin-1-yl)-butyl]-[1,4]diazepan-5-one | (rac)-3-methyl-piperidin-4-ol (intermediate 94) | 498.3 |
| 359 | (rac)-1-[(E)-3-(3,4-Dichloro-phenyl)-acryloyl]-4-[3-hydroxy-4-(3-hydroxy-4-methyl-piperidin-1-yl)-butyl]-[1,4]diazepan-5-one | (rac)-4-methyl-piperidin-3-ol (intermediate 91) | 498.3 |
| 360 | (rac)-1-[(E)-3-(3,4-Dichloro-phenyl)-acryloyl]-4-[3-hydroxy-4-(4-methoxymethyl-piperidin-1-yl)-butyl]-[1,4]diazepan-5-one | 4-methoxymethyl-piperidine | 512.3 |
| 361 | (rac)-1-[(E)-3-(3,4-Dichloro-phenyl)-acryloyl]-4-[3-hydroxy-4-(3-methoxymethyl-piperidin-1-yl)-butyl]-[1,4]diazepan-5-one | (rac)-3-methoxymethyl-piperidine | 512.3 |
| 362 | 1-[(E)-3-(3,4-Dichloro-phenyl)-acryloyl]-4-[3-hydroxy-4-(trans-3-hydroxy-2-methyl-piperidin-1-yl)-butyl]-[1,4]diazepan-5-one | (rac,trans)-2-methyl-piperidin-3-ol (intermediate 87) | 498.3 |
| 363 | (rac)-1-[(E)-3-(3,4-Dichloro-phenyl)-acryloyl]-4-[3-hydroxy-4-(2-hydroxymethyl-2-methyl-piperidin-1-yl)-butyl]-[1,4]diazepan-5-one | (rac)-(2-methyl-piperidin-2-yl)-methanol (intermediate 34) | 512.3 |
| 364 | (rac)-[1-(4-{4-[(E)-3-(3,4-Dichloro-phenyl)-acryloyl]-7-oxo-[1,4]diazepan-1-yl}-2-hydroxy-butyl)-piperidin-4-yl]-carbamic acid methyl ester | Piperidin-4-yl-carbamic acid methylester (intermediate 38) | 541.3 |
| 365 | (rac)-1-[(E)-3-(3,4-Dichloro-phenyl)-acryloyl]-4-[4-(trans-4-fluoro-3-hydroxy-piperidin-1-yl)-3-hydroxy-butyl]-[1,4]diazepan-5-one | (rac,trans)-4-Fluoro-piperidin-3-ol (intermediate 89) | 502.3 |
| 366 | (rac)-1-[(E)-3-(3,4-Dichloro-phenyl)-acryloyl]-4-[3-hydroxy-4-(4-hydroxy-3-hydroxymethyl-piperidin-1-yl)-butyl]-[1,4]diazepan-5-one | (rac)-3-hydroxymethyl-piperidin-4-ol (intermediate 35) | 514.5 |
| 367 | (rac)-1-[(E)-3-(3,4-Dichloro-phenyl)-acryloyl]-4-[3-hydroxy-4-(4-hydroxy-3-methoxymethyl-piperidin-1-yl)-butyl]-[1,4]diazepan-5-one | (rac)-3-methoxymethyl-piperidin-4-ol (intermediate 36) | 528.5 |
| 368 | (rac)-1-[(E)-3-(3,4-Dichloro-phenyl)-acryloyl]-4-[3-hydroxy-4-(4-methoxy-3-methoxymethyl-piperidin-1-yl)-butyl]-[1,4]diazepan-5-one | (rac)-4-methoxy-3-methoxymethyl piperidine (intermediate 37) | 542.5 |
| 369 | (rac)-1-[(E)-3-(3,4-Dichloro-phenyl)-acryloyl]-4-[3-hydroxy-4-(trans-4-hydroxy-2-hydroxymethyl-piperidin-1-yl)-butyl]-[1,4]diazepan-5-one | (rac,trans)-2-hydroxymethyl-piperidin-4-ol (intermediate 46) | 514.5 |
| 370 | (rac)-N-[1-(4-{4-[(E)-3-(3,4-Dichloro-phenyl)-acryloyl]-7-oxo-[1,4]diazepan-1-yl}-2-hydroxy-butyl)-piperidin-4-yl]-acetamide | N-Piperidin-4-yl-acetamide | 525.5 |
| 371 | (rac)-1-[(E)-3-(3,4-Dichloro-phenyl)-acryloyl]-4-[3-hydroxy-4-(trans-3-hydroxy-4-methyl-piperidin-1-yl)-butyl]-[1,4]diazepan-5-one | (rac,trans)-4-methyl-piperidin-3-ol (intermediate 100) | 498.5 |
| 372 | (rac)-1-[(E)-3-(3,4-Dichloro-phenyl)-acryloyl]-4-[3-hydroxy-4-(trans-4-hydroxy-3-methyl-piperidin-1-yl)-butyl]-[1,4]diazepan-5-one | (rac,trans)-3-methyl-piperidin-4-ol (intermediate 95) | 498.5 |
| 373 | (rac)-1-[(E)-3-(3,4-Dichloro-phenyl)-acryloyl]-4-[3-hydroxy-4-(2-methoxymethyl-piperidin-1-yl)-butyl]-[1,4]diazepan-5-one | (rac)-2-methoxymethyl-piperidine | 512.3 |

| Example No. | Compound Name | Amine | MS: (MH+) |
|---|---|---|---|
| 374 | (rac)-1-[(E)-3-(3,4-Dichloro-phenyl)-acryloyl]-4-[3-hydroxy-4-(2-hydroxymethyl-piperidin-1-yl)-butyl]-[1,4]diazepan-5-one | (rac)-2-hydroxymethyl-piperidine | 498.3 |
| 375 | (rac)-1-[(E)-3-(3,4-Dichloro-phenyl)-acryloyl]-4-[3-hydroxy-4-(2-methyl-piperidin-1-yl)-butyl]-[1,4]diazepan-5-one | (rac)-2-methylpiperidine | 482.3 |
| 376 | (rac)-1-[(E)-3-(3,4-Dichloro-phenyl)-acryloyl]-4-[3-hydroxy-4-(3-methyl-piperidin-1-yl)-butyl]-[1,4]diazepan-5-one | (rac)-3-methylpiperidine | 482.3 |
| 377 | (rac)-1-[(E)-3-(3,4-Dichloro-phenyl)-acryloyl]-4-[3-hydroxy-4-(4-methyl-piperidin-1-yl)-butyl]-[1,4]diazepan-5-one | 4-methylpiperidine | 482.3 |
| 378 | (rac)-1-[(E)-3-(3,4-Dichloro-phenyl)-acryloyl]-4-[3-hydroxy-4-(3-hydroxymethyl-piperidin-1-yl)-butyl]-[1,4]diazepan-5-one | (rac)-3-hydroxymethyl-piperidine | 498.3 |
| 379 | (rac)-1-[(E)-3-(3,4-Dichloro-phenyl)-acryloyl]-4-[3-hydroxy-4-(4-hydroxymethyl-piperidin-1-yl)-butyl]-[1,4]diazepan-5-one | 4-hydroxymethyl-piperidine | 498.3 |
| 380 | (rac)-1-[(E)-3-(3,4-Dichloro-phenyl)-acryloyl]-4-[3-hydroxy-4-(3-methoxymethyl-3-methyl-piperidin-1-yl)-butyl]-[1,4]diazepan-5-one | (rac)-3-methoxymethyl-3-methyl-piperidine (intermediate 31) | 526.4 |
| 381 | (rac)-1-[(E)-3-(3,4-Dichloro-phenyl)-acryloyl]-4-[3-hydroxy-4-(2-hydroxymethyl-2-methyl-pyrrolidin-1-yl)-butyl]-[1,4]diazepan-5-one | (rac)-2-hydroxymethyl-2-methyl-pyrrolidine | 498.3 |

Examples 382-409

General Procedure for Examples 382-409

A solution of 1-[(E)-3-(3-Chloro-4-fluoro-phenyl)-acryloyl]-4-(4-iodo-butyl)-[1,4]diazepan-5-one (intermediate 99) (0.1 mmol) in DMA (0.5 ml) was added to the appropriate amine (0.15 mmol), which are either commercially available or are described in the intermediate section, and a generous spatula of cesium carbonate and sodium iodide added. The reaction was then shaken at room termperature for 1 h, then raised to 80° C. for a further 1 h, filtered, and directly purifed purified by preparative HPLC.

| Example No. | Compound Name | Amine | MS: (MH+) |
|---|---|---|---|
| 382 | 1-[(E)-3-(3-Chloro-4-fluoro-phenyl)-acryloyl]-4-(4-piperidin-1-yl-butyl)-[1,4]diazepan-5-one | Piperidine | 436.3 |
| 383 | (rac)-1-[(E)-3-(3-Chloro-4-fluoro-phenyl)-acryloyl]-4-[4-(3-hydroxy-piperidin-1-yl)-butyl]-[1,4]diazepan-5-one | (rac)-piperidin-3-ol | 452.3 |
| 384 | 1-[(E)-3-(3-Chloro-4-fluoro-phenyl)-acryloyl]-4-[4-(4-hydroxy-piperidin-1-yl)-butyl]-[1,4]diazepan-5-one | Piperidin-4-ol | 452.3 |
| 385 | (rac)-1-[(E)-3-(3-Chloro-4-fluoro-phenyl)-acryloyl]-4-[4-(3-hydroxymethyl-piperidin-1-yl)-butyl]-[1,4]diazepan-5-one | (rac)-3-hydroxymethyl-piperidine | 466.3 |
| 386 | 1-[(E)-3-(3-Chloro-4-fluoro-phenyl)-acryloyl]-4-[4-(4-hydroxymethyl-piperidin-1-yl)-butyl]-[1,4]diazepan-5-one | 4-hydroxymethyl-piperidine | 466.3 |
| 387 | (rac)-1-[(E)-3-(3-Chloro-4-fluoro-phenyl)-acryloyl]-4-[4-(2-hydroxymethyl-piperidin-1-yl)-butyl]-[1,4]diazepan-5-one | (rac)-2-hydroxymethyl-piperidine | 466.3 |
| 388 | (rac,trans)-1-[(E)-3-(3-Chloro-4-fluoro-phenyl)-acryloyl]-4-[4-(3-hydroxy-2-methyl-piperidin-1-yl)-butyl]-[1,4]diazepan-5-one | (rac,trans)-2-methyl-piperidin-3-ol (intermediate 87) | 466.3 |

-continued

| Example No. | Compound Name | Amine | MS: (MH+) |
|---|---|---|---|
| 389 | (rac,trans)-1-[(E)-3-(3-Chloro-4-fluoro-phenyl)-acryloyl]-4-[4-(4-fluoro-3-hydroxy-piperidin-1-yl)-butyl]-[1,4]diazepan-5-one | (rac,trans)-4-Fluoro-piperidin-3-ol (intermediate 89) | 470.3 |
| 390 | (rac,cis)-1-[(E)-3-(3-Chloro-4-fluoro-phenyl)-acryloyl]-4-[4-(3-fluoro-4-hydroxy-piperidin-1-yl)-butyl]-[1,4]diazepan-5-one | (rac,cis)-3-fluoro-piperidin-4-ol (intermediate 93) | 470.3 |
| 391 | (rac)-1-[(E)-3-(3-Chloro-4-fluoro-phenyl)-acryloyl]-4-[4-(3-hydroxy-3-methyl-piperidin-1-yl)-butyl]-[1,4]diazepan-5-one | (rac)-3-methyl-piperidin-3-ol (intermediate 101) | 466.3 |
| 392 | (rac)-1-[(E)-3-(3-Chloro-4-fluoro-phenyl)-acryloyl]-4-[4-(3-methoxymethyl-piperidin-1-yl)-butyl]-[1,4]diazepan-5-one | (rac)-3-methoxymethyl-piperidine | 480.3 |
| 393 | (rac)-1-[(E)-3-(3-Chloro-4-fluoro-phenyl)-acryloyl]-4-[4-(3-hydroxy-pyrrolidin-1-yl)-butyl]-[1,4]diazepan-5-one | (rac)-3-hydroxy-pyrrolidine | 438.3 |
| 394 | (rac,trans)-1-[(E)-3-(3-Chloro-4-fluoro-phenyl)-acryloyl]-4-[4-(3-fluoro-4-hydroxy-piperidin-1-yl)-butyl]-[1,4]diazepan-5-one | (rac,trans)-3-fluoro-piperidin-4-ol (intermediate 90) | 470.3 |
| 395 | (rac)-1-[(E)-3-(3-Chloro-4-fluoro-phenyl)-acryloyl]-4-[4-(3-methoxy-piperidin-1-yl)-butyl]-[1,4]diazepan-5-one | (rac)-3-methoxypiperidine | 466.3 |
| 396 | 1-[(E)-3-(3-Chloro-4-fluoro-phenyl)-acryloyl]-4-[4-(4-isopropyl-piperazin-1-yl)-butyl]-[1,4]diazepan-5-one | 1-Isopropyl-piperazine | 479.4 |
| 397 | 1-[(E)-3-(3-Chloro-4-fluoro-phenyl)-acryloyl]-4-[4-(4-cyclopropyl-piperazin-1-yl)-butyl]-[1,4]diazepan-5-one | 1-Cyclopropyl-piperazine | 477.3 |
| 389 | 1-[(E)-3-(3-Chloro-4-fluoro-phenyl)-acryloyl]-4-[4-(4-cyclopentyl-piperazin-1-yl)-butyl]-[1,4]diazepan-5-one | 1-Cyclopentyl-piperazine | 505.4 |
| 399 | 1-[(E)-3-(3-Chloro-4-fluoro-phenyl)-acryloyl]-4-{4-[4-(2-methoxy-ethyl)-piperazin-1-yl]-butyl}-[1,4]diazepan-5-one | 1-(2-Methoxy-ethyl)-piperazine | 495.4 |
| 400 | (rac)-1-[(E)-3-(3-Chloro-4-fluoro-phenyl)-acryloyl]-4-[4-(4-hydroxy-3-methyl-piperidin-1-yl)-butyl]-[1,4]diazepan-5-one | (rac)-3-methyl-piperidin-4-ol (intermediate 94) | 466.3 |
| 401 | [1-(4-{4-[(E)-3-(3-Chloro-4-fluoro-phenyl)-acryloyl]-7-oxo-[1,4]diazepan-1-yl}-butyl)-piperidin-4-yl]-carbamic acid methyl ester | Piperidin-4-yl-carbamic acid methylester (intermediate 38) | 509.3 |
| 402 | [1-(4-{4-[(E)-3-(3-Chloro-4-fluoro-phenyl)-acryloyl]-7-oxo-[1,4]diazepan-1-yl}-butyl)-piperidin-4-yl]-methyl carbamic acid methyl ester | Methyl-piperidin-4-yl-carbamic acid methyl ester (intermediate 39) | 523.3 |
| 403 | (rac)-1-[(E)-3-(3-Chloro-4-fluoro-phenyl)-acryloyl]-4-[4-(4-isopropyl-3-methyl-piperazin-1-yl)-butyl]-[1,4]diazepan-5-one | (rac)-1-Isopropyl-2-methyl-piperazine | 493.4 |
| 404 | 1-[(E)-3-(3-Chloro-4-fluoro-phenyl)-acryloyl]-4-[4-(4-methoxymethyl-piperidin-1-yl)-butyl]-[1,4]diazepan-5-one | 4-methoxymethyl-piperidine | 480.4 |
| 405 | (rac)-1-[(E)-3-(3-Chloro-4-fluoro-phenyl)-acryloyl]-4-[4-(3-hydroxy-3-methyl-piperidin-1-yl)-butyl]-[1,4]diazepan-5-one | (rac)-(3-methyl-piperidin-3-yl)-methanol (intermediate 30) | 480.4 |
| 406 | (rac)-1-[(E)-3-(3-Chloro-4-fluoro-phenyl)-acryloyl]-4-[4-(3-methoxymethyl-3-methyl-piperidin-1-yl)-butyl]-[1,4]diazepan-5-one | (rac)-3-methoxymethyl-3-methyl-piperidine (intermediate 31) | 494.4 |
| 407 | (rac)-1-[(E)-3-(3-Chloro-4-fluoro-phenyl)-acryloyl]-4-[4-(2-hydroxymethyl-2-methyl-piperidin-1-yl)-butyl]-[1,4]diazepan-5-one | (rac)-(2-methyl-piperidin-2-yl)-methanol (intermediate 34) | 480.4 |

-continued

| Example No. | Compound Name | Amine | MS: (MH+) |
|---|---|---|---|
| 408 | (rac)-1-[(E)-3-(3-Chloro-4-fluoro-phenyl)-acryloyl]-4-[4-(cis-4-hydroxy-2-hydroxymethyl-piperidin-1-yl)-butyl]-[1,4]diazepan-5-one | (rac,cis)-2-hydroxymethyl-piperidin-4-ol) (intermediate 45) | 482.3 |
| 409 | (rac)-1-[(E)-3-(3-Chloro-4-fluoro-phenyl)-acryloyl]-4-[4-(4-hyroxy-3-methyl-piperidin-1-yl)-butyl]-[1,4]diazepan-5-one | (rac)-4-methyl-piperidin-3-ol (intermediate 91) | 466.3 |

Examples 410-421

General Procedure for Examples 410-421

A solution of 1-[(E)-3-(4-Chloro-3-fluoro-phenyl)-acryloyl]-4-(4-iodo-butyl)-[1,4]diazepan-5-one (intermediate 57) (0.1 mmol) in DMA (0.5 ml) was added to the appropriate amine (0.15 mmol), which are either commercially available or are described in the intermediate section, and a generous spatula of cesium carbonate and sodium iodide added. The reaction was then shaken at room termperature for 1 h, then raised to 80° C. for a further 1 h, filtered, and directly purifed purified by preparative HPLC.

| Example No. | Compound Name | Amine | MS: (MH+) |
|---|---|---|---|
| 410 | (rac)-1-[(E)-3-(4-Chloro-3-fluoro-phenyl)-acryloyl]-4-[4-(cis-3-methoxy-4-hydroxymethyl-piperidin-1-yl)-butyl]-[1,4]diazepan-5-one | (rac,cis)-(3-methoxy-piperidin-4-yl)-methanol (intermediate 50) | 496.4 |
| 411 | (rac)-1-[(E)-3-(4-Chloro-3-fluoro-phenyl)-acryloyl]-4-[4-(cis-3-hydroxy-4-hydroxymethyl-4-methyl-piperidin-1-yl)-butyl]-[1,4]diazepan-5-one | (rac,cis)-4-hydroxymethyl-4-methyl-piperidin-3-ol (intermediate 52) | 496.4 |
| 412 | (rac)-1-[(E)-3-(4-Chloro-3-fluoro-phenyl)-acryloyl]-4-[4-(trans-3-hydroxy-4-hydroxymethyl-4-methyl-piperidin-1-yl)-butyl]-[1,4]diazepan-5-one | (rac,trans)-4-hydroxymethyl-4-methyl-piperidin-3-ol (intermediate 53) | 496.4 |
| 413 | (rac)-1-[(E)-3-(4-Chloro-3-fluoro-phenyl)-acryloyl]-4-[4-(5-hydroxy-2-methyl-piperidin-1-yl)-butyl]-[1,4]diazepan-5-one | (rac)-6methyl-piperidin-3-ol (intermediate 66) | 466.4 |
| 414 | (rac)-1-[(E)-3-(4-Chloro-3-fluoro-phenyl)-acryloyl]-4-[4-(5-hydroxy-2-hydroxymethyl-piperidin-1-yl)-butyl]-[1,4]diazepan-5-one | (rac)-6-ydroxymethyl-piperidin-3-ol (intermediate 65) | 482.4 |
| 415 | 1-[(E)-3-(4-Chloro-3-fluoro-phenyl)-acryloyl]-4-[4-((+)-4-hydroxy-6-aza-spiro[2.5]oct-6-yl)-butyl]-[1,4]diazepan-5-one | (+)-6-Aza-spiro[2.5]octan-4-ol (intermediate 82) | 478.4 |
| 416 | 1-[(E)-3-(4-Chloro-3-fluoro-phenyl)-acryloyl]-4-[4-((−)-4-hydroxy-6-aza-spiro[2.5]oct-6-yl)-butyl]-[1,4]diazepan-5-one | (−)-6-Aza-spiro[2.5]octan-4-ol (intermediate 83) | 478.4 |
| 417 | (rac)-1-[(E)-3-(4-Chloro-3-fluoro-phenyl)-acryloyl]-4-[4-(2-hydroxymethyl-5-methoxy-piperidin-1-yl)-butyl]-[1,4]diazepan-5-one | (rac)-(5-methoxy-piperidin-2-yl)-methanol (intermediate 67) | 496.3 |
| 418 | (rac)-1-[(E)-3-(4-Chloro-3-fluoro-phenyl)-acryloyl]-4-[4-(5-hydroxy-2-methoxymethyl-piperidin-1-yl)-butyl]-[1,4]diazepan-5-one | (rac)-6-methoxymethyl-pipeirdin-3-ol (intermediate 74) | 496.4 |
| 419 | (rac)-1-[(E)-3-(4-Chloro-3-fluoro-phenyl)-acryloyl]-4-[4-(cis-3-hydroxy-2-hydroxymethyl-piperidin-1-yl)-butyl]-[1,4]diazepan-5-one | (rac,cis)-2-hydroxymethyl-piperidin-3-ol (intermediate 62) | 482.3 |
| 420 | (rac)-1-[(E)-3-(4-Chloro-3-fluoro-phenyl)-acryloyl]-4-[4-(3-hydroxy-4,4-dimethyl-piperidin-1-yl)-butyl]-[1,4]-diazepan-5-one | (rac)-4,4-dimethyl-piperidin-3-ol (intermediate 84) | 480.3 |
| 421 | (rac,cis)-1-[(E)-3-(4-Chloro-3-fluoro-phenyl)-acryloyl]-4-[4-(3-hydroxy-5-methyl-piperidin-1-yl)-butyl]-[1,4]diazepan-5-one | (rac,cis)-5-methyl-piperidin-3-ol (intermediate 75) | 466.3 |

Examples 422-490

General Procedure for Examples 422-490

A solution of 1-[(E)-3-(3,4-Dichloro-phenyl)-acryloyl]-4-(4-iodo-butyl)-[1,4]diazepan-5-one (Example 9B) (0.1 mmol) in DMA (0.5 ml) was added to the appropriate amine (0.15 mmol), which are either commercially available or are described in the intermediate section, and a generous spatula of cesium carbonate and sodium iodide added. The reaction was then shaken at room termperature for 1 h, then raised to 80° C. for a further 1 h, filtered, and directly purifed purified by preparative HPLC.

| Example No. | Compound Name | Amine | MS: (MH+) |
|---|---|---|---|
| 422 | 1-[(E)-3-(3,4-Dichloro-phenyl)-acryloyl]-4-[4-(4-hydroxymethyl-piperidin-1-yl)-butyl]-[1,4]diazepan-5-one | 4-hydroxymethyl-piperidine | 482.3 |
| 423 | 1-[(E)-3-(3,4-Dichloro-phenyl)-acryloyl]-4-[4-(3-methoxymethyl-piperidin-1-yl)-butyl]-[1,4]diazepan-5-one | (rac)-3-methoxymethyl-piperidine | 496.3 |
| 424 | 1-[(E)-3-(3,4-Dichloro-phenyl)-acryloyl]-4-[4-(4-hydroxy-piperidin-1-yl)-butyl]-[1,4]diazepan-5-one | piperidin-4-ol | 468.3 |
| 425 | (rac)-1-[(E)-3-(3,4-Dichloro-phenyl)-acryloyl]-4-[4-(3-hydroxymethyl-piperidin-1-yl)-butyl]-[1,4]diazepan-5-one | (rac)-3-hydroxymethyl-piperidine | 482.3 |
| 426 | 1-[(E)-3-(3,4-Dichloro-phenyl)-acryloyl]-4-[4-(4-hydroxymethyl-piperidin-1-yl)-butyl]-[1,4]diazepan-5-one | 4-hydroxymethyl-piperidine | 482.3 |
| 427 | (rac)-1-[(E)-3-(3,4-Dichloro-phenyl)-acryloy]-4-[4-(2-hydroxymethyl-piperidin-1-yl)-butyl]-[1,4]diazepan-5-one | (rac)-2-hydroxymethyl-piperidine | 482.3 |
| 428 | (rac,trans)-1-[(E)3-(3,4-Dichloro-phenyl)-acryloyl]-4-[4-(3-hydroxy-2-methyl-piperidin-1-yl)-butyl]-[1,4]diazepan-5-one | (rac,trans)-2-methyl-piperidin-3-ol (intermediate 87) | 482.3 |
| 429 | (rac,trans)-1-[(E)-3-(3,4-Dichloro-phenyl)-acryloyl]-4-[4-(4-fluoro-3-hydroxy-piperidin-1-yl)-butyl]-[1,4]diazepan-5-one | (rac,trans)-4-Fluoro-piperidin-3-ol (intermediate 89) | 486.2 |
| 430 | (rac,cis)-1-[(E)-3-(3,4-Dichloro-phenyl)-acryloyl]-4-[4-(3-fluoro-4-hydroxy-piperidin-1-yl)-butyl]-[1,4]diazepan-5-one | (rac,cis)-3-fluoro-piperidin-4-ol (intermediate 93) | 486.2 |
| 431 | (rac)-1-[(E)-3-(3,4-Dichloro-phenyl)-acryloyl]-4-[4-(3-hydroxy-3-methyl-piperidin-1-yl)-butyl]-[1,4]diazepan-5-one | (rac)-3-methyl-piperidin-3-ol (intermediate 101) | 482.3 |
| 432 | (rac)-1-[(E)-3-(3,4-Dichloro-phenyl)-acryloyl]-4-[4-(3-methoxymethyl-piperidin-1-yl)-butyl]-[1,4]diazepan-5-one | (rac)-3-Methoxymethyl-piperidine | 496.3 |
| 433 | (rac)-1-[(E)-3-(3,4-Dichloro-phenyl)-acryloyl]-4-[4-(3-hydroxy-pyrrolidin-1-yl)-butyl]-[1,4]diazepan-5-one | (rac)-Pyrrolidin-3-ol | 454.2 |
| 434 | (rac,trans)-1-[(E)-3-(3,4-Dichloro-phenyl)-acryloyl]-4-[4-(3-fluoro-4-hydroxy-piperidin-1-yl)-butyl]-[1,4]diazepan-5-one | (rac,trans)-3-fluoro-piperidin-4-ol (intermediate 90) | 486.2 |
| 435 | (rac)-1-[(E)-3-(3,4-Dichloro-phenyl)-acryloyl]-4-[4-(3-methoxy-piperidin-1-yl)-butyl]-[1,4]diazepan-5-one | (rac)-3-methoxypiperidine | 482.3 |
| 436 | 1-[(E)-3-(3,4-Dichloro-phenyl)-acryloyl]-4-[4-(4-isopropyl-piperazin-1-yl)-butyl]-[1,4]diazepan-5-one | 1-Isopropyl-piperazine | 495.3 |
| 437 | 1-[(E)-3-(3,4-Dichloro-phenyl)-acryloyl]-4-[4-(4-cyclopropyl-piperazin-1-yl)-butyl]-[1,4]diazepan-5-one | 1-Cyclopropyl-piperazine | 493.3 |
| 438 | 1-[(E)-3-(3,4-Dichloro-phenyl)-acryloyl]-4-[4-(4-cyclopentyl-piperazin-1-yl)-butyl]-[1,4]diazepan-5-one | 1-Cyclopentyl-piperazine | 521.3 |
| 439 | 1-[(E)-3-(3,4-Dichloro-phenyl)-acryloyl]-4-{4-[4-(2-methoxy-ethyl)-piperazin-1-yl]-butyl}-[1,4]diazepan-5-one | 1-(2-Methoxy-ethyl)-piperazine | 511.3 |

-continued

| Example No. | Compound Name | Amine | MS: (MH+) |
|---|---|---|---|
| 440 | (rac)-1-[(E)-3-(3,4-Dichloro-phenyl)-acryloyl]-4-[4-(4-hydroxy-3-methyl-piperidin-1-yl)-butyl]-[1,4]diazepan-5-one | (rac)-3-methyl-piperidin-4-ol (intermediate 94) | 482.3 |
| 441 | [1-(4-{4-[(E)-3-(3,4-Dichloro-phenyl)-acryloyl]-7-oxo-[1,4]diazepan-1-yl}-butyl)-piperidin-4-yl]-carbamic acid methyl ester | Piperidin-4-yl-carbamic acid methylester (intermediate 38) | 525.3 |
| 442 | [1-(4-{4-[(E)-3-(3,4-Dichloro-phenyl)-acryloyl]-7-oxo-[1,4]diazepan-1-yl}-butyl)-piperidin-4-yl]-methyl-carbamic acid methyl ester | Methyl-piperidin-4-yl-carbamic acid methyl ester (intermediate 39) | 539.3 |
| 443 | (rac)-1-[(E)-3-(3,4-Dichloro-phenyl)-acryloyl]-4-[4-(4-isopropyl-3-methyl-piperazin-1-yl)-butyl]-[1,4]diazepan-5-one | (rac)-1-Isopropyl-2-methyl-piperazine | 509.3 |
| 444 | 1-[(E)-3-(3,4-Dichloro-phenyl)-acryloyl]-4-[4-(4-methoxymethyl-3-piperidin-1-yl)-butyl]-[1,4]diazepan-5-one | 4-methoxymethyl-piperidine | 496.3 |
| 445 | (rac)-1-[(E)-3-(3,4-Dichloro-phenyl)-acryloyl]-4-[4-(3-hydroxymethyl-3-methyl-piperidin-1-yl)-butyl]-[1,4]diazepan-5-one | (rac)-(3-methyl-piperidin-3-yl)-methanol (intermediate 30) | 496.4 |
| 446 | (rac)-1-[(E)-3-(3,4-Dichloro-phenyl)-acryloyl]-4-[4-(3-methoxymethyl-3-methyl-piperidin-1-yl)-butyl]-[1,4]diazepan-5-one | (rac)-3-methoxymethyl-3-methyl-piperidine (intermediate 31) | 510.4 |
| 447 | (rac)-1-[(E)-3-(3,4-Dichloro-phenyl)-acryloyl]-4-[4-(2-hydroxymethyl-2-methyl-piperidin-1-yl)-butyl]-[1,4]diazepan-5-one | (rac)-(2-methyl-piperidin-2-yl)-methanol (intermediate 34) | 496.3 |
| 448 | (rac)-1-[(E)-3-(3,4-Dichloro-phenyl)-acryloyl]-4-[4-(3-hydroxy-4-methyl-piperidin-1-yl)-butyl]-[1,4]diazepan-5-one | (rac)-4-methyl-piperidin-3-ol (intermediate 91) | 482.3 |
| 449 | (rac)-1-[(E)-3-(3,4-Dichloro-phenyl)-acryloyl]-4-[4-(2-methoxymethyl-piperidin-1-yl)-butyl]-[1,4]diazepan-5-one | (rac)-2-methoxymethyl-piperidine | 496.4 |
| 450 | (rac)-1-[(E)-3-(3,4-Dichloro-phenyl)-acryloyl]-4-[4-(4-hydroxy-3-hydroxymethyl-piperidin-1-yl)-butyl]-[1,4]diazepan-5-one | (rac)-3-hydroxymethyl-piperidin-4-ol (intermediate 35) | 498.5 |
| 451 | (rac)-1-[(E)-3-(3,4-Dichloro-phenyl)-acryloyl]-4-[4-(4-hydroxy-3-methoxymethyl-piperidin-1-yl)-butyl]-[1,4]diazepan-5-one | (rac)-3-methoxymethyl-piperidin-4-ol (intermediate 36) | 512.5 |
| 452 | (rac)-1-[(E)-3-(3,4-Dichloro-phenyl)-acryloyl]-4-[4-(4-methoxy-3-methoxymethyl-piperidin-1-yl)-butyl]-[1,4]diazepan-5-one | (rac)-4-methoxy-3-methoxymethyl-piperidine (intermediate 37) | 526.6 |
| 453 | N-[1-(4-{4-[(E)-3-(3,4-Dichloro-phenyl)-acryloyl]-7-oxo-[1,4]diazepan-1-yl}-butyl)-piperidin-4-yl]-acetamide | N-Piperidin-4-yl-acetamide | 509.5 |
| 454 | (rac)-1-[(E)-3-(3,4-Dichloro-phenyl)-acryloyl]-4-[4-(trans-3-hydroxy-4-methyl-piperidin-1-yl)-butyl]-[1,4]diazepan-5-one | (rac,trans)-4-methyl-piperidin-3-ol (intermediate 100) | 482.5 |
| 455 | (rac)-1-[(E)-3-(3,4-Dichloro-phenyl)-acryloyl]-4-[4-(trans-4-hydroxy-3-methyl-piperidin-1-yl)-butyl]-[1,4]diazepan-5-one | (rac,trans)-3-methyl-piperidin-4-ol (intermediate 95) | 482.5 |
| 456 | (rac)-1-[(E)-3-(3,4-Dichloro-phenyl)-acryloyl]-4-[4-(4-hydroxy-6-aza-spiro[2.5]oct-6-yl)-butyl]-[1,4]diazepan-5-one | (rac)-6-Aza-spiro[2.5]octan-4-ol (intermediate 81) | 494.3 |
| 457 | (rac)-1-[(E)-3-(3,4-Dichloro-phenyl)-acryloyl]-4-[4-(8-hydroxy-5-aza-spiro[2.5]oct-5-yl)-butyl]-[1,4]diazepan-5-one | (rac)-5-Aza-spiro[2.5]octan-8-ol (intermediate 98) | 494.3 |
| 458 | (rac)-1-[(E)-3-(3,4-Dichloro-phenyl)-acryloyl]-4-[4-(cis-4-hydroxy-3-methyl-piperidin-1-yl)-butyl]-[1,4]diazepan-5-one | (rac,cis)-3-methyl-piperidin-4-ol (intermediate 96) | 482.3 |

-continued

| Example No. | Compound Name | Amine | MS: (MH+) |
|---|---|---|---|
| 459 | (rac)-1-[(E)-3-(3,4-Dichloro-phenyl)-acryloyl]-4-[4-(4-hydroxymethyl-4-methyl-piperidin-1-yl)-butyl]-[1,4]diazepan-5-one | (4-methyl-piperidin-4-yl)-methanol (intermediate 32) | 496.3 |
| 460 | 1-[(E)-3-(3,4-Dichloro-phenyl)-acryloyl]-4-{4-[(2-hydroxy-ethyl)-methyl-amino]-butyl}-[1,4]diazepan-5-one | 2-Methylamino-ethanol | 442.3 |
| 461 | 1-[(E)-3-(3,4-Dichloro-phenyl)-acryloyl]-4-{4-[(2-hydroxy-ethyl)-ethyl-amino]-butyl}-[1,4]diazepan-5-one | 2-Ethylamino-ethanol | 456.3 |
| 462 | (rac)-1-[(E)-3-(3,4-Dichloro-phenyl)-acryloyl]-4-[4-(2-hydroxymethyl-2-methyl-pyrrolidin-1-yl)-butyl]-[1,4]diazepan-5-one | (rac)-(2-methyl-pyrrolidin-2-yl)-methanol (intermediate 34) | 482.3 |
| 463 | (rac)-N-[1-(4-{4-[(E)-3-(3,4-Dichloro-phenyl)-acryloyl]-7-oxo-[1,4]diazepan-1-yl}-butyl)-piperidin-3-yl]-acetamide | (rac)-Piperidin-3-yl-carbamic acid methyl ester (intermediate 40) | 525.4 |
| 464 | (rac)-1-[(E)-3-(3,4-Dichloro-phenyl)-acryloyl]-4-[4-(4-hydroxy-3,3-dimethyl-piperidin-1-yl)-butyl]-[1,4]diazepan-5-one | (rac)-3,3-dimethyl-piperidin-4-ol (intermediate 97) | 496.4 |
| 465 | 1-[(E)-3-(3,4-Dichloro-phenyl)-acryloyl]-4-[4-(4-isobutyl-piperazin-1-yl)-butyl]-[1,4]diazepan-5-one | 1-Isobutyl-piperazine | 509.4 |
| 466 | (rac)-N-[1-(4-{4-[(E)-3-(3,4-Dichloro-phenyl)-acryloyl]-7-oxo-[1,4]diazepan-1-yl}-butyl)-piperidin-3-yl]-acetamide | (rac)-N-Piperidin-3-yl-acetamide | 509.4 |
| 467 | (rac)-1-[(E)-3-(3,4-Dichloro-phenyl)-acryloyl]-4-[4-(1-oxa-8-aza-Spiro[4.5]dec-8-yl)-butyl]-[1,4]diazepan-5-one | 1-Oxa-8-aza-spiro[4.5]decane (intermediate 27) | 508.4 |
| 468 | (rac)-1-[(E)-3-(3,4-Dichloro-phenyl)-acryloyl]-4-[4-(cis-3-hydroxy-4-hydroxymethyl-piperidin-1-yl)-butyl]-[1,4]diazepan-5-one | (rac,cis)-4-hydroxymethyl-piperidin-3-ol (intermediate 47) | 498.4 |
| 469 | (rac)-1-[(E)-3-(3,4-Dichloro-phenyl)-acryloyl]-4-[4-(cis-3-hydroxy-4-methoxymethyl-piperidin-1-yl)-butyl]-[1,4]diazepan-5-one | (rac,cis)-4-methoxymethyl-piperidin-3-ol (intermediate 49) | 512.4 |
| 470 | (rac)-1-[(E)-3-(3,4-Dichloro-phenyl)-acryloyl]-4-[4-(cis-3-methoxy-4-methoxymethyl-piperidin-1-yl)-butyl]-[1,4]diazepan-5-one | (rac,cis)-3-methoxy-4-methoxymethyl-piperidine (intermediate 51) | 526.4 |
| 471 | (rac)-1-[(E)-3-(3,4-Dichloro-phenyl)-acryloyl]-4-[4-(trans-3-hydroxy-4-hydroxymethyl-piperidin-1-yl)-butyl]-[1,4]diazepan-5-one | (rac,trans)-4-hydroxymethyl-piperidin-3-ol (intermediate 48) | 498.4 |
| 472 | (rac)-1-[(E)-3-(3,4-Dichloro-phenyl)-acryloyl]-4-[4-(cis-3-methoxy-4-hydroxymethyl-piperidin-1-yl)-butyl]-[1,4]diazepan-5-one | (rac,cis)-(3-methoxy-piperidin-4-yl)-methanol (intermediate 50) | 512.4 |
| 473 | (rac)-1-[(E)-3-(3,4-Dichloro-phenyl)-acryloyl]-4-[4-(cis-3-hydroxy-4-hydroxymethyl-4-methyl-piperidin-1-yl)-butyl]-[1,4]diazepan-5-one | (rac,cis)-4-hydroxymethyl-4-methyl-piperidin-3-ol (intermediate 52) | 512.4 |

-continued

| Example No. | Compound Name | Amine | MS: (MH+) |
|---|---|---|---|
| 474 | (rac)-1-[(E)-3-(3,4-Dichloro-phenyl)-acryloyl]-4-[4-(trans-3-hydroxy-4-hydroxymethyl-4-methyl-piperidin-1-yl)-butyl]-[1,4]diazepan-5-one | (rac,trans)-4-hydroxymethyl-4-methyl-piperidin-3-ol (intermediate 53) | 512.4 |
| 475 | (rac)-1-[(E)-3-(3,4-Dichloro-phenyl)-acryloyl]-4-[4-(5-hydroxy-2-methyl-piperidin-1-yl)-butyl]-[1,4]diazepan-5-one | (rac)-6-methyl-piperidin-3-ol (intermediate 66) | 482.4 |
| 476 | (rac)-1-[(E)-3-(3,4-Dichloro-phenyl)-acryloyl]-4-[4-(5-hydroxy-2-hydroxymethyl-piperidin-1-yl)-butyl]-[1,4]diazepan-5-one | (rac)-6-hydroxymethyl-piperidin-3-ol (intermediate 65) | 498.4 |
| 477 | (rac)-1-[(E)-3-(3,4-Dichloro-phenyl)-acryloyl]-4-[4-(2-hydroxymethyl-5-methoxy-piperidin-1-yl)-butyl]-[1,4]diazepan-5-one | (rac)-(5-methoxy-piperidin-2-yl)-methanol (intermediate 67) | 512.3 |
| 478 | (rac)-1-[(E)-3-(3,4-Dichloro-phenyl)-acryloyl]-4-[4-(5-hydroxy-4-methoxy-2-methoxymethyl-piperidin-1-yl)-butyl]-[1,4]diazepan-5-one | (rac)-4-methoxy-6-methoxymethyl-piperidin-3-ol (intermediate 68) | 542.3 |
| 479 | (rac)-1-[(E)-3-(3,4-Dichloro-phenyl)-acryloyl]-4-[4-(5-hydroxy-2-methoxymethyl-piperidin-1-yl)-butyl]-[1,4]diazepan-5-one | (rac)-6-methoxymethyl-piperidin-3-ol (intermediate 63) | 512.3 |
| 480 | (rac)-1-[(E)-3-(3,4-Dichloro-phenyl)-acryloyl]-4-[4-(cis-3-hydroxy-2-hydroxymethyl-piperidin-1-yl)-butyl]-[1,4]diazepan-5-one | (rac,cis)-2-hydroxymethyl-piperidin-3-ol (intermediate 62) | 498.3 |
| 481 | (rac)-1-[(E)-3-(3,4-Dichloro-phenyl)-acryloyl]-4-[4-(4-hydroxy-4,4-dimethyl-piperidin-1-yl)-butyl]-[1,4]diazepan-5-one | (rac)-4,4-dimethyl-piperidin-3-ol (intermediate 84) | 496.3 |
| 482 | (rac,cis)-1-[(E)-3-(3,4-Dichloro-phenyl)-acryloyl]-4-[4-(3-hydroxy-5-methyl-piperidin-1-yl)-butyl]-[1,4]diazepan-5-one | (rac,cis)-5-methyl-piperidin-3-ol (intermediate 75) | 482.3 |
| 483 | (rac)-N-[(2RS,4SR,5RS)-1-(4-{4-[(E)-3-(3,4-Dichloro-phenyl)-acryloyl]-7-oxo-[1,4]diazepan-1-yl}-butyl)-5-methoxy-2-methoxymethyl-piperidin-4-yl]-acetamide | N-((2RS,4SR,5RS)-5-Methoxy-2-methoxymethyl-piperidin-4-yl)-acetamide (intermediate 69) | 583.3 |
| 484 | (rac,trans)-1-[(E)-3-(3,4-Dichloro-phenyl)-acryloyl]-4-[4-(5-hydroxy-2-methoxymethyl-piperidin-1-yl)-butyl]-[1,4]diazepan-5-one | (rac,trans)-6-methoxymethyl-piperidin-3-ol (intermediate 74) | 512.3 |
| 485 | (rac)-2-[1-(4-{4-[(E)-3-(3,4-Dichloro-phenyl)-acryloyl]-7-oxo-[1,4]diazepan-1-yl}-butyl)-6-hydroxymethyl-piperidin-3-yloxy]-acetamide | (rac)-2-(6-Hydroxymethyl-piperidin-3-yloxy)-acetamide (intermediate 72) | 555.3 |
| 486 | (rac)-1-[(E)-3-(3,4-Dichloro-phenyl)-acryloyl]-4-[4-(3-hydroxy-2-methoxymethyl-piperidin-1-yl)-butyl]-[1,4]diazepan-5-one | (rac)-2-Methoxymethyl-piperidin-3-ol (intermediate 73) | 512.3 |
| 487 | (rac)-1-[(E)-3-(3,4-Dichloro-phenyl)-acryloyl]-4-[4-(5-hydroxy-2-methyl-piperidin-1-yl)-butyl]-[1,4]diazepan-5-one | (rac,trans)-6-Methyl-piperidin-3-ol (intermediate 70) | 482.3 |
| 488 | (rac,cis)-1-[(E)-3-(3,4-Dichloro-phenyl)-acryloyl]-4-[4-(3-hydroxy-2-methoxymethyl-6-methyl-piperidin-1-yl)-butyl]-[1,4]diazepan-5-one | (rac,cis)-2-Methoxymethyl-6-methyl-piperidin-3-ol (intermediate 64) | 526.3 |

-continued

| Example No. | Compound Name | Amine | MS: (MH+) |
|---|---|---|---|
| 489 | (rac)-1-[(E)-3-(3,4-Dichloro-phenyl)-acryloyl]-4-[4-(3-hydroxy-2,6-bis-methoxymethyl-piperidin-1-yl)-butyl]-[1,4]diazepan-5-one | (rac)-2,6-Bis-methoxymethyl-piperidin-3-ol (intermediate 71) | 556.3 |
| 490 | (rac)-1-[(E)-3-(3,4-Dichloro-phenyl)-acryloyl]-4-[4-(3-hydroxy-5-methoxymethyl-piperidin-1-yl)-butyl]-[1,4]diazepan-5-one | (rac)-5-Methoxymethyl-piperidin-3-ol (intermediate 76) | 498.3 |

Examples 491-494

General Procedure for Examples 491-494

A solution of 3-{4-[(E)-3-(4-Chloro-3-fluoro-phenyl)-acryloyl]-7-oxo-[1,4]diazepan-1-yl}-propionaldehyde (intermediate 60) (0.1 mmol) in DCE (0.5 ml) was added to the appropriate amine (0.1 mmol), which are either commercially available or are described in the intermediate section, followed by a freshly prepared solution of pyridine-borane complex (25 ul, 8M in pyridine, 0.2 mmol) and acetic acid (25 ul) in EtOH (0.5 ml). The reaction was then shaken overnight, concentrated and the residue purified by preparative HPLC.

| Example No. | Compound Name | Amine | MS: (MH+) |
|---|---|---|---|
| 491 | 1-[(E)-3-(4-Chloro-3-fluoro-phenyl)-acryloyl]-4-[3-((+,cis)-3-hydroxy-4-methyl-piperidin-1-yl)-propyl]-[1,4]diazepan-5-one | (+,cis)-4-Methyl-piperidin-3-ol (intermediate 85) | 452.3 |
| 492 | 1-[(E)-3-(4-Chloro-3-fluoro-phenyl)-acryloyl]-4-[3-((−,cis)-3-hydroxy-4-methyl-piperidin-1-yl)-propyl]-[1,4]diazepan-5-one | (−,cis)-4-Methyl-piperidin-3-ol (intermediate 86) | 452.3 |
| 493 | 1-[(E)-3-(4-Chloro-3-fluoro-phenyl)-acryloyl]-4-[3-((+)-4-hydroxy-6-aza-spiro[2.5]oct-6-yl)-propyl]-[1,4]diazepan-5-one | (+)-6-Aza-spiro[2.5]octan-4-ol (intermediate 82) | 464.3 |
| 494 | 1-[(E)-3-(4-Chloro-3-fluoro-phenyl)-acryloyl]-4-[3-((−)-4-hydroxy-6-aza-spiro[2.5]oct-6-yl)-propyl]-[1,4]diazepan-5-one | (−)-6-Aza-spiro[2.5]octan-4-ol (intermediate 83) | 464.3 |

Examples 495-498

General Procedure for Examples 495-498

To a suspension of 4-[3-((−)-4-hydroxy-6-aza-spiro[2.5]oct-6-yl)-propyl]-[1,4]diazepan-5-one dihydrochloride (intermediate 92, 0.1 mmol), O-(7-azabenotriazol-1-yl)-1,1,3,3-tetramethyluronium hexafluorophosphate (46 mg, 0.12 mmol), the appropriate carboxylic acid in DMF (1 ml) was added Et$_3$N (21 ul, 0.15 mmol) and the mixture shaken for 1 h. The reaction was then directly purified by preparative HPLC.

| Example No. | Compound Name | Acid | MS: (MH+) |
|---|---|---|---|
| 495 | 1-[(E)-3-(3,4-Difluoro-phenyl)-acryloyl]-4-[3-((−)-4-hydroxy-6-aza-spiro[2.5]oct-6-yl)-propyl]-[1,4]diazepan-5-one | (E)-3-(3,4-Difluoro-phenyl)-acrylic acid | 448.4 |
| 496 | 1-[(E)-3-(3-Chloro-phenyl)-acryloyl]-4-[3-((−)-4-hydroxy-6-aza-spiro[2.5]oct-6-yl)-propyl]-[1,4]diazepan-5-one | (E)-3-(3-Chloro-phenyl)-acrylic acid | 446.4 |
| 497 | 1-[(E)-3-(5,6-Dichloro-pyridin-3-yl)-acryloyl]-4-[3-((−)-4-hydroxy-6-aza-spiro[2.5]oct-6-yl)-propyl]-[1,4]diazepan-5-one | (E)-3-(5,6-Dichloro-pyridin-3-yl)-acrylic acid (Example 12B) | 481.3 |
| 498 | 1-[(E)-3-(4-Chloro-phenyl)-acryloyl]-4-[3-((−)-4-hydroxy-6-aza-spiro[2.5]oct-6-yl)-propyl]-[1,4]diazepan-5-one | (E)-3-(4-Chloro-phenyl)-acrylic acid | 446.4 |

Examples 499-501

General Procedure for Examples 499-501

A solution of (rac)-4,4-dimethyl-piperidin-3-ol hydrochloride (intermediate 84) (0.15 mmol) in DMA (0.5 ml) was added to the appropriate epoxide (0.10 mmol) and a generous spatula of cesium carbonate added. The reaction was then shaken overnight at 80° C., filtered, and directly purifed purified by preparative HPLC.

| Example No. | Compound Name | Epoxide | MS: (MH+) |
|---|---|---|---|
| 499 | (rac)-1-[(E)-3-(3,4-Difluoro-phenyl)-acryloyl]-4-[2-hydroxy-3-(3-hydroxy-4,4-dimethyl-piperidin-1-yl)-propyl]-[1,4]diazepan-5-one | (rac)-1-[(E)-3-(3,4-Difluoro-phenyl)-acryloyl]-4-oxiranylmethyl-[1,4]diazepan-5-one (Example 177A) | 466.3 |
| 500 | 1-[(E)-3-(3-Chloro-4-fluoro-phenyl)-acryloyl]-4-[(R)-3-hydroxy-4-(3-hydroxy-4,4-dimethyl-piperidin-1-yl)-butyl]-[1,4]diazepan-5-one | 1-[(E)-3-(3-Chloro-4-fluoro-phenyl)-acryloyl]-4-((R)-2-oxiranyl-ethyl)-[1,4]diazepan-5-one (intermediate 56) | 496.3 |
| 501 | 1-[(E)-3-(3,4-Dichloro-phenyl)-acryloyl]-4-[(R)-3-hydroxy-4-(3-hydroxy-4,4-dimethyl-piperidin-1-yl)-butyl]-[1,4]diazepan-5-one | 1-[(E)-3-(3,4-Dichloro-phenyl)-acryloyl]-4-((R)-2-oxiranyl-ethyl)-[1,4]diazepan-5-one (Example 172C) | 512.3 |

Examples 502-505

General Procedure for Examples 502-505

A solution of (rac, cis)-5-methyl-piperidine-3-ol hydrochloride (intermediate 75) (0.15 mmol) in DMA (0.5 ml) was added to the appropriate epoxide (0.10 mmol) and a generous spatula of cesium carbonate added. The reaction was then shaken overnight at 80° C., filtered, and directly purifed purified by preparative HPLC.

| Example No. | Compound Name | Epoxide | MS: (MH+) |
|---|---|---|---|
| 502 | 1-[(E)-3-(3-Chloro-4-fluoro-phenyl)-acryloyl]-4-[(R)-3-hydroxy-4-(cis-3-hydroxy-5-methyl-piperidin-1-yl)-butyl]-[1,4]diazepan-5-one | 1-[(E)-3-(3-Chloro-4-fluoro-phenyl)-acryloyl]-4-((R)-2-oxiranyl-ethyl)-[1,4]diazepan-5-one (intermediate 56) | 482.3 |
| 503 | 1-[(E)-3-(3,4-Dichloro-phenyl)-acryloyl]-4-[(R)-3-hydroxy-4-(cis-3-hydroxy-5-methyl-piperidin-1-yl)-butyl]-[1,4]diazepan-5-one | 1-[(E)-3-(3,4-Dichloro-phenyl)-acryloyl]-4-((R)-2-oxiranyl-ethyl)-[1,4]diazepan-5-one (Example 172C) | 498.3 |
| 504 | (rac)-1-[(E)-3-(3,4-Difluoro-phenyl)-acryloyl]-4-[2-hydroxy-3-(cis-3-hydroxy-5-methyl-piperidin-1-yl)-propyl]-[1,4]diazepan-5-one | (rac)-1-[(E)-3-(3,4-Difluoro-phenyl)-acryloyl]-4-oxiranylmethyl-[1,4]diazepan-5-one (Example 177A) | 452.3 |
| 505 | (rac)-1-[(E)-3-(3,4-Difluoro-phenyl)-acryloyl]-4-[3-hydroxy-4-(cis-3-hydroxy-5-methyl-piperidin-1-yl)-butyl]-[1,4]diazepan-5-one | (rac)-1-[(E)-3-(3,4-Difluoro-phenyl)-acryloyl]-4-(2-oxiranyl-ethyl)-[1,4]diazepan-5-one (intermediate 58) | 466.3 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

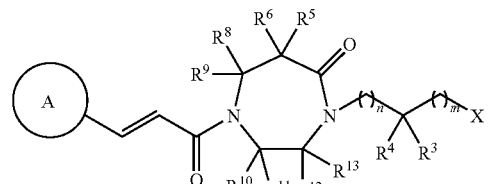

wherein

A is aryl or heteroaryl, said aryl and said heteroaryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said aryl and said heteroaryl being optionally substituted by $C_{1-6}$ alkylenedioxy;

X is —N($R^1$)($R^2$) or —N$^+$($R^1$)($R^2$)($R^7$);

i) $R^1$ and $R^2$ are, independently to each other, hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$; or $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl;

$R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen; or ii) $R^1$ is hydrogen, $C_{1-6}$ alkyl, $C_{3-6}$ alkenyl, $C_{3-6}$ alkinyl, hydroxy $C_{1-6}$ alkyl, $C_{1-6}$ alkoxy $C_{1-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$;

$R^3$ is hydrogen, $C_{1-6}$ alkyl, $C_{3-7}$ cycloalkyl, $C_{3-7}$ cycloalkyl $C_{1-6}$ alkyl, halogen or halo $C_{1-6}$ alkyl;

$R^2$ and $R^4$, together with the nitrogen atom to which $R^2$ is attached, the carbon atom to which $R^4$ is attached and the $C_{1-2}$ alkylene between said nitrogen atom and said carbon atom, if any, form heterocyclyl optionally substituted by one to three substituents independently selected from the group consisting of $C_{1-6}$ alkyl and fluorine;

$R^5$ and $R^6$ are, independently to each other, hydrogen, fluoro, $C_{1-6}$ alkyl or $C_{3-7}$ cycloalkyl;

$R^7$ is $C_{1-6}$ alkyl;

$R^8$, $R^9$, $R^{10}$, $R^{11}$, $R^{12}$ and $R^{13}$ are, independently to each other, hydrogen, $C_{1-6}$ alkyl or $C_{3-7}$ cycloalkyl;

$R^d$ is hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and the phenyl of said phenyl and said phenyl $C_{1-3}$ alkyl, the heteroaryl of said heteroaryl and said heteroaryl $C_{1-3}$ alkyl, and the heterocyclyl being optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^aSO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of the heterocyclyl being optionally replaced with a carbonyl group;

$R^a$, $R^b$ and $R^c$ are independently hydrogen or $C_{1-6}$ alkyl;

n is an integer of 0 to 3;

m is an integer of 0 to 3;

m+n is an integer of 1 to 5;

or a pharmaceutically acceptable salts thereof;

wherein, unless otherwise indicated, the term "aryl" means phenyl or naphthyl;

the term "heterocyclyl" means non-aromatic mono- or bicyclic radicals of four to nine ring atoms in which one to three ring atoms are heteroatoms independently selected from N, O and S(O)$_n$ (where n is an integer from 0 to 2), the remaining ring atoms being C;

the term "heteroaryl" means a monocyclic or bicyclic radical of 5 to 10 ring atoms having one to three ring heteroatoms independently selected from N, O, and S, the remaining ring atoms being C;

the term "acyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

2. The compounds of claim 1 wherein A is aryl, said aryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said aryl being optionally substituted by $C_{1-6}$ alkylenedioxy.

3. The compounds of claim 2 wherein $R^1$ and $R^2$ are, independently to each other, hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl;

and $R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

4. The compounds of claim 3 wherein the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are substituted by one to three substituents independently selected from the group consisting of $R^d$.

5. The compounds of claim 2 wherein $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group;

and $R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

6. The compounds of claim 5 wherein one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl.

7. The compounds of claim 2 wherein $R^1$ is hydrogen, $C_{1-6}$ alkyl, $C_{3-6}$ alkenyl, $C_{3-6}$ alkinyl, hydroxy $C_{1-6}$ alkyl, $C_{1-6}$ alkoxy $C_{1-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl.

8. The compounds of claim 7 wherein the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$.

9. The compounds of claim 1 wherein A is heteroaryl, said heteroaryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said heteroaryl being optionally substituted by $C_{1-6}$ alkylenedioxy.

10. The compounds of claim 9 wherein $R^1$ and $R^2$ are, independently to each other, hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl;

and wherein $R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

11. The compounds of claim 10 wherein the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are substituted by one to three substituents independently selected from the group consisting of $R^d$.

12. The compounds of claim 9 wherein $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group;

and $R^3$ and $R^4$ are, independently to each other, hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, hydroxy-$C_{1-6}$ alkyl, $C_{1-6}$ alkoxy-$C_{1-6}$ alkyl, halogen or halo $C_{1-6}$ alkyl; or $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

13. The compounds of claim 12 wherein one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl.

14. The compounds of claim 9 wherein $R^1$ is hydrogen, $C_{1-6}$ alkyl, $C_{3-6}$ alkenyl, $C_{3-6}$ alkinyl, hydroxy $C_{1-6}$ alkyl, $C_{1-6}$ alkoxy $C_{1-6}$ alkyl, $C_{3-7}$ cycloalkyl, $C_{3-7}$ cycloalkyl $C_{1-6}$ alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl.

15. The compounds of claim 14 wherein the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$.

16. The compounds of claim 1, wherein $R^3$ and $R^4$ are, independently to each other, hydrogen, $C_{1-6}$ alkyl, $C_{3-7}$ cycloalkyl, $C_{3-7}$ cycloalkyl $C_{1-6}$ alkyl, halogen or halo $C_{1-6}$ alkyl;

$R^8$, $R^9$, $R^{10}$, $R^{11}$, $R^{12}$ and $R^{13}$ are hydrogen;

$R^d$ is hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^aSO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and the phenyl of said phenyl and said phenyl $C_{1-3}$ alkyl, the heteroaryl of said heteroaryl and said heteroaryl $C_{1-3}$ alkyl, and the heterocyclyl being optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of the heterocyclyl being optionally replaced with a carbonyl group.

17. The compounds of claim 1, wherein A is phenyl optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or A is phenyl optionally substituted by $C_{1-6}$ alkylenedioxy.

18. The compounds of claim 1, wherein A is phenyl substituted by one or two halogen atoms independently selected from the group consisting of chlorine and fluorine.

19. The compounds of claim 1, wherein A is phenyl substituted by two halogen atoms independently selected from the group consisting of chlorine and fluorine at its 3,4 or 3,5 position.

20. The compounds of claim 1, wherein X is —N($R^1$)($R^2$).

21. The compounds of claim 20, wherein at least one of $R^1$ and $R^2$ is other than hydrogen.

22. The compounds of claim 20, wherein $R^1$ is hydrogen, $C_{1-6}$ alkyl, or hydroxy $C_{2-6}$ alkyl and $R^2$ is $C_{3-7}$ cycloalkyl, heterocyclyl, heterocyclyl $C_{1-6}$ alkyl, $C_{7-10}$ bicycloalkyl, hydroxy $C_{2-6}$ alkyl or $C_{1-6}$ alkoxy $C_{2-6}$ alkyl, in which the cycloalkyl and the heterocyclyl of said heterocyclyl and said heterocyclyl $C_{1-6}$ alkyl are optionally substituted by one or two substituents independently selected from the group consisting of $C_{1-6}$ alkyl, hydroxy, heteroaryl and $C_{1-6}$ alkoxy.

23. The compounds of claim 20, wherein $R^1$ is hydrogen and $R^2$ is heterocyclyl.

24. The compounds of claim 20, wherein m+n is an integer of 1 or 2.

25. The compounds of claim 20, wherein $R^3$, $R^4$, $R^5$ and $R^6$ are hydrogen.

26. The compounds of claim 20, wherein $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or
one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl.

27. The compounds of claim 26, wherein the heterocyclyl formed by $R^1$ and $R^2$, together with the nitrogen atom to which they are attached, is a mono-cyclic radical of five or six ring atoms in which one more ring atom, in addition to the nitrogen atom, may be a heteroatom independently selected from N, O and $S(O)_n$ (where n is an integer from 0 to 2).

28. The compounds of claim 26, wherein the heterocyclyl formed by $R^1$ and $R^2$, together with the nitrogen atom to which they are attached, is piperidyl, pyrrolidinyl, piperazinyl, morpholinyl, thiomorpholinyl or 1,1-dioxo-hiomorphlinyl.

29. The compounds of claim 26, wherein the heterocyclyl formed by $R^1$ and $R^2$, together with the nitrogen atom to which they are attached, is piperidyl or pyrrolidinyl.

30. The compounds of claim 26, wherein the heterocyclyl formed by $R^1$ and $R^2$, together with the nitrogen atom to which they are attached, is optionally substituted by one or two substituents independently selected from the group consisting of hydroxy, phenyl and hydroxy $C_{1-6}$ alkyl, and/or
one of the ring carbon atoms of the heterocyclyl formed by $R^1$ and $R^2$ may be shared by another ring which is five or six membered mono-cyclic heterocyclyl, one or two ring carbon atoms of said another ring being optionally replaced by a carbonyl group.

31. The compounds of claim 26, wherein m+n is an integer of 1 to 3.

32. The compounds of claim 26, wherein $R^3$, $R^4$, $R^5$ and $R^6$ are hydrogen.

33. The compounds of claim 1, which is
1-[(E)-3-(3,4-Dichloro-phenyl)-acryloyl]-4-(4-piperidin-1-yl-butyl)-[1,4]diazepan-5-one,
1-[(E)-3-(3-Chloro-4-fluoro-phenyl)-acryloyl]-4-(3-piperidin-1-yl-propyl)-[1,4]diazepan-5-one,
1-[(E)-3-(4-Chloro-3-fluoro-phenyl)-acryloyl]-4-(3-piperidin-1-yl-propyl)-[1,4]diazepan-5-one,
8-(3-{4-[(E)-3-(3,4-Dichloro-phenyl)-acryloyl]-7-oxo-[1,4]diazepan-1-yl}-propyl)-1,3,8-triaza-spiro[4.5]decane-2,4-dione,
1-[(E)-3-(3,4-Dichloro-phenyl)-acryloyl]-4-[3-(4-hydroxy-4-phenyl-piperidin-1yl)-propyl]-[1,4]diazepan-5-one,
(+/−)-1-[(E)-3-(3,4-Dichloro-phenyl)-acryloyl]-4-[3-(3-hydroxy-piperidin-1-yl)-propyl]-[1,4]diazepan-5-one,
8-(3-{4-[(E)-3-(3,4-Dichloro-phenyl)-acryloyl]-7-oxo-[1,4]diazepan-1-yl}-propyl)-1-oxa-3,8-diaza-spiro[4.5]decan-2-one,
1-[(E)-3-(3,4-Dichloro-phenyl)-acryloyl]-4-[3-(tetrahydro-pyran-4-ylamino)-ethyl]-[1,4]diazepan-5-one,
(S)-1-[(E)-3-(3,4-Dichloro-phenyl)-acryloyl]-4-[3-(2-hydroxymethyl-pyrrolidin-1-yl)-ethyl]-[1,4]diazepan-5-one, or
1-[(E)-3-(3,4-Dichloro-phenyl)-acryloyl]-4-(2-pyrrolidin-1-yl-ethyl)-[1,4]diazepan-5-one.

34. The compounds of claim 1, which is
1-[(E)-3-(3-Chloro-4-fluoro-phenyl)-acryloyl]-4-[3-((−,cis)-3-hydroxy-4-methyl-piperidin-1-yl)-propyl]-[1,4]diazepan-5-one,
1-[(E)-3-(3-Chloro-4-fluoro-phenyl)-acryloyl]-4-[3-(3-hydroxy-4,4-dimethyl-piperidin-1-yl)-propyl]-[1,4]diazepan-5-one,
(cis)-1-[(E)-3-(3-Chloro-4-fluoro-phenyl)-acryloyl]-4-[3-(3-hydroxy-5-methyl-piperidin-1-yl)-propyl]-[1,4]diazepan-5-one,
1-[(E)-3-(3,4-Dichloro-phenyl)-acryloyl]-4-[2-hydroxy-3-(3-hydroxy-4-methyl-piperidin-1-yl)-propyl]-[1,4]diazepan-5-one,
1-[(E)-3-(3,4-Dichloro-phenyl)-acryloyl]-4-[(S)-2-hydroxy-3-((−)-4-hydroxy-6-aza-spiro[2.5]oct-6-yl)-propyl]-[1,4]diazepan-5-one,
1-[(E)-3-(3-Chloro-4-fluoro-phenyl)-acryloyl]-4-[(S)-2-hydroxy-3-(3-hydroxy-4,4-dimethyl -piperidin-1-yl)-propyl]-[1,4]diazepan-5-one,
1-[(E)-3-(3-Chloro-4-fluoro-phenyl)-acryloyl]-4-[(S)-2-hydroxy-3-(cis-3-hydroxy-5-methyl-piperidin-1-yl)-propyl]-[1,4]diazepan-5-one,
1-[(E)-3-(4-Chloro-3-fluoro-phenyl)-acryloyl]-4-[4-((−)-4-hydroxy-6-aza-spiro[2.5]oct-6-yl)-butyl]-[1,4]diazepan-5-one,
(cis)-1-[(E)-3-(3-Chloro-4-fluoro-phenyl)-acryloyl]-4-[4-(3-hydroxy-5-methyl-piperidin-1-yl)-butyl]-[1,4]diazepan-5-one,
1-[(E)-3-(3-Chloro-phenyl)-acryloyl]-4-[3-((−)-4-hydroxy-6-aza-spiro[2.5]oct-6-yl)-propyl]-[1,4]diazepan-5-one, or
1-[(E)-3-(5,6-Dichloro-pyridin-3-yl)-acryloyl]-4-[3-((−)-4-hydroxy-6-aza-spiro[2.5]oct-6-yl)-propyl]-[1,4]diazepan-5-one.

35. A pharmaceutical composition comprising a compound of claim 1 and a pharmaceutically acceptable excipient.

* * * * *